United States Patent
Weinstabl et al.

(10) Patent No.: US 11,304,929 B2
(45) Date of Patent: Apr. 19, 2022

(54) TOSYLACETATE BASED COMPOUNDS AND DERIVATIVES THEREOF AS PHGDH INHIBITORS

(71) Applicant: Boehringer Ingelheim International GmbH, Ingelheim am Rhein (DE)

(72) Inventors: Harald Weinstabl, Vienna (AT); Georg Dahmann, Biberach an der Riss (DE); Matthias Treu, Vienna (AT); Bernd Wellenzohn, Friedrichshafen (DE); Stephan Karl Zahn, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 359 days.

(21) Appl. No.: 16/493,346

(22) PCT Filed: Mar. 13, 2018

(86) PCT No.: PCT/EP2018/056170
§ 371 (c)(1),
(2) Date: Sep. 12, 2019

(87) PCT Pub. No.: WO2018/167019
PCT Pub. Date: Sep. 20, 2018

(65) Prior Publication Data
US 2022/0008386 A1  Jan. 13, 2022

(30) Foreign Application Priority Data
Mar. 14, 2017 (EP) ..................... 17160838

(51) Int. Cl.
| | | |
|---|---|---|
| *C07D 209/42* | (2006.01) | |
| *C07D 403/04* | (2006.01) | |
| *C07D 209/60* | (2006.01) | |
| *C07D 471/04* | (2006.01) | |
| *C07D 401/12* | (2006.01) | |
| *C07D 231/14* | (2006.01) | |
| *C07D 405/12* | (2006.01) | |
| *A61K 31/404* | (2006.01) | |
| *A61K 9/20* | (2006.01) | |
| *A61K 31/4155* | (2006.01) | |
| *A61K 31/437* | (2006.01) | |
| *A61K 31/5377* | (2006.01) | |
| *A61K 31/496* | (2006.01) | |
| *A61K 45/06* | (2006.01) | |

(52) U.S. Cl.
CPC .......... *A61K 31/404* (2013.01); *A61K 9/2013* (2013.01); *A61K 9/2018* (2013.01); *A61K 9/2027* (2013.01); *A61K 9/2059* (2013.01); *A61K 31/4155* (2013.01); *A61K 31/437* (2013.01); *A61K 31/496* (2013.01); *A61K 31/5377* (2013.01); *A61K 45/06* (2013.01); *C07D 209/42* (2013.01); *C07D 209/60* (2013.01); *C07D 231/14* (2013.01); *C07D 401/12* (2013.01); *C07D 403/04* (2013.01); *C07D 405/12* (2013.01); *C07D 471/04* (2013.01)

(58) Field of Classification Search
CPC ... C07D 209/42; C07D 231/14; C07D 403/04
See application file for complete search history.

(56) References Cited

U.S. PATENT DOCUMENTS 8,293,917 B2 * 10/2012 Cook .................. A61P 37/08
546/275.4

FOREIGN PATENT DOCUMENTS

| WO | 2000042213 A1 | 7/2000 |
|---|---|---|
| WO | 2002080899 A1 | 10/2002 |
| WO | 2011106632 | 9/2011 |
| WO | 2016040449 A1 | 3/2016 |

OTHER PUBLICATIONS

Fuller, An Improved model for Fragment-based lead generation at Astra Zeneca, Drug Discovery today, vol. 21, 2016.
Mullarky, Identifcation of a small molecule inhibitor of 3-phosphoglycerate dehydrogenase to target serine biosynthesis in cancers, PNASm 2016.
Pacold, A PHGDH inhibitor reveals coordination of serine synthesis and one-carbon unit fate, Nature Chern Biology, 2016.
Wang, Rational design of selective allosteric inhibitors of PHDGH and serine synthesis with in vivo activity, Cell Chem Biol. vol. 19, 2017.

* cited by examiner

*Primary Examiner* — Kamal A Saeed
(74) *Attorney, Agent, or Firm* — Wendy M. Gombert

(57) ABSTRACT

The present invention encompasses compounds of formula (I), wherein the groups $R^1$ to R, $A^1$ to $A^4$ and n have the meanings given in the claims and specification, their use as inhibitors of PHGDH, pharmaceutical compositions which contain compounds of this kind and their use as medicaments, especially as agents for treatment and/or prevention of oncological diseases.

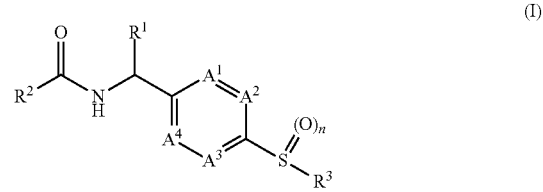

16 Claims, No Drawings

TOSYLACETATE BASED COMPOUNDS AND DERIVATIVES THEREOF AS PHGDH INHIBITORS

FIELD OF THE INVENTION

The present invention relates to new tosylacetate based compounds and derivatives of formula (I)

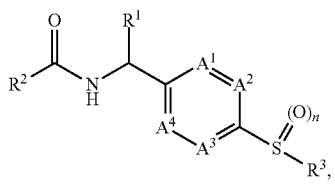

wherein the groups $R^1$ to $R^3$, $A^1$ to $A^4$ and n have the meanings given in the claims and specification, their use as inhibitors of PHGDH, pharmaceutical compositions which contain compounds of this kind and their use as medicaments, especially as agents for treatment and/or prevention of oncological diseases.

BACKGROUND OF THE INVENTION

The essential contribution of the serine synthetic pathway (SSP) to tumorigenesis has been shown by a plethora of studies. Although serine (Ser) is classified as a nutritionally nonessential amino acid, Ser is indispensable and displays a critical role in several cellular processes that are of particular importance for tumor cells: (i) Ser can be converted to glycine via the action of the serine hydroxymethyltransferase (SHMT) providing carbon units for purine nucleotide synthesis (Kalhan & Hanson, J Biol Chem. (2012) 287: 19786-19791; Locasale, Nat Rev Cancer. (2013) 13:572-583; Amelio et al., Trends Biochem Sci. (2014) 39:191-198; Mehrmohamadi & Locasale Mol Cell Oncol. (2015) 2:e996418; Tedeschi et al., Cell Death Dis. (2013) 4:e877). (ii) Ser can react with palmitoyl-CoA to provide sphingosine required for the generation of sphingolipids that constitute the cell membrane (Ravez et al., J Med Chem. (2016) e-pub ahead; Xu et al., J Biol Chem. (1991) 266: 2143-2150). (iii) Ser serves as a precursor of several amino acids like glycine and cysteine (Vazquez et al., Cancer Res. (2013) 73: 478-482; Ravez et al., J Med Chem. (2016) e-pub ahead). (iv) Ser plays a crucial role in the regulation of the redox status due to the fact that serine is involved in the production of NADPH (Tedeschi et al., Cell Death Dis. (2013) 4:e877). (v) Last but not least, PHGDH, the key enzyme of the de novo SSP was shown to produce the oncometabolite D-2-hydroxyglutarate (D-2HG) which has been linked with epigenetic de-regulation in tumor cells (Mondesir et al., J Blood Med. (2016) 7: 171-180; Fan et al., ACS Chem Biol. (2015) 10: 510-516). The SSP not only provides essential building blocks/metabolites but also epigenetic regulators, Ser and its synthesis pathway essentially contributes to cell proliferation, tumor homeostasis and to de-differentiation of cancer cells (Mattaini et al., J Cell Biol. (2016) 214: 249-257; El-Hattab, Mol Genet Metab. (2016) 118: 153-159).

De novo synthesis of Ser is triggered via the SSP. The SSP diverts of the 3-PG from glycolysis to generate Ser as well as equimolar amounts of reduced nicotinamide adenine dinucleotide (NADH) and α-ketoglutarate (α-KG). The SSP consists of three successive enzymatic reactions Phosphoglycerate dehydrogenase (PHGDH) catalyzes the first step and produces 3-phosphohydroxypyruvate (3-PPyr) by NAD+-coupled oxidation of 3-PG. Next, 3-PPyr is converted in phosphoserine by the phosphoserine aminotransferase 1 (PSAT-1) and then into serine by the action of phosphoserine phosphatase (PSPH). Finally, Ser can be converted into glycine by SHMT.

Elevated rates of SSP have been observed in neoplastic tissues of different origins (Snell & Weber, Biochem J. (1986) 233: 617-620; DeBerardinis, Cell Metab. (2011) 14: 285-286) and have been linked with tumorigenesis (DeBerardinis, Cell Metab. (2011) 14: 285-286) with PHGDH being the key enzyme. PHGDH was shown to be amplified/overexpressed in melanoma and breast cancer (Beroukhim et al., Nature. (2010) 463: 899-8905; Locasale et al., Nat Genet. (2011) 43: 869-874; Possemato et al., Nature. (2011) 476: 346-350). In addition, recent studies identified several factors as activators of the SSP in cancer cells which also determine cancer pathogenesis, such as the general control nonderepressible 2 kinase (GCN2) leading to expression of the activating transcription factor 4 (ATF4). Similarly, ATF4 can also be induced by the transcription factor nuclear factor erythroid-2-related factor 2 (NRF2) in human non-small-cell lung cancer (Wang et al., Neoplasia. (2013) 15: 989-997; DeNicola et al., Nat Genet. (2015) 47: 1475-1481). Also MYC activates the SSP by transcriptional upregulation of the expression of SSP enzymes under deprivation of glucose or glutamine (Sun et al., Cell Res. (2015) 25: 429-444). Most importantly, a recent study demonstrated that hypoxia induces the expression of SSP enzymes, and this phenomenon is mediated by HIF-1 and HIF-2 in a large panel of breast cancer cell lines (Samanta et al., Cancer Res. (2016) 76: 4430-4442). Finally, it was reported that tumor suppressors PKC-ζ and p53 repress the expression of PHGDH (Ma et al., Cell. (2013) 152: 599-611; Ou et al., J Biol Chem. (2015) 290: 457-466; Maddocks et al., Nature. (2013) 493: 542-546). Thus, deficiency of PKC-ζ or p53 in cancer cells promotes the activity of PHGDH and drives the SSP.

The knockdown of PHGDH inhibited the growth of cancer cell lines that harbor PHGDH amplification and/or PHGDH overexpression but had no effect on lines expressing PHGDH at a normal level (Luo, Breast Cancer Res. (2011) 13: 317; Possemato et al., Nature. (2011) 476: 346-350). A negative-selection RNAi screening using a human breast cancer xenograft model at an orthotopic site in mouse was developed by Possemato et al. in 2011 for identifying novel cancer targets (Possemato et al., Nature. (2011) 476: 346-350). This method highlighted PHGDH as a gene required for in vivo tumorigenesis and breast cancer progression (Samanta et al., Cancer Res. (2016) 76: 4430-4442) and that this gene is localized in a genomic region of recurrent copy number gain in breast cancer. Subsequently, it was shown that the most abundantly expressed SSP enzymes in basal-like TNBC tissues was PHGDH and that the expression levels of PHGDH were inversely correlated with clinical prognostic factors (Noh et al., Tumour Biol. (2014) 35: 4457-4468; Ravez et al., J Med Chem. (2016) e-pub ahead). Also Knockdown of PHGDH in melanoma cells selectively inhibited the growth of cells that exhibit PHGDH amplification versus those that lack this amplification (Locasale et al., Nat Genet. (2011) 43: 869-874; Mullarky et al., Pigment Cell Melanoma Res. (2011) 24: 1112-1115). The prognostic significance of amplification/overexpression of PHGDH has clearly been demonstrated for colon cancer (Yoon et al., Oncology. (2015) 89: 351-359; Jia et al., Transl Oncol. (2016) 9: 191-196), glioma (Liu et al., J Neurooncol. (2013) 111: 245-255), cervical adenocarcinoma (Jing et al., Cancer Biol Ther. (2015) 16: 541-548)

and lung adeno carcinoma (DeNicola et al., Nat Genet. (2015) 47: 1475-1481; Amelio et al., Oncogene. (2014) 33: 5039-5046). In thyroid cancer it was shown that a B-Raf V600E mutation was associated with a higher rate of PHGDH expression compared to non-mutant cases (Chen et al., Int J Mol Med. (2015) 36: 1607-1614; Sun et al., J Transl Med. (2016) 14: 168).

Interestingly, in leukemia an increase in oxidative stress upon inhibition of glutamine metabolism was identified as the trigger of the up-regulation of PHGDH. Silencing of PHGDH inhibited leukemia cell growth, thereby identifying serine as a key pro-survival factor (Polet et al., Oncotarget. (2016) 7: 1765-1776).

Most recently, it was demonstrated that PHGDH catalyzes NADH-dependent reduction of α-ketoglutarate to the oncometabolite D-2-hydroxyglutarate (D-2HG) (Fan et al., ACS Chem Biol. (2015) 10: 510-516). Originally D-2HG was identified as an oncometabolite leading to inhibition of several de-methylases thereby changing the epigentic landscape in tumor cells (Prensner & Chinnaiyan, Nature Medicine (2011) 17: 291-293). D-2HG is produced in large amounts by isocitrate dehydrogenase mutants in glioma (Xu et al., Cancer Cell. (2011) 19: 17-30; Rossetto et al., Rev Neurol (Paris) (2011) 167: 699-703) and acute myeloid leukemia (Ward et al., Cancer Cell. (2010) 17: 225-234; Ward et al., Oncogene. (2012) 31: 2491-2498). Most interestingly, in breast cancer PHGDH was identified as an enzymatic driver of D-2HG production (Fan et al., ACS Chem Biol. (2015) 10: 510-516). Terunuma and colleagues performed a detailed metabolic profiling of human breast tumors and uncovered intrinsic metabolite signatures in these tumors using an untargeted discovery approach and validation of key metabolites. D-2HG accumulated at high levels in those breast cancer tumors where MYC pathway activation was observed. Most importantly, MYC-driven accumulation of D-2HG is associated with a poor prognosis in breast cancer (Terunuma et al., J Clin Invest. (2014) 124: 398-412). As it was shown that MYC—among others—regulate enzymes of the glycolytic pathway (Stine et al., Cancer Discov. (2015) 5: 1024-39) PHGDH amplification and/or overexpression in breast cancer could potentially influence cell physiology by overproduction of D-2HG in a similar way (e.g. DNA methylation) as it was shown for glioma and AML (see above).

The mechanism(s) by which PHGDH supports tumorigenesis might be manifold but the enzymatic function of PHGDH is a prerequisite to essentially contribute to cell proliferation, invasion, and tumorigenicity of cancer cells. All these data strongly support PHGDH as an attractive drug target in tumors that overexpress PHGDH or exhibit PHGDH gene amplification.

Indole-2-carboxamide based NAD+-competitive PHGDH inhibitors have been disclosed in 2015 and published in 2016 illustrating fragment based drug discovery at AstraZeneca (Drug discovery today (2016), 21(8), 1272-83). These compounds lack cellular potency.

The allosteric PHGDH inhibitors CBR-5884 with low micromolar potency was reported by Cantley et al. (Proceedings of the National Academy of Sciences of the United States of America (2016), 113(7), 1778-1783) Further allosteric binders (NCT-503 and NCT-502) were reported by Sabatini et al. (Nature Chemical Biology (2016), 12(6), 452-458) and by Locasale and Lai (PKUMDL-WQ-2101, PKUMDL-WQ-2201, PKUMDL-WQ-2202, PKUMDL-WQ-2203) in Wang, et al. (Rational Design of Selective Allosteric Inhibitors of PHGDH and Serine Synthesis with Anti-tumor Activity, Cell Chemical Biology, 2017, Vol. 24-1 p. 55-65).

In WO2016040449, RAZE THERAPEUTICS INC. disclosed pyrazole based NAD+-competitive PHGDH inhibitors or acid-bioisosteric inhibitors.

None of the above mentioned inhibitors were able to show nanomolar cellular biomarker modulation ($^{13}$C-serine).

The aim of the present invention is to provide alternative PHGDH inhibitors which are also selective and potent compounds having nanomolar biomarker modulation. This is achieved by the compounds of the invention via intracellular release of potent carboxylic acids (drug) from their permeable ester precursors (prodrug).

DETAILED DESCRIPTION OF THE INVENTION

It has now been found that, surprisingly, compounds of formula (I)

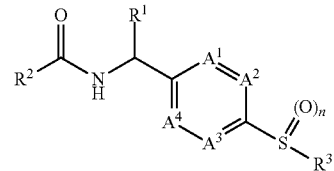

wherein the groups $R^1$ to $R^3$, $A^1$ to $A^4$ and n have the meanings given hereinafter act as inhibitors of PHGDH which are involved in modulating cell proliferation. Thus, the compounds according to the invention may be used for example for the treatment of diseases characterised by excessive or abnormal cell proliferation.

The present invention therefore relates to a compound of formula (I)

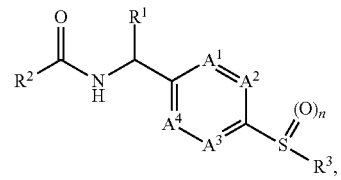

wherein
n is 1 or 2;
$A^1$, $A^2$, $A^3$ and $A^4$ are independently selected from —N═ and —CR$^{13}$═ and wherein none, one or two independently selected $A^1$, $A^2$, $A^3$ and $A^4$ can be —N═;
$R^{13}$ is hydrogen, halogen, —C$_{1-3}$alkyl, —O—C$_{1-3}$alkyl;
$R^1$ is selected from the group consisting of hydrogen, —C$_{1-3}$alkyl and —C$_{1-3}$alkyl-OH;
$R^2$ is

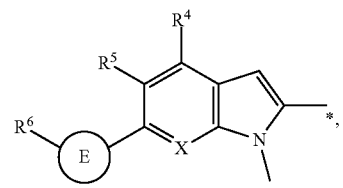

wherein

X is —N= or —CR$^7$—;

R$^7$ is selected from hydrogen, halogen, —C$_{1-3}$alkyl and —O—C$_{1-3}$alkyl;

R$^4$ is selected from the group consisting of hydrogen, halogen, —C$_{1-3}$haloalkyl, —C$_{1-3}$alkyl;

R$^5$ is selected from the group consisting of hydrogen, halogen, —C$_{1-3}$haloalkyl, —C$_{1-3}$alkyl;

or R$^4$ and R$^5$ taken together form a ring selected from a 5 or 6 membered heteroaryl, a 5 or 6 membered heterocyclyl and phenyl;

E is selected from a bond, —C$_{1-3}$alkylene-, —C$_{1-3}$haloalkylene-, —C$_{2-3}$alkynylene, 5 or 6 membered -heteroarylene- and 5 or 6 membered -heterocyclylene-;

R$^6$ is selected from hydrogen, halogen, —C$_{1-3}$alkyl, which —C$_{1-3}$alkyl is optionally substituted with one group selected from —NH$_2$, —N(C$_{1-3}$alkyl)$_2$ and 5 or 6 membered heterocycloalkyl;

or R$^2$ is

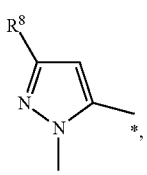

wherein

R$^8$ is selected from indolyl or phenyl, each of which group is optionally substituted with one, two or three substituents independently selected from halogen, —C$_{1-3}$haloalkyl, —C$_{1-3}$alkyl, —O—C$_{1-3}$alkyl;

R$^3$ is

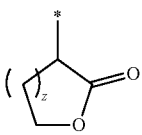

and z is 1 or 2;

or R$^3$ is —C(R$^9$R$^{10}$)—COO—R$^{11}$ and

R$^9$ and R$^{10}$ are the same or different, independently selected from hydrogen, —C$_{1-3}$alkyl, —C$_{1-3}$alkyl-O—C$_{1-3}$alkyl;

or R$^9$ and R$^{10}$ taken together form a —C$_{3-5}$cycloalkyl or a 6 membered heterocycloalkyl, which heterocycloalkyl is optionally substituted with —C(O)—C$_{1-3}$alkyl;

R$^{11}$ is selected from the group consisting of hydrogen, —C$_{3-6}$cycloalkyl, 4-6 membered heterocycloalkyl and —C$_{1-5}$alkyl, which —C$_{1-5}$alkyl group is optionally and independently substituted with one or two the same or different substituents, selected from R$^{12}$;

R$^{12}$ is selected from the group consisting of —C$_{3-6}$cycloalkyl, halogen, —OH, —O—C$_{1-4}$alkyl, —O—C$_{1-4}$alkyl-O—C$_{1-4}$alkyl, —O—C$_{1-4}$alkyl-OH, —OC(O)—C$_{1-4}$alkyl, —NHCOO—C$_{1-4}$alkyl, —SO$_2$—C$_{1-3}$alkyl, —N(C$_{1-3}$alkyl)$_2$, 5 or 6 membered heteroaryl and phenyl, which phenyl group is optionally substituted with —C$_{1-3}$haloalkyl, or R$^{12}$ is a 4 to 6 membered heterocycloalkyl, which heterocycloalkyl is optionally substituted with halogen or —C$_{1-3}$ alkyl.

The example compounds as disclosed herein have chiral centres. Although not separately depicted in the tables all stereoisomers of such example compounds are meant to be embodiments of the invention and shall be deemed to be specifically disclosed, i.e. the compound as depicted in the tables, the corresponding enantiomer and/or diastereoisomers not specifically depicted in the tables and the racemate of both enantiomers are separate embodiments of the invention. The preferred embodiments are the compounds disclosed in the examples.

Synthetic intermediates generically defined as well as specifically disclosed herein and their salts are also part of the invention.

The present invention further relates to hydrates, solvates, polymorphs, metabolites, derivatives, isomers and prodrugs of a compound of formula (I).

In an aspect the present invention relates to compounds of Formula (I')

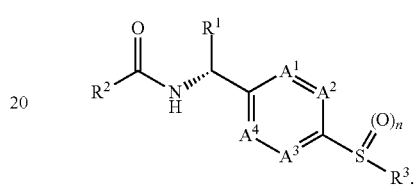

It is to be understood that compounds of Formula (I') is a subset of compounds of Formula (I) and that whenever the term "compound(s) of Formula (I)" is used this also includes compound(s) (1') unless stated otherwise. Furthermore all aspects of the invention relating to a compound of Formula (I) or compounds of Formula (I) also in addition corresponds to an aspect of the invention relating to a compound of Formula (I') or compounds of Formula (I').

The present invention further relates to a hydrate of a compound of formula (I).

The present invention further relates to a solvate of a compound of formula (I).

The present invention further relates to a polymorph of a compound of formula (I).

In another aspect the present invention relates to a compound of formula (I), or a salt thereof, wherein each of A$^1$, A$^2$, A$^3$ and A$^4$ is —CH=.

In another aspect the present invention relates to a compound of formula (I), or a salt thereof, wherein each of A$^1$, A$^2$ and A$^4$ is —CH= and A$^3$ is —N=.

In another aspect the present invention relates to a compound of formula (I), or a salt thereof, wherein each of A$^2$, A$^3$ and A$^4$ is —CH= and A$^1$ is —N=.

In another aspect the present invention relates to a compound of formula (I), or a salt thereof, wherein n is 2.

In another aspect the present invention relates to a compound of formula (I), or a salt thereof, wherein n is 1.

In another aspect the present invention relates to a compound of formula (I), or a salt thereof, wherein R$^1$ is selected from among hydrogen, —CH$_3$ and —CH$_2$OH.

In another aspect the present invention relates to a compound of formula (I), or a salt thereof, wherein R$^1$ is selected from among —CH$_3$ and —CH$_2$OH.

In another aspect the present invention relates to a compound of formula (I), or a salt thereof, wherein X is —N=.

In another aspect the present invention relates to a compound of formula (I), or a salt thereof, wherein X is —CR$^7$— and R$^7$ is selected from hydrogen, halogen, —C$_{1-3}$alkyl and —O—C$_{1-3}$alkyl.

In another aspect the present invention relates to a compound of formula (I), or a salt thereof, wherein X is —CR$^7$— and R$^7$ is selected from hydrogen, halogen and —C$_{1-3}$alkyl.

In another aspect the present invention relates to a compound of formula (I), or a salt thereof, wherein X is —CR$^7$— and R$^7$ is selected from hydrogen and —O—C$_{1-3}$alkyl.

In another aspect the present invention relates to a compound of formula (I), or a salt thereof, wherein X is —CR$^7$— and R$^7$ is selected from among hydrogen, —Cl and —CH$_3$.

In another aspect the present invention relates to a compound of formula (I), or a salt thereof, wherein R$^2$ is

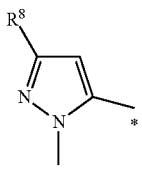

and

R$^8$ is selected from indolyl and phenyl, wherein the phenyl is optionally substituted with halogen, —O—C$_{1-3}$alkyl and —C$_{1-3}$alkyl.

In another aspect the present invention relates to a compound of formula (I), or a salt thereof, wherein R$^2$ is

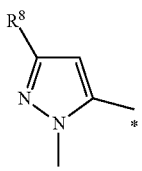

and

R$^8$ is selected from indolyl and phenyl, wherein the phenyl is optionally substituted with —F, —Cl, —O—CH$_3$, —CH$_3$.

In another aspect the present invention relates to a compound of formula (I), or a salt thereof, wherein R$^4$ is selected from among hydrogen and halogen.

In another aspect the present invention relates to a compound of formula (I), or a salt thereof, wherein R$^4$ is selected from among hydrogen, —F and —Cl.

In another aspect the present invention relates to a compound of formula (I), or a salt thereof, wherein R$^5$ is selected from among hydrogen, —F, —Cl, —CF$_3$.

In another aspect the present invention relates to a compound of formula (I), or a salt thereof, wherein R$^5$ is selected from among hydrogen, halogen and —C$_{1-3}$haloalkyl.

In another aspect the present invention relates to a compound of formula (I), or a salt thereof, wherein R$^5$ and R$^4$ taken together form a phenyl ring.

In another aspect the present invention relates to a compound of formula (I), or a salt thereof, wherein E is a bond and R$^6$ is selected from hydrogen, —C$_{1-3}$alkyl and halogen; or E is a 5 membered -heteroarylene- and R$^6$ is —C$_{1-3}$alkyl substituted with a 6 membered heterocycloalkyl; or E is a 6 membered -heterocycloalkylene- and R$^6$ is —C$_{1-3}$alkyl, E is —C$_{2-3}$alkynylene- and R$^6$ is hydrogen;

In another aspect the present invention relates to a compound of formula (I), or a salt thereof, wherein E is a bond and R$^6$ is —C$_{1-3}$alkyl.

In another aspect the present invention relates to a compound of formula (I), or a salt thereof, wherein E is a bond and R$^6$ is —CH$_3$.

In another aspect the present invention relates to a compound of formula (I), or a salt thereof, wherein R$^{11}$ is selected from the group consisting of hydrogen, 4 to 6 membered heterocycloalkyl, or —C$_{1-5}$alkyl, which —C$_{1-5}$alkyl is optionally and independently substituted with 1 or 2 the same or different substituents selected from R$^{12}$; and R$^{12}$ is selected from the group consisting of -cyclopropyl, halogen, —OH, —O—C$_{1-4}$alkyl, —O—C$_{1-4}$alkyl-OH, —O—C$_{1-4}$alkyl-O—C$_{1-4}$alkyl, —OC(O)—C$_{1-4}$alkyl, —NHCOO—C$_{1-4}$alkyl, —SO$_2$—C$_{1-3}$alkyl, —N(C$_{1-3}$alkyl)$_2$,

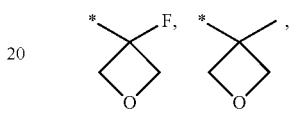

pyridyl, 4 to 6 membered heterocycloalkyl and phenyl, which phenyl group is optionally substituted with —C$_{1-3}$haloalkyl.

In another aspect the present invention relates to a compound of formula (I), or a salt thereof, wherein R$^3$ is selected from the group consisting of —C(R$^9$R$^{10}$)—COO—R$^{11}$,

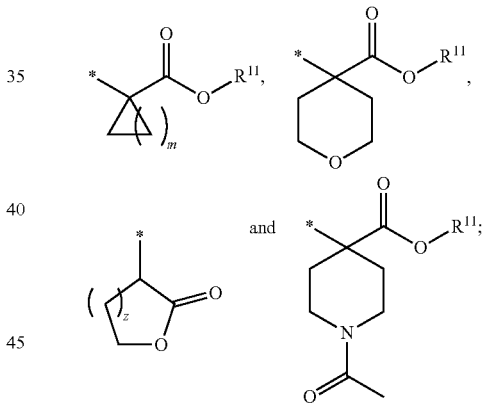

z is 1 or 2;

m is 1, 2, 3 or 4;

R$^9$ and R$^{10}$ are the same or different, independently selected from hydrogen, —C$_{1-3}$alkyl, —C$_{1-3}$alkyl-O—C$_{1-3}$alkyl;

R$^{11}$ is selected from the group consisting of hydrogen, —C$_{3-6}$cycloalkyl, 4-6 membered heterocycloalkyl and —C$_{1-5}$alkyl, which —C$_{1-5}$alkyl group is optionally and independently substituted with one or two the same or different substituents, selected from R$^{12}$;

R$^{12}$ is selected from the group consisting of —C$_{3-6}$cycloalkyl, halogen, —OH, —O—C$_{1-4}$alkyl, —O—C$_{1-4}$alkyl-O—C$_{1-4}$alkyl, —O—C$_{1-4}$alkyl-OH, —OC(O)—C$_{1-4}$alkyl, —NHCOO—C$_{1-4}$alkyl, —SO$_2$—C$_{1-3}$alkyl, —N(C$_{1-3}$alkyl)$_2$, 5 or 6 membered heteroaryl and phenyl, which phenyl group is optionally substituted with —C$_{1-3}$haloalkyl, or R$^{12}$ is a 4 to 6 membered heterocycloalkyl,

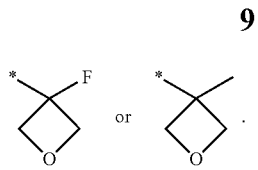

In another aspect the present invention relates to a compound of formula (I), or a salt thereof, wherein $R^{11}$ is H or —$C_{1-5}$alkyl.

In another aspect the present invention relates to a compound of formula (I), or a salt thereof, wherein $R^{11}$ is —$C_{1-5}$alkyl.

In another aspect the present invention relates to a compound of formula (I), or a salt thereof, wherein $R^9$ and $R^{10}$ are the same or different, independently selected from hydrogen and —$C_{1-3}$alkyl.

In another aspect the present invention relates to a compound of formula (I), or a salt thereof, wherein $R^3$ is selected from the group consisting of —C($R^9R^{10}$)—COO—$R^{11}$;

$R^9$ and $R^{10}$ are the same or different, independently selected from hydrogen, —$C_{1-3}$alkyl; and $R^{11}$ is hydrogen or —$C_{1-5}$alkyl.

In another aspect the present invention relates to a compound of formula (I), or a salt thereof, wherein E is a bond and $R^6$ is selected from hydrogen, —$CH_3$ and —I; or E is -pyrazolylene- and $R^6$ is —$CH_2CH_3$ substituted with morpholine; or E is a -piperazinylene- and $R^6$ is —$CH_3$.

E is —CC—$R^6$ is hydrogen.

In another aspect the present invention relates to a compound of formula (I), or a salt thereof, wherein $R^2$ is

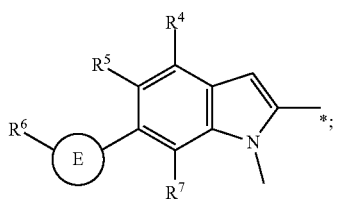

$R^7$ is hydrogen;

$R^4$ is selected from the group consisting of —F, —Cl, Br and —$C_{1-3}$alkyl;

$R^5$ is selected from the group consisting of —F, —Cl and Br;

E is a bond and $R^6$ is —$C_{1-3}$alkyl.

In another aspect the present invention relates to a compound of formula (I), or a salt thereof, wherein $R^3$ is selected from among

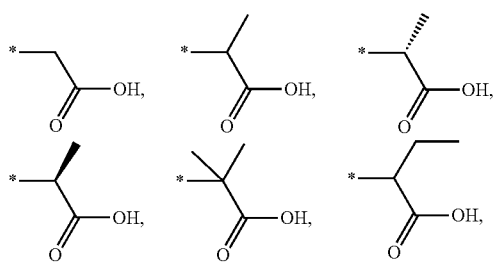

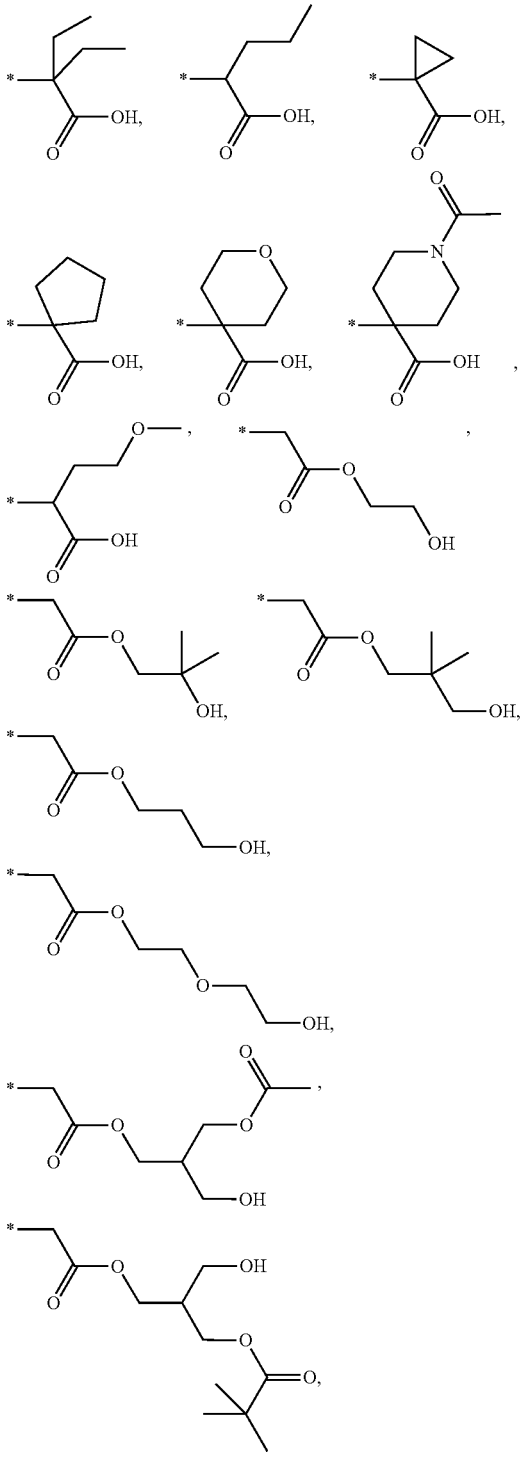

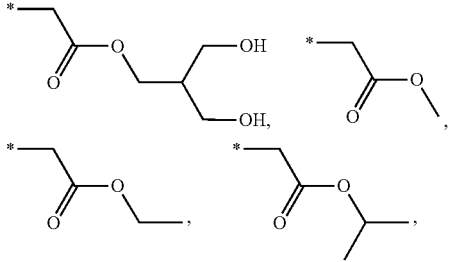

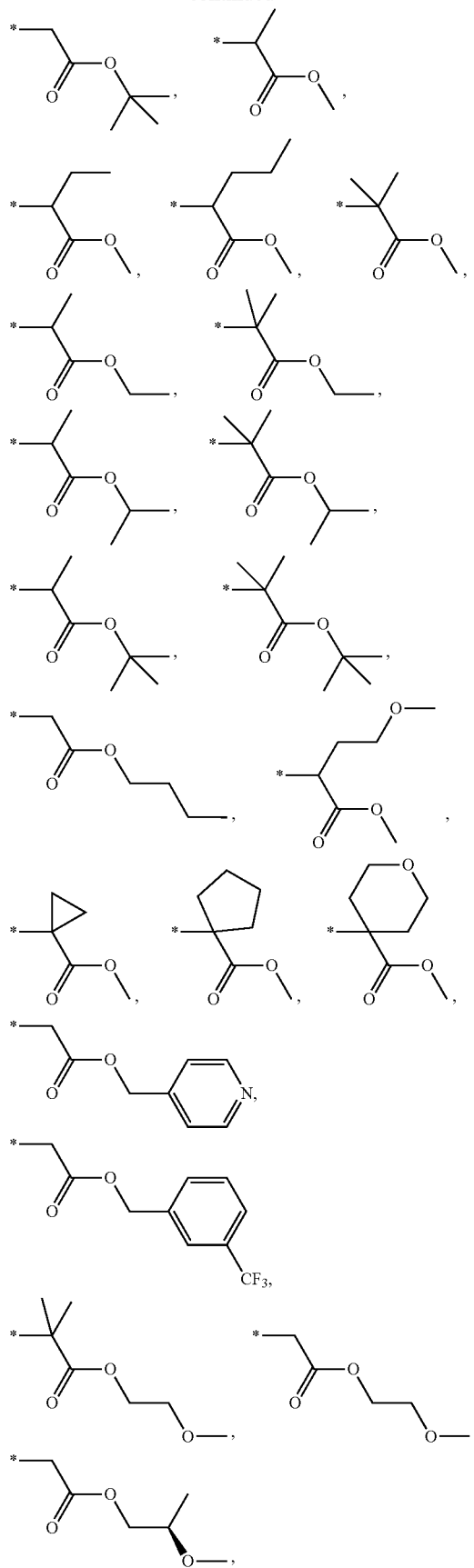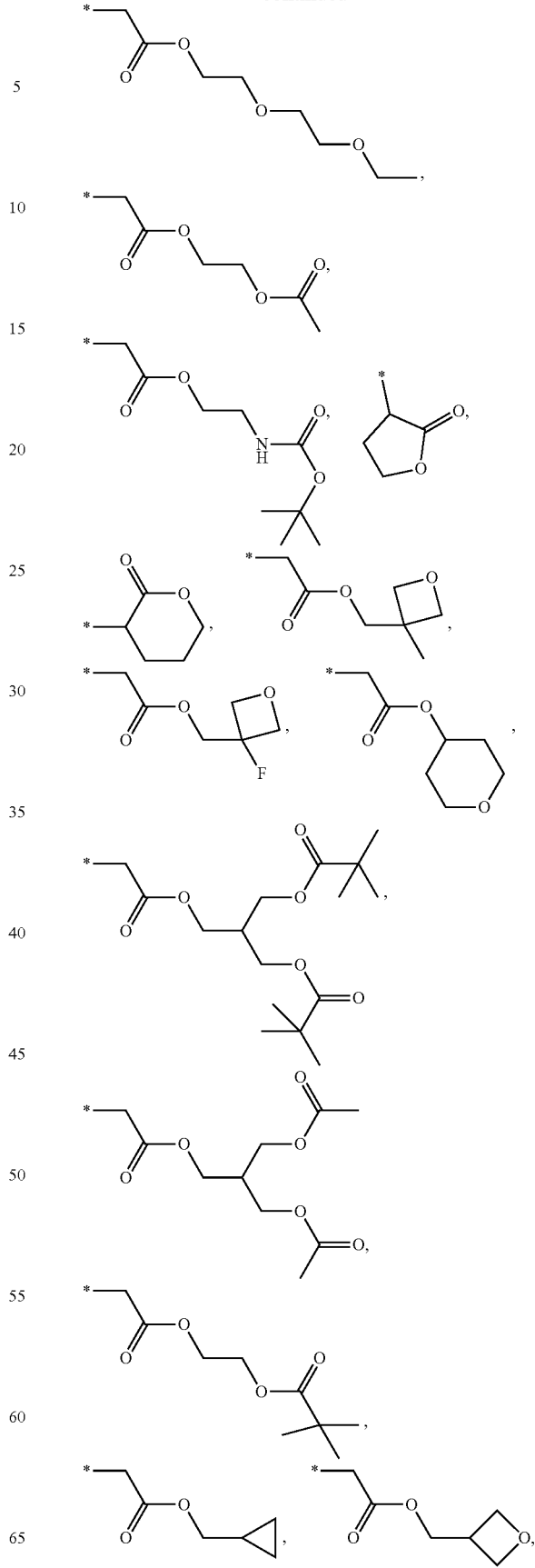

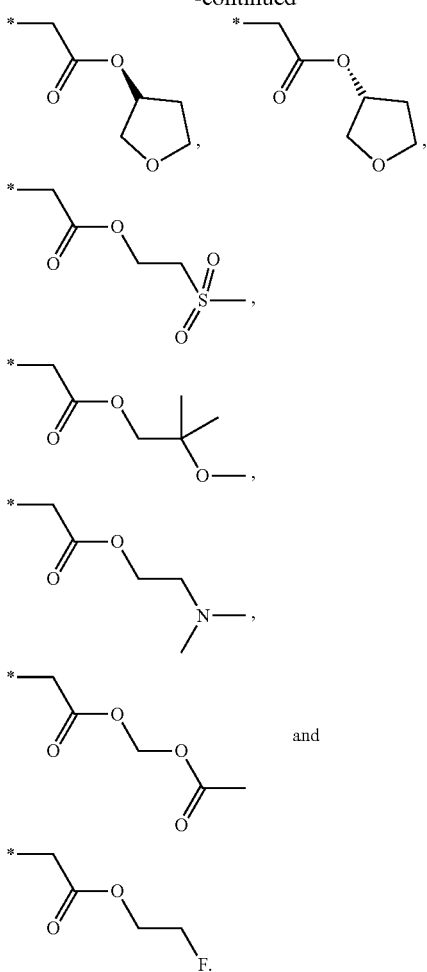

In another aspect the present invention relates to a compound of formula (I), or a salt thereof, wherein R³ is selected from

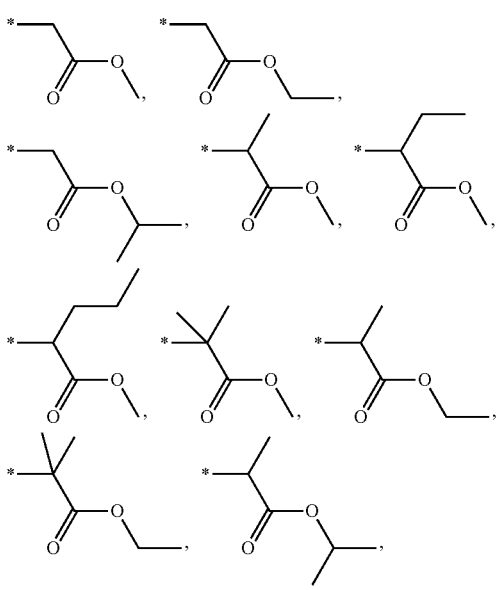

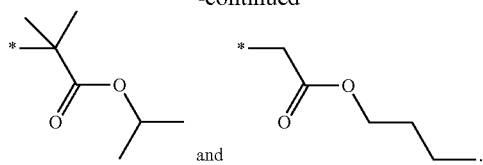

In another aspect the present invention relates to a compound of formula (I), or a salt thereof, wherein R³ is selected from

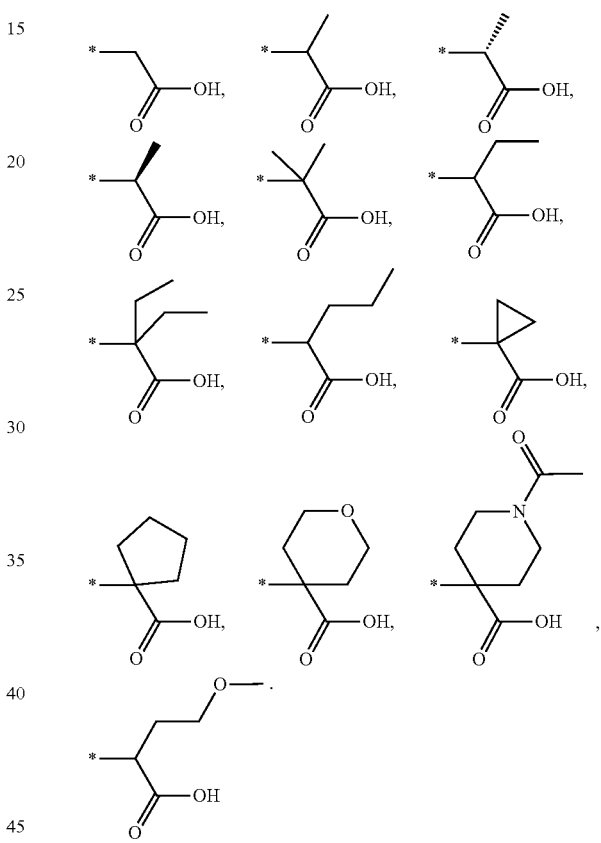

Carboxylic acids according to formula (I) are up to three log-units more potent compared to published chemical matter due to unique structural features of the —S(O)n-R3- moiety. However, these acids are badly cell permeable and therefore only micromolar serine modulators.

In addition, esters according to formula (I) are capable to release corresponding potent carboxylic acids intracellularly but the esters themselves are less potent PHGDH inhibitors than the corresponding carboxylic acids. Due to the permeable nature of the esters they can penetrate the cell wall and thus show the ability of low nanomolar intracellular biomarker modulation ($^{13}$Cserine).

The present invention further relates to a pharmaceutically acceptable salt of a compound of formula (I).

The present invention further relates to a co-crystal, preferably a pharmaceutically acceptable co-crystal, of a compound of formula (I).

The present invention further relates to a pharmaceutically acceptable salt of a compound of formula (I) with anorganic or organic acids or bases.

The present invention is directed to compounds of formula (I) which are useful in the prevention and/or treatment of a disease and/or condition wherein the inhibition of PHGDH is of therapeutic benefit, including but not limited to the treatment and/or prevention of cancer.

In another aspect the invention relates to a compound of formula (I)—or a pharmaceutically acceptable salt thereof—for use as a medicament.

In another aspect the invention relates to a compound of formula (I)—or a pharmaceutically acceptable salt thereof—for use in a method of treatment of the human or animal body.

In another aspect the invention relates to a compound of formula (I)—or a pharmaceutically acceptable salt thereof—for use in the treatment and/or prevention of a disease and/or condition wherein the inhibition of PHGDH is of therapeutic benefit.

In another aspect the invention relates to a compound of formula (I)—or a pharmaceutically acceptable salt thereof—for use in the treatment and/or prevention of cancer, infections, inflammations or autoimmune diseases.

In another aspect the invention relates to a compound of formula (I)—or a pharmaceutically acceptable salt thereof—for use in a method of treatment and/or prevention of cancer, infections, inflammations or autoimmune diseases in the human or animal body.

In another aspect the invention relates to the use of a compound of formula (I)—or a pharmaceutically acceptable salt thereof—for preparing a pharmaceutical composition for the treatment and/or prevention of cancer, infections, inflammations or autoimmune diseases.

In another aspect the invention relates to a compound of formula (I)—or a pharmaceutically acceptable salt thereof—for use in the treatment and/or prevention of cancer.

In another aspect the invention relates to the use of a compound of formula (I)—or a pharmaceutically acceptable salt thereof—for preparing a pharmaceutical composition for the treatment and/or prevention of cancer.

In another aspect the invention relates to a compound of formula (I)—or a pharmaceutically acceptable salt thereof—for use in a method of treatment and/or prevention of cancer in the human or animal body.

In another aspect the invention relates to a compound of formula (I)—or a pharmaceutically acceptable salt thereof—for use in the treatment and/or prevention of a hematological cancer.

In another aspect the invention relates to a compound of formula (I)—or a pharmaceutically acceptable salt thereof—for use in the treatment and/or prevention of glioma, breast cancer, melanoma, non-small cell lung cancer (NSCLC), colorectal cancer, cervical carcinoma, thyroid cancer, preferably BRAF mutated and leukemia.

In another aspect the invention relates to a compound of formula (I)—or a pharmaceutically acceptable salt thereof—for use in the treatment and/or prevention of p53 mutated cancer, MYC-driven cancers and/or cancers with a high level of D-2-hydroxyglutarate (D-2HG).

In another aspect the invention relates to the use of a compound of formula (I)—or a pharmaceutically acceptable salt thereof—for preparing a pharmaceutical composition for the treatment and/or prevention of a hematological cancer.

In another aspect the invention relates to the use of a compound of formula (I)—or a pharmaceutically acceptable salt thereof—for preparing a pharmaceutical composition for the treatment and/or prevention of glioma, breast cancer, melanoma, non-small cell lung cancer (NSCLC), colorectal cancer, cervical carcinoma, thyroid cancer, preferably BRAF mutated and leukemia.

In another aspect the invention relates to the use of a compound of formula (I)—or a pharmaceutically acceptable salt thereof—for preparing a pharmaceutical composition for the treatment and/or prevention of p53 mutated cancer, MYC-driven cancers and/or cancers with a high level of 2DHG.

In another aspect the invention relates to a method for the treatment and/or prevention of a disease and/or condition wherein the inhibition of PHGDH is of therapeutic benefit comprising administering a therapeutically effective amount of a compound of formula (I)—or a pharmaceutically acceptable salt thereof—to a human being.

In another aspect the invention relates to a method for the treatment and/or prevention of cancer comprising administering a therapeutically effective amount of a compound of formula (I)—or a pharmaceutically acceptable salt thereof—to a human being.

In another aspect the invention relates to a pharmaceutical composition comprising at least one compound of formula (I)—or a pharmaceutically acceptable salt thereof—and a pharmaceutically acceptable carrier.

In another aspect the invention relates to a pharmaceutical preparation comprising a compound of formula (I)—or a pharmaceutically acceptable salt thereof—and at least one other cytostatic and/or cytotoxic active substance.

In another aspect the invention relates to a compound of formula (I)—or a pharmaceutically acceptable salt thereof—for use in the treatment and/or prevention of cancer, infections, inflammations or autoimmune diseases wherein said compound is administered before, after or together with at least one other cytostatic or cytotoxic active substance.

In another aspect the invention relates to the use of a compound of formula (I)—or a pharmaceutically acceptable salt thereof—for preparing a medicament for the treatment and/or prevention of cancer, infections, inflammations or autoimmune diseases wherein said compound is administered before, after or together with at least one other cytostatic or cytotoxic active substance.

In another aspect the invention relates to a cytostatic or cytotoxic active substance prepared for being administered before, after or together with a compound of formula (I)—or a pharmaceutically acceptable salt thereof—for use in the treatment and/or prevention of cancer, infections, inflammations or autoimmune diseases.

In another aspect the invention relates to a method for the treatment and/or prevention of cancer, infections, inflammations or autoimmune diseases comprising administering to a patient in need thereof a therapeutically effective amount of a compound of formula (I)—or a pharmaceutically acceptable salt thereof—before, after or together with at least one other cytostatic or cytotoxic active substance.

Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to:

All different depictions of $R^x$ without superscript such as $R_x$ or Rx herein shall refer to and be understood as $R^x$, e.g. $R_1$ or $R1$ should refer to $R^1$.

All different depictions of $A^x$ without superscript such as $A_x$ or Ax herein shall refer to and be understood as $A^x$, e.g. $A_1$ or A1 should refer to $A^1$.

The use of the prefix $C_{x-y}$, wherein x and y each represent a natural number (x<y), indicates that the chain or ring structure or combination of chain and ring structure as a whole, specified and mentioned in direct association, may consist of a maximum of y and a minimum of x carbon atoms.

The indication of the number of members in groups that contain one or more heteroatom(s) (e.g. heteroalkyl, heteroaryl, heteroarylalkyl, heterocyclyl, heterocycylalkyl) relates to the total number of atoms of all the ring members or chain members or the total of all the ring and chain members.

The indication of the number of carbon atoms in groups that consist of a combination of carbon chain and carbon ring structure (e.g. cycloalkylalkyl, arylalkyl) relates to the total number of carbon atoms of all the carbon ring and carbon chain members. Obviously, a ring structure has at least three members.

In general, for groups comprising two or more subgroups (e.g. heteroarylalkyl, heterocycylalkyl, cycloalkylalkyl, arylalkyl) the last named subgroup is the radical attachment point, for example, the substituent aryl-$C_{1-6}$alkyl means an aryl group which is bound to a $C_{1-6}$alkyl group, the latter of which is bound to the core or to the group to which the substituent is attached.

In groups like OH, $NH_2$, S(O), $S(O)_2$, CN (cyano), COOH, $CF_3$ or the like, the skilled artisan can see the radical attachment point(s) to the molecule from the free valences of the group itself.

As it will be clear to the person skilled in the art, the radical attachment point(s) to the molecule from the free valences of the group itself is indicated with the following symbols "-" or "*".

Alkyl denotes monovalent, saturated hydrocarbon chains, which may be present in both straight-chain (unbranched) and branched form. If an alkyl is substituted, the substitution may take place independently of one another, by mono- or polysubstitution in each case, on all the hydrogen-carrying carbon atoms.

The term "$C_{1-5}$alkyl" includes for example $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—CH($CH_3$)—, $H_3C$—$CH_2$—$CH(CH_3)$—$CH_2$—, $H_3C$—CH($CH_3$)—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

Further examples of alkyl are methyl (Me; —$CH_3$), ethyl (Et; —$CH_2CH_3$), 1-propyl (n-propyl; n-Pr; —$CH_2CH_2CH_3$), 2-propyl (i-Pr; iso-propyl; —$CH(CH_3)_2$), 1-butyl (n-butyl; n-Bu; —$CH_2CH_2CH_2CH_3$), 2-methyl-1-propyl (iso-butyl; i-Bu; —$CH_2CH(CH_3)_2$), 2-butyl (sec-butyl; sec-Bu; —$CH(CH_3)CH_2CH_3$), 2-methyl-2-propyl (tert-butyl; t-Bu; —$C(CH_3)_3$), 1-pentyl (n-pentyl; —$CH_2CH_2CH_2CH_2CH_3$), 2-pentyl (—$CH(CH_3)$$CH_2CH_2CH_3$), 3-pentyl (—$CH(CH_2CH_3)_2$), 3-methyl-1-butyl (iso-pentyl; —$CH_2CH_2CH(CH_3)_2$), 2-methyl-2-butyl (—$C(CH_3)_2CH_2CH_3$), 3-methyl-2-butyl (—$CH(CH_3)CH(CH_3)_2$), 2,2-dimethyl-1-propyl (neo-pentyl; —$CH_2C(CH_3)_3$), 2-methyl-1-butyl (—$CH_2CH(CH_3)CH_2CH_3$), 1-hexyl (n-hexyl; —$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 2,3-dimethyl-1-butyl (—$CH_2CH(CH_3)CH(CH_3)CH_3$), 2,2-dimethyl-1-butyl (—$CH_2C(CH_3)_2CH_2CH_3$), 3,3-dimethyl-1-butyl (—$CH_2CH_2C(CH_3)_3$), 2-methyl-1-pentyl (—$CH_2CH(CH_3)CH_2CH_2CH_3$), 3-methyl-1-pentyl (—$CH_2CH_2CH(CH_3)CH_2CH_3$), 1-heptyl (n-heptyl), 2-methyl-1-hexyl, 3-methyl-1-hexyl, 2,2-dimethyl-1-pentyl, 2,3-dimethyl-1-pentyl, 2,4-dimethyl-1-pentyl, 3,3-dimethyl-1-pentyl, 2,2,3-trimethyl-1-butyl, 3-ethyl-1-pentyl, 1-octyl (n-octyl), 1-nonyl (n-nonyl); 1-decyl (n-decyl) etc.

By the terms propyl, butyl, pentyl, hexyl, heptyl, octyl, nonyl, decyl etc. without any further definition are meant saturated hydrocarbon groups with the corresponding number of carbon atoms, wherein all isomeric forms are included.

The above definition for alkyl also applies if alkyl is a part of another (combined) group such as for example $C_{x-y}$alkylamino or $C_{x-y}$alkyloxy.

The term alkylene can also be derived from alkyl. Alkylene is bivalent, unlike alkyl, and requires two binding partners. Formally, the second valency is produced by removing a hydrogen atom in an alkyl. Corresponding groups are for example —$CH_3$ and —$CH_2$—, —$CH_2CH_3$ and —$CH_2CH_2$—or >$CHCH_3$ etc.

The term "$C_{1-4}$alkylene" includes for example —($CH_2$)—, —($CH_2$—$CH_2$)—, —(CH($CH_3$))—, —($CH_2$—$CH_2$—$CH_2$)—, —($C(CH_3)_2$)—, —(CH($CH_2CH_3$))—, —(CH($CH_3$)—$CH_2$)—, —($CH_2$—CH($CH_3$))—, —($CH_2$—$CH_2$—$CH_2$—$CH_2$)—, —($CH_2$—$CH_2$—CH($CH_3$))—, —(CH($CH_3$)—$CH_2$—$CH_2$)—, —($CH_2$—CH($CH_3$)—$CH_2$)—, —($CH_2$—C($CH_3)_2$)—, —($C(CH_3)_2$—$CH_2$)—, —(CH($CH_3$)—CH($CH_3$))—, —($CH_2$—CH($CH_2CH_3$))—, —(CH($CH_2CH_3$)—$CH_2$)—, —(CH($CH_2CH_2CH_3$))—, —(CH(CH($CH_3$))$_2$)—and —C($CH_3$)($CH_2CH_3$)—.

Other examples of alkylene are methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene, hexylene etc.

By the generic terms propylene, butylene, pentylene, hexylene etc. without any further definition are meant all the conceivable isomeric forms with the corresponding number of carbon atoms, i.e. propylene includes 1-methylethylene and butylene includes 1-methylpropylene, 2-methylpropylene, 1,1-dimethylethylene and 1,2-dimethylethylene.

The above definition for alkylene also applies if alkylene is part of another (combined) group such as for example in HO—$C_{x-y}$alkyleneamino or $H_2N$—$C_{x-y}$alkyleneoxy.

Unlike alkyl, alkenyl consists of at least two carbon atoms, wherein at least two adjacent carbon atoms are joined together by a C—C double bond and a carbon atom can only be part of one C—C double bond. If in an alkyl as hereinbefore defined having at least two carbon atoms, two hydrogen atoms on adjacent carbon atoms are formally removed and the free valencies are saturated to form a second bond, the corresponding alkenyl is formed.

Examples of alkenyl are vinyl (ethenyl), prop-1-enyl, allyl (prop-2-enyl), isopropenyl, but-1-enyl, but-2-enyl, but-3-enyl, 2-methyl-prop-2-enyl, 2-methyl-prop-1-enyl, 1-methyl-prop-2-enyl, 1-methyl-prop-1-enyl, 1-methylidenepropyl, pent-1-enyl, pent-2-enyl, pent-3-enyl, pent-4-enyl, 3-methyl-but-3-enyl, 3-methyl-but-2-enyl, 3-methyl-but-1-enyl, hex-1-enyl, hex-2-enyl, hex-3-enyl, hex-4-enyl, hex-5-enyl, 2,3-dimethyl-but-3-enyl, 2,3-dimethyl-but-2-enyl, 2-methylidene-3-methylbutyl, 2,3-dimethyl-but-1-enyl, hexa-1,3-dienyl, hexa-1,4-dienyl, penta-1,4-dienyl, penta-1,3-dienyl, buta-1,3-dienyl, 2,3-dimethylbuta-1,3-diene etc.

By the generic terms propenyl, butenyl, pentenyl, hexenyl, butadienyl, pentadienyl, hexadienyl, heptadienyl, octadienyl, nonadienyl, decadienyl etc. without any further definition are meant all the conceivable isomeric forms with the corresponding number of carbon atoms, i.e. propenyl includes prop-1-enyl and prop-2-enyl, butenyl includes but-1-enyl, but-2-enyl, but-3-enyl, 1-methyl-prop-1-enyl, 1-methyl-prop-2-enyl etc.

Alkenyl may optionally be present in the cis or trans or E or Z orientation with regard to the double bond(s).

The above definition for alkenyl also applies when alkenyl is part of another (combined) group such as for example in $C_{x-y}$alkenylamino or $C_{x-y}$alkenyloxy.

Unlike alkylene, alkenylene consists of at least two carbon atoms, wherein at least two adjacent carbon atoms are joined together by a C—C double bond and a carbon atom can only be part of one C—C double bond. If in an alkylene as hereinbefore defined having at least two carbon atoms, two hydrogen atoms at adjacent carbon atoms are formally removed and the free valencies are saturated to form a second bond, the corresponding alkenylene is formed.

Examples of alkenylene are ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene, hexenylene etc.

By the generic terms propenylene, butenylene, pentenylene, hexenylene etc. without any further definition are meant all the conceivable isomeric forms with the corresponding number of carbon atoms, i.e. propenylene includes 1-methylethenylene and butenylene includes 1-methylpropenylene, 2-methylpropenylene, 1,1-dimethylethenylene and 1,2-dimethylethenylene.

Alkenylene may optionally be present in the cis or trans or E or Z orientation with regard to the double bond(s).

The above definition for alkenylene also applies when alkenylene is a part of another (combined) group as for example in HO—$C_{x-y}$alkenyleneamino or $H_2N$—$C_{x-y}$alkenyleneoxy.

Unlike alkyl, alkynyl consists of at least two carbon atoms, wherein at least two adjacent carbon atoms are joined together by a C—C triple bond. If in an alkyl as hereinbefore defined having at least two carbon atoms, two hydrogen atoms in each case at adjacent carbon atoms are formally removed and the free valencies are saturated to form two further bonds, the corresponding alkynyl is formed.

Examples of alkynyl are ethynyl, prop-1-ynyl, prop-2-ynyl, but-1-ynyl, but-2-ynyl, but-3-ynyl, 1-methyl-prop-2-ynyl, pent-1-ynyl, pent-2-ynyl, pent-3-ynyl, pent-4-ynyl, 3-methyl-but-1-ynyl, hex-1-ynyl, hex-2-ynyl, hex-3-ynyl, hex-4-ynyl, hex-5-ynyl etc.

By the generic terms propynyl, butynyl, pentynyl, hexynyl, heptynyl, octynyl, nonynyl, decynyl etc. without any further definition are meant all the conceivable isomeric forms with the corresponding number of carbon atoms, i.e. propynyl includes prop-1-ynyl and prop-2-ynyl, butynyl includes but-1-ynyl, but-2-ynyl, but-3-ynyl, 1-methyl-prop-1-ynyl, 1-methyl-prop-2-ynyl, etc.

If a hydrocarbon chain carries both at least one double bond and also at least one triple bond, by definition it belongs to the alkynyl subgroup.

The above definition for alkynyl also applies if alkynyl is part of another (combined) group, as for example in $C_{x-y}$alkynylamino or $C_{x-y}$alkynyloxy.

Unlike alkylene, alkynylene consists of at least two carbon atoms, wherein at least two adjacent carbon atoms are joined together by a C—C triple bond. If in an alkylene as hereinbefore defined having at least two carbon atoms, two hydrogen atoms in each case at adjacent carbon atoms are formally removed and the free valencies are saturated to form two further bonds, the corresponding alkynylene is formed.

Examples of alkynylene are ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene, hexynylene etc.

By the generic terms propynylene, butynylene, pentynylene, hexynylene etc. without any further definition are meant all the conceivable isomeric forms with the corresponding number of carbon atoms, i.e. propynylene includes 1-methylethynylene and butynylene includes 1-methylpropynylene, 2-methylpropynylene, 1,1-dimethylethynylene and 1,2-dimethylethynylene.

The above definition for alkynylene also applies if alkynylene is part of another (combined) group, as for example in HO—$C_{x-y}$alkynyleneamino or $H_2N$—$C_{x-y}$alkynyleneoxy.

By heteroatoms are meant oxygen, nitrogen and sulphur atoms.

Haloalkyl (haloalkenyl, haloalkynyl) is derived from the previously defined alkyl (alkenyl, alkynyl) by replacing one or more hydrogen atoms of the hydrocarbon chain independently of one another by halogen atoms, which may be identical or different. If a haloalkyl (haloalkenyl, haloalkynyl) is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —$CF{=}CF_2$, —$CCl{=}CH_2$, —$CBr{=}CH_2$, —$C{\equiv}C$—$CF_3$, —$CHFCH_2CH_3$, —$CHFCH_2CF_3$ etc.

From the previously defined haloalkyl (haloalkenyl, haloalkynyl) are also derived the terms haloalkylene (haloalkenylene, haloalkynylene). Haloalkylene (haloalkenylene, haloalkynylene), unlike haloalkyl (haloalkenyl, haloalkynyl), is bivalent and requires two binding partners. Formally, the second valency is formed by removing a hydrogen atom from a haloalkyl (haloalkenyl, haloalkynyl).

Corresponding groups are for example —$CH_2F$ and —CHF—, —$CHCH_2F$ and —CHFCHF— or >$CFCH_2F$ etc.

The above definitions also apply if the corresponding halogen-containing groups are part of another (combined) group.

Halogen relates to fluorine, chlorine, bromine and/or iodine atoms.

Cycloalkyl is made up of the subgroups monocyclic hydrocarbon rings, bicyclic hydrocarbon rings and spirohydrocarbon rings. The systems are saturated. In bicyclic hydrocarbon rings two rings are joined together so that they have at least two carbon atoms in common. In spirohydrocarbon rings one carbon atom (spiroatom) belongs to two rings together.

If a cycloalkyl is to be substituted, the substitutions may take place independently of one another, in the form of mono- or polysubstitutions in each case, on all the hydrogen-carrying carbon atoms. Cycloalkyl itself may be linked as a substituent to the molecule via every suitable position of the ring system.

Examples of cycloalkyl are cyclopropyl, cyclobutyl, cyclopentyl, cyclohexyl, cycloheptyl, bicyclo[2.2.0]hexyl, bicyclo[3.2.0]heptyl, bicyclo[3.2.1]octyl, bicyclo[2.2.2]octyl, bicyclo[4.3.0]nonyl (octahydroindenyl), bicyclo[4.4.0]decyl (decahydronaphthyl), bicyclo[2.2.1]heptyl (norbornyl), bicyclo[4.1.0]heptyl (norcaranyl), bicyclo[3.1.1]heptyl (pinanyl), spiro[2.5]octyl, spiro[3.3]heptyl etc.

The above definition for cycloalkyl also applies if cycloalkyl is part of another (combined) group as for example in $C_{x-y}$cycloalkylamino, $C_{x-y}$cycloalkyloxy or $C_{x-y}$cycloalkylalkyl.

If the free valency of a cycloalkyl is saturated, then an alicyclic group is obtained.

The term cycloalkylene can thus be derived from the previously defined cycloalkyl. Cycloalkylene, unlike cycloalkyl, is bivalent and requires two binding partners. Formally, the second valency is obtained by removing a hydrogen atom from a cycloalkyl. Corresponding groups are for example:

cyclohexyl and

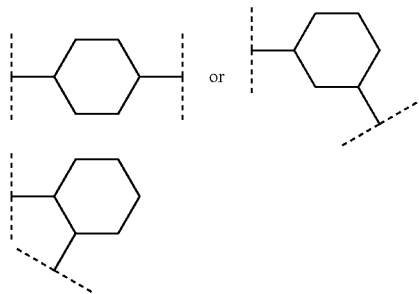

(cyclohexylene).

The above definition for cycloalkylene also applies if cycloalkylene is part of another (combined) group as for example in HO—$C_{x-y}$cycloalkyleneamino or $H_2N$—$C_{x-y}$cycloalkyleneoxy.

Cycloalkenyl is also made up of the subgroups monocyclic hydrocarbon rings, bicyclic hydrocarbon rings and spiro-hydrocarbon rings. However, the systems are unsaturated, i.e. there is at least one C—C double bond but no aromatic system. If in a cycloalkyl as hereinbefore defined two hydrogen atoms at adjacent cyclic carbon atoms are formally removed and the free valencies are saturated to form a second bond, the corresponding cycloalkenyl is obtained.

If a cycloalkenyl is to be substituted, the substitutions may take place independently of one another, in the form of mono- or polysubstitutions in each case, on all the hydrogen-carrying carbon atoms. Cycloalkenyl itself may be linked as a substituent to the molecule via every suitable position of the ring system.

Examples of cycloalkenyl are cycloprop-1-enyl, cycloprop-2-enyl, cyclobut-1-enyl, cyclobut-2-enyl, cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, cyclobuta-1,3-dienyl, cyclopenta-1,4-dienyl, cyclopenta-1,3-dienyl, cyclopenta-2,4-dienyl, cyclohexa-1,3-dienyl, cyclohexa-1,5-dienyl, cyclohexa-2,4-dienyl, cyclohexa-1,4-dienyl, cyclohexa-2,5-dienyl, bicyclo[2.2.1]hepta-2,5-dienyl (norborna-2,5-dienyl), bicyclo[2.2.1]hept-2-enyl (norbornenyl), spiro[4,5]dec-2-enyl etc.

The above definition for cycloalkenyl also applies when cycloalkenyl is part of another (combined) group as for example in $C_{x-y}$cycloalkenylamino, $C_{x-y}$cycloalkenyloxy or $C_{x-y}$cycloalkenylalkyl.

If the free valency of a cycloalkenyl is saturated, then an unsaturated alicyclic group is obtained.

The term cycloalkenylene can thus be derived from the previously defined cycloalkenyl. Cycloalkenylene, unlike cycloalkenyl, is bivalent and requires two binding partners. Formally, the second valency is obtained by removing a hydrogen atom from a cycloalkenyl. Corresponding groups are for example:

cyclopentenyl and

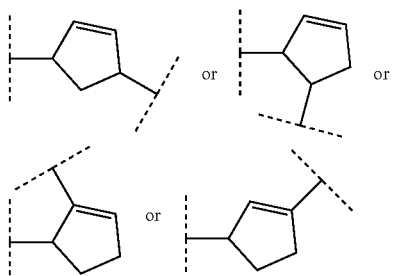

(cyclopentenylene) etc.

The above definition for cycloalkenylene also applies if cycloalkenylene is part of another (combined) group as for example in HO—$C_{x-y}$cycloalkenyleneamino or $H_2N$—$C_{x-y}$cycloalkenyleneoxy.

Aryl denotes mono-, bi- or tricyclic carbocycles with at least one aromatic carbocycle. Preferably, it denotes a monocyclic group with six carbon atoms (phenyl) or a bicyclic group with nine or ten carbon atoms (two six-membered rings or one six-membered ring with a five-membered ring), wherein the second ring may also be aromatic or, however, may also be partially saturated.

If an aryl is to be substituted, the substitutions may take place independently of one another, in the form of mono- or polysubstitutions in each case, on all the hydrogen-carrying carbon atoms. Aryl itself may be linked as a substituent to the molecule via every suitable position of the ring system.

Examples of aryl are phenyl, naphthyl, indanyl (2,3-dihydroindenyl), indenyl, anthracenyl, phenanthrenyl, tetrahydronaphthyl (1,2,3,4-tetrahydronaphthyl, tetralinyl), dihydronaphthyl (1,2-dihydronaphthyl), fluorenyl etc. Most preferred is phenyl.

The above definition of aryl also applies if aryl is part of another (combined) group as for example in arylamino, aryloxy or arylalkyl.

If the free valency of an aryl is saturated, then an aromatic group is obtained.

The term arylene can also be derived from the previously defined aryl. Arylene, unlike aryl, is bivalent and requires two binding partners. Formally, the second valency is formed by removing a hydrogen atom from an aryl. Corresponding groups are for example:

phenyl and

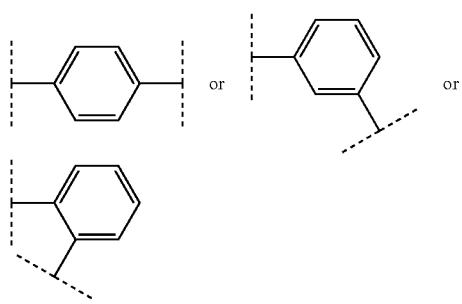

(o, m, p-phenylene),
naphthyl and

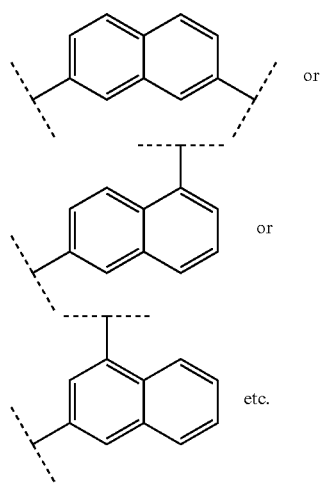

etc.

The above definition for arylene also applies if arylene is part of another (combined) group as for example in HO-aryleneamino or H$_2$N-aryleneoxy.

Heterocyclyl denotes ring systems, which are derived from the previously defined cycloalkyl, cycloalkenyl and aryl by replacing one or more of the groups —CH$_2$— independently of one another in the hydrocarbon rings by the groups —O—, —S— or —NH— or by replacing one or more of the groups =CH— by the group =N—, wherein a total of not more than five heteroatoms may be present, at least one carbon atom must be present between two oxygen atoms and between two sulphur atoms or between an oxygen and a sulphur atom and the ring as a whole must have chemical stability. Heteroatoms may optionally be present in all the possible oxidation stages (sulphur→sulphoxide —SO—, sulphone —SO$_2$—; nitrogen→N-oxide).

As it will be clear to the person skilled in the art, Heterocycloalkyl is derived from cycloalkyl and heterocycloalkenyl is derived from cycloalkenyl, as described above.

A direct result of the derivation from cycloalkyl, cycloalkenyl and aryl is that heterocyclyl is made up of the subgroups monocyclic heterorings, bicyclic heterorings, tricyclic heterorings and spiro-heterorings, which may be present in saturated or unsaturated form.

By unsaturated is meant that there is at least one double bond in the ring system in question, but no heteroaromatic system is formed. In bicyclic heterorings two rings are linked together so that they have at least two (hetero)atoms in common. In spiro-heterorings one carbon atom (spiroatom) belongs to two rings together.

If a heterocyclyl is substituted, the substitutions may take place independently of one another, in the form of mono- or polysubstitutions in each case, on all the hydrogen-carrying carbon and/or nitrogen atoms. Heterocyclyl itself may be linked as a substituent to the molecule via every suitable position of the ring system.

Examples of heterocyclyl are tetrahydrofuryl, pyrrolidinyl, pyrrolinyl, imidazolidinyl, thiazolidinyl, imidazolinyl, pyrazolidinyl, pyrazolinyl, piperidinyl, piperazinyl, oxiranyl, aziridinyl, azetidinyl, 1,4-dioxanyl, azepanyl, diazepanyl, morpholinyl, thiomorpholinyl, homomorpholinyl, homopiperidinyl, homopiperazinyl, homothiomorpholinyl, thiomorpholinyl-S-oxide, thiomorpholinyl-S,S-dioxide, 1,3-dioxolanyl, tetrahydropyranyl, tetrahydrothiopyranyl, [1,4]-oxazepanyl, tetrahydrothienyl, homothiomorpholinyl-S,S-dioxide, oxazolidinonyl, dihydropyrazolyl, dihydropyrrolyl, dihydropyrazinyl, dihydropyridyl, dihydro-pyrimidinyl, dihydrofuryl, dihydropyranyl, tetrahydrothienyl-S-oxide, tetrahydrothienyl-S,S-dioxide, homothiomorpholinyl-S-oxide, 2,3-dihydroazet, 2H-pyrrolyl, 4H-pyranyl, 1,4-dihydropyridinyl, 8-aza-bicyclo[3.2.1]octyl, 8-aza-bicyclo[5.1.0]octyl, 2-oxa-5-azabicyclo[2.2.1]heptyl, 8-oxa-3-aza-bicyclo[3.2.1]octyl, 3,8-diaza-bicyclo[3.2.1]octyl, 2,5-diaza-bicyclo[2.2.1]heptyl, 1-aza-bicyclo[2.2.2]octyl, 3,8-diaza-bicyclo[3.2.1]octyl, 3,9-diaza-bicyclo[4.2.1]nonyl, 2,6-diaza-bicyclo[3.2.2]nonyl, 1,4-dioxa-spiro[4.5]decyl, 1-oxa-3,8-diaza-spiro[4.5]decyl, 2,6-diaza-spiro[3.3]heptyl, 2,7-diaza-spiro[4.4]nonyl, 2,6-diaza-spiro[3.4]octyl, 3,9-diaza-spiro[5.5]undecyl, 2,8-diaza-spiro[4.5]decyl etc.

Further examples are the structures illustrated below, which may be attached via each hydrogen-carrying atom (exchanged for hydrogen):

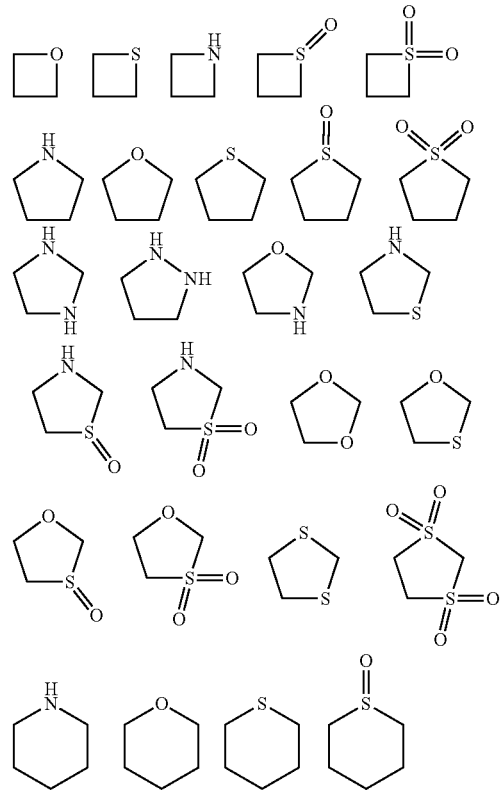

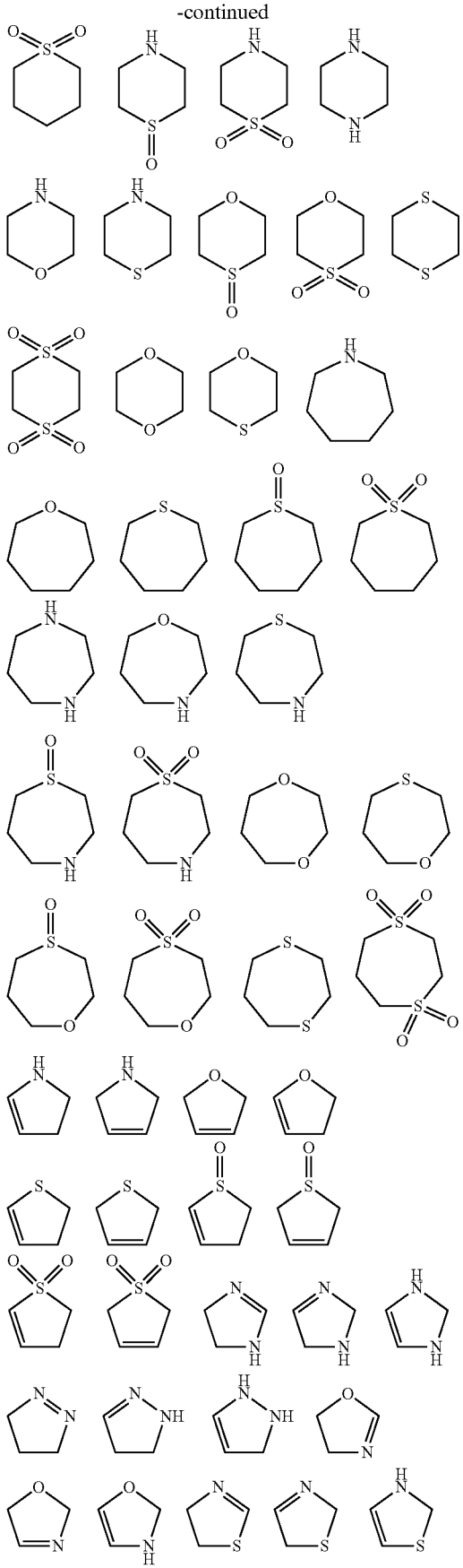
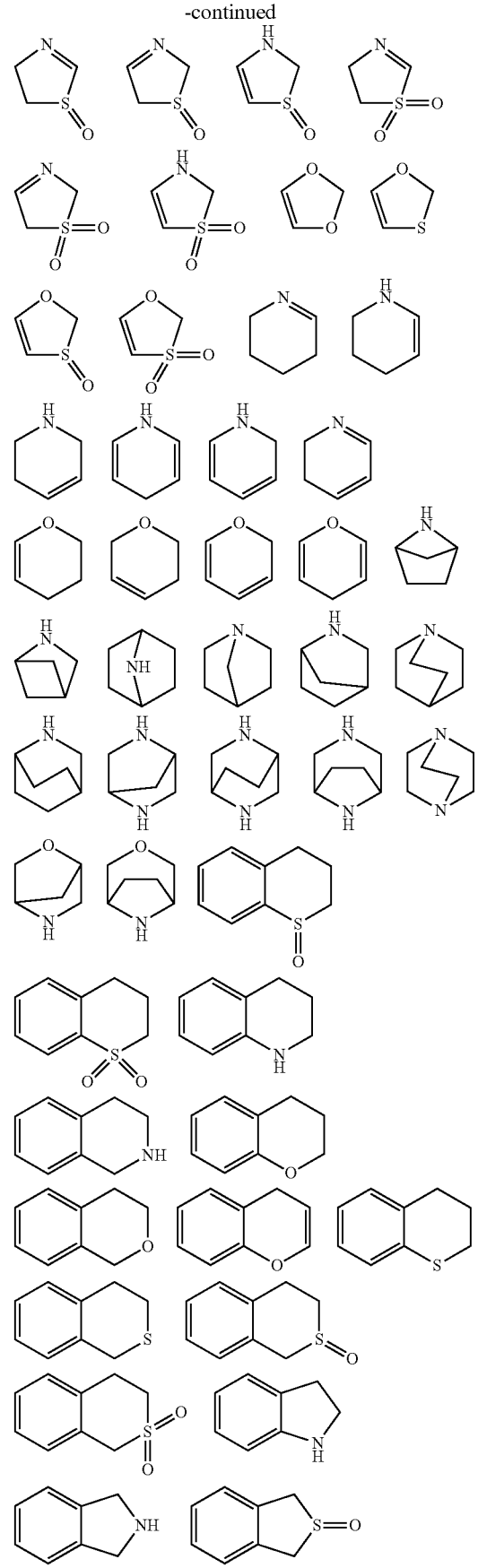

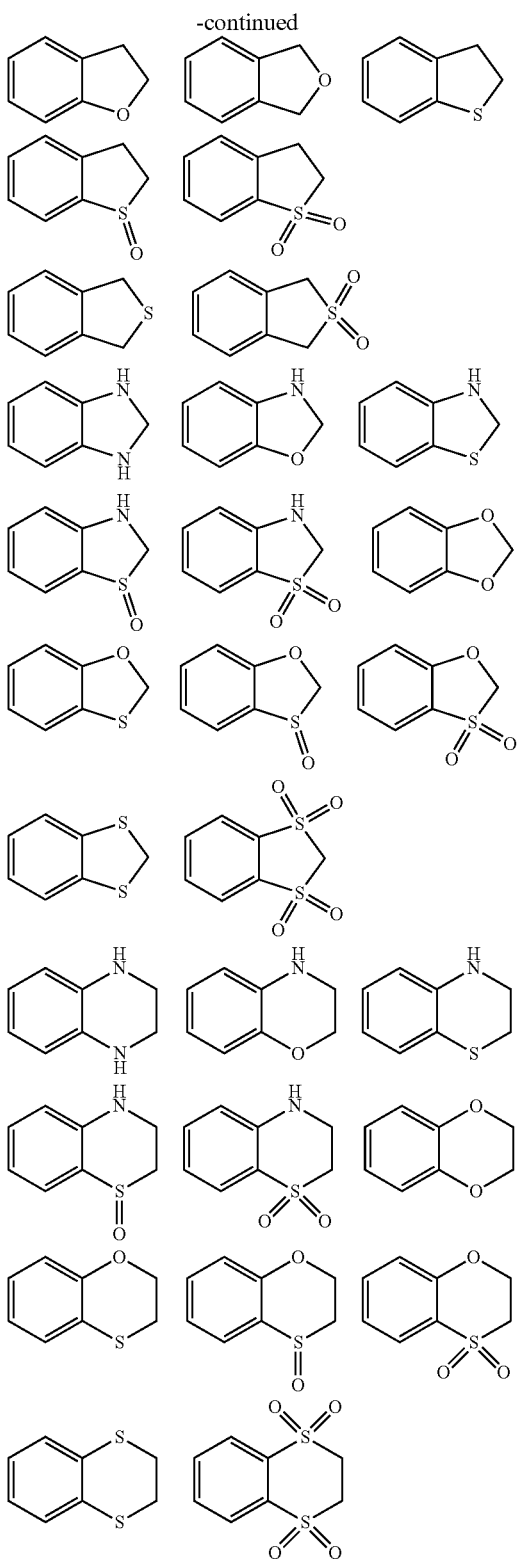

Preferably, heterocyclyls are 4 to 8 membered, monocyclic and have one or two heteroatoms independently selected from oxygen, nitrogen and sulfur.

Preferred heterocyclyls are: piperazinyl, piperidinyl, morpholinyl, pyrrolidinyl, azetidinyl, tetrahydropyranyl, tetrahydrofuranyl.

The above definition of heterocyclyl also applies if heterocyclyl is part of another (combined) group as for example in heterocyclylamino, heterocyclyloxy or heterocyclylalkyl.

If the free valency of a heterocyclyl is saturated, then a heterocyclic group is obtained.

The term heterocyclylene is also derived from the previously defined heterocyclyl. Heterocyclylene, unlike heterocyclyl, is bivalent and requires two binding partners. Formally, the second valency is obtained by removing a hydrogen atom from a heterocyclyl. Corresponding groups are for example:

piperidinyl and

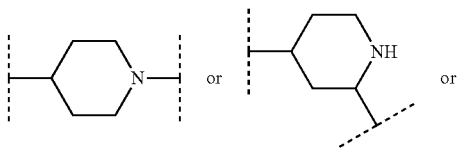

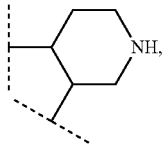

2,3-dihydro-1H-pyrrolyl and

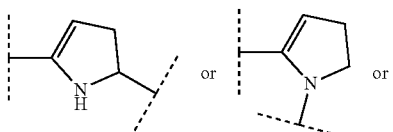

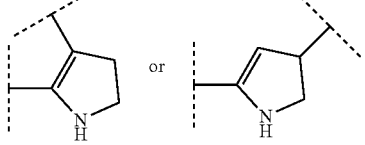

etc.

The above definition of heterocyclylene also applies if heterocyclylene is part of another (combined) group as for example in HO-heterocyclyleneamino or $H_2N$-heterocyclyleneoxy.

Heteroaryl denotes monocyclic heteroaromatic rings or polycyclic rings with at least one heteroaromatic ring, which compared with the corresponding aryl or cycloalkyl (cycloalkenyl) contain, instead of one or more carbon atoms, one or more identical or different heteroatoms, selected independently of one another from among nitrogen, sulphur and oxygen, wherein the resulting group must be chemically stable. The prerequisite for the presence of heteroaryl is a heteroatom and a heteroaromatic system.

If a heteroaryl is to be substituted, the substitutions may take place independently of one another, in the form of mono- or polysubstitutions in each case, on all the hydrogen-carrying carbon and/or nitrogen atoms. Heteroaryl itself may be linked as a substituent to the molecule via every suitable position of the ring system, both carbon and nitrogen.

Examples of heteroaryl are furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl, triazinyl, pyridyl-N-oxide, pyrrolyl-N-oxide, pyrimidinyl-N-oxide, pyridazinyl-N- oxide, pyrazinyl-N-oxide, imidazolyl-N-oxide, isoxazolyl-N-oxide, oxazolyl-N-oxide, thiazolyl-N-oxide, oxadiazolyl-N-oxide, thiadiazolyl-N-oxide, triazolyl-N-oxide, tetrazolyl-N-oxide, indolyl, isoindolyl, benzofuryl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl, benzotriazinyl, indolizinyl, oxazolopyridyl, imidazopyridyl, naphthyridinyl, benzoxazolyl, pyridopyridyl, pyrimidopyridyl, purinyl, pteridinyl, benzothiazolyl, imidazopyridyl, imidazothiazolyl, quinolinyl-N-oxide, indolyl-N-oxide, isoquinolyl-N-oxide, quinazolinyl-N-oxide, quinoxalinyl-N-oxide, phthalazinyl-N-oxide, indolizinyl-N-oxide, indazolyl-N-oxide, benzothiazolyl-N-oxide, benzimidazolyl-N-oxide etc.

Further examples are the structures illustrated below, which may be attached via each hydrogen-carrying atom (exchanged for hydrogen):

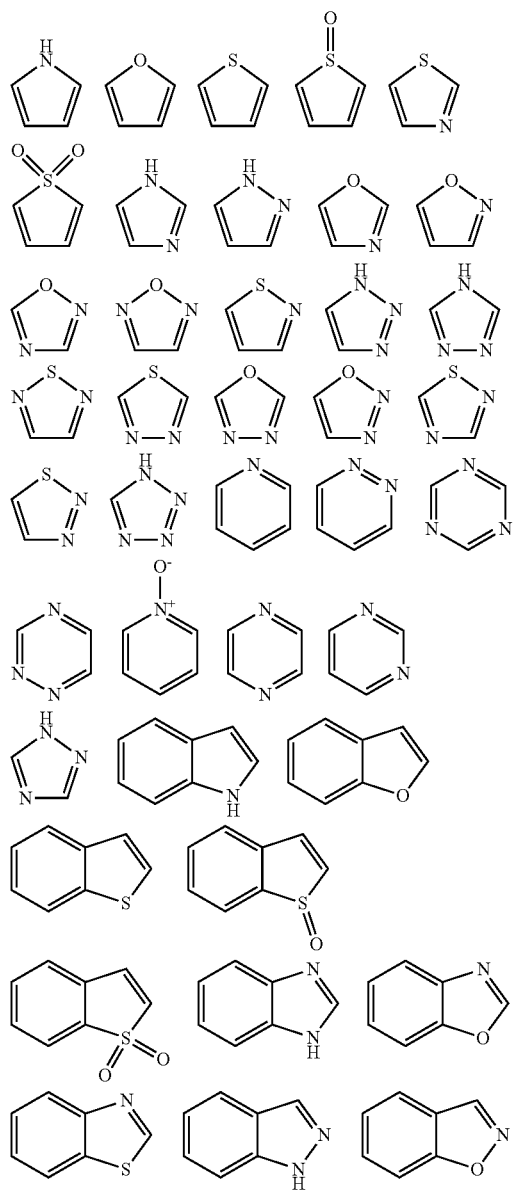

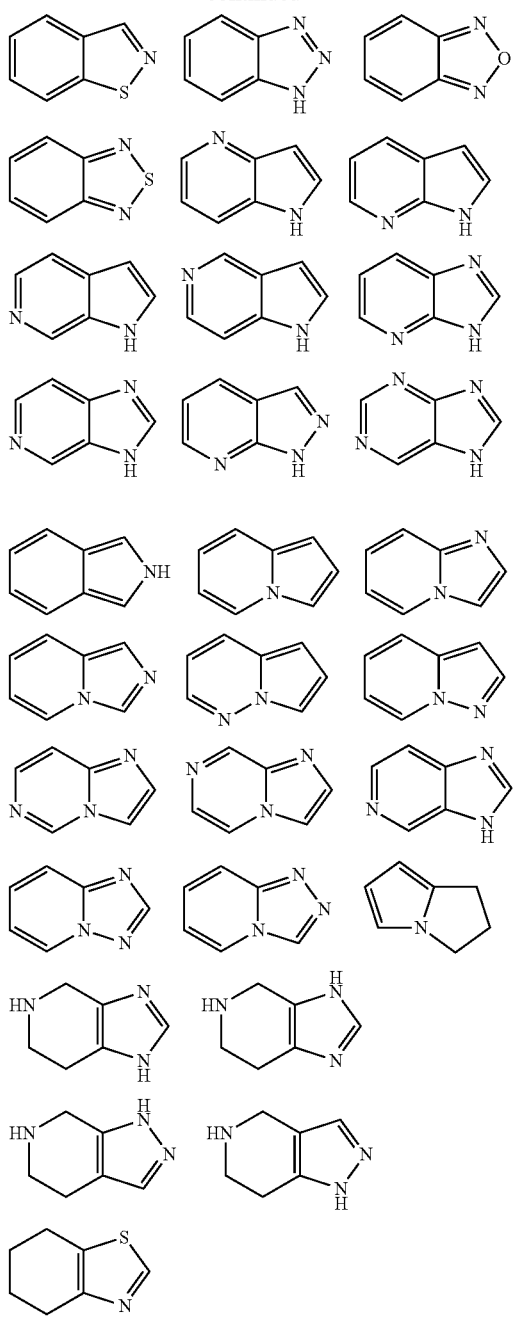

Preferably, heteroaryls are 5-6 membered monocyclic or 9-10 membered bicyclic, each with 1 to 4 heteroatoms independently selected from oxygen, nitrogen and sulfur.

The above definition of heteroaryl also applies if heteroaryl is part of another (combined) group as for example in heteroarylamino, heteroaryloxy or heteroarylalkyl.

If the free valency of a heteroaryl is saturated, a heteroaromatic group is obtained.

The term heteroarylene is also derived from the previously defined heteroaryl. Heteroarylene, unlike heteroaryl, is bivalent and requires two binding partners. Formally, the second valency is obtained by removing a hydrogen atom from a heteroaryl. Corresponding groups are for example:

pyrrolyl and

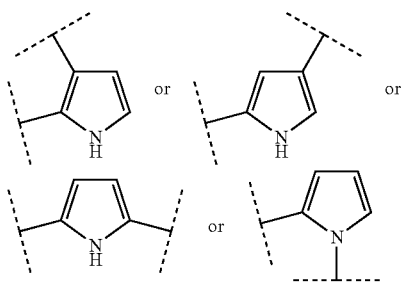

etc.

The above definition of heteroarylene also applies if heteroarylene is part of another (combined) group as for example in HO-heteroaryleneamino or H₂N-heteroaryleneoxy.

By substituted is meant that a hydrogen atom which is bound directly to the atom under consideration, is replaced by another atom or another group of atoms (substituent). Depending on the starting conditions (number of hydrogen atoms) mono- or polysubstitution may take place on one atom. Substitution with a particular substituent is only possible if the permitted valencies of the substituent and of the atom that is to be substituted correspond to one another and the substitution leads to a stable compound (i.e. to a compound which is not converted spontaneously, e.g. by rearrangement, cyclisation or elimination).

Bivalent substituents such as =S, =NR, =NOR, =NNRR, =NN(R)C(O)NRR, =N₂ or the like, may only be substituents on carbon atoms, whereas the bivalent substituent =O may also be a substituent on sulphur. Generally, substitution may be carried out by a bivalent substituent only at ring systems and requires replacement of two geminal hydrogen atoms, i.e. hydrogen atoms that are bound to the same carbon atom that is saturated prior to the substitution. Substitution by a bivalent substituent is therefore only possible at the group —CH₂— or sulphur atoms (=O only) of a ring system.

Stereochemistry/solvates/hydrates: Unless specifically indicated, throughout the specification and appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates and hydrates of the free compound or solvates and hydrates of a salt of the compound.

In general, substantially pure stereoisomers can be obtained according to synthetic principles known to a person skilled in the field, e.g. by separation of corresponding mixtures, by using stereochemically pure starting materials and/or by stereoselective synthesis. It is known in the art how to prepare optically active forms, such as by resolution of racemic forms or by synthesis, e.g. starting from optically active starting materials and/or by using chiral reagents.

Enantiomerically pure compounds of this invention or intermediates may be prepared via asymmetric synthesis, for example by preparation and subsequent separation of appropriate diastereomeric compounds or intermediates which can be separated by known methods (e.g. by chromatographic separation or crystallization) and/or by using chiral reagents, such as chiral starting materials, chiral catalysts or chiral auxiliaries. Further, it is known to the person skilled in the art how to prepare enantiomerically pure compounds from the corresponding racemic mixtures, such as by chromatographic separation of the corresponding racemic mixtures on chiral stationary phases, or by resolution of a racemic mixture using an appropriate resolving agent, e.g. by means of diastereomeric salt formation of the racemic compound with optically active acids or bases, subsequent resolution of the salts and release of the desired compound from the salt, or by derivatization of the corresponding racemic compounds with optically active chiral auxiliary reagents, subsequent diastereomer separation and removal of the chiral auxiliary group, or by kinetic resolution of a racemate (e.g. by enzymatic resolution); by enantioselective crystallization from a conglomerate of enantiomorphous crystals under suitable conditions, or by (fractional) crystallization from a suitable solvent in the presence of an optically active chiral auxiliary.

Salts: The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, and commensurate with a reasonable benefit/risk ratio.

As used herein "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include salts from benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid.

Further pharmaceutically acceptable salts can be formed with cations from ammonia, L-arginine, calcium, 2,2'-iminobisethanol, L-lysine, magnesium, N-methyl-D-glucamine, potassium, sodium and tris(hydroxymethyl)-aminomethane.

The pharmaceutically acceptable salts of the present invention can be synthesized from the parent compound which contains a basic or acidic moiety by conventional chemical methods. Generally, such salts can be prepared by reacting the free acid or base form of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts), also comprise a part of the invention.

In a representation such as for example

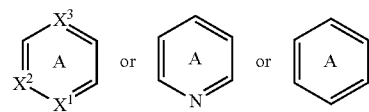

the letter A has the function of a ring designation in order to make it easier, for example, to indicate the attachment of the ring in question to other rings.

For bivalent groups in which it is crucial to determine which adjacent groups they bind and with which valency, the corresponding binding partners are indicated in brackets where necessary for clarification purposes, as in the following representations:

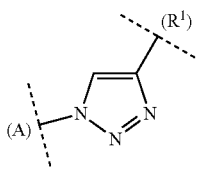

or (R²)—C(O)NH— or (R²)—NHC(O)—;

Groups or substituents are frequently selected from among a number of alternative groups/substituents with a corresponding group designation (e.g. $R^a$, $R^b$ etc). If such a group is used repeatedly to define a compound according to the invention in different parts of the molecule, it is pointed out that the various uses are to be regarded as totally independent of one another.

By a therapeutically effective amount for the purposes of this invention is meant a quantity of substance that is capable of obviating symptoms of illness or of preventing or alleviating these symptoms, or which prolong the survival of a treated patient.

The compounds according to the invention are prepared by the methods of synthesis described hereinafter in which the substituents of the general formulae have the meanings given hereinbefore. These methods are intended as an illustration of the invention without restricting its subject matter and the scope of the compounds claimed to these examples. Where the preparation of starting compounds is not described, they are commercially obtainable or may be prepared analogously to known prior art compounds or methods described herein. Substances described in the literature are prepared according to or in analogy to the published methods of synthesis.

General Reaction Scheme and Summary of the Synthesis Route

List of Abbreviations

| | |
|---|---|
| Ac | acetyl |
| ACN, AN | acetonitrile |
| aq. | aquatic, aqueous |
| ATP | adenosine triphosphate |
| BINAP | 2,2'-bis(diphenylphosphino)-1,1'-binaphthyl |
| BiPh | biphenyl |
| Bn | benzyl |
| Boc | tert-butyloxycarbonyl |
| Bu | butyl |
| c | concentration |
| d | day(s) |
| dba | dibenzylideneacetone |
| TLC | thin layer chromatography |
| DABSO | 1,4-Diazabicyclo[2.2.2]octane bis(sulfur dioxide) adduct |
| Davephos | 2-dimethylamino-2'-dicyclohexylaminophosphinobiphenyl |
| DBA | dibenzylideneacetone |
| DCM | dichloromethane |
| DEA | diethylamine |
| DIPEA | N-ethyl-N,N-diisopropylamine (Hünig's base) |
| DMAP | 4-N,N-dimethylaminopyridine |
| DME | 1,2-dimethoxyethane |
| DMF | N,N-dimethylformamide |
| DMSO | dimethylsulphoxide |
| DPPA | diphenylphosphorylazide |
| dppf | 1,1'-bis(diphenylphosphino)ferrocene |
| EDTA | ethylenediaminetetraacetic acid |
| EGTA | ethyleneglycoltetraacetic acid |
| ADAC | Allgemeiner Deutscher Automobil-Club e.V. |
| eq | eguivalent(s) |
| ESI | electron spray ionization |
| Et | ethyl |
| Et₂O | diethyl ether |
| EtOAc | ethyl acetate |
| EtOH | ethanol |
| h | hour |
| HATU | O-(7-azabenzotriazol-1-yl)-N,N,N',N'-tetramethyl-uronium hexafluorophosphate |
| HPLC | high performance liquid chromatography |
| i | iso |
| Kat., kat. | catalyst, catalytic |
| conc. | concentrated |
| LC | liquid chromatography |
| LiHMDS | lithium bis(trimethylsilyl)amide |
| sln. | solution |
| Me | methyl |
| MeCN | acetonitrile |
| MeOH | methanol |
| min | minutes |
| MPLC | medium pressure liquid chromatography |
| MS | mass spectrometry |
| NBS | N-bromo-succinimide |
| NIS | N-iodo-succinimide |
| NMM | N-methylmorpholine |
| NMP | N-methylpyrrolidone |
| NP | normal phase |
| n.a. | not available |
| PBS | phosphate-buffered saline |
| Ph | phenyl |
| Pr | propyl |
| Py | pyridine |
| rac | racemic |
| red. | reduction |
| Rf (R$_f$) | retention factor |
| RP | reversed phase |
| rt | ambient temperature |
| S$_N$ | nucleophilic substitution |
| TBAF | tetrabutylammonium fluoride |
| TBDMS | tert-butyldimethylsilyl |
| TBME | tert-butylmethylether |
| TBTU | O-(benzotriazol-1-yl)-N,N,N',N'-tetramethyl-uronium tetrafluoroborate |
| tBu | tert-butyl |
| TEA | triethylamine |
| temp. | temperature |
| tert | tertiary |
| Tf | triflate |
| TFA | trifluoroacetic acid |
| THF | tetrahydrofuran |
| TMS | trimethylsilyl |
| t$_{Ret.}$ | retention time (HPLC) |
| TRIS | tris(hydroxymethyl)-aminomethane |
| TsOH | p-toluenesulphonic acid |
| UV | ultraviolet |

General Reaction Scheme:
Indol-2-carboxamides; synthesis of R11-Esters; for commercially available halo acetic acid derivatives
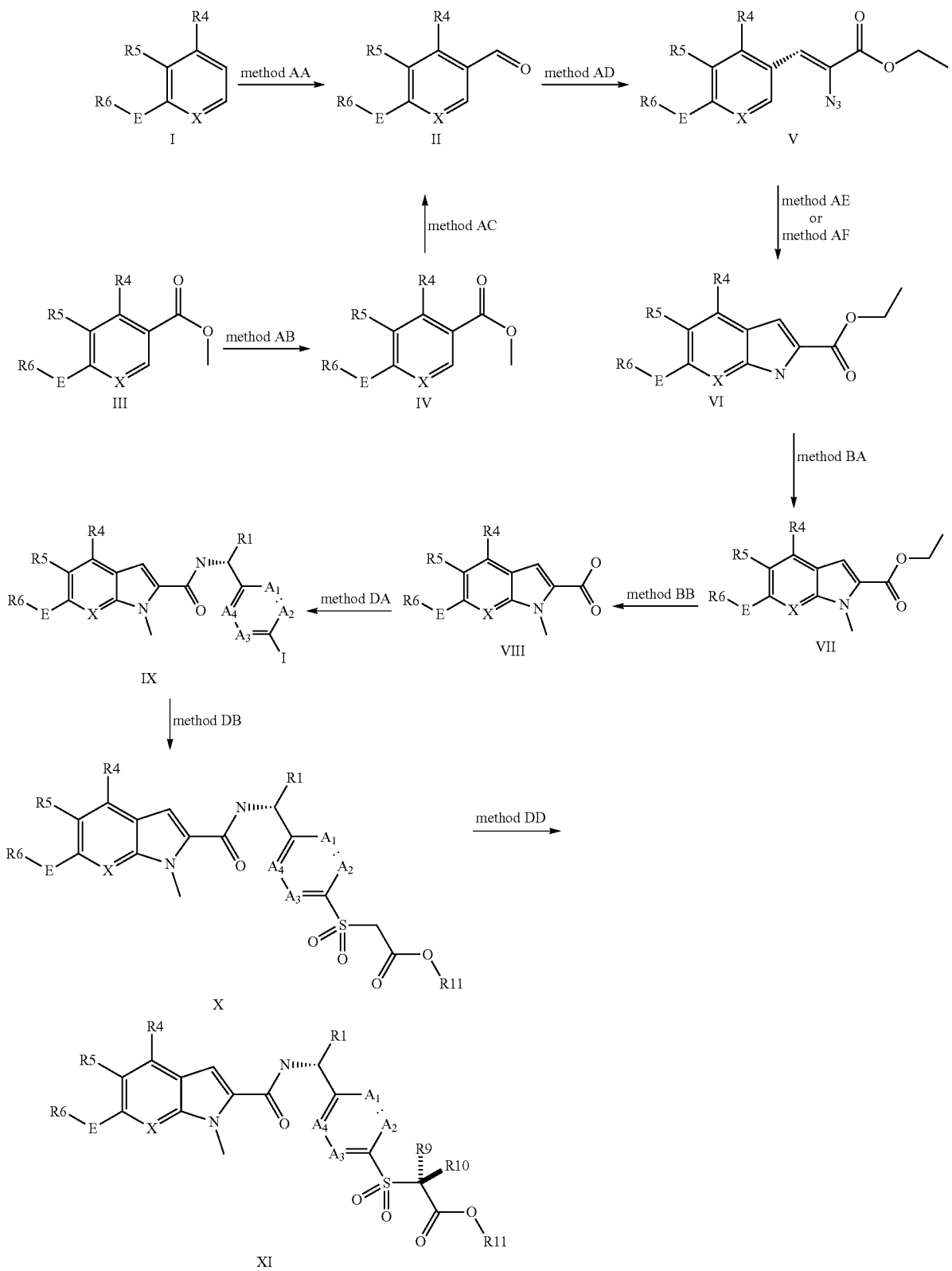

Indol-2-carboxamides; synthesis of sulfoxide derivatives
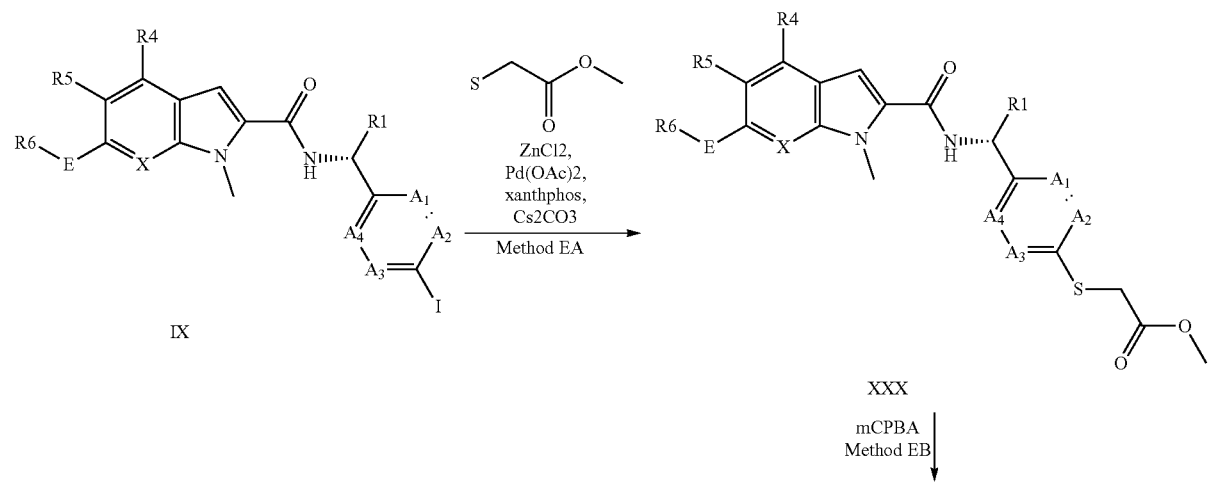
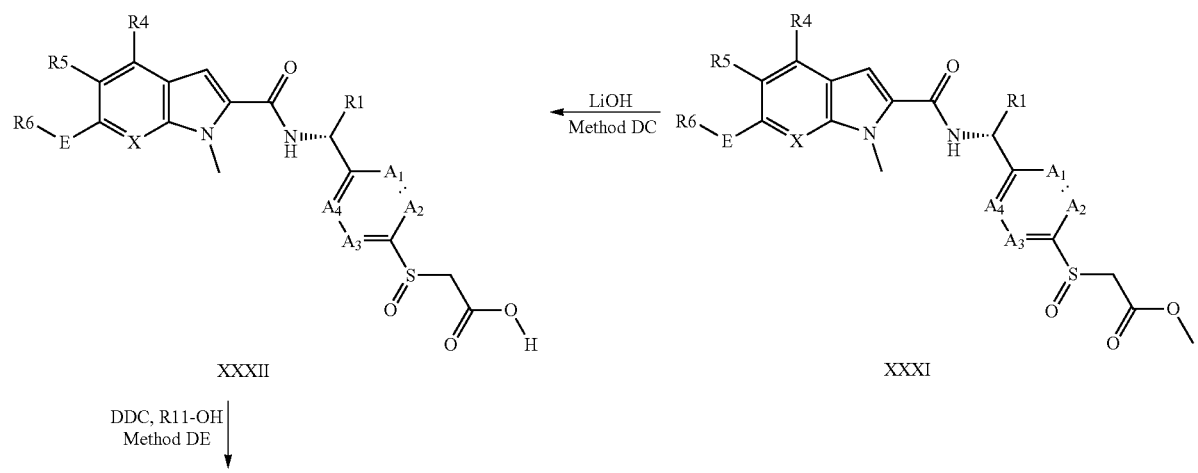
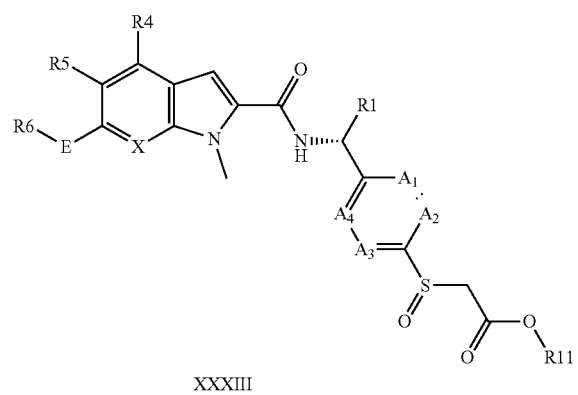

Indol-2-carboxamides; alternative ester synthesis for non-commercially available halo-acetic acid derivatives
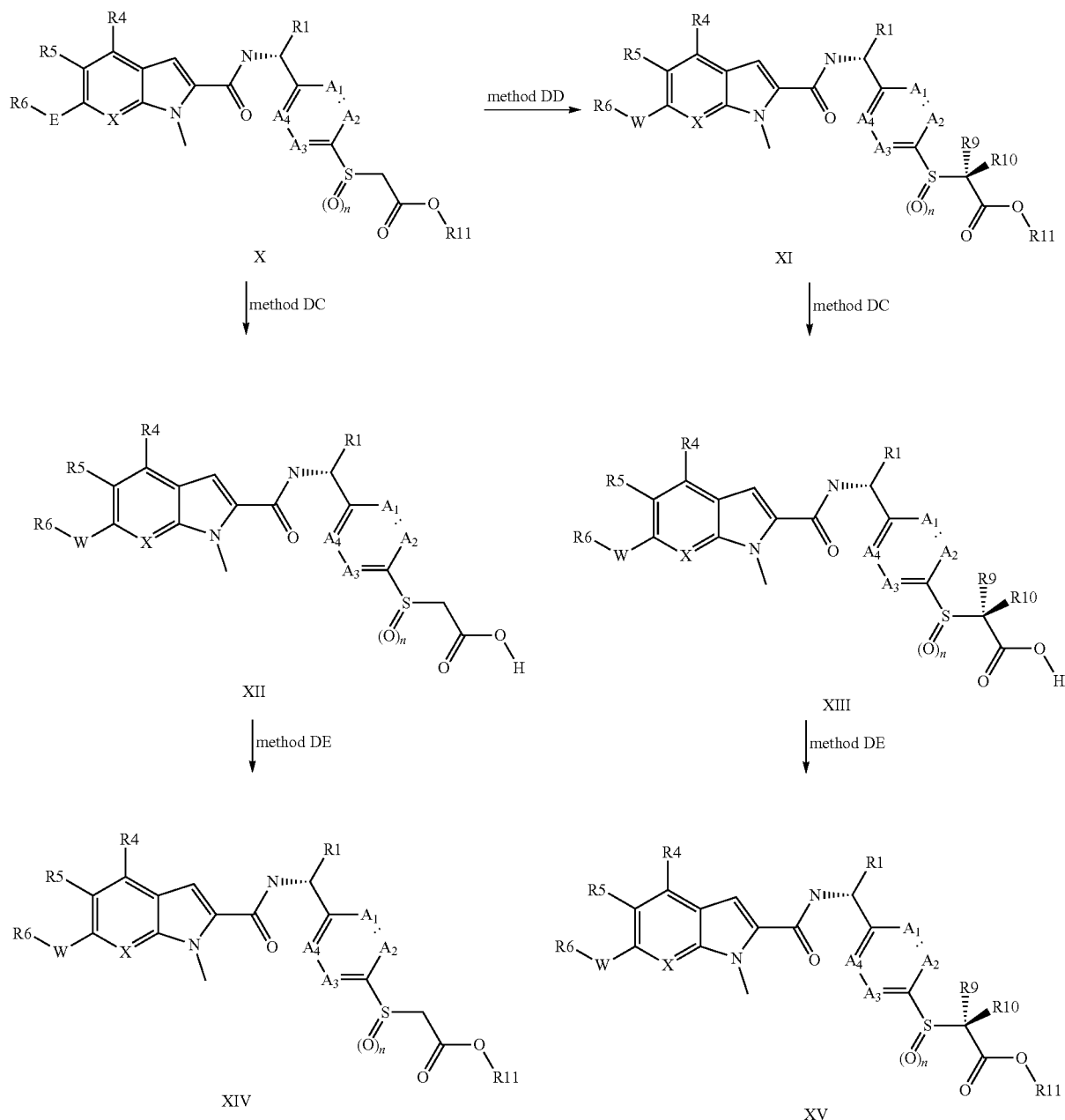
Pyrrazol-5-Carboxamides; Route 1 for branched esters
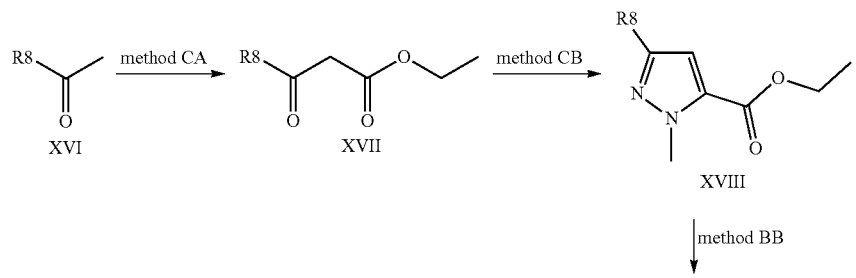

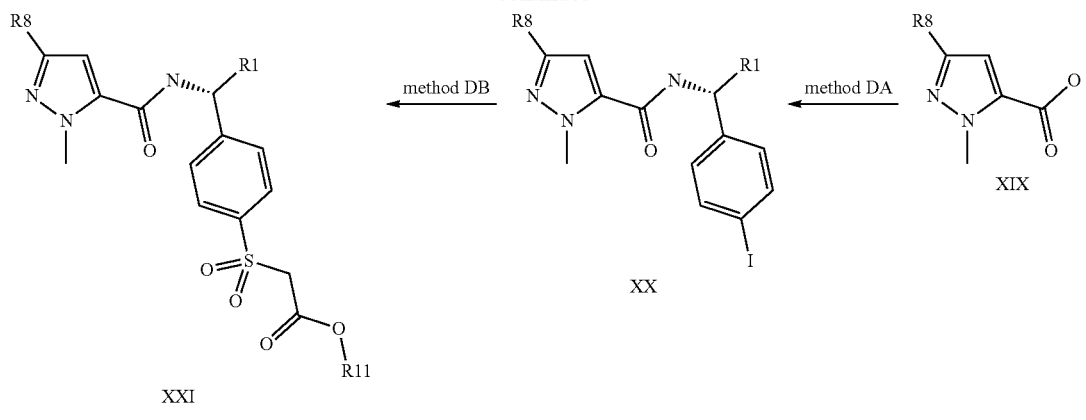
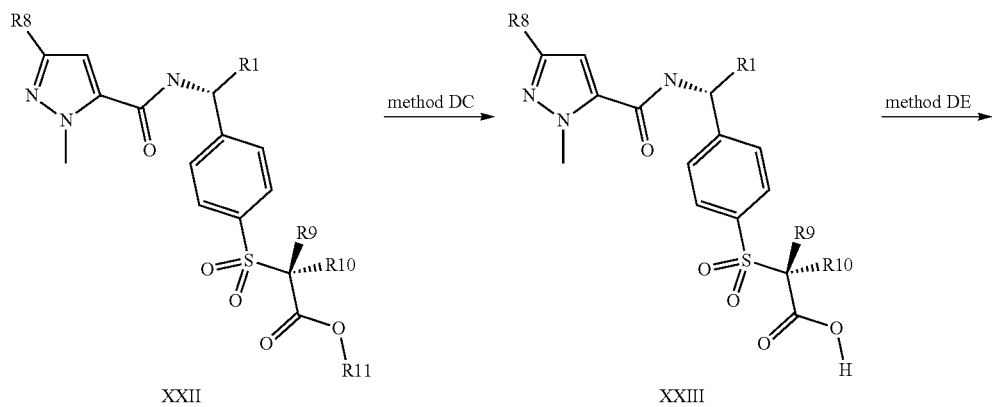
XXIV
route for non commercially available halo acetic esters.

• Pyrrazol-5-Carboxamides; Route 2, starting from XXV

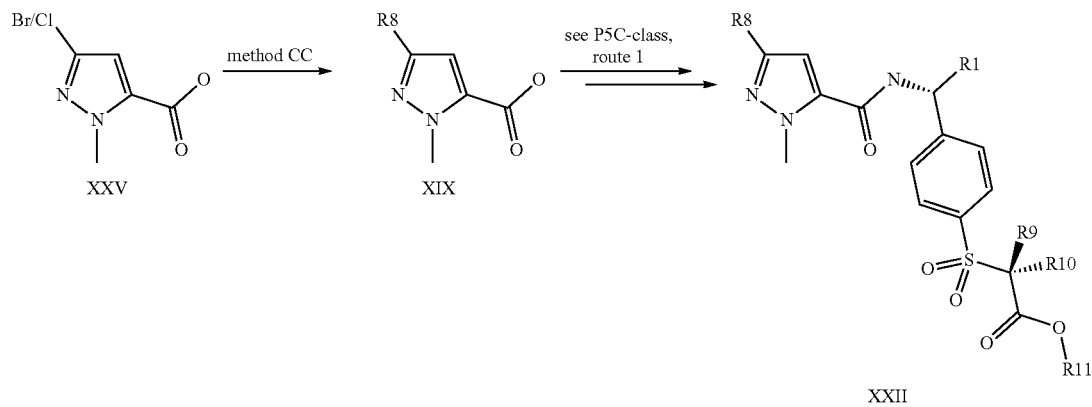

Features and advantages of the present invention will become apparent from the following detailed examples which illustrate the fundamentals of the invention by way of example without restricting its scope:

Preparation of the Compounds According to the Invention

General

Unless stated otherwise, all the reactions are carried out in commercially obtainable apparatus using methods that are commonly used in chemical laboratories. Starting materials that are sensitive to air and/or moisture are stored under protective gas and corresponding reactions and manipulations therewith are carried out under protective gas (nitrogen or argon).

The compounds according to the invention are named in accordance with CAS rules using the software Autonom (Beilstein) or Marvin Sketch. If a compound is to be represented both by a structural formula and by its nomenclature, in the event of a conflict the structural formula is decisive.

Microwave reactions are carried out in an initiator/reactor made by Biotage or in an Explorer made by CEM or in Synthos 3000 or Monowave 300 made by Anton Paar in sealed containers (preferably 2, 5 or 20 mL), preferably with stirring.

Chromatography

The thin layer chromatography is carried out on ready-made silica gel 60 TLC plates on glass (with fluorescence indicator F-254) made by Merck.

The preparative high pressure chromatography (RP HPLC) of the example compounds according to the invention is carried out with columns made by Waters (names: XTerra Prep. MS C18, 5 µm, 30×100 mm or XTerra Prep. MS C18, 5 µm, 50×100 mm OBD or Symmetrie C18, 5 µm, 19×100 mm or Sunfire C18 OBD, 19×100 mm, 5 µm or Sunfire Prep C 10 µm OBD 50×150 mm or X-Bridge Prep C18 5 µm OBD 19×50 mm) or X-Bridge Prep C18 10 µm OBD 50×150 mm), Agilent (name: Zorbax SB-C8 5 µm PrepHT 21.2×50 mm) and Phenomenex (names: Gemini C18 5 µm AXIA 21.2×50 mm or Gemini C18 10 µm 50×150 mm). Different gradients of $H_2O$/acetonitrile or $H_2O$/MeOH are used to elute the compounds, while 0.1% HCOOH is added to the water (acidic conditions). For the chromatography under basic conditions $H_2O$/acetonitrile gradients are used as well, while the water is made alkaline as follows: 5 mL $NH_4HCO_3$ solution (158 g in 1 L $H_2O$) and 2 mL $NH_3$ (7 M in MeOH) are replenished to 1 L with $H_2O$.

The analytical HPLC (reaction control) of intermediate compounds is carried out using columns made by Agilent (names: Zorbax SB-C8, 5 µm, 21.2×50 mm or Zorbax SB-C8 3.5 µm 2.1×50 mm), Phenomenex (name: Gemini C18 3 µm 2×30 mm) and Waters (names: XBridge™ C18, 3.5 µm, 2.1×50 mm, XBridge™ C18, 5 µm, 2.1×50 mm, XBridge™ C18, 2.5 µm, 2.1×20 mm or Sunfire™ C18, 3.5 µm, 2.1×50 mm. The analytical equipment is also equipped with a mass detector in each case.

HPLC-Mass Spectroscopy/UV-Spectrometry

The retention times/MS-ESI for characterizing the example compounds according to the invention are produced using an HPLC-MS apparatus (high performance liquid chromatography with mass detector). Compounds that elute at the injection peak are given the retention time $t_{Ret.}=0.00$.

Method 1

| HPLC | Agilent 1100/1200 system |
|---|---|
| MS | 1200 Series LC/MSD (API-ES +/− 3000 V, Quadrupol, G6140) |
| MSD signal settings | Scan pos 150-750 |
| column | YMC; Part. No. TA12S03-0302WT; Triart C18, 3 µm, 12 nm; 30 × 2.0 mm column |
| eluant | A: H2O + 0.11% formic acid |
| | B: MeCN + 0.1% formic acid (HPLC grade) |
| detection signal | UV 254 nm (bandwidth 10, reference off) |
| spectrum | range: 190-400 nm; step: 4 nm |
| peak width | >0.005 min (0.1 s) |
| injection | 0.5 µL standard injection |
| flow | 1.4 mL/min |
| column temperature | 45° C. |
| gradient | 0.0-1.0 min    15% → 100% B |
| | 1.0-1.1 min    100% B |
| | Stop time: 1.23 min |

Method 2

| HPLC | Agilent 1100/1200 system |
|---|---|
| MS | 1200 Series LC/MSD (API-ES +/− 3000 V, Quadrupol, G6140) |
| MSD signal settings | Scan pos 150-750, Scan neg 150-750 |
| column | YMC; Part. No. TA12S03-0302WT; Triart C18, 3 µm, 12 nm; 30 × 2.0 mm column |
| eluant | A: H2O + 0.11% formic acid |
| | B: MeCN + 0.1% formic acid (HPLC grade) |
| detection signal | UV 254 nm (bandwidth 10, reference off) |
| spectrum | range: 190-400 nm; step: 4 nm |
| peak width | >0.005 min (0.1 s) |

-continued

| | |
|---|---|
| injection | 0.5 μL standard injection |
| flow | 1.4 mL/min |
| column temperature | 45° C. |
| gradient | 0.0-1.0 min    15% → 100% B |
| | 1.0-1.1 min    100% B |
| | Stop time: 1.23 min |

Method 3

| | |
|---|---|
| HPLC | Agilent 1100/1200 system |
| MS | 1200 Series LC/MSD (MM-ES + APCI +/− 4000 V, Quadrupol, G6130) |
| MSD signal settings | Scan pos 150-800, Scan neg 150-800 |
| column | Waters; Part. No. 186006028; XBridge BEH C18 XP, 2.5 μm, 30 × 2.1 mm column |
| eluant | 5 mM NH4HCO3/18 mM NH3 (pH = 9.2) |
| | B: acetonitrile (HPLC grade) |
| detection signal | UV 254 nm (bandwidth 8, reference off) |
| spectrum | range: 190-400 nm; step: 4 nm |
| peak width | 0.0025 min (0.05 s) |
| injection | 0.5 μL standard injection |
| flow | 1.4 mL/min |
| column temperature | 45° C. |
| gradient | 0.0-1.0 min    15% → 95% B |
| | 1.0-1.3 min    95% B |
| | Stop time: 1.3 min |

Method 4

| | |
|---|---|
| HPLC | Agilent 1100/1200 system |
| MS | 1200 Series LC/MSD (MM-ES + APCI +/− 3000 V, Quadrupol, G6130) |
| MSD signal settings | Scan pos 150-750 |
| column | Waters; Part. No. 186006028; XBridge BEH C18 XP, 2.5 μm, 30 × 2.1 mm column |
| eluant | 5 mM NH4HCO3/18 mM NH3 (pH = 9.2) |
| | B: acetonitrile (HPLC grade) |
| detection signal | UV 254 nm (bandwidth 8, reference off) |
| spectrum | range: 190-400 nm; step: 4 nm |
| peak width | 0.0025 min (0.05 s) |
| injection | 0.5 μL standard injection |
| flow | 1.4 mL/min |
| column temperature | 45° C. |
| gradient | 0.0-1.0 min    15% → 95% B |
| | 1.0-1.3 min    95% B |
| | Stop time: 1.3 min |

Method 5

| | |
|---|---|
| HPLC | Agilent 1100 system |
| MS | 1200 Series LC/MSD (API-ES +/− 3000 V, Quadrupol, G6130) |
| MSD signal settings | Scan pos/neg 120-900 m/z |
| column | Waters, Xbridge C18, 2.5 μm, 2.1 × 20 mm column |
| eluant | A: 20 mM NH4HCO3/NH3 pH 9 |
| | B: acetonitrile HPLC grade |
| detection signal | 315 nm (bandwidth 170 nm, reference off) |
| spectrum | range: 230-400 nm |
| peak width | <0.01 min |
| injection | 5 μL standard injection |
| column temperature | 60° C. |
| flow | 1.00 mL/min |
| gradient | 0.00-1.50 min    10% → 95% B |
| | 1.50-2.00 min    95% B |
| | 2.00-2.10 min    95% → 10% B |

Method 6

| | |
|---|---|
| LC | Agilent Infinity 1290 series |
| MS | Agilent 6150 Quadruple lcms(SQ) |
| MSD signal settings | Scan pos/neg 100-1200 |
| column | Aquity BEH C18 2.1 × 50 mm, 1.7 μm |
| eluant | A: water + 0.1% formic acid |
| | B: acetonitrile (HPLC grade) + 0.1% formic acid |
| detection signal | UV 215/254 nm (bandwidth 4, reference off) |
| spectrum | range: 200-400 nm; step: 2.0 nm |
| peak width | >0.01 min (0.2 s) |
| injection | 0.5 μL standard injection |
| flow | 0.6 mL/min |
| column temperature | 25° C. |
| gradient | 0.0-0.4 min    3% B |
| | 0.4-3.2 min    3% → 98% B |
| | 3.2-3.8 min    98% B |
| | 3.8-4.2 min    98% → 3% B |
| | 4.2-4.5 min    3% B |

Method 7

| | |
|---|---|
| LC | Waters UPLC Acquity |
| MS | Micromass Quattro micro ™ |
| MSD signal settings | Scan pos/neg 100-1200 |
| column | Kinetex C18, 2.1 × 100 mm, 1.7 μm |
| eluant | A: water + 0.1% formic acid |
| | B: acetonitrile (HPLC grade) + 0.1% formic acid |
| detection signal | UV 215/254 nm (bandwidth 4, reference off) |
| spectrum | range: 200-400 nm; Resolution: 1.2 nm |
| Sampling rate | 5 points/sec |
| injection | 0.5 μL standard injection |
| flow | 0.4 mL/min |
| column temperature | 35° C. |
| gradient | 0.0-0.3 min    5% B |
| | 0.3-1.5 min    5% → 50% B |
| | 1.5-3.0 min    50% → 100% B |
| | 3.0-4.5 min    100% B |
| | 4.5-5.0 min    100% → 5% B |
| | 5.0-6.0 min    5% B |

Method 8

| | |
|---|---|
| LC | Waters UPLC Acquity |
| MS | Micromass Quattro micro ™ |
| MSD signal settings | Scan pos/neg 100-1000 |
| column | Aquity BEH C18 2.1 × 50 mm, 1.7 μm |
| eluant | A: water + 0.1% formic acid |
| | B: acetonitrile (HPLC grade) + 0.1% formic acid |
| detection signal | UV 215/254 nm |
| spectrum | range: 200-400 nm; Resolution: 1.2 nm |
| Sampling rate | 5 points/sec |
| injection | 0.5 μL standard injection |
| flow | 0.4 mL/min |
| column temperature | 35° C. |
| gradient | 0.0-0.5 min    5% B |
| | 0.5-2.0 min    5% → 50% B |
| | 2.0-3.5 min    50% → 100% B |
| | 3.5-5.0 min    100% B |
| | 5.0-5.1 min    5% B |

Method 9

| | |
|---|---|
| LC | Agilent RRLC 1200 series |
| MS | Agilent 6130 Quadruple lcms(SQ) |
| MSD signal settings | Scan pos/neg 90-1200 |
| column | Xbridge C18, 4.6 × 50 mm, 2.5μ |
| eluant | A: 5 mM Ammonium Acetate |
| | B: acetonitrile |
| detection signal | UV 215/254 nm (bandwidth 4, reference off) |
| spectrum | range: 200-400 nm; step: 2.0 nm |
| peak width | >0.10 min (2 s) |
| injection | 0.5 μL standard injection |

-continued

| | | |
|---|---|---|
| flow | 0.6 mL/min | |
| column temperature | 35° C. | |
| gradient | 0.0-1.0 min | 5% B |
| | 1.0-1.8 min | 5% → 55% B |
| | 1.8-3.5 min | 55% → 98% B |
| | 3.5-5.5 min | 98% B |
| | 5.5-6.0 min | 98% → 5% B |

Method 10

| | |
|---|---|
| HPLC | Agilent RRLC (1200 Series) |
| MS | Agilent SQD -6130 (API-ES/APCI (Multi Mode) +/− 3000 V, Corona Current 4 µA) |
| MSD signal settings | Scan pos 90-1000, Scan neg 90-1000 |
| Column | X-bridge C18, 4.6 × 50 mm, 2.5µ |
| Eluent | A: 5 mM Ammonium Acetate<br>B: Acetonitrile |
| Detection signal | UV 215 nm (bandwidth 4, reference off) |
| Spectrum | range: 200-400 nm; step: 2 nm |
| Peak width | >0.1 min (2.0 S) |
| Injection | 5 µL injection with needle wash. |
| Flow rate | 0.6 mL/min |
| Column temperature | 35° C. |
| Gradient | 0.0-1.0 min        5% B |
| | 1.0-1.8 min        5% → 55% B |
| | 1.8-3.5 min        55% → 98% B |
| | 3.5-5.5 min        98% B |
| | 5.5-6.0 min        98% → 5% B |

Method 11

| | |
|---|---|
| LC | Agilent Infinity 1290 series |
| MS | Agilent 6150 Quadruple lcms(SQ) |
| MSD signal settings | Scan pos/neg 80-1200 |
| column | Aquity BEH C18 2.1 × 50 mm, 1.7 µm |
| eluant | A: water + 0.1% formic acid<br>B: acetonitrile (HPLC grade) + 0.1% formic acid |
| detection signal | UV 215/254 nm (bandwidth 4, reference off) |
| spectrum | range: 200-400 nm; step: 2.0 nm |
| peak width | >0.01 min (0.2 s) |
| injection | 0.5 µL standard injection |
| flow | 0.8 mL/min |
| column temperature | 60° C. |
| gradient | 0.0-0.2 min       3% B |
| | 0.2-1.5 min       3% → 95% B |
| | 1.5-2.5 min       95% B |
| | 2.5-2.6 min       95% → 3% B |
| | 2.6-3.2 min       3% B |

Method 12

| | |
|---|---|
| HPLC | Agilent Infinity-1290 Series |
| MS | Agilent SQD -6130 (API-ES +/− 3000 V) |
| MSD signal settings | Scan pos 100-1000, Scan neg 100-1000 |
| Column | Aquity BEH C18, 2.1 × 50 mm, 1.7 µm |
| Eluent | A: 0.1% Formic Acid in Acetonitrile<br>B: 0.1% Formic Acid in water |
| Detection signal | UV 215 nm (bandwidth 4, reference off) |
| Spectrum | range: 200-400 nm; step: 2 nm |
| Peak width | >0.025 min (0.5 S) |
| Injection | 0.5 µL injection with needle wash at flush port. |
| Flow rate | 0.8 mL/min |
| Column temperature | 60° C. |
| Gradient | 0.0-0.2 min       3% B |
| | 0.2-1.5 min       3% → 95% B |
| | 1.5-2.5 min       95% B |
| | 2.5-2.6 min       95% →3% B |

Method 13

| | |
|---|---|
| HPLC | Agilent Infinity-1290 Series |
| MS | Agilent SQD -6150 (API-ES +/− 3000 V) |
| MSD signal settings | Scan pos 100-1000, Scan neg 100-1000 |
| Column | Aquity BEH C18, 2.1 × 50 mm, 1.7 µm |
| Eluent | A: 0.1% Formic Acid in Acetonitrile<br>B: 0.1% Formic Acid in water |
| Detection signal | UV 215 nm (bandwidth 4, reference off) |
| Spectrum | range: 200-400 nm; step: 2 nm |
| Peak width | >0.025 min (0.5 S) |
| Injection | 0.5 µL injection with needle wash at flush port. |
| Flow rate | 0.8 mL/min |
| Column temperature | 45° C. |
| Gradient | 0.0-0.2 min       2% B |
| | 0.2-1.5 min       2% → 98% B |
| | 1.5-2.6 min       98% B |
| | 2.6-2.61 min      98% →2% B |
| | 2.61-3.2 min      2% B |

Method 14

| | |
|---|---|
| LC | Waters UPLC Acquity |
| MS | Micromass Quattro micro ™ |
| MSD signal settings | Scan pos/neg 100-1200 |
| column | Aquity BEH C18 2.1 × 50 mm, 1.7 µm |
| eluant | A: acetonitrile (HPLC grade) + 0.1% formic acid<br>B: water + 0.1% formic acid |
| detection signal | UV 215/254 nm |
| spectrum | range: 200-400 nm; Resolution: 1.2 nm |
| Sampling rate | 10 points/sec |
| injection | 0.5 µL standard injection |
| flow | 0.6 mL/min |
| column temperature | 35° C. |
| gradient | 0.0-0.3 min       97% B |
| | 0.3-3.5 min       97% → 2% B |
| | 3.5-4.8 min       2% B |
| | 4.8-5.0 min       2% → 97% B |
| | 5.0-5.1 min       97% B |

Method 15

| | |
|---|---|
| HPLC | Agilent Infinity-1290 Series |
| MS | Agilent SQD -6130 (API-ES +/− 3000 V) |
| MSD signal settings | Scan pos 100-1000, Scan neg 100-1000 |
| Column | Aquity BEH C18, 2.1 × 50 mm, 1.7 µm |
| Eluent | A: 0.1% Formic Acid in Acetonitrile<br>B: 0.1% Formic Acid in water |
| Detection signal | UV 215 nm (bandwidth 4, reference off) |
| Spectrum | range: 200-400 nm; step: 2 nm |
| Peak width | >0.025 min (0.5 S) |
| Injection | 0.5 µL injection with needle wash at flush port. |
| Flow rate | 0.8 mL/min |
| Column temperature | 60° C. |
| Gradient | 0.0-0.2 min       3% B |
| | 0.2-1.5 min       3% → 95% B |
| | 1.5-2.5 min       95% B |
| | 2.5-2.6 min       95% →3% B |

Method 16

| | |
|---|---|
| HPLC | Agilent Infinity-1290 Series |
| MS | Agilent SQD -6130 (API-ES +3500 V/−3000 V) |
| MSD signal settings | Scan pos 100-1200, Scan neg 100-1200 |
| Column | Aquity BEH C18, 2.1 × 50 mm, 1.7 µm |
| Eluent | A: 0.1% Formic Acid in Acetonitrile<br>B: 0.1% Formic Acid in water |
| Detection signal | UV 215/254 nm (bandwidth 4, reference off) |
| Spectrum | range: 200-400 nm; step: 2 nm |
| Peak width | >0.025 min (0.5 S) |
| Injection | 0.5 µL injection with needle wash at flush port. |
| Flow rate | 0.8 mL/min |
| Column temperature | 60° C. |

| Gradient | 0.0-0.4 min | 97% B |
| --- | --- | --- |
| | 0.4-2.2 min | 97% → 2% B |
| | 2.2-2.6 min | 2% B |
| | 2.6-2.61 min | 2% → 97% B |
| | 2.61-3.0 min | 97% B |

Synthesis of Benzaldehyde Derivatives by Lithiation

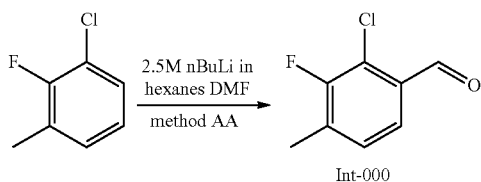

Int-000

Synthesis of Int-000 (Method AA):

To a stirred solution of 1-Chloro-2-fluoro-3-methyl-benzene (500 mg; 0.003 mol) in anhydrous THF (5 ml) n-BuLi (1.750 ml; 2.5 m in hexanes) is added at −78° C. The reaction mixture is stirred for 30 min before DMF (0.200 ml) is added. The reaction mixture is allowed to warm to rt within 2 h and subsequently quenched with sat. aq NH$_4$Cl solution, extracted with EtOAc, and dried under reduced pressure. The residual solid is purified by column chromatography (100-200 mesh).

The following benzaldehyde derivatives are prepared according to the above described procedure:

| Example | Structure | NMR |
| --- | --- | --- |
| Int-000 | 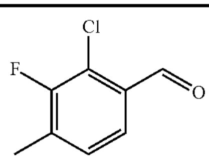 | $^1$H-NMR (400 MHz; DMSO): δ 10.22 (s, 1H); 7.66-7.64 (d, 1H, J = 8.8 Hz); 7.49-7.46 (t, 1H, J = 14.8 Hz); 2.37-2.37 (s, 3H, J = 2 Hz) |

By Reduction—Re-Oxidation

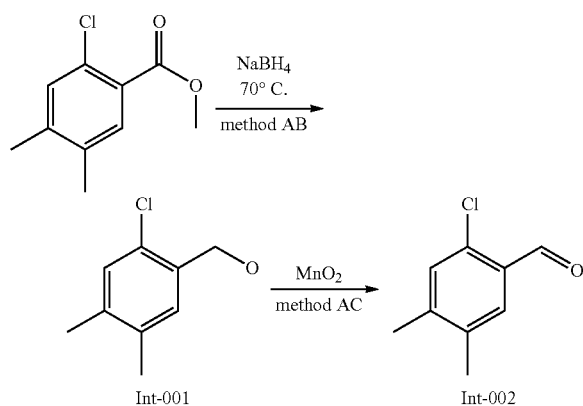

Synthesis of Int-001 (Method AB).

Sodiumborohydride (805.00 mg, 0.02 mol) is added to a stirred solution methyl 2-chloro-4,5-dimethylbenzoate (705.00 mg, 3.55 mmol) in anhydrous THF (20 mL) at rt. The reaction mixture is stirred for 15 min, methanol (3.60 ml) is added and the mixture is stirred at 70° C. for 4 hrs. HPLC/MS shows complete conversion. The reaction mixture is poured into water and extracted with DCM. The organic layer is dried over MgSO$_4$ and concentrated under reduced pressure. The residue is loaded onto Isolute and chromatographed.

The following benzyl alcohol derivatives are prepared according to the above described procedure:

| Example | Structure | t$_{ret}$ [min] | M + H | HPLC Method |
| --- | --- | --- | --- | --- |
| Int-001 | 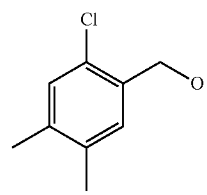 | 1.03 | not detectable | 5 |

Synthesis of Int-002 (Method AC).

(2-Chloro-4,5-dimethyl-phenyl)-methanol (526.00 mg, 0.003 mol) is dissolved in DCM, manganese dioxide (3.05 g, 0.031 mol) is added and the mixture is stirred at r.t. for two days. HPLC/MS shows complete conversion. The mixture is filtered and concentrated under reduced pressure and used without further purification.

The following benzaldehyde derivatives are prepared according to the above described procedure:

| Example | Structure | t$_{ret}$ [min] | M + H | HPLC Method |
| --- | --- | --- | --- | --- |
| Int-002 | 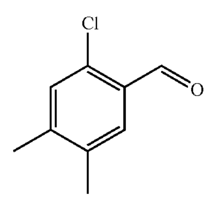 | 1.22 | not detectable | 5 |

Synthesis of indole carboxylate intermediates Hemetsberger-Knittel Synthesis

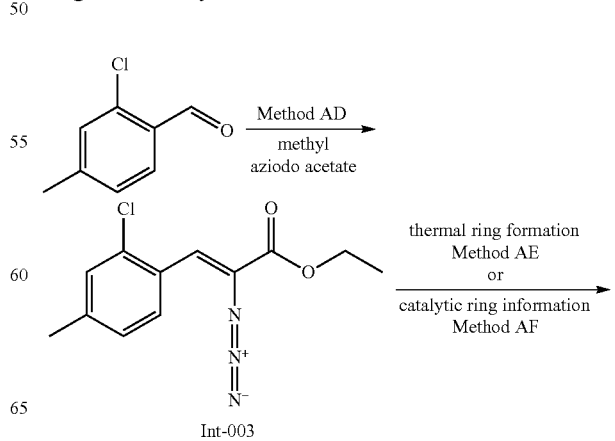

Int-003

-continued

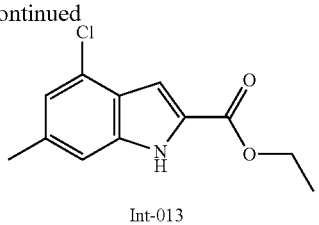

Int-013

Synthesis of Int-003 (Method AD)

To sodium ethoxide (25% in ethanol, 293.3 g, 906 mmol) and 2-chloro-4-methylbenzaldehyde (35.0 g, 226 mmol) ethyl azido acetate (116.8 g, 906 mmol) in THF (70 mL)/ethanol (700 mL) is added at −30° C. and stirred for 1 h at ambient temperature. Ice water is added, and the solid is collected by filtration.

The following azido esters are available in an analogous manner starting from different aldehydes.

| Example | Structure | NMR |
|---|---|---|
| Int-003 | 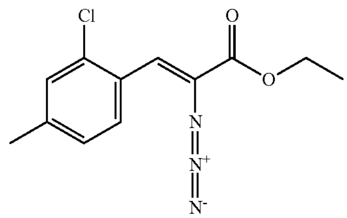 [SMILES: CCOC(=O)/C(=C/c1ccc(C)cc1Cl)N=[N+]=[N-]] | $^1$H-NMR (400 MHz; CDCl$_3$): δ 8.07-8.09 (d, 1H J = 8 Hz); 7.29 (s, 1H); 7.24-7.260 (d, 1H, J = 8.8 Hz;); 7.09-7.11 (d, 1H, J = 8 Hz); 4.35-4.41 (m, 2H); 2.34 (s, 3H); 1.38-1.42 (t, 3H) |
| Int-004 | 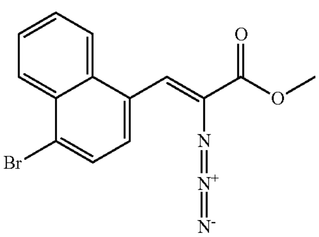 [SMILES: COC(=O)/C(=C/c1ccc(Br)c2ccccc12)N=[N+]=[N-]] | $^1$H-NMR (400 MHz; CDCl$_3$): 8.28-8.31 (m, 1H); 8.28-8.31 (m, 1H); 7.98-8.01 (m, 1H); 7.81-7.83 (d, 1H, J = 8 Hz); 7.58-7.66 (m, 3H); 3.98 (s, 3H) |
| Int-005 | 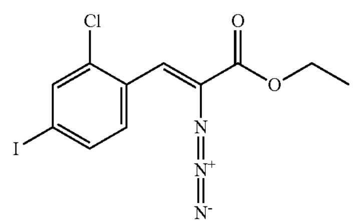 [SMILES: CCOC(=O)/C(=C/c1ccc(I)cc1Cl)N=[N+]=[N-]] | $^1$H-NMR (400 MHz; CDCl$_3$): δ 7.91-7.93 (d, 1H, J = 8.4 Hz); 7.60-7.63 (d, 1H, J = 8.4 Hz); 7.18 (s, 1H); 4.35-4.41 (m, 2H); 1.32-1.45 (t, 3H) |
| Int-006 | 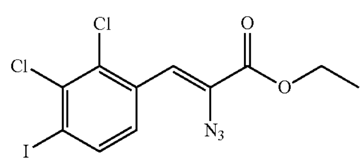 [SMILES: CCOC(=O)/C(=C/c1ccc(I)c(Cl)c1Cl)N=[N+]=[N-]] | $^1$H-NMR (500 MHz; CDCl$_3$): δ 7.81-7.80 (d, 1H J = 8.5 Hz); 7.75-7.74 (d, 1H, J = 8.5 Hz); 7.16 (s, 1H); 4.42-4.38 (m, 2H); 1.43-1.28 (t, 3H) |
| Int-007 | 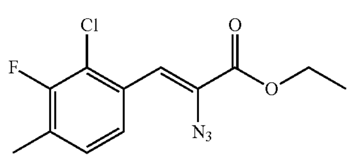 [SMILES: CCOC(=O)/C(=C/c1ccc(C)c(F)c1Cl)N=[N+]=[N-]] | $^1$H-NMR (400 MHz; DMSO): δ 7.97-7.95 (d, 1H, J = 8 Hz); 7.37-7.33 (t, 1H, J = 14.8 Hz); 7.07 (s, 1H); 3.88 (s, 3H); 2.30 (s, 3H). |

| Example | Structure | t$_{ret}$ [min] | M + H | HPLC Method |
|---|---|---|---|---|
| Int-008 | 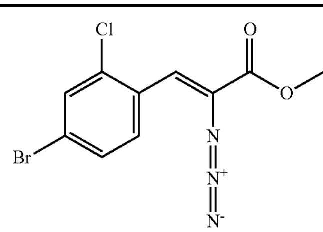 | 0.94 | not detectable | 3 |

| | | | | | |
|---|---|---|---|---|---|
| Int-009 | [structure: methyl 2-azido-3-(2,3-dichloro-4-methylphenyl)acrylate] | 0.95 | not detectable | | 2 |
| Int-010 | [structure: methyl 2-azido-3-(2,3-difluoro-4-methylphenyl)acrylate] | 0.87 | 267 | | 1 |
| Int-011 | [structure: methyl 2-azido-3-(4,5-dichloro-6-methylpyridin-3-yl)acrylate] | 0.82 | 287/ 289 | | 2 |
| Int-012 | [structure: methyl 2-azido-3-(2-chloro-4,5-dimethylphenyl)acrylate] | 0.92 | not detectable | | 2 |

Synthesis of Int-013 (Method AE)

Int-004 (26.0 g, 265.7 mmol) in xylene (20 mL) is added to xylene (520 mL) at 160° C. over a period of 20 min. and stirred for 3 h at this temperature. The reaction mixture is concentrated in vacuo and triturated with pentane (100 mL).

Synthesis of Int-014 (Method AF)

To Int-008 (1.40 g, 4.43 mmol) in toluene (250 ml) rhodium(6)heptafluorobutyrate dimer (482 mg, 2.19 mmol) is added and stirred at 60° C. overnight. The reaction mixture is concentrated in vacuo, and the residue is purified by column chromatography.

The following indoles are available in an analogous manner applying the given synthetic method.

| Example | Structure | synthetic method | $t_{ret}$ [min] | M + H | M − H | HPLC Method |
|---|---|---|---|---|---|---|
| Int-013 | [structure: ethyl 4-chloro-6-methyl-1H-indole-2-carboxylate] | AE | 2.79 | 238 | | 6 |

-continued
| Example | Structure | synthetic method | $t_{ret}$ [min] | M + H | M − H | HPLC Method |
|---|---|---|---|---|---|---|
| Int-014 | 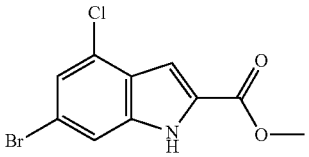 | AF | 0.79 | | 286/288 | 3 |
| Int-015 | 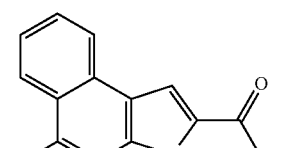 | AE | 2.65 | 304 | | 7 |
| Int-016 | 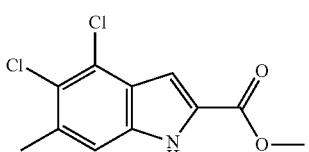 | AF | 0.81 | 258 | | 2 |
| Int-017 | 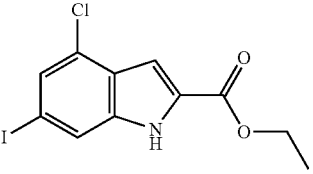 | AE | 3.03 | | 348 | 6 |
| Int-018 | 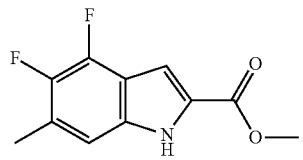 | AF | 0.70 | 226 | | 1 |
| Int-019 | 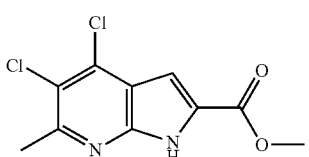 | AE | 0.72 | 259/261 | | 2 |
| Int-020 | 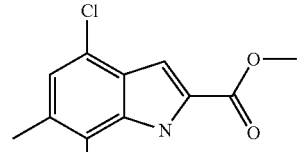 | AE | 1.43 | 238 | | 5 |
| Int-021 | 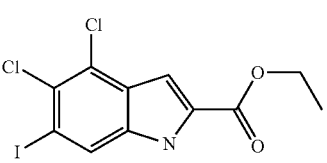 [SMILES: CCOC(=O)c1cc2c(Cl)c(Cl)c(I)cc2[nH]1] | AE | 2.22 | 384 | | 16 |
| Int-022 | 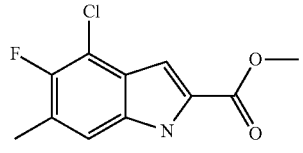 | AE | 2.62 | 240 | | 8 |

Synthesis of Aza-Indoles

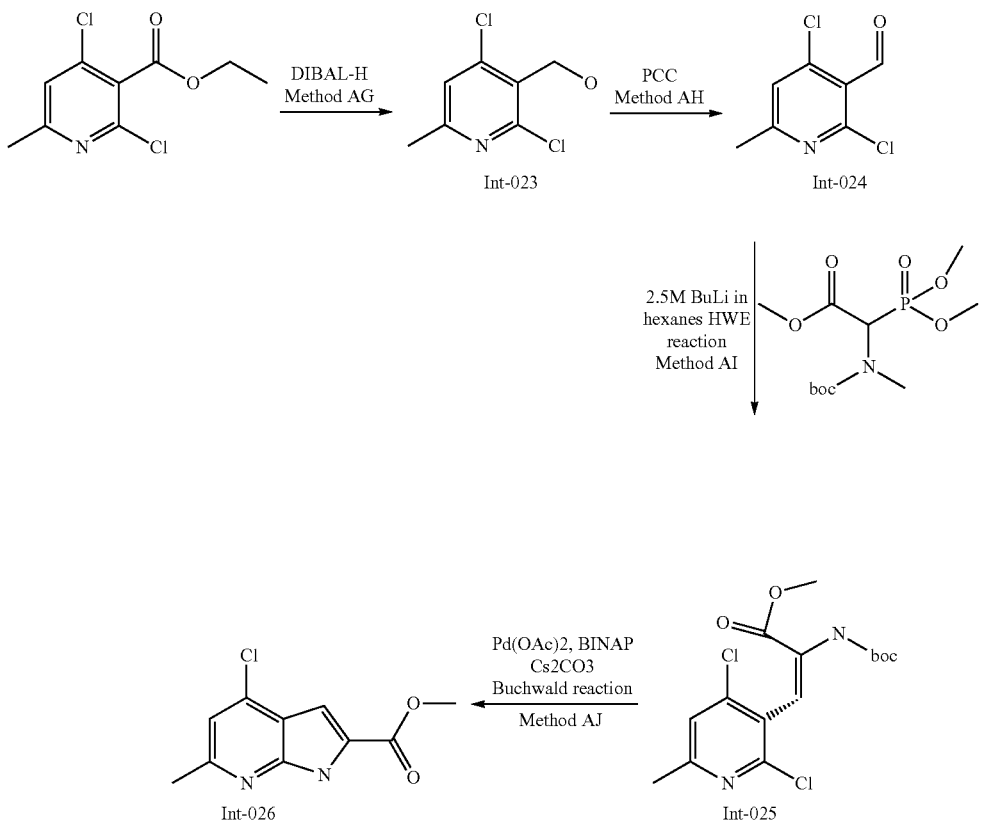

Synthesis of Int-023 (Method AG)

To a stirred solution of 2,4-Dichloro-6-methyl-nicotinic acid ethyl ester (2.5 g, 0.01 mol) in anhydrous THF (25 mL) DIBALH (21 mL, 0.021 mol, 1.0 M in toluene) is slowly added at 0° C. The reaction mixture is allowed to warm to rt and stirring is continued for 16 h. The reaction mixture is cooled 0° C. and aq. sat. ammonium chloride solution is added. Ethyl acetate is added and the layers are separated. The organic layer is dried over sodium sulphate, filtered and solvents are removed under reduced pressure. The crude product is purified by column chromatography.

| Example | Structure | $t_{ret}$ [min] | M + H | HPLC Method |
|---|---|---|---|---|
| Int-023 | 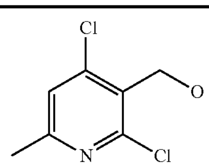 | 1.71 | 193 | 8 |

Synthesis of Int-024 (Method AH)

To a stirred solution of (Int-023; 2,4-Dichloro-6-methyl-pyridin-3-yl)-methanol (1.2 g, 6.0 mmol) in DCM (20 mL) PCC (2.7 g, 12.0 mmol) is added at 0° C. and the reaction mixture is allowed to warm to rt. Stirring is continued at rt for additional 2 h. The reaction mixture is filtered through a plug of Celite®. Solvents are removed under reduced pressure and the crude solid is purified by column chromatography.

| Example | Structure | $t_{ret}$ [min] | M + H | HPLC Method |
|---|---|---|---|---|
| Int-024 | 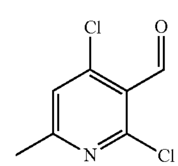 | 2.15 | 191 | 8 |

Synthesis of Int-025 (Method AI)

To a stirred solution of tert-Butoxycarbonylamino-(dimethoxy-phosphoryl)-acetic acid methyl ester (Int-024; 782 mg, 2.63 mmol) in anhydrous THF (8 mL) n-BuLi (2.5M in hexanes, 2.1 mL, 5.3 mmol) is added at 0° C. during a period of time of 15 minutes. Stirring is continued for additional 30 minutes at same temperature, before 2,4-Dichloro-6-methyl-pyridine-3-carbaldehyde (500 mg, 2.6 mmol) dissolved in anhydrous THF (2 mL) is added to the reaction mixture at 0° C. Stirring is continued for 1 h, the reaction mixture is quenched with sat. aq. ammonium chloride solution and the aqueous phase is extracted with ethyl acetate. Phases are separated, the organic phase is dried with MgSO$_4$, filtered and solvents are removed in vacuo. The crude product is purified with column chromatography.

| Example | Structure | t$_{ret}$ [min] | M + H | HPLC Method |
|---|---|---|---|---|
| Int-025 | 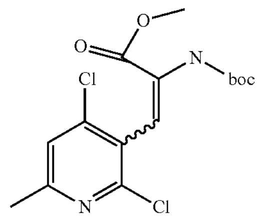 | 1.80 | 361 | 16 |

Synthesis Via Dialkyl Oxalate Condensation

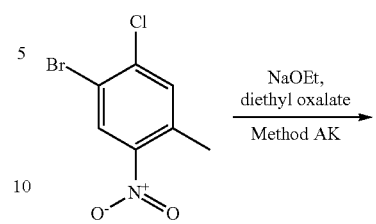

Synthesis of Int-026 (Method AJ)

2-tert-Butoxycarbonylamino-3-(2,4-dichloro-6-methyl-pyridin-3-yl)-acrylic acid methyl ester (Int-025; 6.0 g, 16.6 mmol) is dissolved in anhydrous 1,4-dioxane (60 mL) and methylamine (2 M in THF, 25 mL, 50 mmol), Palladium (II)acetate (373 mg, 2 mmol), BINAP (1.04 g, 2 mmol), and cesium carbonate (10.8 g, 33 mmol) are added and the reaction mixture is degassed with Argon. The reaction mixture is heated to reflux for 16 hours, cooled to rt and solids are filtered off. After washing with ethyl acetate the combined organic extracts are concentrated and the crude product is purified by column chromatography.

| Example | Structure | t$_{ret}$ [min] | M + H | HPLC Method |
|---|---|---|---|---|
| Int-026 | 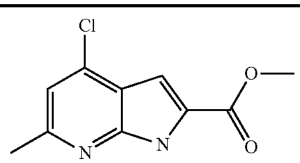 | 2.43 | 225 | 8 |

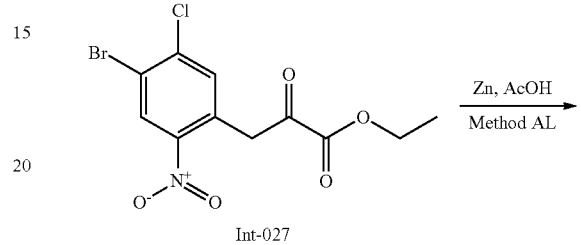

Int-027

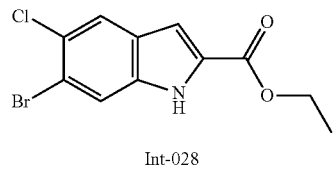

Int-028

Synthesis of Int-027 (Method AK).

1-Bromo-2-chloro-4-methyl-5-nitrobenzene (25.0 g, 100 mmol) in ethanol (100 mL) is added to sodium ethoxide (13.57 g, 110 mmol) in ethanol (200 mL) at ambient temperature. Diethyl oxalate (16.03 g, 110 mmol) is added and stirred for 16 h at ambient temperature. Ice water is added. The formed solid is collected by filtration and triturated with water.

| Example | Structure | t$_{ret}$ [min] | M − H | HPLC Method |
|---|---|---|---|---|
| Int-027 | 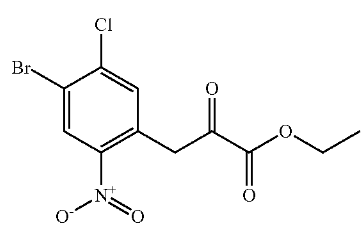 [SMILES: CCOC(=O)C(=O)Cc1cc(Cl)c(Br)cc1[N+](=O)[O-]] | 4.33 | 350 | 9 |

Synthesis of Int-28 (Method AL).

To Int-027 (11.0 g, 31 mmol) in glacial acetic acid (120 mL)/water (80 mL) zinc dust (20.4 g, 314 mmol) is added at 75° C. in small portions. The mixture is stirred at this temperature until the conversion is complete and then cooled to ambient temperature. The mixture is partitioned between water and EtOAc, stirred for 20 min. and filtered. The organic layer is concentrated in vacuo, and the residue is purified by column chromatography.

| Example | Structure | $t_{ret}$ [min] | M + H | HPLC Method |
|---|---|---|---|---|
| Int-028 | 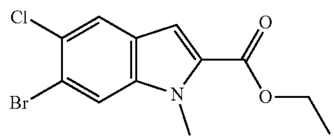 [SMILES: CCOC(=O)c1cc2cc(Cl)c(Br)cc2n1C] | 3.18 | 316 | 8 |

Synthesis of Indole-2-Carboxylic Acid Intermediates

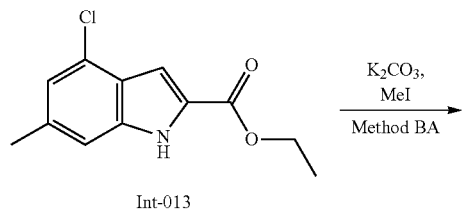

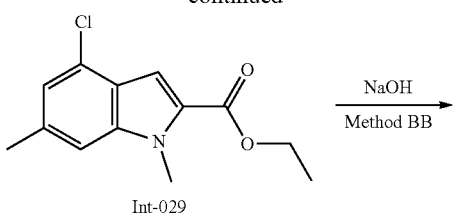

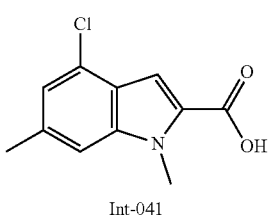

Synthesis of Int-29 (Method BA)

To Int-013 (12.0 g, 50.5 mmol) and K$_2$CO$_3$ (13.96 g, 101 mmol) in DMF (120 ml) methyl iodide (14.34 g, 101 mmol) is added at 0° C. and stirred for 4 h at ambient temperature. Ice water is added. The formed solid is collected by filtration and triturated subsequently with water and pentane.

The following indoles are prepared in an analogous manner.

| Example | Structure | $t_{ret}$ [min] | M + H | M − H | HPLC Method |
|---|---|---|---|---|---|
| Int-029 | 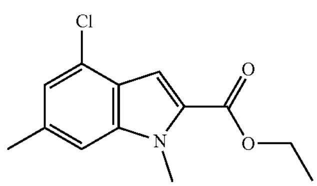 [SMILES: CCOC(=O)c1cc2c(Cl)cc(C)cc2n1C] | 3.12 | 252 | | 6 |
| Int-030 | 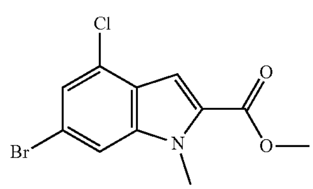 [SMILES: COC(=O)c1cc2c(Cl)cc(Br)cc2n1C] | 0.92 | | 301/303 | 3 |
| Int-031 | 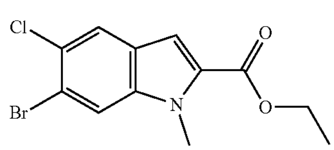 [SMILES: CCOC(=O)c1cc2cc(Cl)c(Br)cc2n1C] | 3.18 | 316 | | 8 |
| Int-032 | 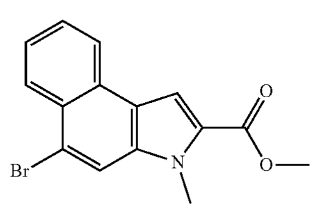 [SMILES: COC(=O)c1cc2c3ccccc3c(Br)cc2n1C] | 3.03 | 318 | | 7 |

| | | | | |
|---|---|---|---|---|
| Int-033 | 4-Cl, 5-Cl, 6-Me, N-Me indole-2-carboxylic acid methyl ester | 0.92 | 272 | 2 |
| Int-034 | 4-F, 5-F, 6-Me, N-Me indole-2-carboxylic acid methyl ester | 0.83 | 240 | 1 |
| Int-035 | 4-Cl, 5-Cl, 6-Me, N-Me 7-azaindole-2-carboxylic acid methyl ester | 0.92 | 273/275 | 2 |
| Int-036 | 4-Cl, 6-Me, N-Me 7-azaindole-2-carboxylic acid methyl ester | 0.78 | 239 | 2 |
| Int-037 | 4-Cl, 6-Me, 7-Me, N-Me indole-2-carboxylic acid methyl ester | 0.89 | 252 | 2 |

| Example | Structure | Name |
|---|---|---|
| Int-038 | 4-Cl, 6-I, N-Me indole-2-carboxylic acid ethyl ester | ¹H-NMR (400 MHz; CDCl₃): δ 7.66 (s, 1H); 7.45 (s, 1H); 7.3 (s, 1H); 4.3-4.4 (m, 2H); 4.04 (s, 3H); 1.2-1.3 (t, 3H) |
| Int-039 | 4-Cl, 5-Cl, 6-I, N-Me indole-2-carboxylic acid ethyl ester | ¹H NMR (500 MHz; CDCl₃): δ 7.87 (s, 1H); 7.28 (s, 1H); 4.41-4.36 (m, 2H); 4.09 (s, 3H); 1.44-1.40 (t, 3H) |
| Int-040 | 4-Cl, 5-F, 6-Me, N-Me indole-2-carboxylic acid methyl ester | ¹H-NMR (300 MHz; CDCl₃): δ 7.30 (s, 1H); 7.06-7.08 (d, 1H, J = 5.1 Hz); 4.04 (s, 3H); 3.92 (s, 3H); 2.45 (s, 3H) |

Synthesis of Int-41 (Method BB)

To Int-029 (12.0 g, 47.7 mmol) in THF (70 mL)/water (25 mL) lithium hydroxide monohydrate (8.01 g, 191 mmol) is added at 0° C. and stirred at ambient temperature for 2 h. 4 N HCl (10 mL) is added, and the mixture is extracted exhaustively with EtOAc. The combined organic layer is washed with water and brine, dried (MgSO₄), filtered and concentrated in vacuo. The residue is triturated with ether and pentane.

The following indole carboxylic acids are prepared in an analogous manner.

| Example | Structure | $t_{ret}$ [min] | M + H | M − H | HPLC Method |
|---|---|---|---|---|---|
| Int-041 | 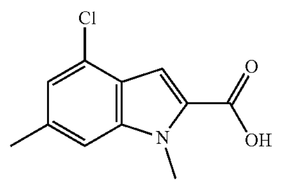 | 2.47 | | 222 | 6 |
| Int-042 | 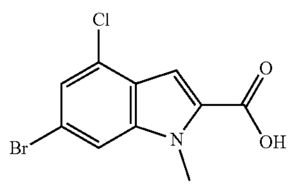 | 0.42 | | 286/ 287 | 3 |
| Int-043 | 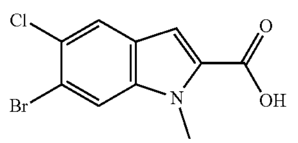 | 3.12 | | 286 | 9 |
| Int-044 | 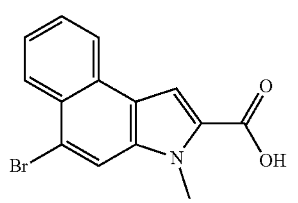 [SMILES: Cn1c(C(=O)O)cc2c3ccccc3c(Br)cc21] | 3.27 | | 302 | 10 |
| Int-045 | 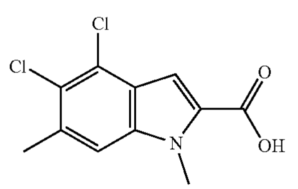 [SMILES: Cc1cc2c(cc(C(=O)O)n2C)c(Cl)c1Cl] | 0.74 | 258 | | 2 |
| Int-046 | 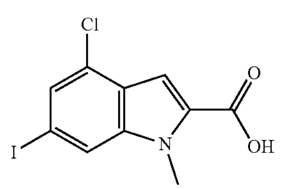 | 1.54 | | 334 | 11 |
| Int-047 | 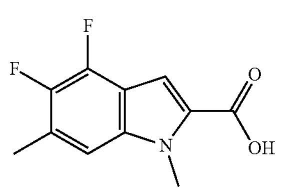 [SMILES: Cc1cc2c(cc(C(=O)O)n2C)c(F)c1F] | 0.64 | 226 | | 1 |

-continued
| Example | Structure | $t_{ret}$ [min] | M + H | M − H | HPLC Method |
|---|---|---|---|---|---|
| Int-048 | 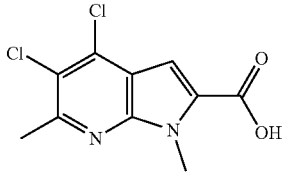 [SMILES: Cc1nc2c(cc(C(=O)O)n2C)c(Cl)c1Cl] | 0.70 | 259/261 | | 2 |
| Int-049 | 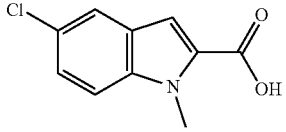 | 0.61 | 210 | | 1 |
| Int-050 | 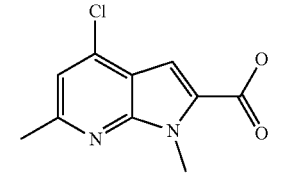 | 0.78 | 239 | | 2 |
| Int-051 | 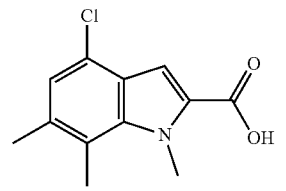 [SMILES: Cc1cc(Cl)c2cc(C(=O)O)n(C)c2c1C] | 0.57 | 225 | | 2 |
| Int-052 | 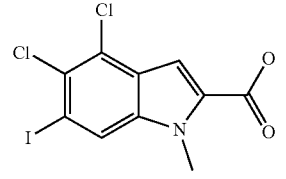 [SMILES: Cn1c(C(=O)O)cc2c(Cl)c(Cl)c(I)cc21] | 1.57 | 370 | | 12 |
| Int-053 | 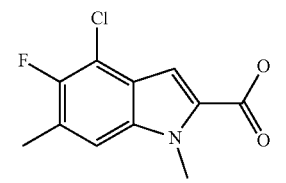 [SMILES: Cc1cc2c(cc(C(=O)O)n2C)c(Cl)c1F] | 2.47 | 240 | | 8 |

Indole Core Derivatisation

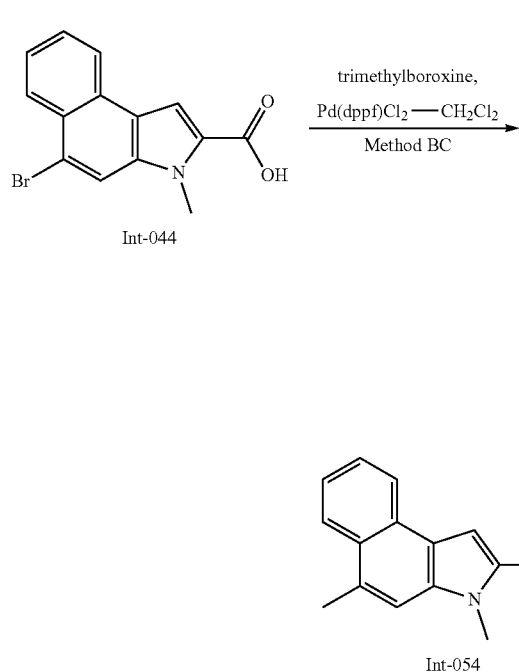

| Example | Structure | $t_{ret}$ [min] | M + H | HPLC Method |
|---|---|---|---|---|
| Int-054 | 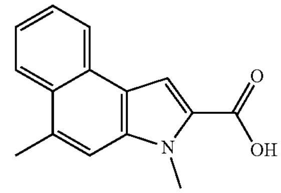 [SMILES: Cc1cc2c(cc(C(=O)O)n2C)c2ccccc12] | 0.69 | 240 | 1 |

Synthesis of Int-054 (Method BC).

Int-044 (200 mg, 0.86 mmol), 2 m aq. K$_2$CO$_3$ (986 µL), trimethylboroxine (138 µL, 0.99 mmol), and Pd(dppf)Cl$_2$—CH$_2$Cl$_2$ (42 mg, 0.05 mmol) in dioxane (3 mL) is stirred for 3 h at 80° C. The reaction mixture is filtered and concentrated in vacuo. Water is added, and the pH is adjusted to 5 using 2 N HCl. The solid is collected by filtration and dried in vacuo.

Synthesis of Int-055 (Method BD).

Int-042 (1.0 g, 2.98 mmol), K$_2$CO$_3$ (0.83 g, 5.96 mmol), 1-methyl-1H-pyrazole-4-boronic acid, pinacol ester (1.24 g, 5.96 mmol), and Pd(dppf)Cl$_2$—CH$_2$Cl$_2$ (243 mg, 0.30 mmol) in DMSO (18 mL)/water (2 mL) is stirred for 1 h at 75° C. The reaction mixture is filtered and concentrated in vacuo. Water is added, and the pH is adjusted to 4 using 2 N HCl. The solid is collected by filtration and purified by column chromatography.

The following pyrazolyl indoles are prepared in an analogous manner.

| Example | Structure | $t_{ret}$ [min] | M + H | HPLC Method |
|---|---|---|---|---|
| Int-055 | 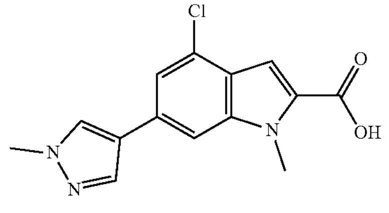 [SMILES: Cn1cc(-c2cc(Cl)c3cc(C(=O)O)n(C)c3c2)cn1] | 0.56 | 290 | 2 |
| Int-056 | 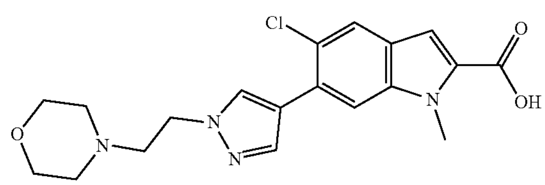 [SMILES: Cn1c(C(=O)O)cc2cc(Cl)c(-c3cnn(CCN4CCOCC4)c3)cc21] | 0.37 | 389 | 2 |

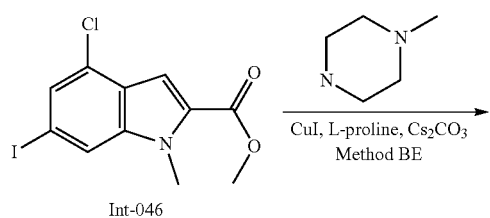

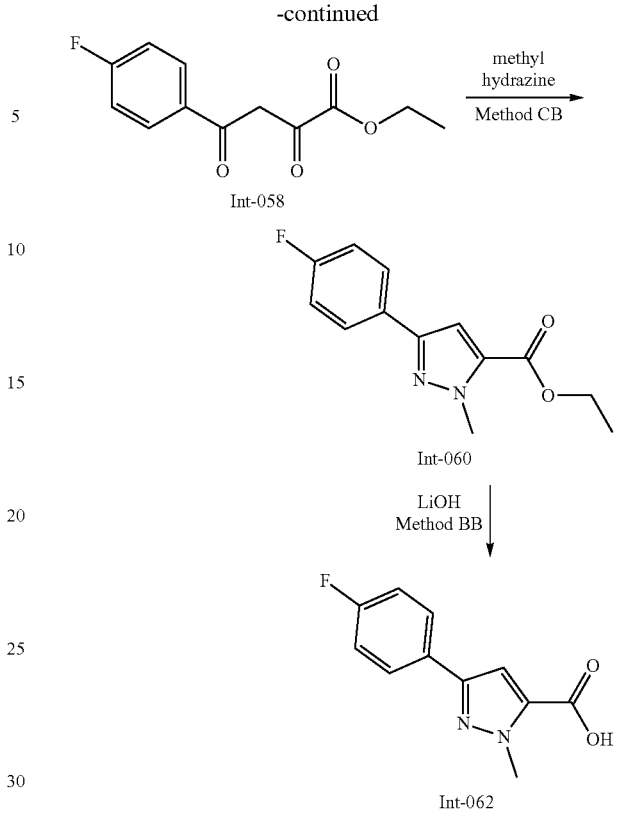

Synthesis of Int-057 (Method BE).

4-Chloro-6-iodo-1-methyl-1H-indole-2-carboxylic acid methyl ester (Int-046; 370 mg, 1.06 mmol), N-methylpiperazine (425 mg, 4.23 mmol), copper(I)iodide (60 mg, 0.32 mmol), L-proline (73.0 mg, 0.64 mmol), and cesium carbonate (690.0 mg, 2.12 mmol) are dissolved in degassed DMSO and stirred for one hour at 90° C. Water is added and the solids are collected by filtration. Reversed phase column chromatography delivers the purified product.

Synthesis of Arylpyrazole Carboxylates and Analogous Intermediates Pyrazole Ring Formation

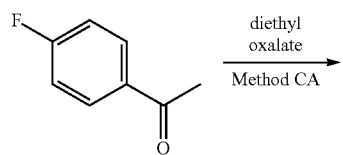

Synthesis of Int-058 (Method CA)

Sodium metal (60%, 15.06 g, 376 mmol) is added to dry ethanol (300 mL), then 1-(4-fluorophenyl)-ethanone (40.0 g, 289 mmol) in dry THF is added at 0° C. and stirred for 10 min. at this temperature. Diethyl oxalate (50.78 g, 347 mmol) is added and stirred for 16 h at ambient temperature. 2 N HCl is added. The formed solid is collected by filtration and dried.

The following diketones are prepared in an analogous manner.

| Example | Structure | $t_{ret}$ [min] | M + H | HPLC Method |
|---|---|---|---|---|
| Int-058 | ![structure] | 2.08 | 239 | 13 |
| Int-059 | ![structure] | 1.54 | 255 | 11 |

Synthesis of Int-060 (Method CB)

To Int-058 (60.0 g, 252 mmol) in ethanol (300 ml) methyl hydrazine (13.9 g, 302 mmol) and acetic acid (126 g, 126 mmol) are added and stirred for 3 h at ambient temperature. Most of the ethanol is evaporated, and water is added. The mixture is extracted exhaustively with EtOAc. The combined organic layer is washed with water and brine, dried ($MgSO_4$), filtered and concentrated in vacuo.

The mixture of isomers is purified by column chromatography.

The following aryl pyrazoles are prepared in an analogous manner.

| Example | Structure | $t_{ret}$ [min] | M + H | HPLC Method |
|---|---|---|---|---|
| Int-060 | 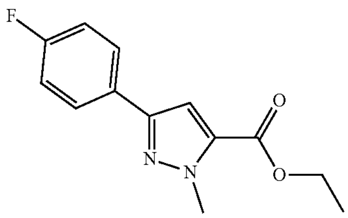 [SMILES: CCOC(=O)c1cc(-c2ccc(F)cc2)nn1C] | 1.35 | 249 | 11 |
| Int-061 | 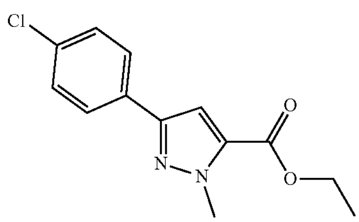 [SMILES: CCOC(=O)c1cc(-c2ccc(Cl)cc2)nn1C] | 1.44 | 266 | 11 |

Carboxylic acids Int-062 and Int-063 are prepared using general Method BB

| Example | Structure | $t_{ret}$ [min] | M + H | HPLC Method |
|---|---|---|---|---|
| Int-062 | 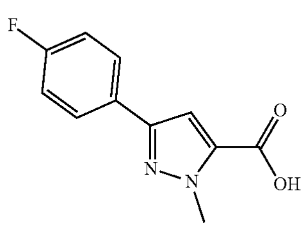 [SMILES: Cn1nc(-c2ccc(F)cc2)cc1C(=O)O] | 2.63 | 221 | 9 |
| Int-063 | 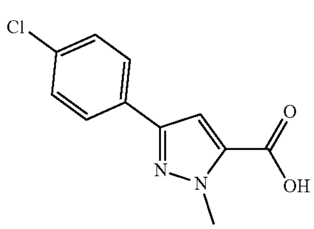 [SMILES: Cn1nc(-c2ccc(Cl)cc2)cc1C(=O)O] | 2.18 | 237 | 14 |

Halo-Pyrazole Functionalization

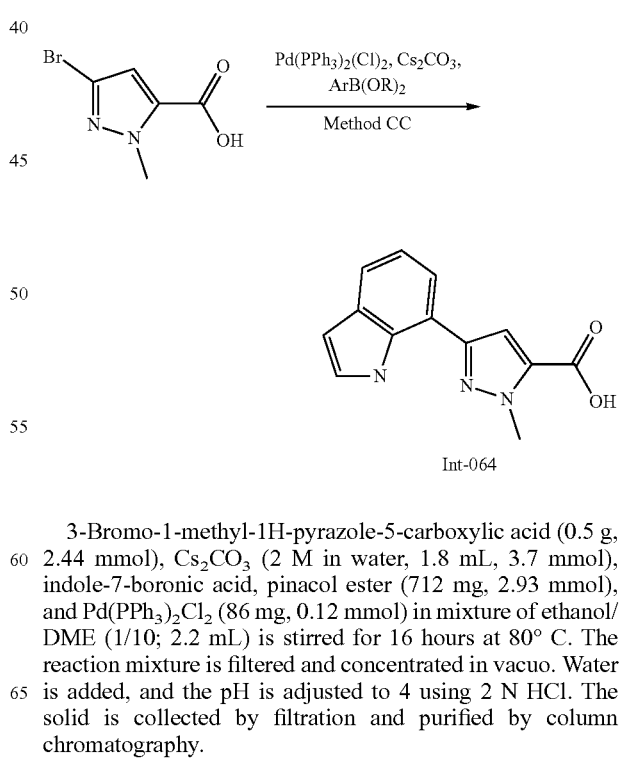

Int-064

3-Bromo-1-methyl-1H-pyrazole-5-carboxylic acid (0.5 g, 2.44 mmol), $Cs_2CO_3$ (2 M in water, 1.8 mL, 3.7 mmol), indole-7-boronic acid, pinacol ester (712 mg, 2.93 mmol), and $Pd(PPh_3)_2Cl_2$ (86 mg, 0.12 mmol) in mixture of ethanol/DME (1/10; 2.2 mL) is stirred for 16 hours at 80° C. The reaction mixture is filtered and concentrated in vacuo. Water is added, and the pH is adjusted to 4 using 2 N HCl. The solid is collected by filtration and purified by column chromatography.

| Example | Structure | $t_{ret}$ [min] | M+H | HPLC Method |
|---|---|---|---|---|
| Int-064 | 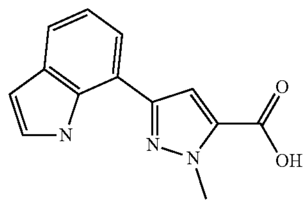 [SMILES: Cn1nc(-c2cccc3cc[nH]c23)cc1C(=O)O] | 0.72 | 242 | 5 |

Synthesis of Examples 01-001-02-017

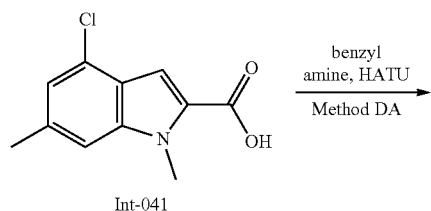

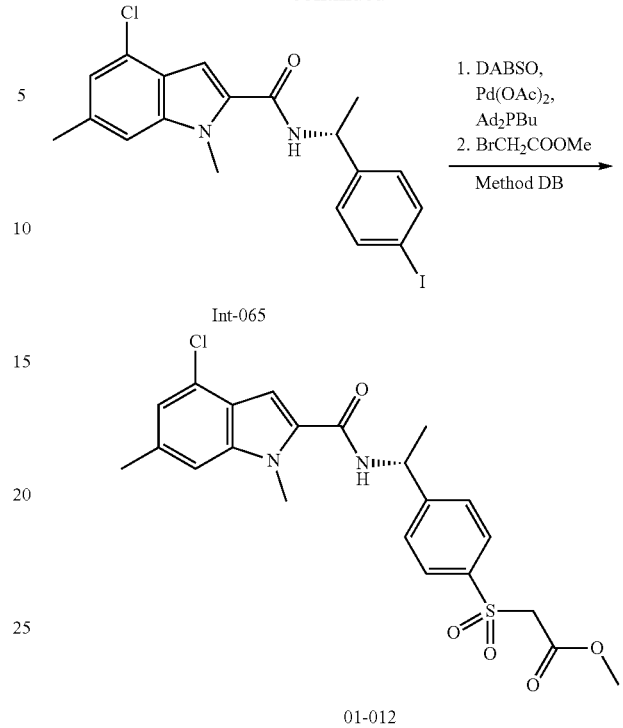

Synthesis of Int-065 (Method DA)

To Int-041 (300 mg, 1.34 mmol) in dry MeCN (10 mL) ethyl diisopropyl amine (432 µL, 2.68 mmol) and HATU (624 mg, 1.61 mmol) are added and stirred for 20 min. at ambient temperature. (1R)-1-(4-iodophenyl)ethanamine (331 mg, 1.34 mmol) is added and stirred for 16 h. Water is added. The formed solid is collected by filtration and triturated with water.

The following amides are prepared in an analogous manner.

| Example | Structure | $t_{ret}$ [min] | M+H | HPLC Method |
|---|---|---|---|---|
| Int-065 | 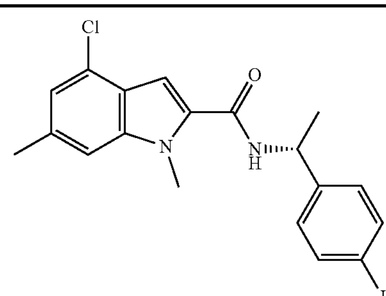 | 0.95 | 453 | 4 |
| Int-066 | 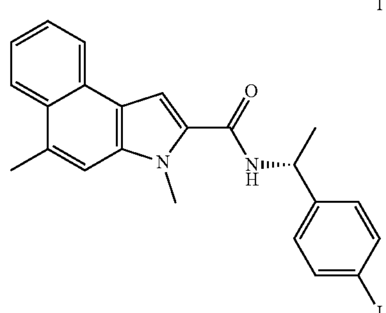 | 0.94 | 469 | 1 |

-continued
| Example | Structure | $t_{ret}$ [min] | M + H | HPLC Method |
|---|---|---|---|---|
| Int-067 | 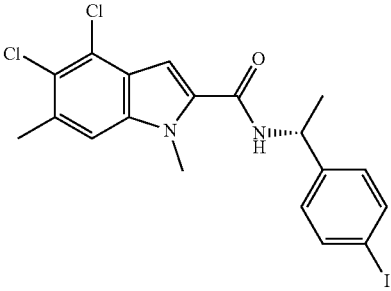 [SMILES: Cc1cc2c(cc(C(=O)N[C@H](C)c3ccc(I)cc3)n2C)c(Cl)c1Cl] | 0.99 | 487 | 2 |
| Int-068 | 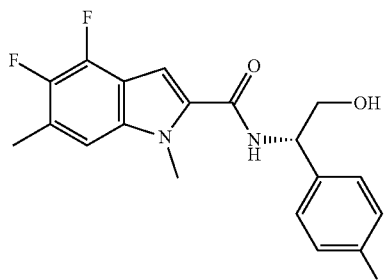 | 0.79 | 471 | 1 |
| Int-068 | 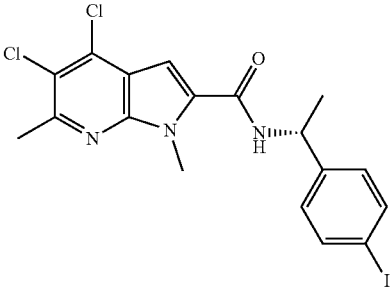 [SMILES: Cc1nc2c(cc(C(=O)N[C@H](C)c3ccc(I)cc3)n2C)c(Cl)c1Cl] | 0.98 | 488/490 | 2 |
| Int-069 | 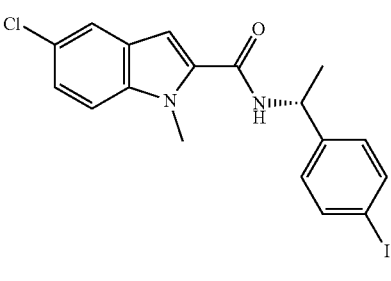 [SMILES: C[C@@H](NC(=O)c1cc2cc(Cl)ccc2n1C)c1ccc(I)cc1] | 0.88 | 439 | 1 |
| Int-070 | 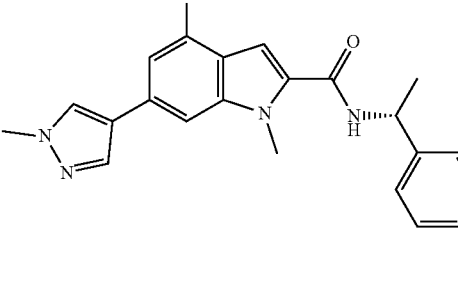 | 0.84 | 519 | 2 |

-continued

| Example | Structure | $t_{ret}$ [min] | M + H | HPLC Method |
|---|---|---|---|---|
| Int-071 | 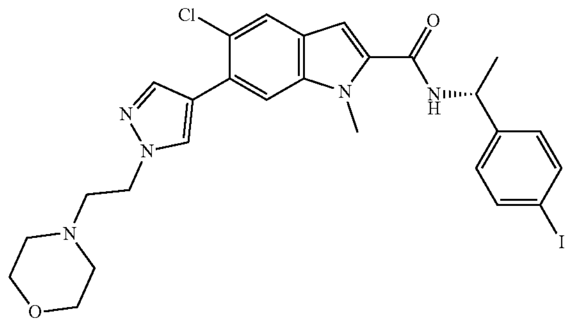 [SMILES: C[C@@H](NC(=O)c1cc2cc(Cl)c(-c3cnn(CCN4CCOCC4)c3)cc2n1C)c1ccc(I)cc1] | 0.62 | 618 | 2 |
| Int-072 | 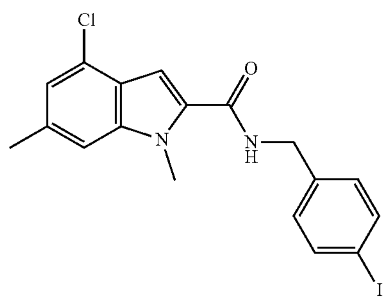 [SMILES: Cc1cc(Cl)c2cc(C(=O)NCc3ccc(I)cc3)n(C)c2c1] | 0.90 | 439 | 1 |
| Int-073 | 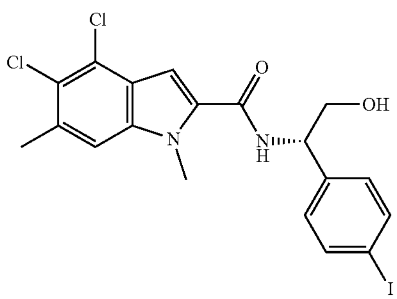 [SMILES: Cc1cc2c(cc(C(=O)N[C@H](CO)c3ccc(I)cc3)n2C)c(Cl)c1Cl] | 0.87 | 503/504 | 2 |
| Int-074 | 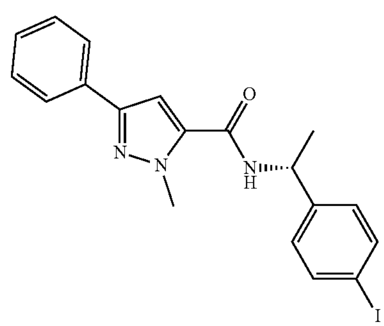 [SMILES: C[C@@H](NC(=O)c1cc(-c2ccccc2)nn1C)c1ccc(I)cc1] | 0.82 | 432 | 1 |
| Int-075 | 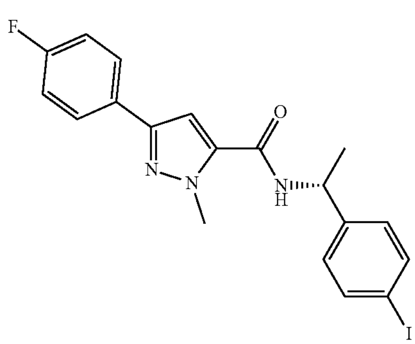 [SMILES: C[C@@H](NC(=O)c1cc(-c2ccc(F)cc2)nn1C)c1ccc(I)cc1] | 0.83 | 450 | 1 |

| Example | Structure | $t_{ret}$ [min] | M + H | HPLC Method |
|---|---|---|---|---|
| Int-076 | 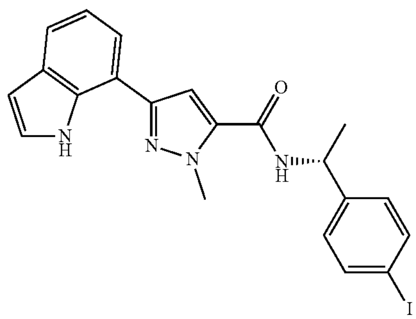 [SMILES: C[C@@H](NC(=O)c1cc(-c2cccc3cc[nH]c23)nn1C)c1ccc(I)cc1] | 0.87 | 471 | 2 |

Synthesis of 01-012 (Method DB).

Int-065 (400 mg, 0.44 mmol), DABSO (123 mg, 0.49 mmol), Pd(OAc)$_2$ (10 mg, 0.04 mmol), butyldi-1-adamantylphosphine (32 mg, 0.09 mmol), triethyl amine (150 µL, 1.33 mmol) and 2-propanol (900 µL) are degassed with argon and stirred for 2 h at 75'00. The mixture is cooled, and methyl bromoacetate (127 µL, 1.33 mmol) is added. The mixture is stirred at ambient temperature overnight. The reaction mixture is concentrated in vacuo, and the residue is partitioned between water and dichloromethane. The aqueous layer is extracted exhaustively with dichloromethane. The combined organic layer is washed with 1 N HCl, dried (MgSO$_4$), filtered and concentrated in vacuo. The residue is purified by column chromatography or by RP-HPLC/MS.

The following sulfonyl acetates are prepared in an analogous manner.

| Example | Structure | | $t_{ret}$ [min] | M + H | M − H | HPLC Method |
|---|---|---|---|---|---|---|
| 01-001 | 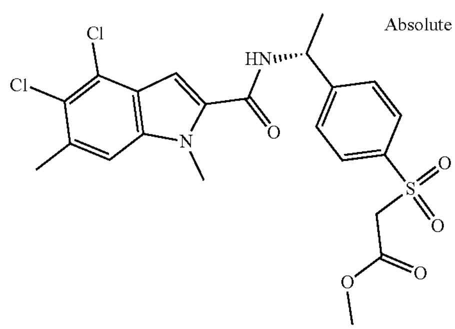 [SMILES: COC(=O)CS(=O)(=O)c1ccc([C@@H](C)NC(=O)c2cc3c(Cl)c(Cl)c(C)cc3n2C)cc1] | Absolute | 1.4 | 497 | | 5 |
| 01-002 | 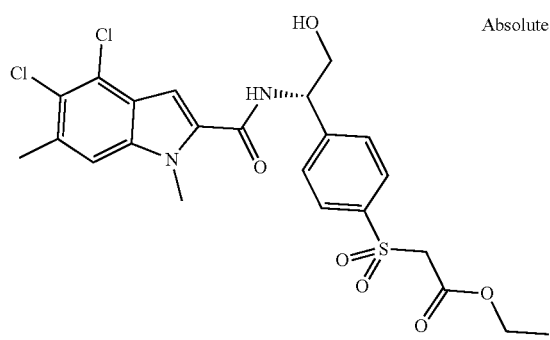 [SMILES: CCOC(=O)CS(=O)(=O)c1ccc([C@@H](CO)NC(=O)c2cc3c(Cl)c(Cl)c(C)cc3n2C)cc1] | Absolute | 1.36 | 527 | | 5 |

-continued
| | | | | | |
|---|---|---|---|---|---|
| 01-003 | 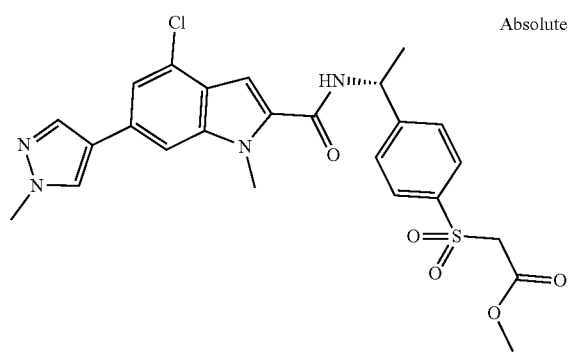 [SMILES: COC(=O)CS(=O)(=O)c1ccc([C@@H](C)NC(=O)c2cc3c(Cl)cc(-c4cnn(C)c4)cc3n2C)cc1] | Absolute | 1.24 | 529 | 5 |
| 01-004 | | Absolute | 1.45 | 477 | 5 |
| 01-005 | 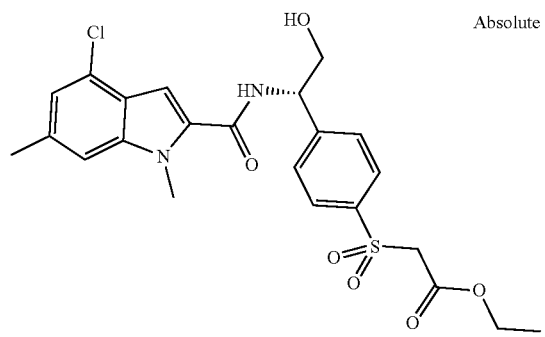 [SMILES: CCOC(=O)CS(=O)(=O)c1ccc([C@@H](CO)NC(=O)c2cc3c(Cl)cc(C)cc3n2C)cc1] | Absolute | 1.29 | 493 | 5 |
| 01-006 | 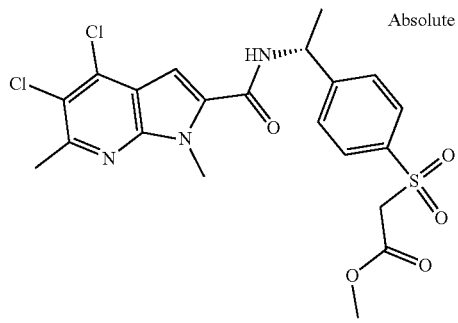 [SMILES: COC(=O)CS(=O)(=O)c1ccc([C@@H](C)NC(=O)c2cc3c(Cl)c(Cl)c(C)nc3n2C)cc1] | Absolute | 1.44 | 498 | 5 |

| | | | | | |
|---|---|---|---|---|---|
| 01-007 | 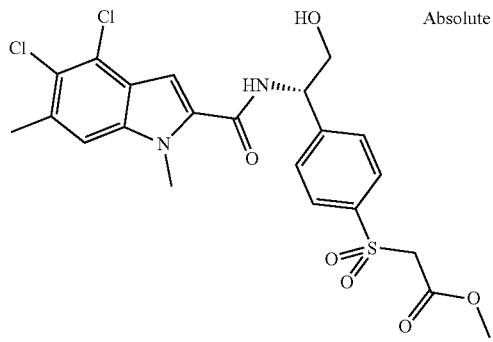 | Absolute | 1.32 | 513 | 5 |
| 01-008 | 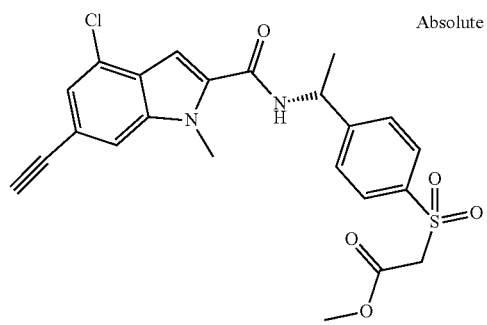 | Absolute | 1.4 | 473 | 5 |
| 01-009 | 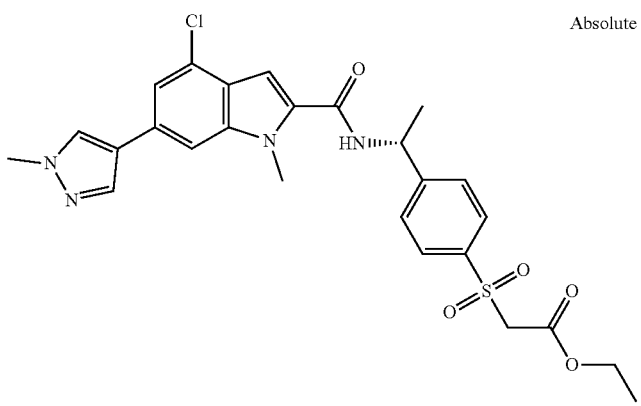 [SMILES: CCOC(=O)CS(=O)(=O)c1ccc([C@@H](C)NC(=O)c2cc3c(Cl)cc(-c4cnn(C)c4)cc3n2C)cc1] | Absolute | 1.28 | 543 | 5 |
| 01-010 | 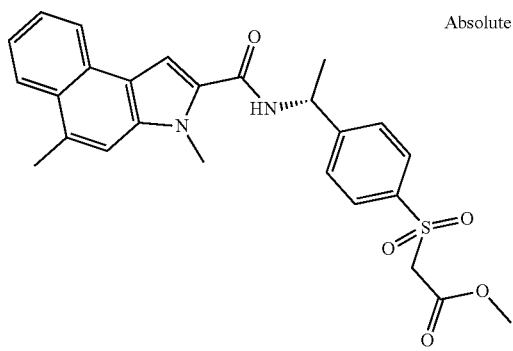 [SMILES: COC(=O)CS(=O)(=O)c1ccc([C@@H](C)NC(=O)c2cc3c4ccccc4c(C)cc3n2C)cc1] | Absolute | 1.42 | 479 | 5 |

-continued
| | | | | | |
|---|---|---|---|---|---|
| 01-011 | 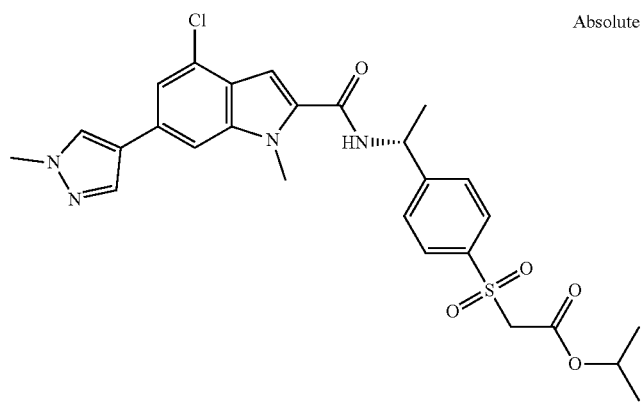 [SMILES: CC(C)OC(=O)CS(=O)(=O)c1ccc([C@@H](C)NC(=O)c2cc3c(Cl)cc(-c4cnn(C)c4)cc3n2C)cc1] | Absolute | 1.32 | 557 | 5 |
| 01-012 | 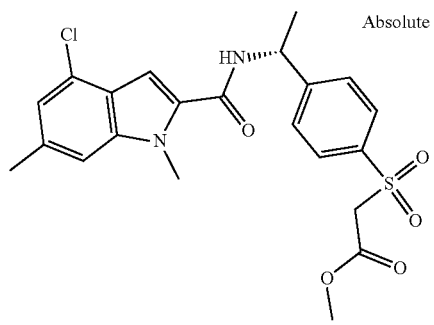 [SMILES: COC(=O)CS(=O)(=O)c1ccc([C@@H](C)NC(=O)c2cc3c(Cl)cc(C)cc3n2C)cc1] | Absolute | 1.41 | 463 | 5 |
| 01-013 | 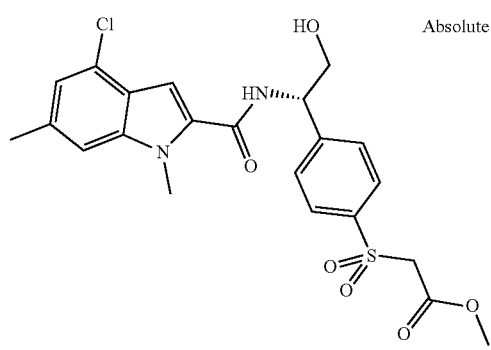 | Absolute | 1.25 | 479 | 5 |
| 01-014 | 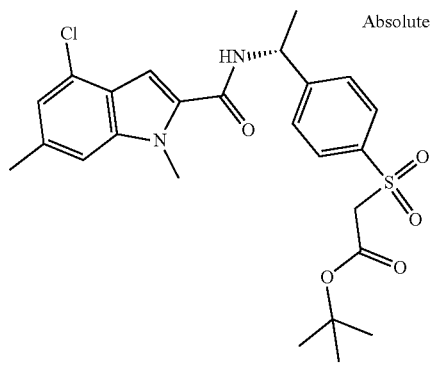 [SMILES: Cc1cc(Cl)c2cc(C(=O)N[C@H](C)c3ccc(S(=O)(=O)CC(=O)OC(C)(C)C)cc3)n(C)c2c1] | Absolute | 1.56 | 503 | 5 |

| | | | | | |
|---|---|---|---|---|---|
| 01-015 | 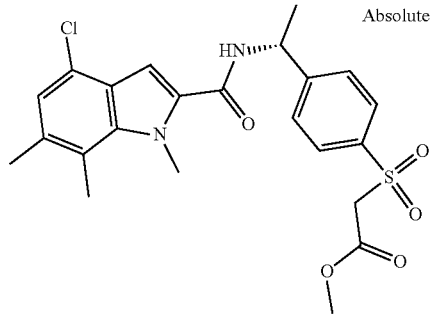 [SMILES: COC(=O)CS(=O)(=O)c1ccc([C@@H](C)NC(=O)c2cc3c(Cl)cc(C)c(C)c3n2C)cc1] | Absolute | 1.44 | 477 | 5 |
| 01-016 | 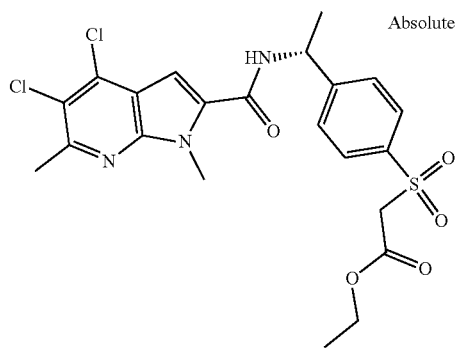 [SMILES: CCOC(=O)CS(=O)(=O)c1ccc([C@@H](C)NC(=O)c2cc3c(Cl)c(Cl)c(C)nc3n2C)cc1] | Absolute | 1.5 | 512 | 5 |
| 01-017 | 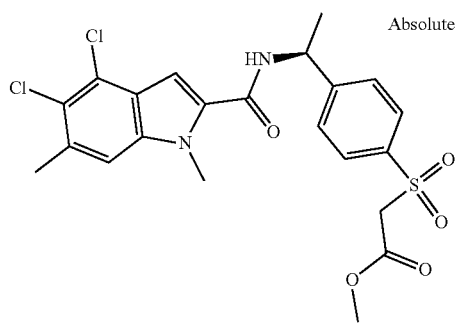 [SMILES: COC(=O)CS(=O)(=O)c1ccc([C@H](C)NC(=O)c2cc3c(Cl)c(Cl)c(C)cc3n2C)cc1] | Absolute | 1.5 | 497 | 5 |
| 01-018 | 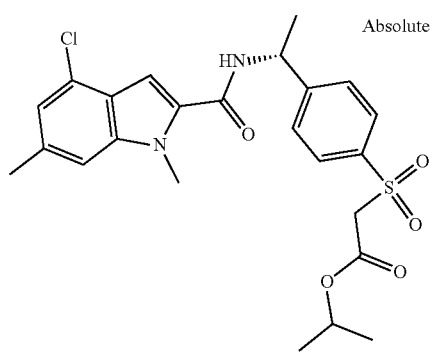 [SMILES: Cc1cc(Cl)c2cc(C(=O)N[C@H](C)c3ccc(S(=O)(=O)CC(=O)OC(C)C)cc3)n(C)c2c1] | Absolute | 1.5 | 491 | 5 |

| | | | | | |
|---|---|---|---|---|---|
| 01-019 | 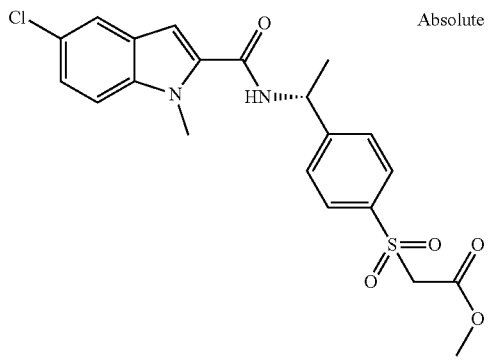 [SMILES: COC(=O)CS(=O)(=O)c1ccc([C@@H](C)NC(=O)c2cc3cc(Cl)ccc3n2C)cc1] | Absolute | 1.28 | 449 | 5 |
| 01-020 | 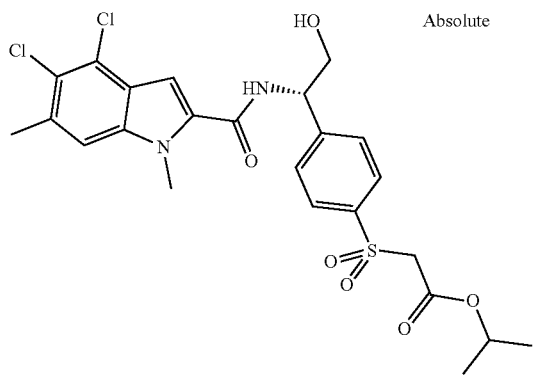 [SMILES: Cc1cc2c(cc(C(=O)N[C@H](CO)c3ccc(S(=O)(=O)CC(=O)OC(C)C)cc3)n2C)c(Cl)c1Cl] | Absolute | 1.51 | 575 | 5 |
| 01-021 | 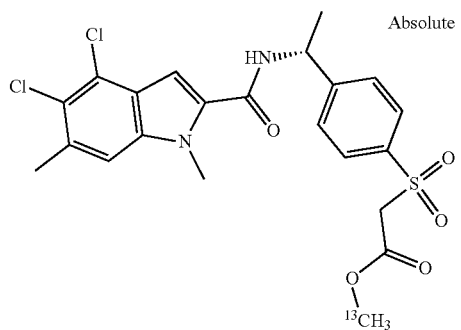 [SMILES: Cc1cc2c(cc(C(=O)N[C@H](C)c3ccc(S(=O)(=O)CC(=O)O[13CH3])cc3)n2C)c(Cl)c1Cl] | Absolute | 1.4 | 541 | 5 |
| 01-022 |  | Absolute | 1.43 | 498 | 5 |

| | | | | | |
|---|---|---|---|---|---|
| 01-023 | 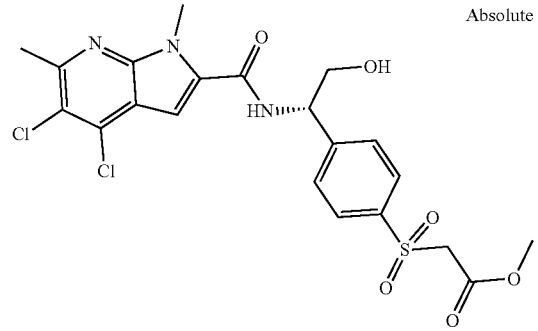 | Absolute | 1.27 | 514 | 5 |
| 01-024 | 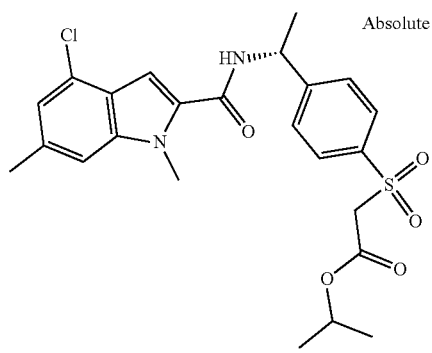 [SMILES: Cc1cc(Cl)c2cc(C(=O)N[C@H](C)c3ccc(S(=O)(=O)CC(=O)OC(C)C)cc3)n(C)c2c1] | Absolute | 1.50 | 491 | 5 |
| 01-025 | 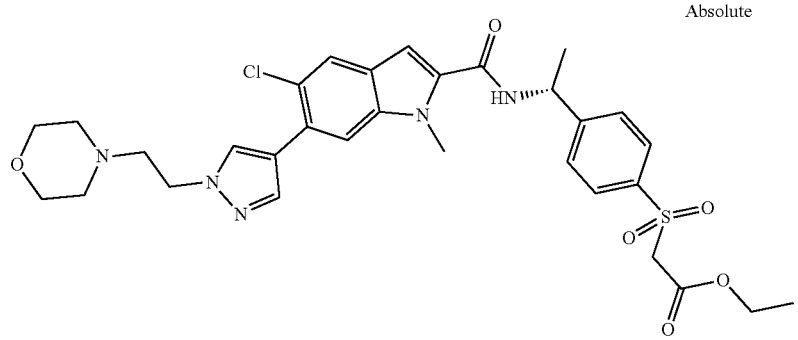 [SMILES: CCOC(=O)CS(=O)(=O)c1ccc([C@@H](C)NC(=O)c2cc3cc(Cl)c(-c4cnn(CCN5CCOCC5)c4)cc3n2C)cc1] | Absolute | 1.23 | 642 | 5 |
| 01-026 | 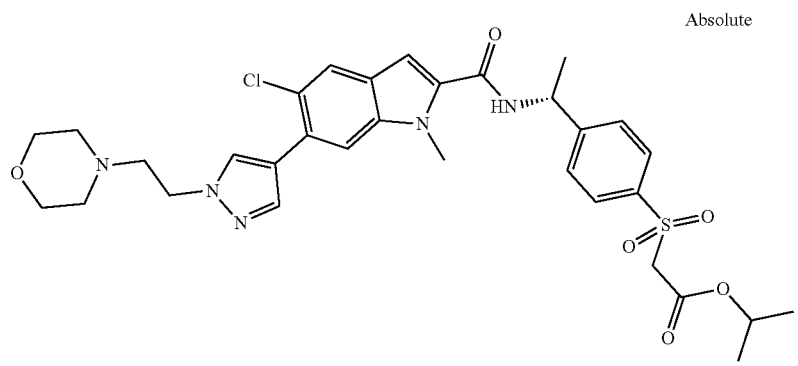 [SMILES: CC(C)OC(=O)CS(=O)(=O)c1ccc([C@@H](C)NC(=O)c2cc3cc(Cl)c(-c4cnn(CCN5CCOCC5)c4)cc3n2C)cc1] | Absolute | 1.26 | 656 | 5 |

-continued
01-027 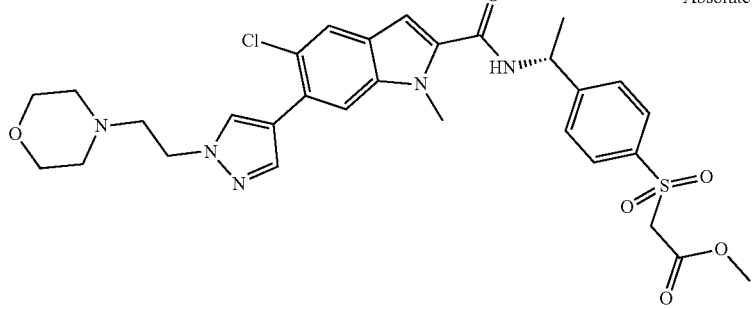 Absolute 1.16 628 5
01-028 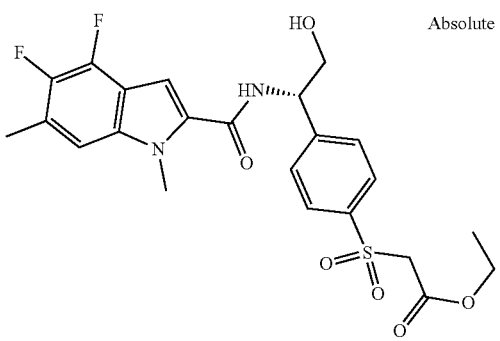 [SMILES: CCOC(=O)CS(=O)(=O)c1ccc([C@@H](CO)NC(=O)c2cc3c(F)c(F)c(C)cc3n2C)cc1] Absolute 1.25 495 5
01-029 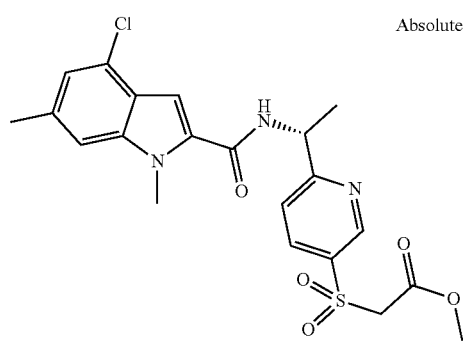 Absolute 2.76 469 6
01-030 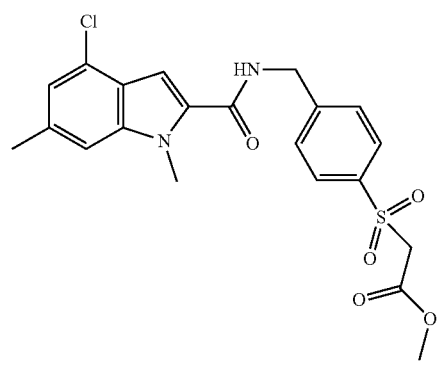 [SMILES: COC(=O)CS(=O)(=O)c1ccc(CNC(=O)c2cc3c(Cl)cc(C)cc3n2C)cc1] n.a. n.a. 5

| | | | | |
|---|---|---|---|---|
| 01-031 | 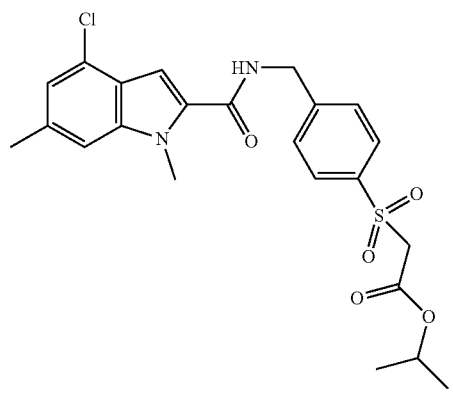 [SMILES: Cc1cc(Cl)c2cc(C(=O)NCc3ccc(S(=O)(=O)CC(=O)OC(C)C)cc3)n(C)c2c1] | 1.65 | 477 | 5 |
| 01-032 | 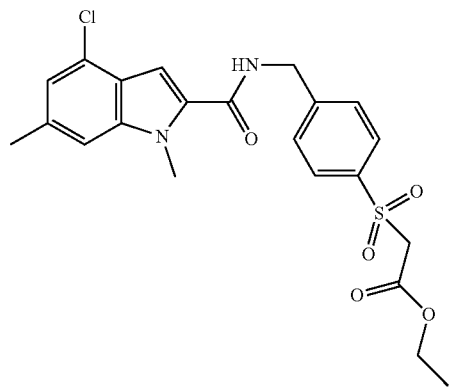 [SMILES: CCOC(=O)CS(=O)(=O)c1ccc(CNC(=O)c2cc3c(Cl)cc(C)cc3n2C)cc1] | 1.37 | 463 | 5 |
| 01-033 | 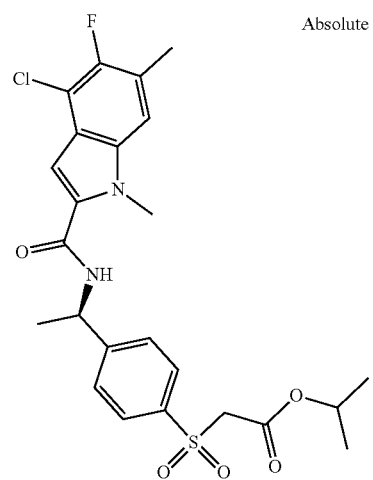 [SMILES: Cc1cc2c(cc(C(=O)N[C@H](C)c3ccc(S(=O)(=O)CC(=O)OC(C)C)cc3)n2C)c(Cl)c1F] Absolute | 1.51 | 509 | 5 |

| | | | | | |
|---|---|---|---|---|---|
| 01-034 | 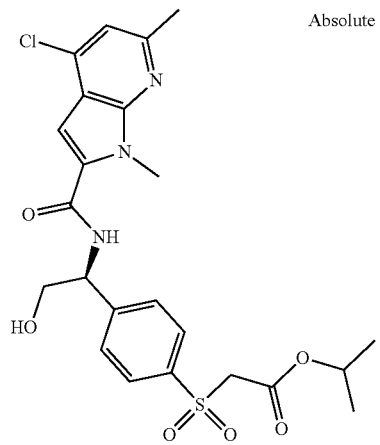 [SMILES: Cc1cc(Cl)c2cc(C(=O)N[C@H](CO)c3ccc(S(=O)(=O)CC(=O)OC(C)C)cc3)n(C)c2n1] | Absolute | 1.22 | 508 | 5 |
| 01-035 | 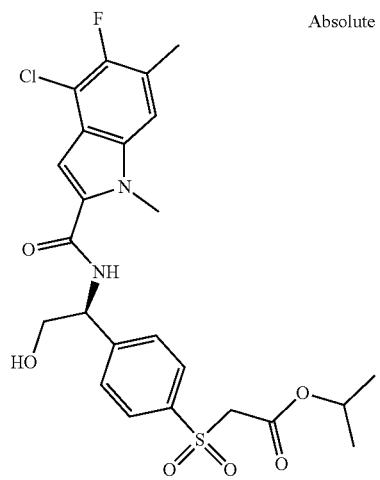 [SMILES: Cc1cc2c(cc(C(=O)N[C@H](CO)c3ccc(S(=O)(=O)CC(=O)OC(C)C)cc3)n2C)c(Cl)c1F] | Absolute | 1.35 | 525 | 5 |
| 01-036 | 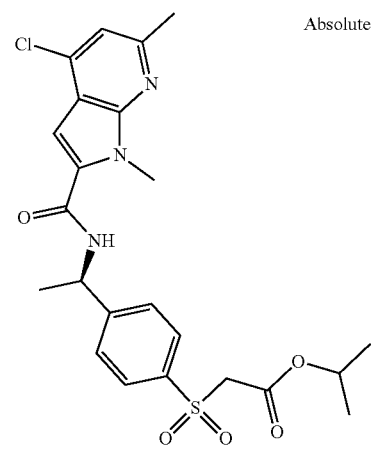 [SMILES: Cc1cc(Cl)c2cc(C(=O)N[C@H](C)c3ccc(S(=O)(=O)CC(=O)OC(C)C)cc3)n(C)c2n1] | Absolute | 1.38 | 492 | 5 |

-continued
| | | | | | |
|---|---|---|---|---|---|
| 01-037 | 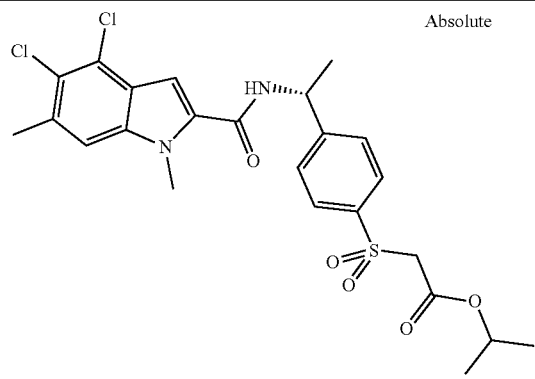 | Absolute | 1.52 | 525 | 5 |
| 01-038 | 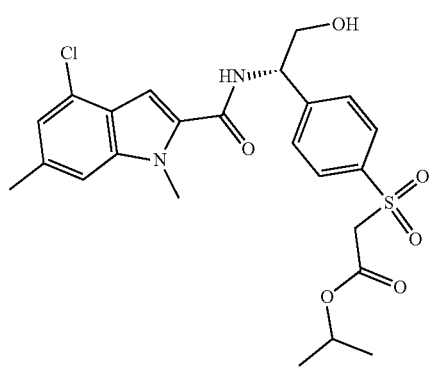 | Absolute | 1.35 | 507 | 5 |
| 01-039 | 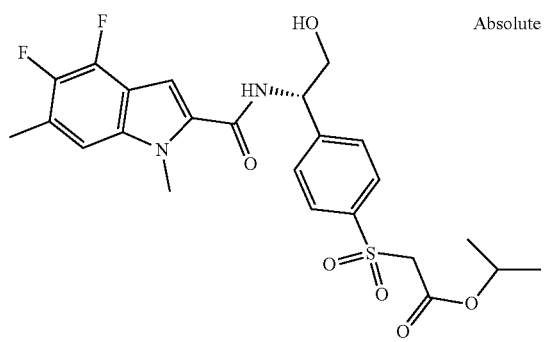 [SMILES: Cc1cc2c(cc(C(=O)N[C@H](CO)c3ccc(S(=O)(=O)CC(=O)OC(C)C)cc3)n2C)c(F)c1F] | Absolute | 1.28 | 509 | 5 |
| 01-040 | 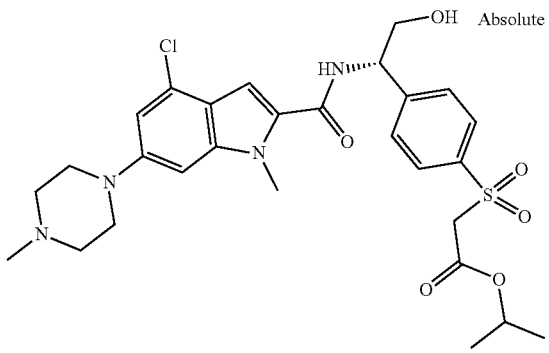 [SMILES: CC(C)OC(=O)CS(=O)(=O)c1ccc([C@@H](CO)NC(=O)c2cc3c(Cl)cc(N4CCN(C)CC4)cc3n2C)cc1] | Absolute | 1.17 | 591 | 5 |

-continued
| Example | Structure | | t Ret | M + H | Method |
|---|---|---|---|---|---|
| 01-041 | 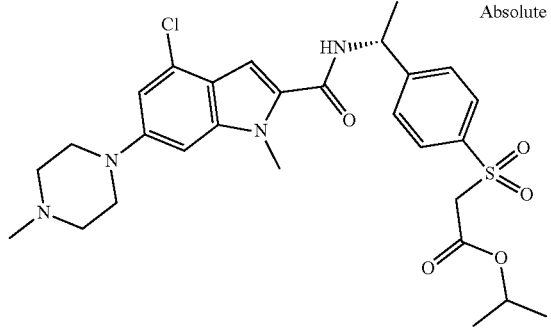 [SMILES: CC(C)OC(=O)CS(=O)(=O)c1ccc([C@@H](C)NC(=O)c2cc3c(Cl)cc(N4CCN(C)CC4)cc3n2C)cc1] | Absolute | 1.33 | 575 | 5 |
| Example | Structure | | t Ret | M + H | Method |
|---|---|---|---|---|---|
| 02-001 | 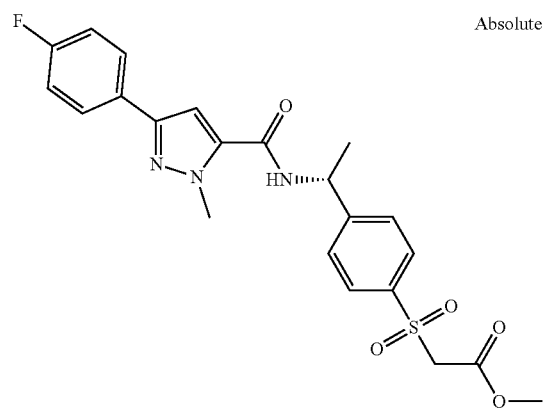 [SMILES: COC(=O)CS(=O)(=O)c1ccc([C@@H](C)NC(=O)c2cc(-c3ccc(F)cc3)nn2C)cc1] | Absolute | 1.25 | 460 | 5 |
| 02-002 | 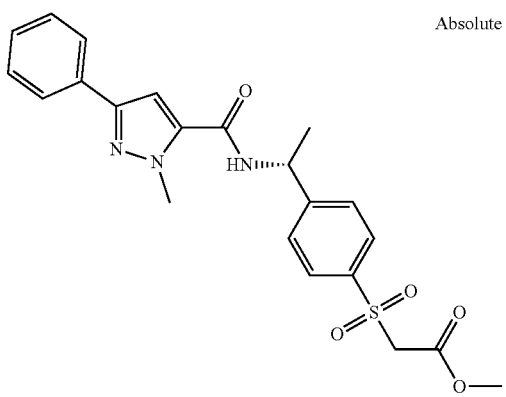 [SMILES: COC(=O)CS(=O)(=O)c1ccc([C@@H](C)NC(=O)c2cc(-c3ccccc3)nn2C)cc1] | Absolute | 1.2 | 442 | 5 |
| 02-003 | 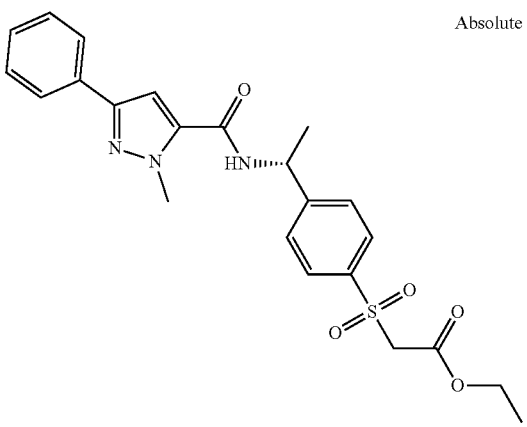 [SMILES: CCOC(=O)CS(=O)(=O)c1ccc([C@@H](C)NC(=O)c2cc(-c3ccccc3)nn2C)cc1] | Absolute | 1.19 | 456 | 5 |

| | | | | | |
|---|---|---|---|---|---|
| 02-004 | 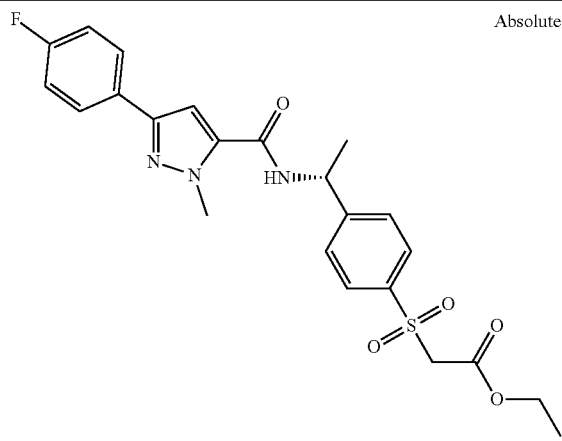 | Absolute | 1.31 | 474 | 5 |
| 02-005 | 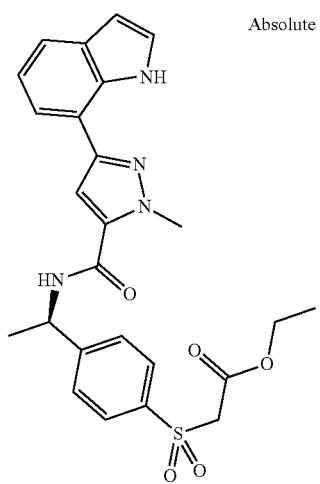 [SMILES: CCOC(=O)CS(=O)(=O)c1ccc([C@@H](C)NC(=O)c2cc(-c3cccc4cc[nH]c34)nn2C)cc1] | Absolute | 1.36 | 495 | 5 |
| 02-006 | 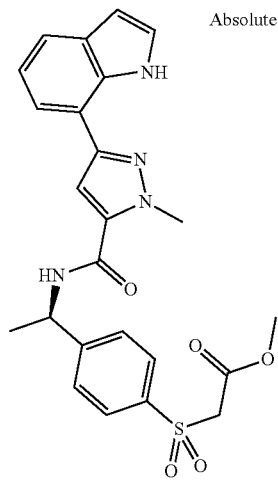 [SMILES: COC(=O)CS(=O)(=O)c1ccc([C@@H](C)NC(=O)c2cc(-c3cccc4cc[nH]c34)nn2C)cc1] | Absolute | 1.32 | 481 | 5 |

| | | | | | |
|---|---|---|---|---|---|
| 02-007 | 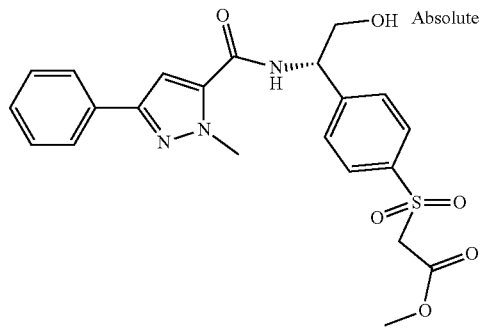 [SMILES: COC(=O)CS(=O)(=O)c1ccc([C@@H](CO)NC(=O)c2cc(-c3ccccc3)nn2C)cc1] | Absolute | 1.05 | 458 | 5 |
| 02-008 | 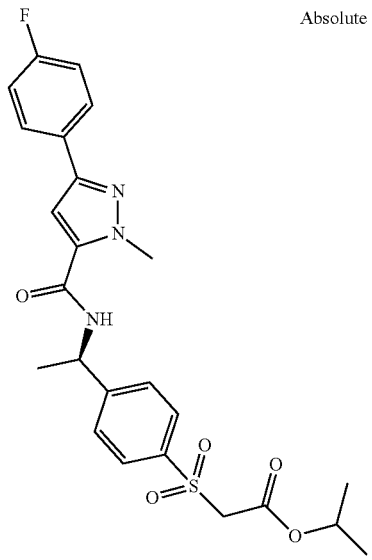 [SMILES: CC(C)OC(=O)CS(=O)(=O)c1ccc([C@@H](C)NC(=O)c2cc(-c3ccc(F)cc3)nn2C)cc1] | Absolute | 1.34 | 488 | 5 |
| 02-009 | 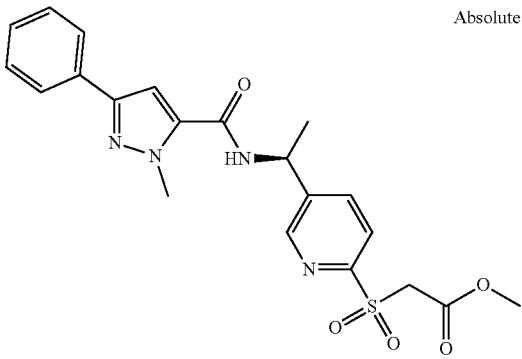 [SMILES: COC(=O)CS(=O)(=O)c1ccc([C@H](C)NC(=O)c2cc(-c3ccccc3)nn2C)cn1] | Absolute | | | 12 |
| 02-010 | 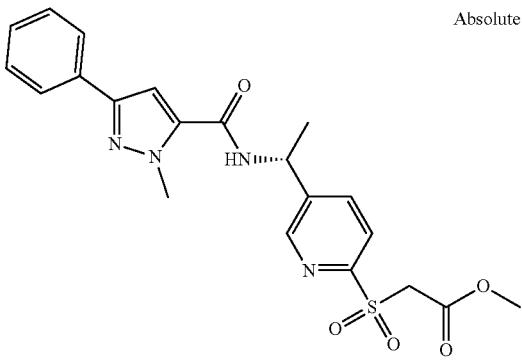 [SMILES: COC(=O)CS(=O)(=O)c1ccc([C@@H](C)NC(=O)c2cc(-c3ccccc3)nn2C)cn1] | Absolute | | | 12 |

| | | | | | |
|---|---|---|---|---|---|
| 02-011 | 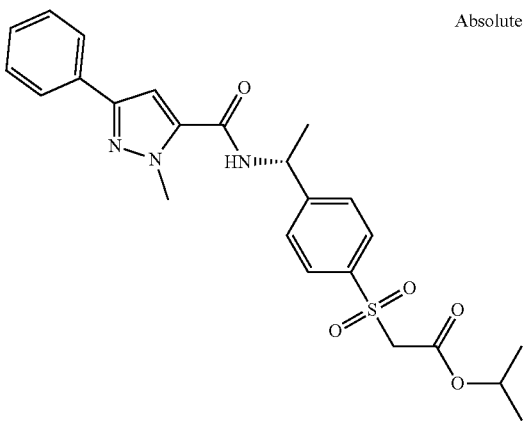 [SMILES: CC(C)OC(=O)CS(=O)(=O)c1ccc([C@@H](C)NC(=O)c2cc(-c3ccccc3)nn2C)cc1] | Absolute | 1.32 | 470 | 5 |
| 02-012 | 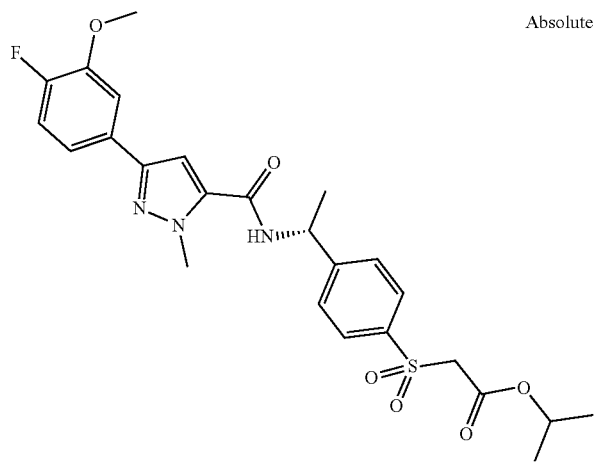 [SMILES: COc1cc(-c2cc(C(=O)N[C@H](C)c3ccc(S(=O)(=O)CC(=O)OC(C)C)cc3)n(C)n2)ccc1F] | Absolute | 1.34 | 518 | 5 |
| 02-013 | 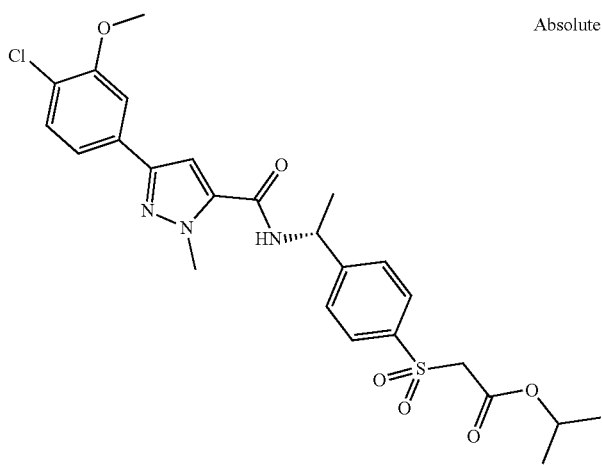 [SMILES: COc1cc(-c2cc(C(=O)N[C@H](C)c3ccc(S(=O)(=O)CC(=O)OC(C)C)cc3)n(C)n2)ccc1Cl] | Absolute | 1.4 | 534 | 5 |

| | | | | | |
|---|---|---|---|---|---|
| 02-014 | 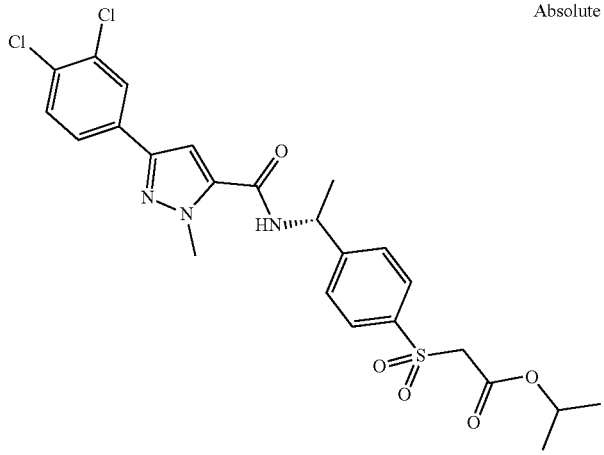 [SMILES: CC(C)OC(=O)CS(=O)(=O)c1ccc([C@@H](C)NC(=O)c2cc(-c3ccc(Cl)c(Cl)c3)nn2C)cc1] | Absolute | 1.54 | 538 | 5 |
| 02-015 | 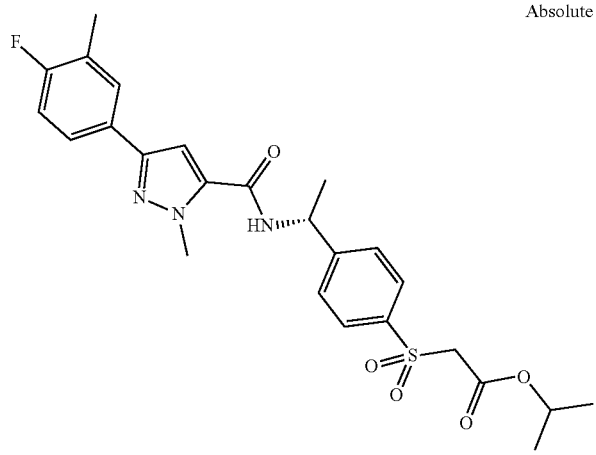 [SMILES: Cc1cc(-c2cc(C(=O)N[C@H](C)c3ccc(S(=O)(=O)CC(=O)OC(C)C)cc3)n(C)n2)ccc1F] | Absolute | 1.41 | 502 | 5 |
| 02-016 | 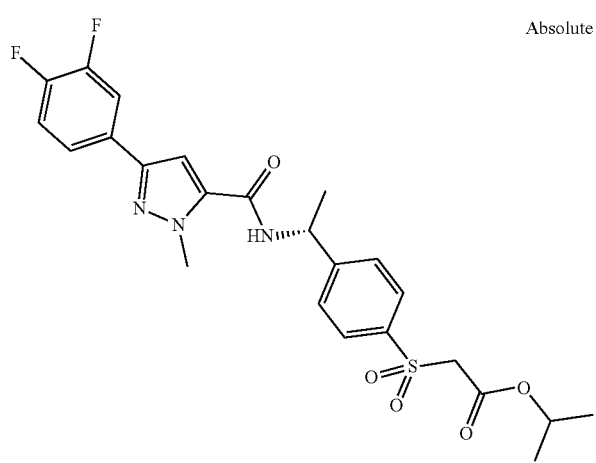 [SMILES: CC(C)OC(=O)CS(=O)(=O)c1ccc([C@@H](C)NC(=O)c2cc(-c3ccc(F)c(F)c3)nn2C)cc1] | Absolute | 1.4 | 506 | 5 |

| | | | | | |
|---|---|---|---|---|---|
| 02-017 | 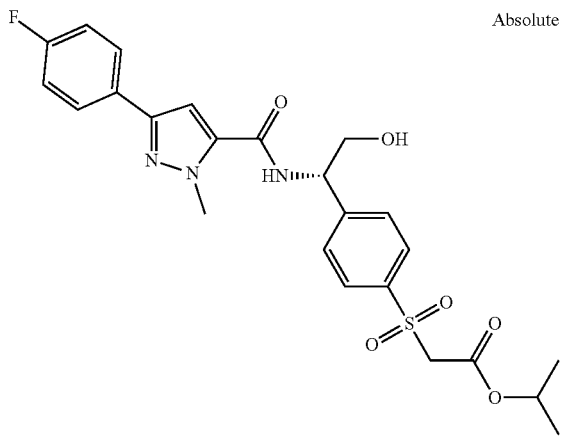 [SMILES: CC(C)OC(=O)CS(=O)(=O)c1ccc([C@@H](CO)NC(=O)c2cc(-c3ccc(F)cc3)nn2C)cc1] | Absolute | 1.2 | 504 | 5 |

Synthesis of Examples 03-001-04-004

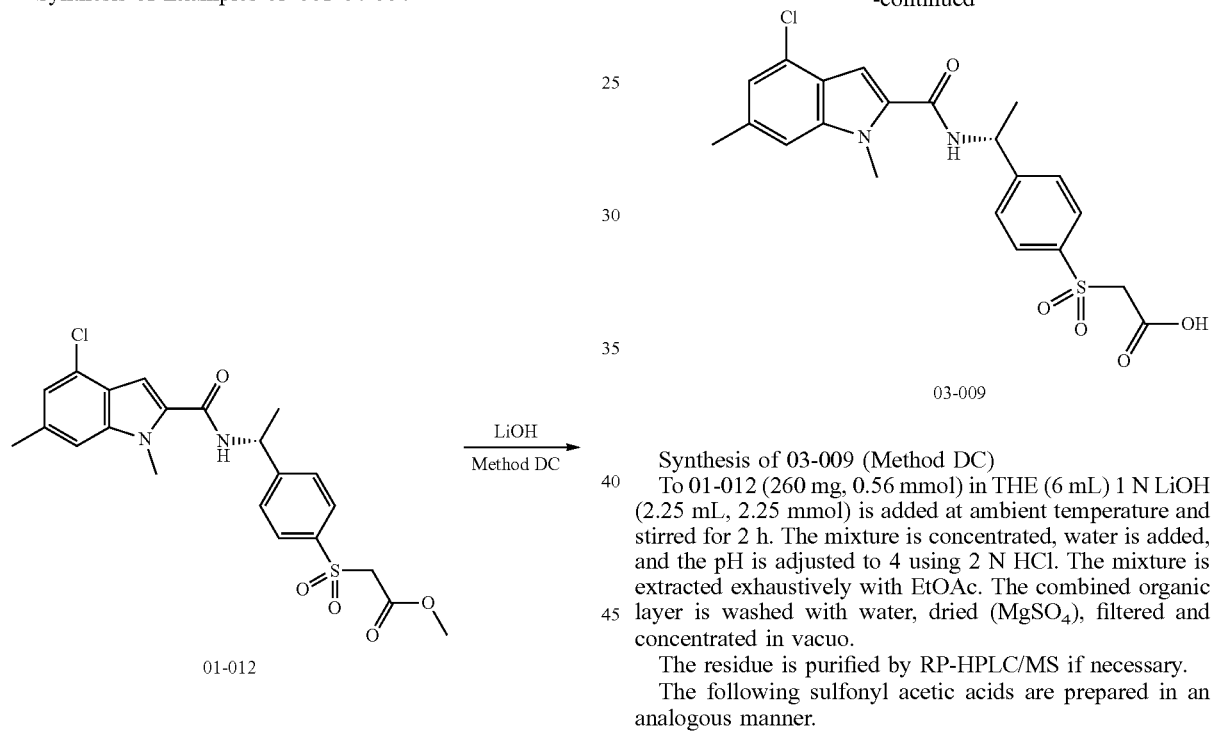

Synthesis of 03-009 (Method DC)

To 01-012 (260 mg, 0.56 mmol) in THF (6 mL) 1 N LiOH (2.25 mL, 2.25 mmol) is added at ambient temperature and stirred for 2 h. The mixture is concentrated, water is added, and the pH is adjusted to 4 using 2 N HCl. The mixture is extracted exhaustively with EtOAc. The combined organic layer is washed with water, dried ($MgSO_4$), filtered and concentrated in vacuo.

The residue is purified by RP-HPLC/MS if necessary.

The following sulfonyl acetic acids are prepared in an analogous manner.

| Example | Structure | | $t_{ret}$ [min] | M + H | HPLC Method |
|---|---|---|---|---|---|
| 03-001 | 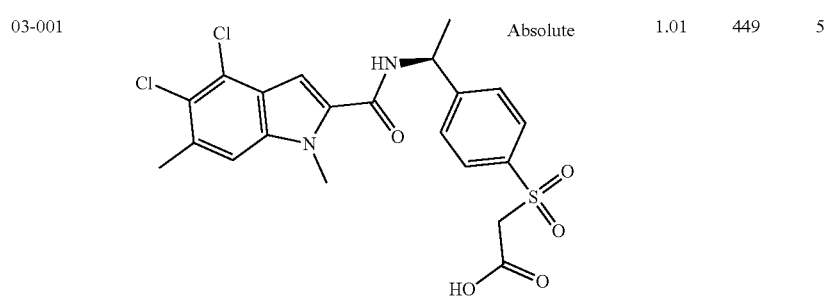 | Absolute | 1.01 | 449 | 5 |

-continued

| Example | Structure | | $t_{ret}$ [min] | M + H | HPLC Method |
|---|---|---|---|---|---|
| 03-002 | 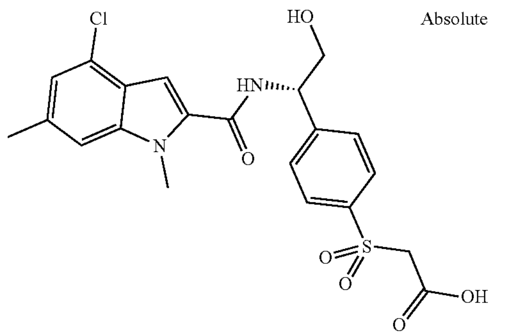 [SMILES: Cc1cc(Cl)c2cc(C(=O)N[C@H](CO)c3ccc(S(=O)(=O)CC(=O)O)cc3)n(C)c2c1] | Absolute | 0.91 | 465 | 5 |
| 03-003 | 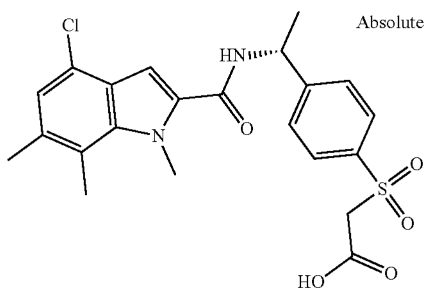 [SMILES: Cc1cc(Cl)c2cc(C(=O)N[C@H](C)c3ccc(S(=O)(=O)CC(=O)O)cc3)n(C)c2c1C] | | 1.01 | 463 | 5 |
| 03-004 | 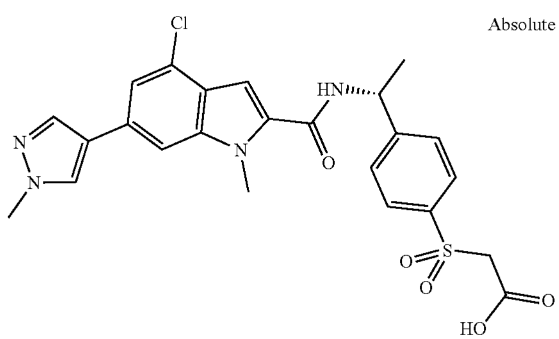 [SMILES: C[C@@H](NC(=O)c1cc2c(Cl)cc(-c3cnn(C)c3)cc2n1C)c1ccc(S(=O)(=O)CC(=O)O)cc1] | Absolute | 0.91 | 515 | 5 |
| 03-005 | 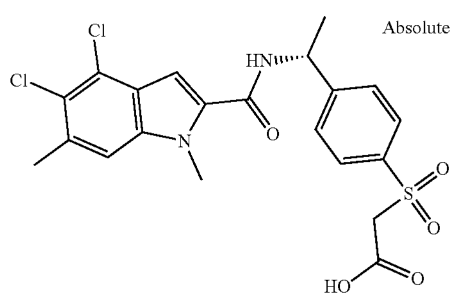 [SMILES: Cc1cc2c(cc(C(=O)N[C@H](C)c3ccc(S(=O)(=O)CC(=O)O)cc3)n2C)c(Cl)c1Cl] | Absolute | 1.03 | 483 | 5 |

-continued

| Example | Structure | | $t_{ret}$ [min] | M + H | HPLC Method |
|---|---|---|---|---|---|
| 03-006 | 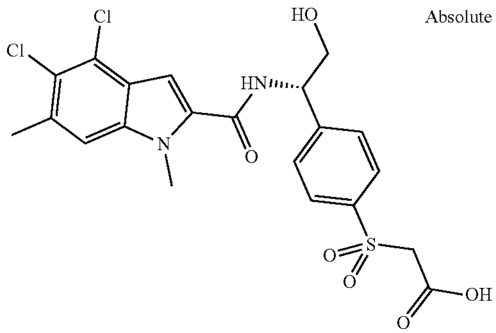 [SMILES: Cc1cc2c(cc(C(=O)N[C@H](CO)c3ccc(S(=O)(=O)CC(=O)O)cc3)n2C)c(Cl)c1Cl] | Absolute | 0.97 | 499 | 5 |
| 03-007 | 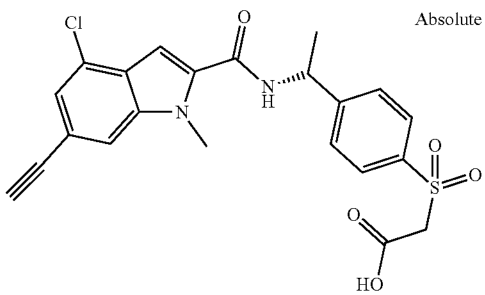 | Absolute | 1 | 459 | 5 |
| 03-008 | 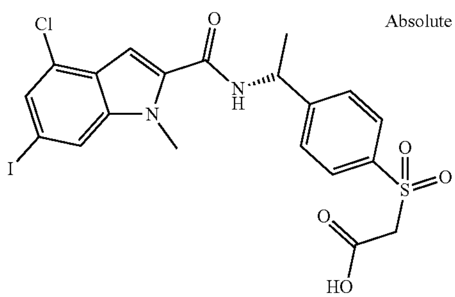 | Absolute | 1.08 | 561 | 5 |
| 03-009 | 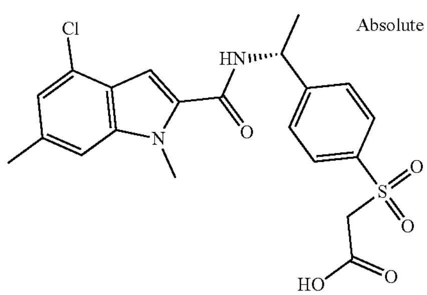 [SMILES: Cc1cc(Cl)c2cc(C(=O)N[C@H](C)c3ccc(S(=O)(=O)CC(=O)O)cc3)n(C)c2c1] | Absolute | 0.9 | 449 | 5 |
| 03-010 | 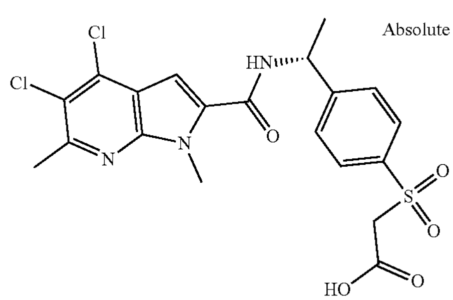 [SMILES: Cc1nc2c(cc(C(=O)N[C@H](C)c3ccc(S(=O)(=O)CC(=O)O)cc3)n2C)c(Cl)c1Cl] | Absolute | 1 | 484 | 5 |

-continued

| Example | Structure | | $t_{ret}$ [min] | M + H | HPLC Method |
|---|---|---|---|---|---|
| 03-011 | 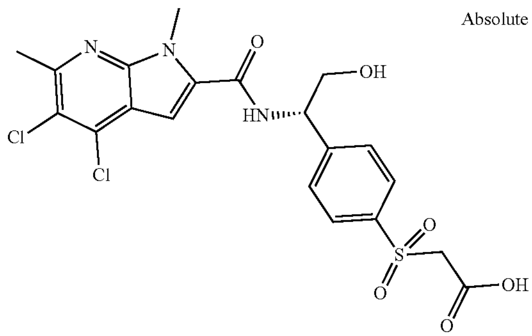 [SMILES: Cc1nc2c(cc(C(=O)N[C@H](CO)c3ccc(S(=O)(=O)CC(=O)O)cc3)n2C)c(Cl)c1Cl] | Absolute | 0.93 | 500 | 5 |
| 03-012 | 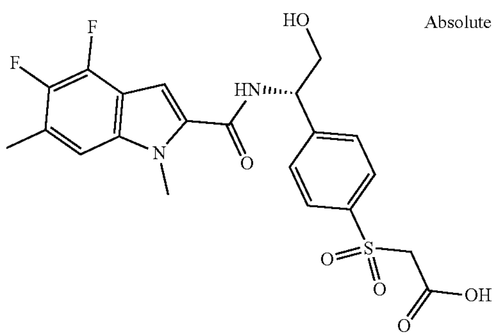 [SMILES: Cc1cc2c(cc(C(=O)N[C@H](CO)c3ccc(S(=O)(=O)CC(=O)O)cc3)n2C)c(F)c1F] | Absolute | 0.88 | 467 | 5 |
| 03-013 | 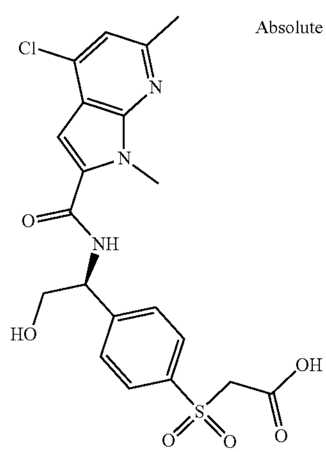 [SMILES: Cc1cc(Cl)c2cc(C(=O)N[C@H](CO)c3ccc(S(=O)(=O)CC(=O)O)cc3)n(C)c2n1] | Absolute | 0.83 | 466 | 5 |
| 03-014 | 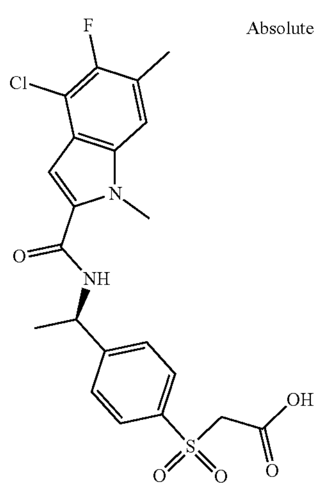 [SMILES: Cc1cc2c(cc(C(=O)N[C@H](C)c3ccc(S(=O)(=O)CC(=O)O)cc3)n2C)c(Cl)c1F] | Absolute | 1.03 | 467 | 5 |

-continued

| Example | Structure | | $t_{ret}$ [min] | M + H | HPLC Method |
|---|---|---|---|---|---|
| 03-015 | 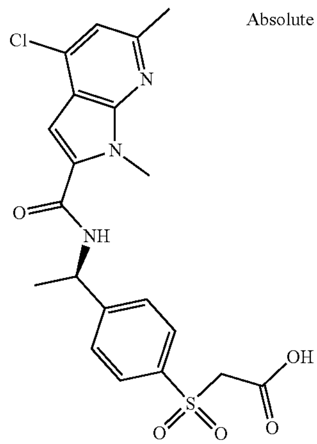 [SMILES: Cc1cc(Cl)c2cc(C(=O)N[C@H](C)c3ccc(S(=O)(=O)CC(=O)O)cc3)n(C)c2n1] | Absolute | 0.93 | 450 | 5 |
| 03-016 | 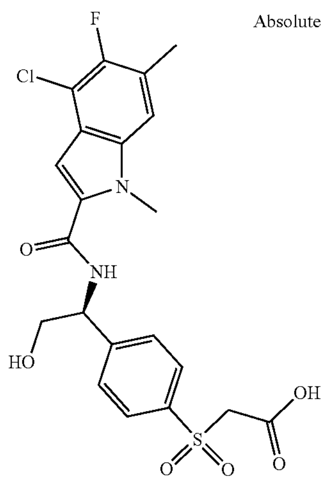 [SMILES: Cc1cc2c(cc(C(=O)N[C@H](CO)c3ccc(S(=O)(=O)CC(=O)O)cc3)n2C)c(Cl)c1F] | Absolute | 0.93 | 483 | 5 |
| 03-017 | 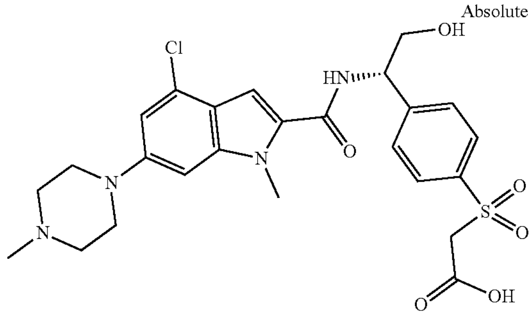 [SMILES: CN1CCN(c2cc(Cl)c3cc(C(=O)N[C@H](CO)c4ccc(S(=O)(=O)CC(=O)O)cc4)n(C)c3c2)CC1] | Absolute | 0.84 | 549 | 5 |
| 03-018 | 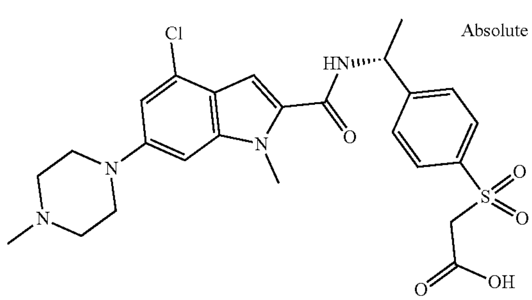 [SMILES: C[C@@H](NC(=O)c1cc2c(Cl)cc(N3CCN(C)CC3)cc2n1C)c1ccc(S(=O)(=O)CC(=O)O)cc1] | Absolute | 0.91 | 533 | 5 |

-continued
| Example | Structure | t_ret [min] | M + H | HPLC Method |
|---------|-----------|-------------|-------|-------------|
| 04-001 | 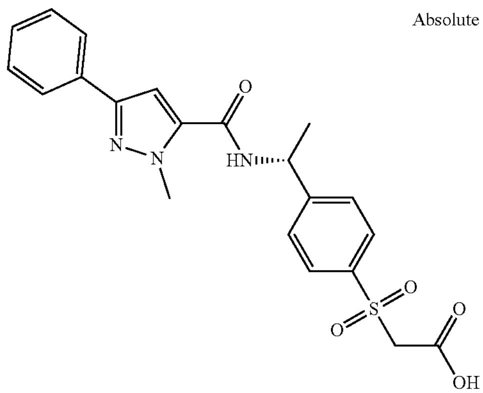 | 0.8 | 428 | 5 |
Absolute
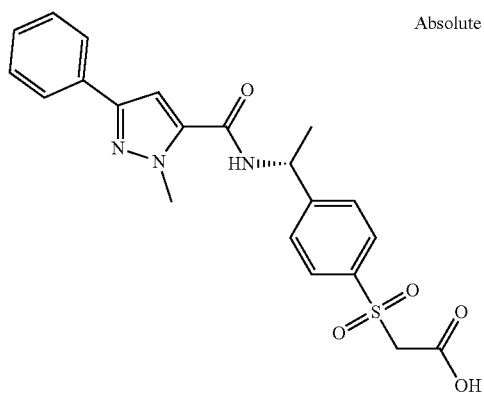 [SMILES: C[C@@H](NC(=O)c1cc(-c2ccccc2)nn1C)c1ccc(S(=O)(=O)CC(=O)O)cc1]
| 04-002 | | 0.88 | 446 | 5 |
Absolute
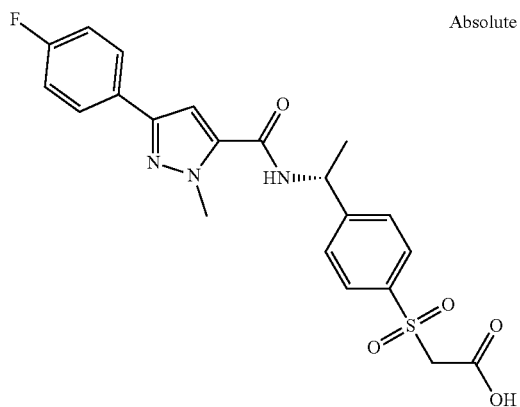 [SMILES: C[C@@H](NC(=O)c1cc(-c2ccc(F)cc2)nn1C)c1ccc(S(=O)(=O)CC(=O)O)cc1]

-continued
| Example | Structure | t_ret [min] | M + H | HPLC Method |
|---|---|---|---|---|
| 04-003 | 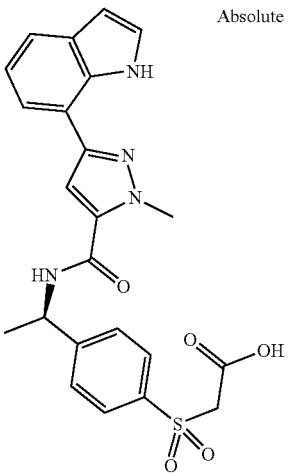 [SMILES: C[C@@H](NC(=O)c1cc(-c2cccc3cc[nH]c23)nn1C)c1ccc(S(=O)(=O)CC(=O)O)cc1] Absolute | 0.97 | 467 | 5 |
| 04-004 | 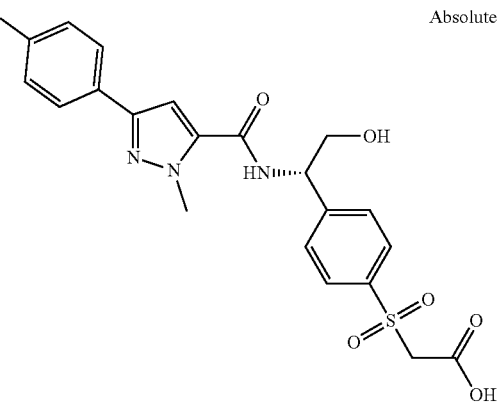 Absolute | 0.82 | 462 | 5 |
Synthesis of Examples 05-001-06-008
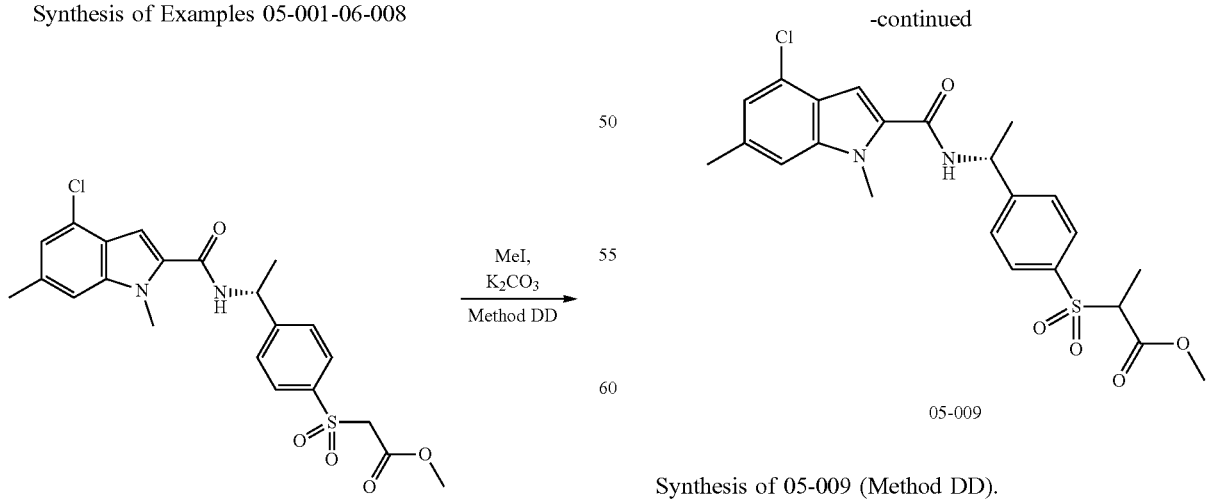
Synthesis of 05-009 (Method DD).
To 01-012 (244 mg, 0.54 mmol) and $K_2CO_3$ (83 mg, 0.60 mmol) in DMF (5 mL) methyl iodide (36 μL, 0.57 mmol) is added and stirred at ambient temperature overnight. The mixture is concentrated, water is added, and the aqueous layer is extracted exhaustively with EtOAc. The combined organic layer is washed with water, dried (MgSO₄), filtered and concentrated in vacuo.

The residue is purified by column chromatography or by RP-HPLC/MS.

The following branched sulfonyl acetic acids are prepared in an analogous manner.

| Example | Structure | Absolute | $t_{ret}$ [min] | M + H | M − H | HPLC Method |
|---|---|---|---|---|---|---|
| 05-001 | 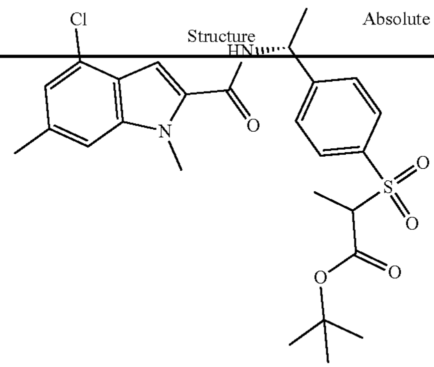 | Absolute | 1.57 | | 517 | 5 |
| 05-002 | 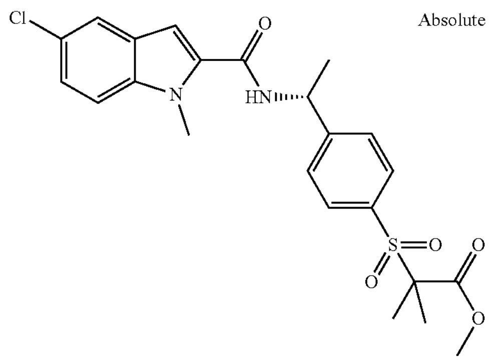 [SMILES: COC(=O)C(C)(C)S(=O)(=O)c1ccc([C@@H](C)NC(=O)c2cc3cc(Cl)ccc3n2C)cc1] | Absolute | 1.33 | 477 | | 5 |
| 05-003 | 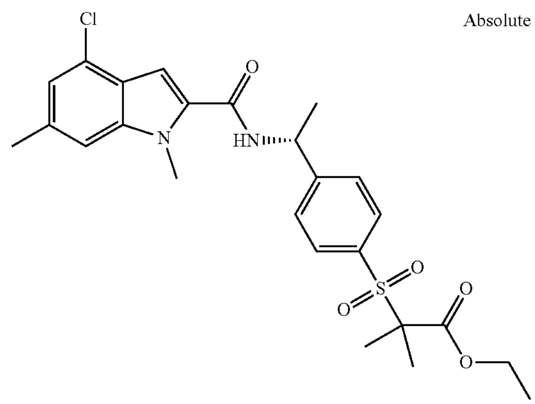 [SMILES: CCOC(=O)C(C)(C)S(=O)(=O)c1ccc([C@@H](C)NC(=O)c2cc3c(Cl)cc(C)cc3n2C)cc1] | Absolute | 1.54 | 505 | | 5 |
| 05-004 | 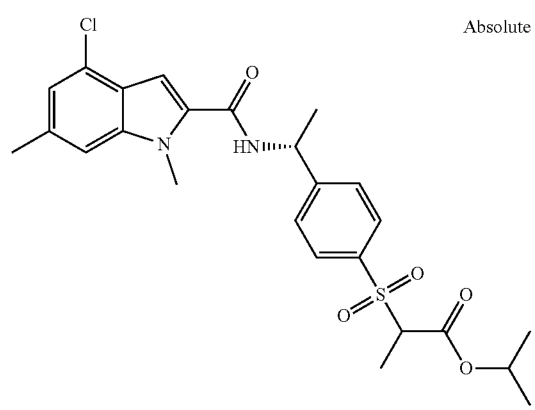 [SMILES: Cc1cc(Cl)c2cc(C(=O)N[C@H](C)c3ccc(S(=O)(=O)C(C)C(=O)OC(C)C)cc3)n(C)c2c1] | Absolute | 1.54 | 505 | | 5 |

-continued

| Example | Structure | | $t_{ret}$ [min] | M + H | M − H | HPLC Method |
|---|---|---|---|---|---|---|
| 05-005 | 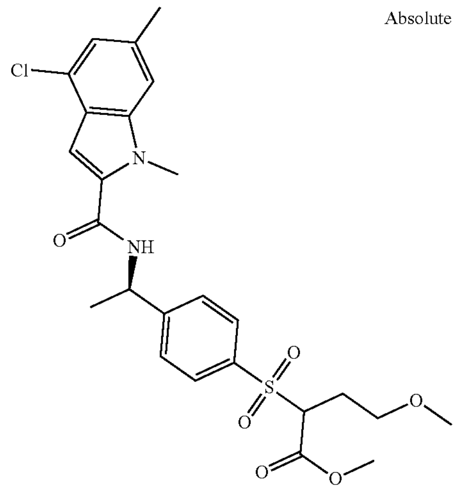 [SMILES: COCCC(C(=O)OC)S(=O)(=O)c1ccc([C@@H](C)NC(=O)c2cc3c(Cl)cc(C)cc3n2C)cc1] | Absolute | 1.46 | 521 | | 5 |
| 05-006 | 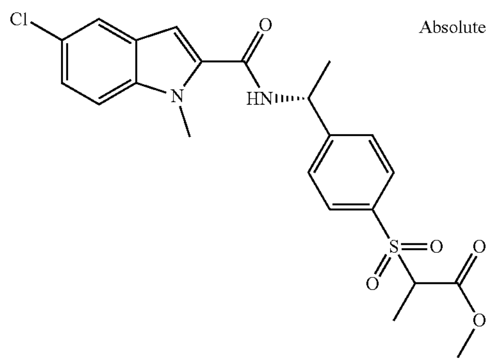 [SMILES: COC(=O)C(C)S(=O)(=O)c1ccc([C@@H](C)NC(=O)c2cc3cc(Cl)ccc3n2C)cc1] | Absolute | 1.29 | 463 | | 5 |
| 05-007 | 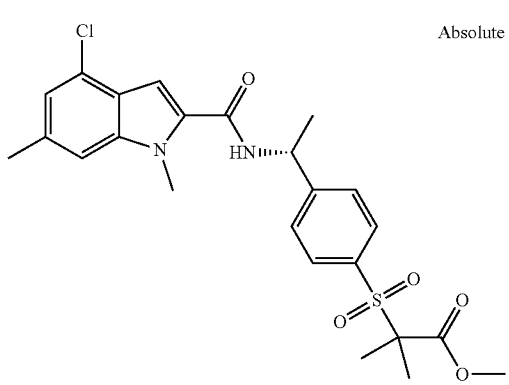 | Absolute | 1.49 | 491 | | 5 |

| Example | Structure | | $t_{ret}$ [min] | M + H | M − H | HPLC Method |
|---|---|---|---|---|---|---|
| 05-008 | 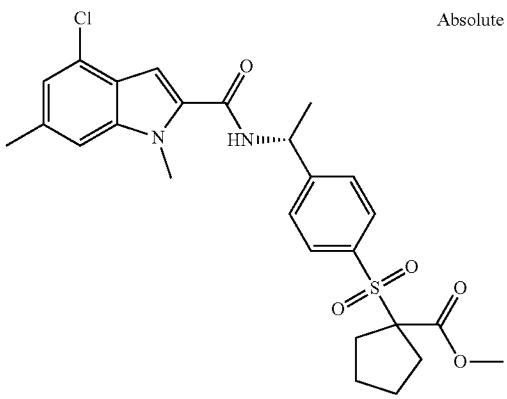 | Absolute | 1.57 | 517 | | 5 |
| 05-009 | 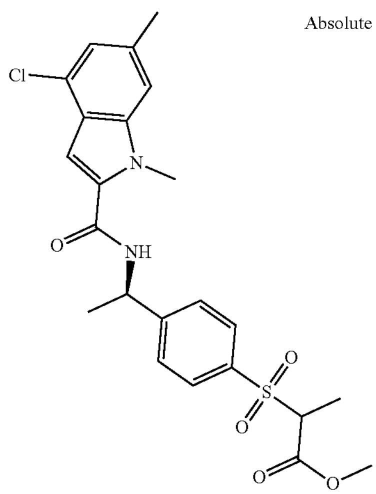 [SMILES: COC(=O)C(C)S(=O)(=O)c1ccc([C@@H](C)NC(=O)c2cc3c(Cl)cc(C)cc3n2C)cc1] | Absolute | 1.43 | 477 | | 5 |
| 05-010 | 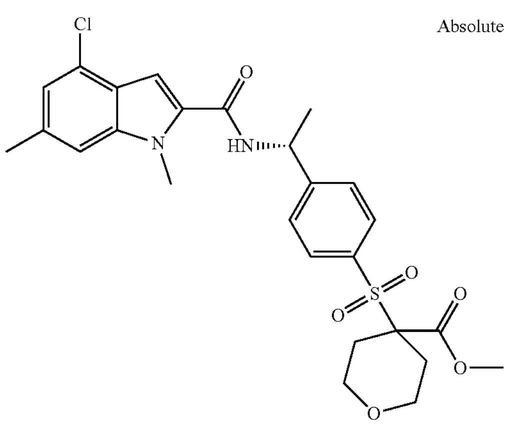 | Absolute | 1.47 | 533 | | 5 |

| Example | Structure | | $t_{ret}$ [min] | M + H | M − H | HPLC Method |
|---|---|---|---|---|---|---|
| 05-011 | 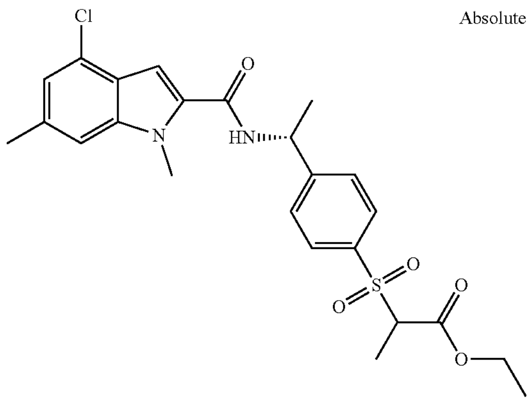 [SMILES: CCOC(=O)C(C)S(=O)(=O)c1ccc([C@@H](C)NC(=O)c2cc3c(Cl)cc(C)cc3n2C)cc1] | Absolute | 1.49 | 491 | | 5 |
| 05-012 | 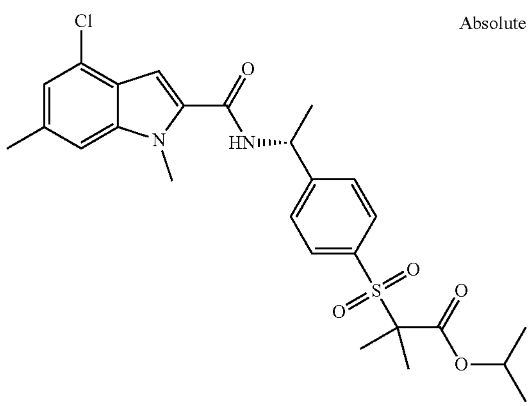 [SMILES: Cc1cc(Cl)c2cc(C(=O)N[C@H](C)c3ccc(S(=O)(=O)C(C)(C)C(=O)OC(C)C)cc3)n(C)c2c1] | Absolute | 1.58 | 519 | | 5 |
| 05-013 | 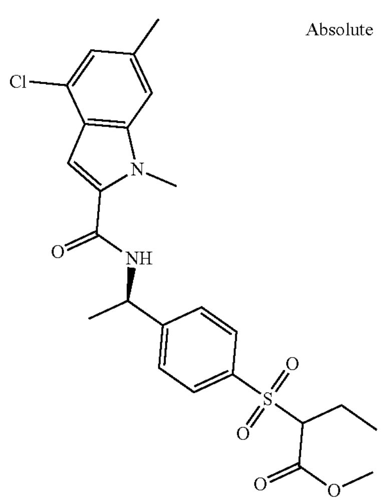 [SMILES: CCC(C(=O)OC)S(=O)(=O)c1ccc([C@@H](C)NC(=O)c2cc3c(Cl)cc(C)cc3n2C)cc1] | Absolute | 1.5 | 491 | | 5 |

| Example | Structure | $t_{ret}$ [min] | M + H | M − H | HPLC Method |
|---|---|---|---|---|---|
| 05-014 | Absolute | 1.63 | 477 | | 5 |
| 05-015 | Absolute | 1.54 | 505 | | 5 |
| 05-016 | Absolute | 1.58 | 540 | | 5 |

| Example | Structure | | $t_{ret}$ [min] | M + H | M − H | HPLC Method |
|---|---|---|---|---|---|---|
| 05-017 | 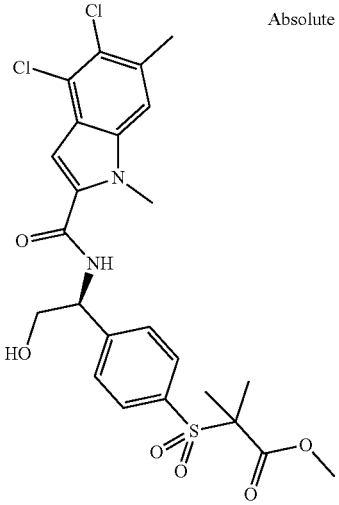 [SMILES: COC(=O)C(C)(C)S(=O)(=O)c1ccc([C@@H](CO)NC(=O)c2cc3c(Cl)c(Cl)c(C)cc3n2C)cc1] | Absolute | 1.4 | 541 | | 5 |
| 05-018 | 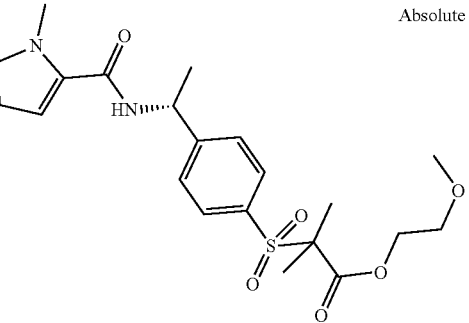 | Absolute | 1.52 | 570 | | 5 |
| 05-019 | 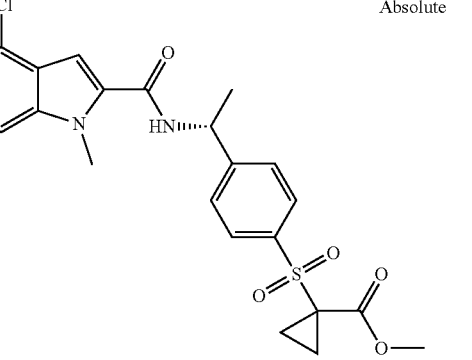 | Absolute | 1.47 | 489 | | 5 |
| 05-020 | 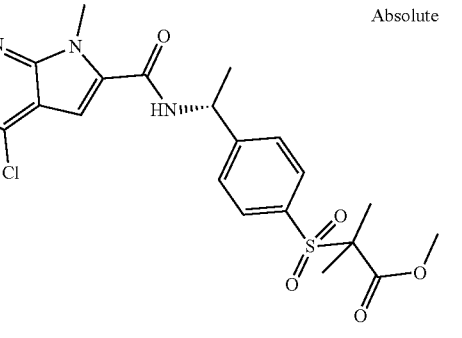 | Absolute | 1.52 | 526 | | 5 |

-continued
| Example | Structure | | t_ret [min] | M + H | M − H | HPLC Method |
|---|---|---|---|---|---|---|
| 05-021 | 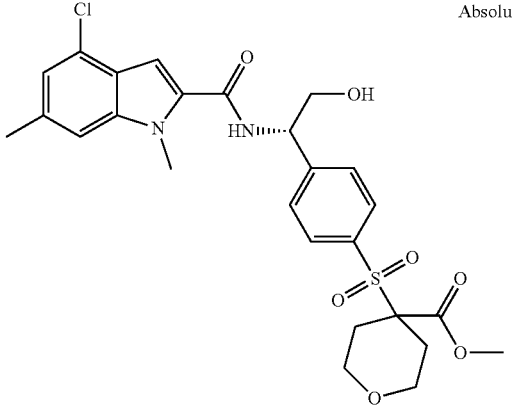 | Absolute | 1.3 | 549 | | 5 |
| 05-022 | 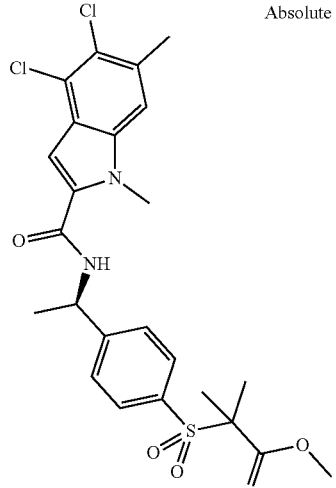 | Absolute | 1.56 | 525 | | 5 |
| 05-023 | 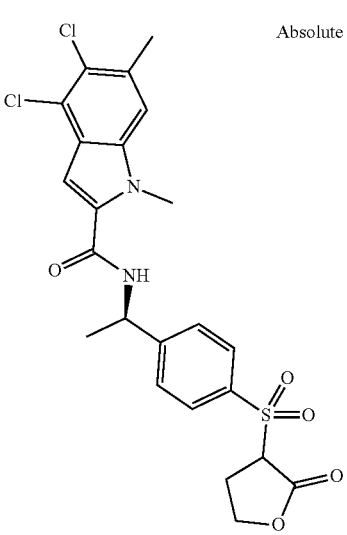 [SMILES: Cc1cc2c(cc(C(=O)N[C@H](C)c3ccc(S(=O)(=O)C4CCOC4=O)cc3)n2C)c(Cl)c1Cl] | Absolute | 1.47 | 509 | | 5 |

| Example | Structure | | $t_{ret}$ [min] | M + H | M − H | HPLC Method |
|---|---|---|---|---|---|---|
| 05-024 | 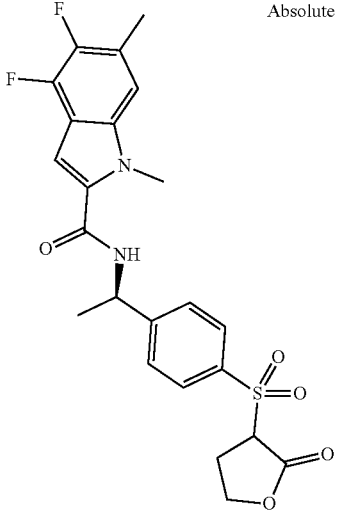 [SMILES: Cc1cc2c(cc(C(=O)N[C@H](C)c3ccc(S(=O)(=O)C4CCOC4=O)cc3)n2C)c(F)c1F] | Absolute | 1.35 | 477 | | 5 |
| 05-025 | 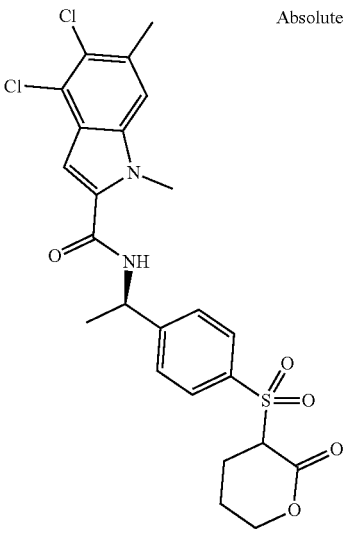 [SMILES: Cc1cc2c(cc(C(=O)N[C@H](C)c3ccc(S(=O)(=O)C4CCCOC4=O)cc3)n2C)c(Cl)c1Cl] | Absolute | 1.47 | 523 | | 5 |
| 06-001 | 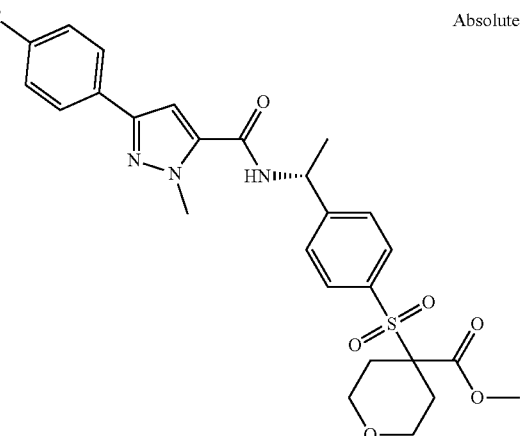 | Absolute | 1.3 | 530 | | 5 |

|Example|Structure| |$t_{ret}$ [min]|M + H|M − H|HPLC Method|
|---|---|---|---|---|---|---|
|06-002|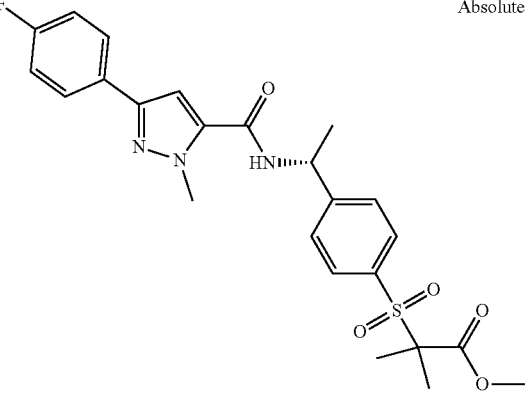|Absolute|1.33|488| |5|
|06-003|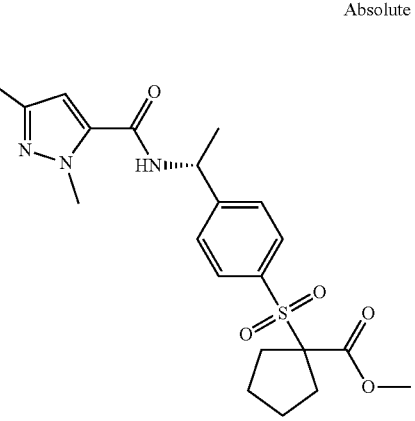|Absolute|1.4|514| |5|
|06-004|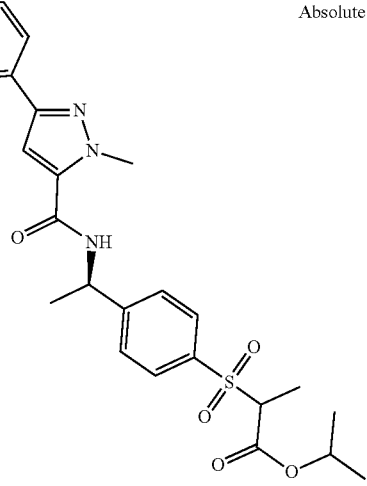|Absolute|1.35|484| |5|

| Example | Structure | | $t_{ret}$ [min] | M + H | M − H | HPLC Method |
|---|---|---|---|---|---|---|
| 06-005 | 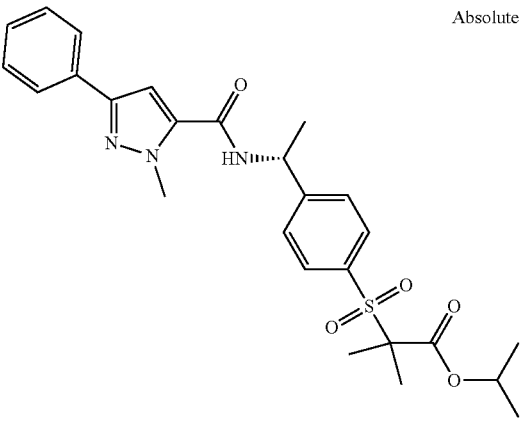 [SMILES: CC(C)OC(=O)C(C)(C)S(=O)(=O)c1ccc([C@@H](C)NC(=O)c2cc(-c3ccccc3)nn2C)cc1] | Absolute | 1.4 | 498 | | 5 |
| 06-006 | 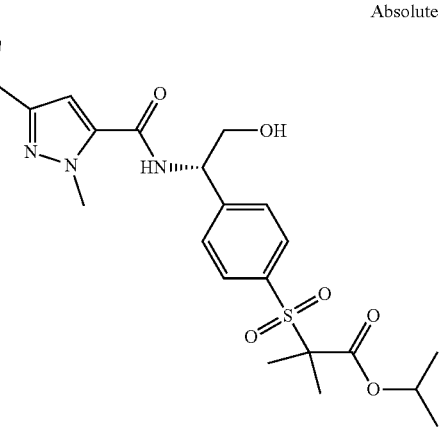 | Absolute | 1.29 | 532 | | 5 |
| 06-007 | 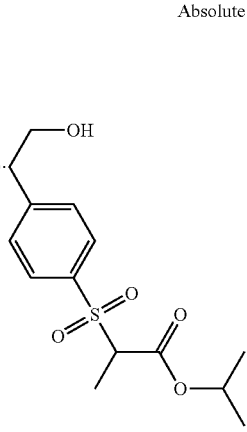 | Absolute | 1.24 | 518 | | 5 |

-continued
| Example | Structure | | $t_{ret}$ [min] | M + H | M − H | HPLC Method |
|---|---|---|---|---|---|---|
| 06-008 | 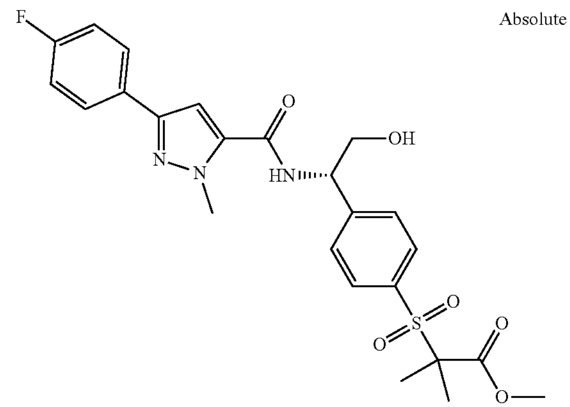 [SMILES: COC(=O)C(C)(C)S(=O)(=O)c1ccc([C@@H](CO)NC(=O)c2cc(-c3ccc(F)cc3)nn2C)cc1] | Absolute | 1.18 | 504 | | 5 |
Synthesis of Examples 07-001-08-003
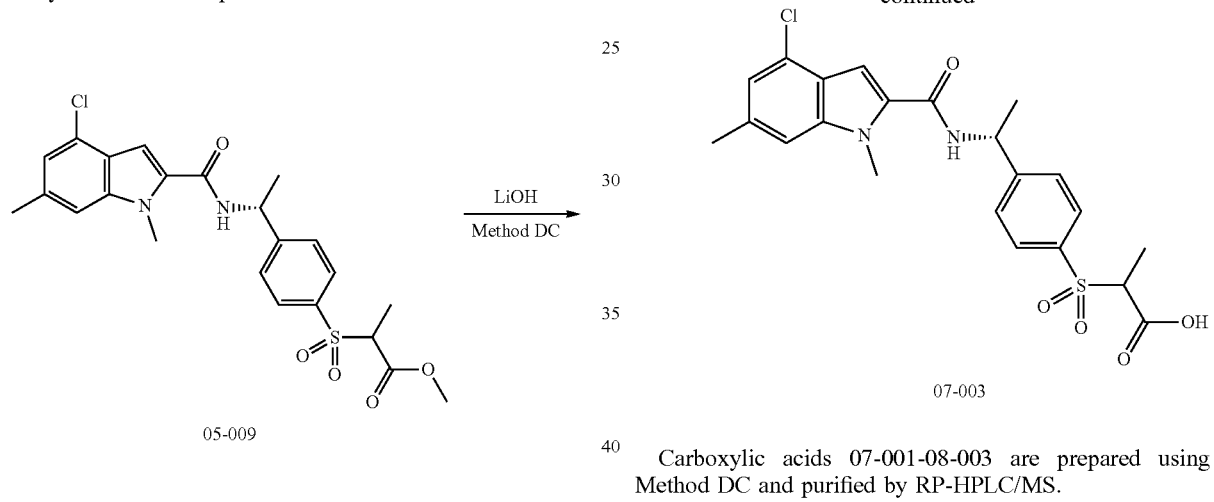
Carboxylic acids 07-001-08-003 are prepared using Method DC and purified by RP-HPLC/MS.
| Example | Structure | | $t_{ret}$ [min] | M + H | HPLC Method |
|---|---|---|---|---|---|
| 07-001 | 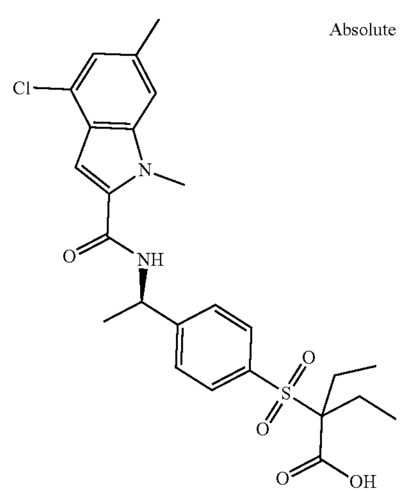 [SMILES: CCC(CC)(C(=O)O)S(=O)(=O)c1ccc([C@@H](C)NC(=O)c2cc3c(Cl)cc(C)cc3n2C)cc1] | Absolute | 1.07 | 505 | 5 |

-continued
| Example | Structure | | $t_{ret}$ [min] | M + H | HPLC Method |
|---|---|---|---|---|---|
| 07-002 | 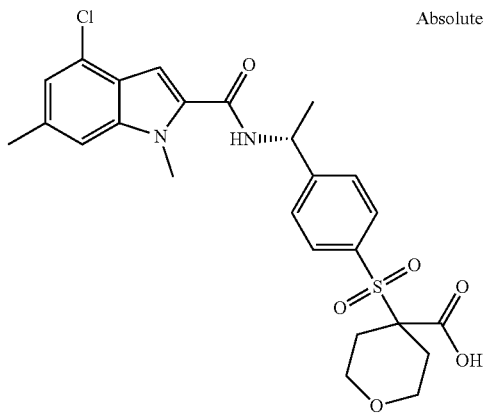 [SMILES: Cc1cc(Cl)c2cc(C(=O)N[C@H](C)c3ccc(S(=O)(=O)C4(C(=O)O)CCOCC4)cc3)n(C)c2c1] | Absolute | 1.01 | 519 | 5 |
| 07-003 | 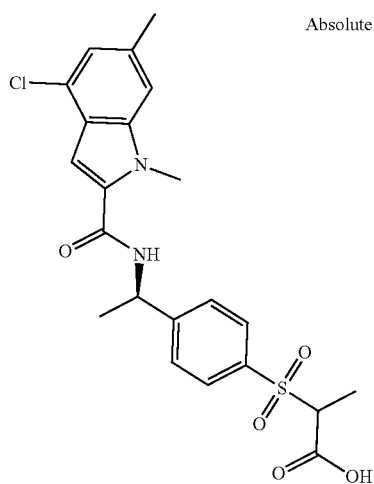 [SMILES: Cc1cc(Cl)c2cc(C(=O)N[C@H](C)c3ccc(S(=O)(=O)C(C)C(=O)O)cc3)n(C)c2c1] | Absolute | 1.01 | 463 | 5 |
| 07-004 | 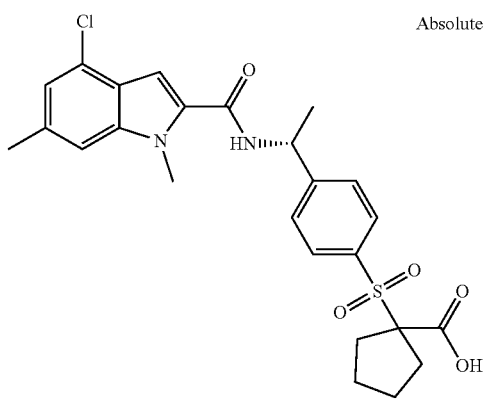 [SMILES: Cc1cc(Cl)c2cc(C(=O)N[C@H](C)c3ccc(S(=O)(=O)C4(C(=O)O)CCCC4)cc3)n(C)c2c1] | Absolute | 1.05 | 503 | 5 |

-continued

| Example | Structure | | $t_{ret}$ [min] | M + H | HPLC Method |
|---|---|---|---|---|---|
| 07-005 | (structure) | Absolute | 1.02 | 477 | 5 |
| 07-006 | (structure) | Absolute | 0.97 | 449 | 5 |
| 07-007 | (structure) | Absolute | 0.93 | 463 | 5 |
| 07-008 | (structure) | Absolute | 0.97 | 449 | 5 |

-continued
| Example | Structure | | $t_{ret}$ [min] | M + H | HPLC Method |
|---|---|---|---|---|---|
| 07-009 | 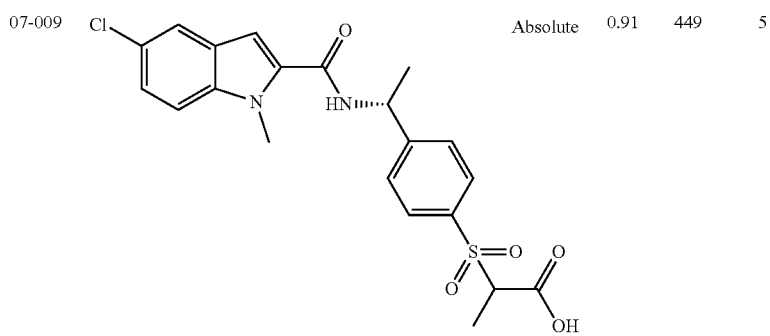 | Absolute | 0.91 | 449 | 5 |
| 07-010 | 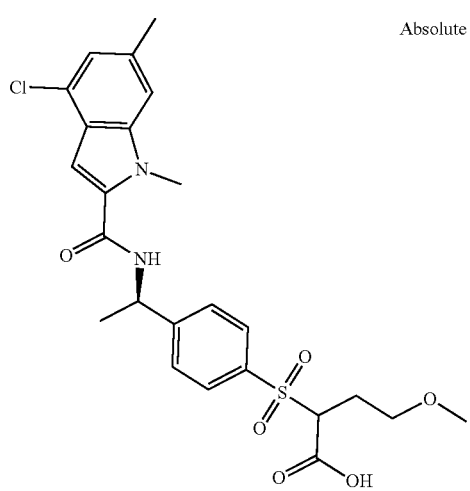 [SMILES: COCCC(C(=O)O)S(=O)(=O)c1ccc([C@@H](C)NC(=O)c2cc3c(Cl)cc(C)cc3n2C)cc1] | Absolute | 1.03 | 507 | 5 |
| 07-011 | 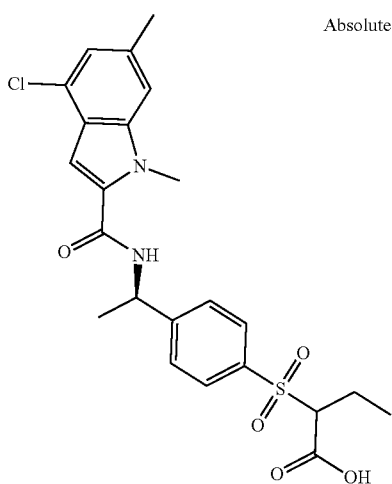 [SMILES: CCC(C(=O)O)S(=O)(=O)c1ccc([C@@H](C)NC(=O)c2cc3c(Cl)cc(C)cc3n2C)cc1] | Absolute | 1.03 | 477 | 5 |

-continued

| Example | Structure | | t_ret [min] | M + H | HPLC Method |
|---------|-----------|---|-------------|-------|-------------|
| 07-012 | 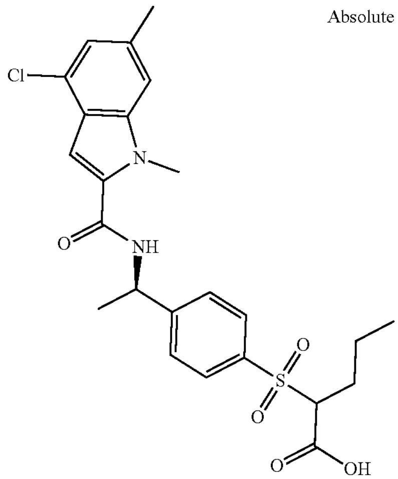 [SMILES: CCCC(C(=O)O)S(=O)(=O)c1ccc([C@@H](C)NC(=O)c2cc3c(Cl)cc(C)cc3n2C)cc1] | Absolute | 1.05 | 491 | 5 |
| 07-013 | 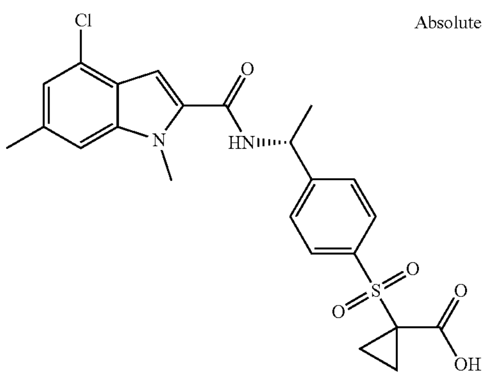 [SMILES: Cc1cc(Cl)c2cc(C(=O)N[C@H](C)c3ccc(S(=O)(=O)C4(C(=O)O)CC4)cc3)n(C)c2c1] | Absolute | 1.02 | 475 | 5 |
| 07-014 | 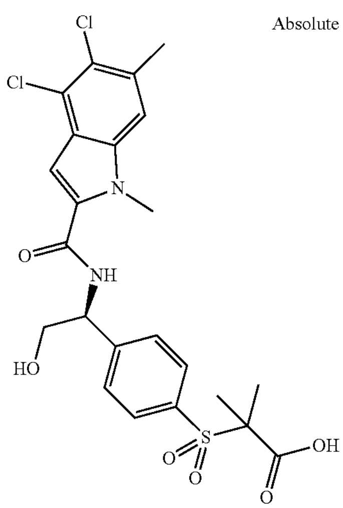 [SMILES: Cc1cc2c(cc(C(=O)N[C@H](CO)c3ccc(S(=O)(=O)C(C)(C)C(=O)O)cc3)n2C)c(Cl)c1Cl] | Absolute | 0.99 | 527 | 5 |

-continued

| Example | Structure | | $t_{ret}$ [min] | M + H | HPLC Method |
|---|---|---|---|---|---|
| 07-015 | (structure) | Absolute | 1.1 | 511 | 5 |
| 07-016 | (structure) | Absolute | 1.09 | 594 | 5 |
| 08-001 | (structure) | Absolute | 0.89 | 474 | 5 |

| Example | Structure | $t_{ret}$ [min] | M + H | HPLC Method |
|---|---|---|---|---|
| 08-002 | Absolute | 0.93 | 500 | 5 |
| 08-003 | Absolute | 0.89 | 516 | 5 |

Syntheses of Esters derived from Structurally Diverse Alcohols 09-001-10-007

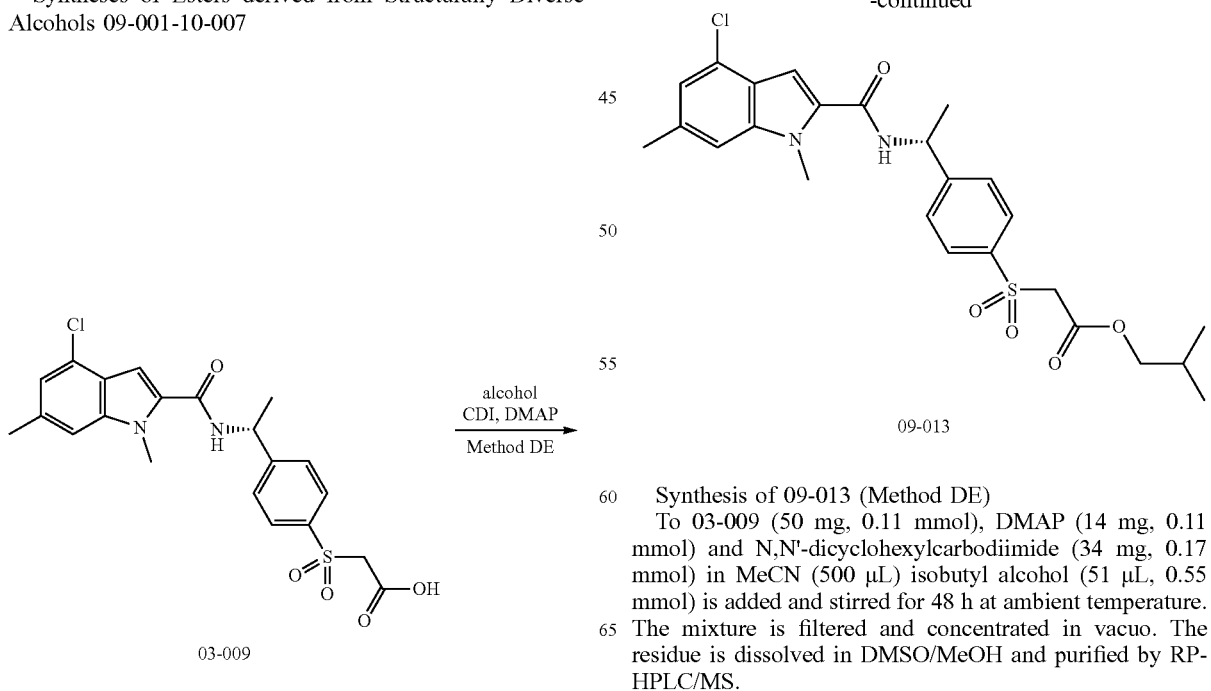

Synthesis of 09-013 (Method DE)

To 03-009 (50 mg, 0.11 mmol), DMAP (14 mg, 0.11 mmol) and N,N'-dicyclohexylcarbodiimide (34 mg, 0.17 mmol) in MeCN (500 μL) isobutyl alcohol (51 μL, 0.55 mmol) is added and stirred for 48 h at ambient temperature. The mixture is filtered and concentrated in vacuo. The residue is dissolved in DMSO/MeOH and purified by RP-HPLC/MS.

The following sulfonyl acetates are prepared in an analogous manner.
| Example | Structure | $t_{ret}$ [min] | M + H | M − H | HPLC Method |
|---|---|---|---|---|---|
| 09-001 | 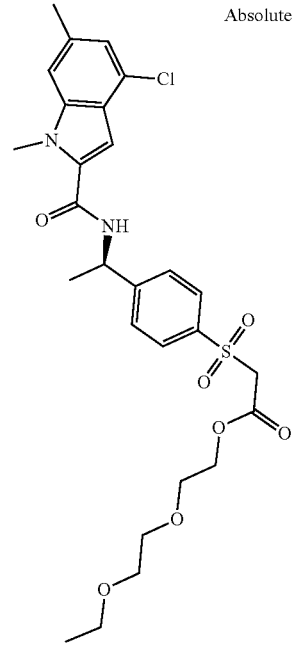 [SMILES: CCOCCOCCOC(=O)CS(=O)(=O)c1ccc([C@@H](C)NC(=O)c2cc3c(Cl)cc(C)cc3n2C)cc1] Absolute | 1.46 | 565 | | 5 |
| 09-002 | 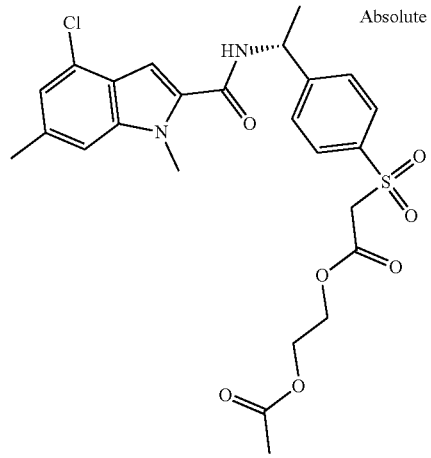 [SMILES: CC(=O)OCCOC(=O)CS(=O)(=O)c1ccc([C@@H](C)NC(=O)c2cc3c(Cl)cc(C)cc3n2C)cc1] Absolute | 1.42 | 535 | | 5 |
| 09-003 | 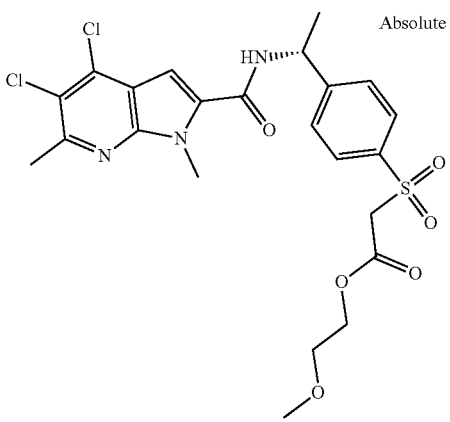 [SMILES: COCCOC(=O)CS(=O)(=O)c1ccc([C@@H](C)NC(=O)c2cc3c(Cl)c(Cl)c(C)nc3n2C)cc1] Absolute | 1.45 | 542 | | 5 |

| | | | | | |
|---|---|---|---|---|---|
| 09-004 | 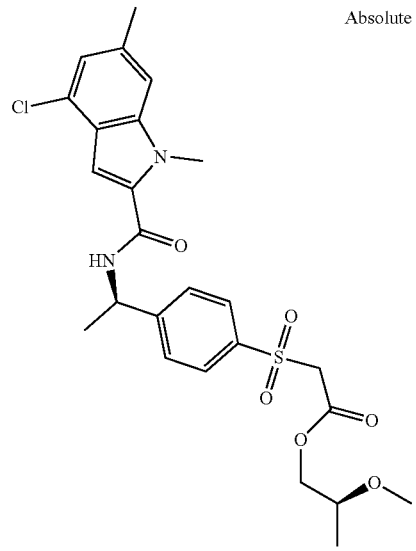 [SMILES: CO[C@@H](C)COC(=O)CS(=O)(=O)c1ccc([C@@H](C)NC(=O)c2cc3c(Cl)cc(C)cc3n2C)cc1] | Absolute | 1.46 | 521 | 5 |
| 09-005 | 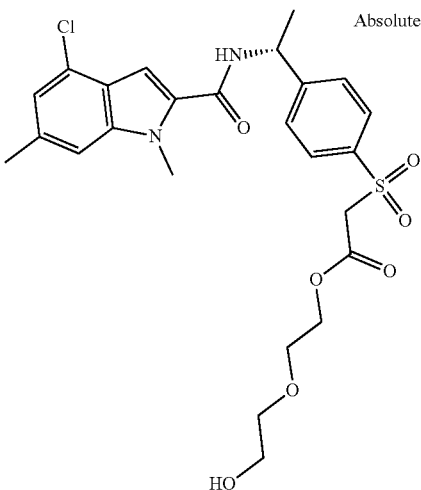 [SMILES: Cc1cc(Cl)c2cc(C(=O)N[C@H](C)c3ccc(S(=O)(=O)CC(=O)OCCOCCO)cc3)n(C)c2c1] | Absolute | 1.3 | 537 | 5 |
| 09-006 | 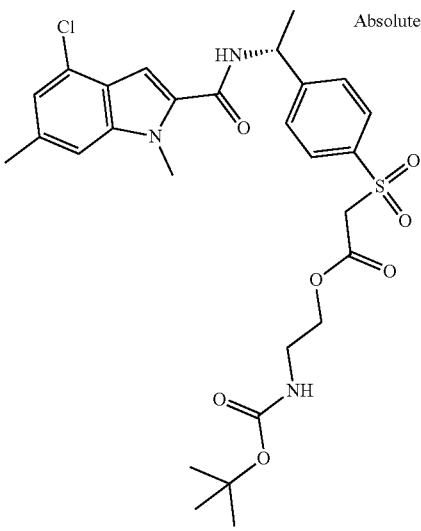 [SMILES: Cc1cc(Cl)c2cc(C(=O)N[C@H](C)c3ccc(S(=O)(=O)CC(=O)OCCNC(=O)OC(C)(C)C)cc3)n(C)c2c1] | Absolute | 1.54 | 492 | 5 |

| | | | | | |
|---|---|---|---|---|---|
| 09-007 | 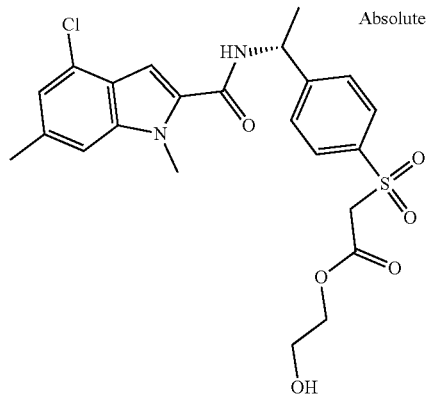 [SMILES: Cc1cc(Cl)c2cc(C(=O)N[C@H](C)c3ccc(S(=O)(=O)CC(=O)OCCO)cc3)n(C)c2c1] | Absolute | 1.29 | 493 | 5 |
| 09-008 | 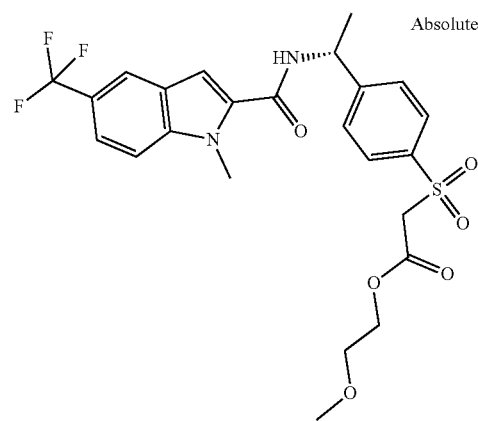 [SMILES: COCCOC(=O)CS(=O)(=O)c1ccc([C@@H](C)NC(=O)c2cc3cc(C(F)(F)F)ccc3n2C)cc1] | Absolute | 1.36 | 527 | 5 |
| 09-009 | 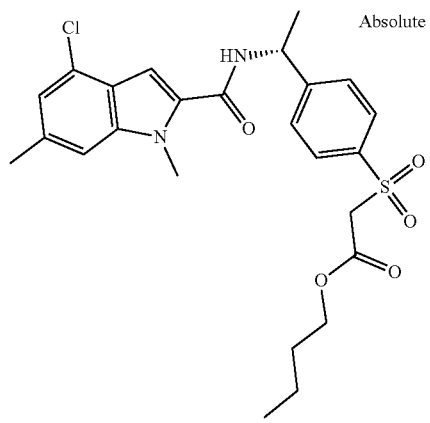 [SMILES: CCCCOC(=O)CS(=O)(=O)c1ccc([C@@H](C)NC(=O)c2cc3c(Cl)cc(C)cc3n2C)cc1] | Absolute | 1.56 | 505 | 5 |
| 09-010 | 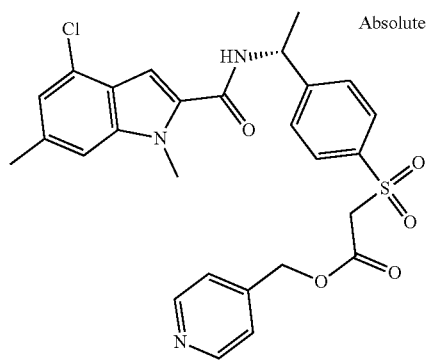 [SMILES: Cc1cc(Cl)c2cc(C(=O)N[C@H](C)c3ccc(S(=O)(=O)CC(=O)OCc4ccncc4)cc3)n(C)c2c1] | Absolute | 1.37 | 540 | 5 |

-continued
| | | | | | |
|---|---|---|---|---|---|
| 09-011 | 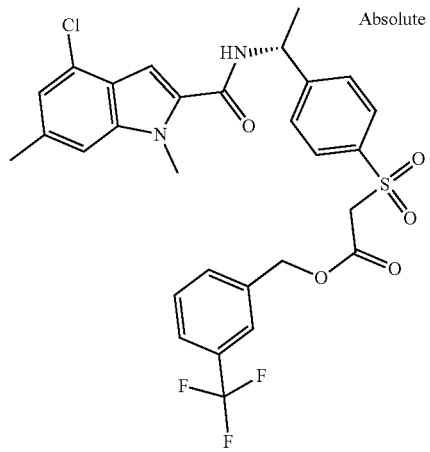 [SMILES: Cc1cc(Cl)c2cc(C(=O)N[C@H](C)c3ccc(S(=O)(=O)CC(=O)OCc4cccc(C(F)(F)F)c4)cc3)n(C)c2c1] | Absolute | 1.63 | 607 | 5 |
| 09-012 | 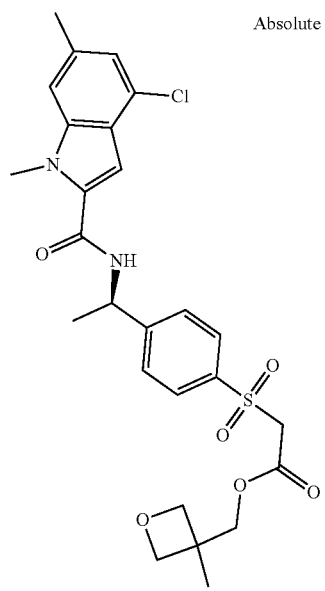 [SMILES: Cc1cc(Cl)c2cc(C(=O)N[C@H](C)c3ccc(S(=O)(=O)CC(=O)OCC4(C)COC4)cc3)n(C)c2c1] | Absolute | 1.41 | 533 | 5 |
| 09-013 | 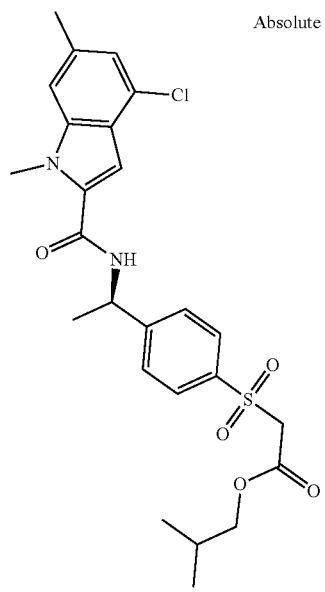 [SMILES: Cc1cc(Cl)c2cc(C(=O)N[C@H](C)c3ccc(S(=O)(=O)CC(=O)OCC(C)C)cc3)n(C)c2c1] | Absolute | 1.57 | 505 | 5 |

| | | | | | |
|---|---|---|---|---|---|
| 09-014 | 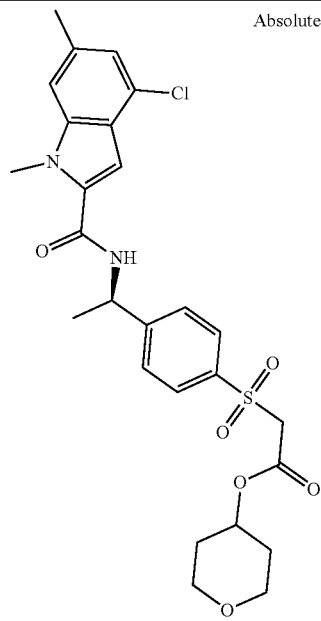 | Absolute | 1.42 | 533 | 5 |
| 09-015 | 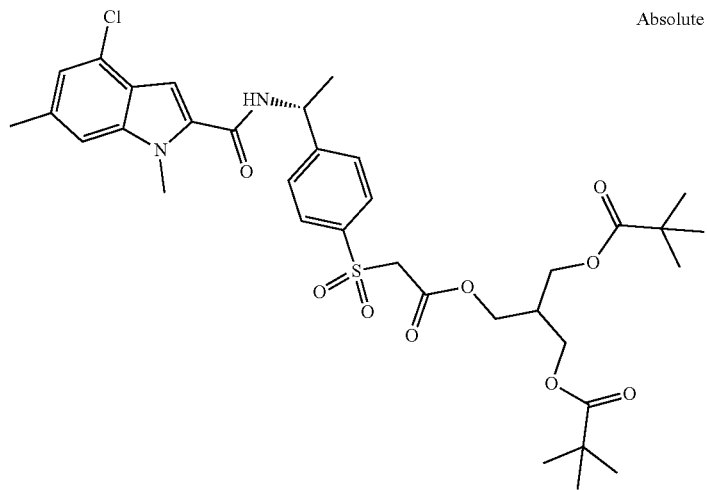 [SMILES: Cc1cc(Cl)c2cc(C(=O)N[C@H](C)c3ccc(S(=O)(=O)CC(=O)OCC(COC(=O)C(C)(C)C)COC(=O)C(C)(C)C)cc3)n(C)c2c1] | Absolute | 1.77 | 705 | 5 |
| 09-016 | 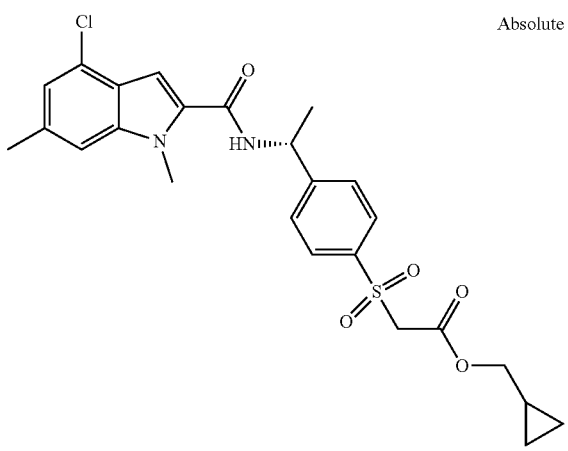 [SMILES: Cc1cc(Cl)c2cc(C(=O)N[C@H](C)c3ccc(S(=O)(=O)CC(=O)OCC4CC4)cc3)n(C)c2c1] | Absolute | 1.51 | 503 | 5 |

| | | | | | |
|---|---|---|---|---|---|
| 09-017 | 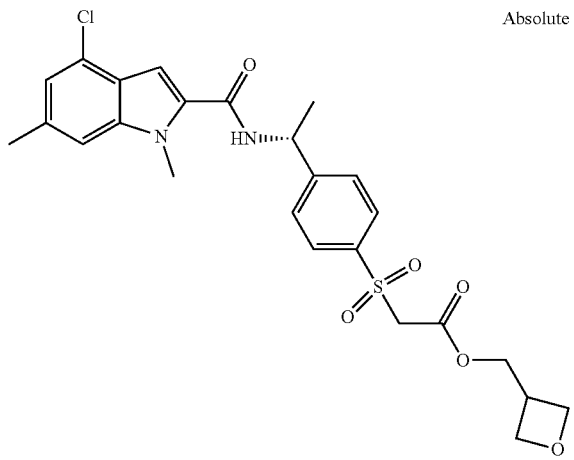 [SMILES: Cc1cc(Cl)c2cc(C(=O)N[C@H](C)c3ccc(S(=O)(=O)CC(=O)OCC4COC4)cc3)n(C)c2c1] | Absolute | 1.37 | 519 | 5 |
| 09-018 | 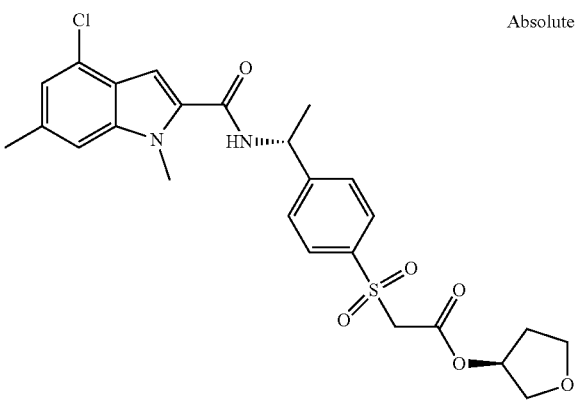 [SMILES: Cc1cc(Cl)c2cc(C(=O)N[C@H](C)c3ccc(S(=O)(=O)CC(=O)O[C@H]4CCOC4)cc3)n(C)c2c1] | Absolute | 1.4 | 519 | 5 |
| 09-019 | 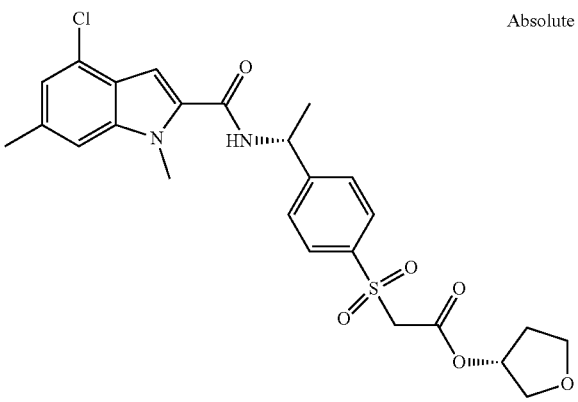 [SMILES: Cc1cc(Cl)c2cc(C(=O)N[C@H](C)c3ccc(S(=O)(=O)CC(=O)O[C@@H]4CCOC4)cc3)n(C)c2c1] | Absolute | 1.4 | 519 | 5 |

-continued
| 09-020 | 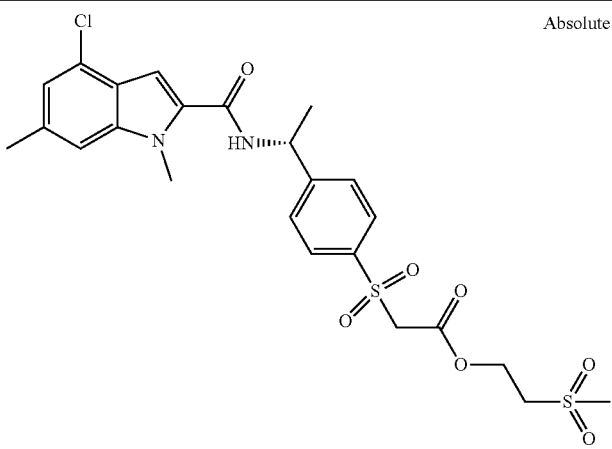 | Absolute | 1.3 | 555 | 5 |
| 09-021 | 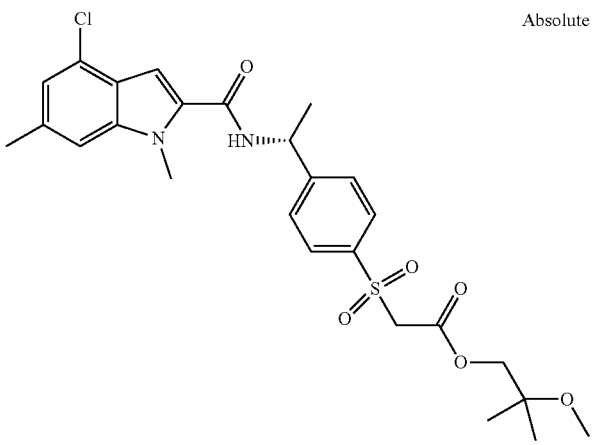 | Absolute | 1.48 | 557 (M + Na) | 5 |
| 09-022 | 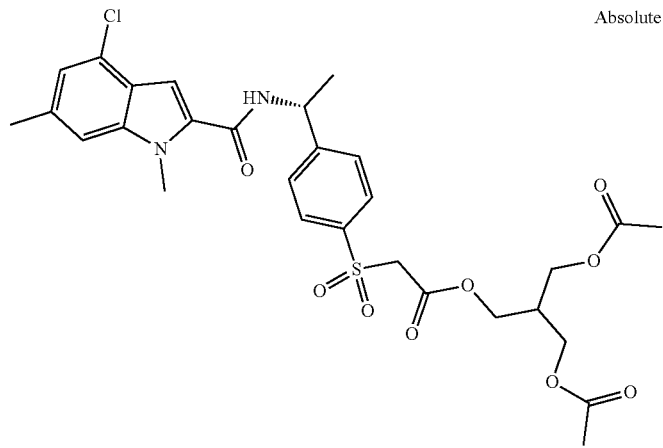 [SMILES: CC(=O)OCC(COC(C)=O)COC(=O)CS(=O)(=O)c1ccc([C@@H](C)NC(=O)c2cc3c(Cl)cc(C)cc3n2C)cc1] | Absolute | 1.47 | 621 | 5 |

-continued
| | | | | | |
|---|---|---|---|---|---|
| 09-023 | 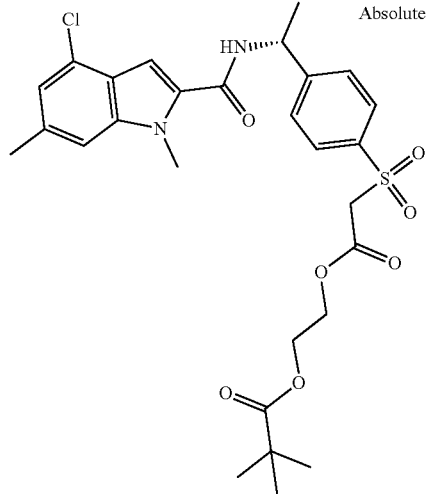 [SMILES: Cc1cc(Cl)c2cc(C(=O)N[C@H](C)c3ccc(S(=O)(=O)CC(=O)OCCOC(=O)C(C)(C)C)cc3)n(C)c2c1] | Absolute | 1.58 | 577 | 5 |
| 09-024 | | | 1.35 | 577 | 5 |
| 09-025 | | Absolute | 1.38 | 505 | 5 |

-continued

| | | | | | |
|---|---|---|---|---|---|
| 09-026 | | Absolute | 1.5 | 621 | 5 |
| 09-027 | | Absolute | 1.23 | 537 | 5 |
| 09-028 | | Absolute | 1.24 | 547 | 5 |
| 09-029 | | Absolute | 1.22 | 520 | 5 |

| | | | | | |
|---|---|---|---|---|---|
| 09-030 | 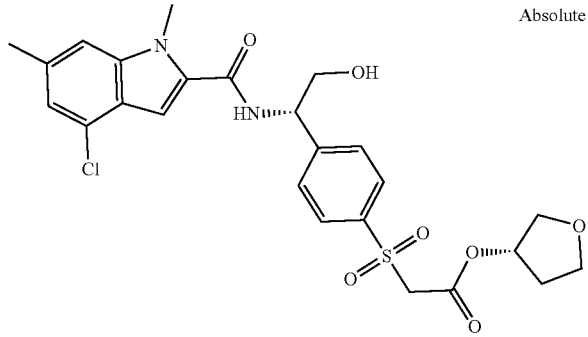 [SMILES: Cc1cc(Cl)c2cc(C(=O)N[C@H](CO)c3ccc(S(=O)(=O)CC(=O)O[C@H]4CCOC4)cc3)n(C)c2c1] | Absolute | 1.21 | 535 | 5 |
| 09-031 | 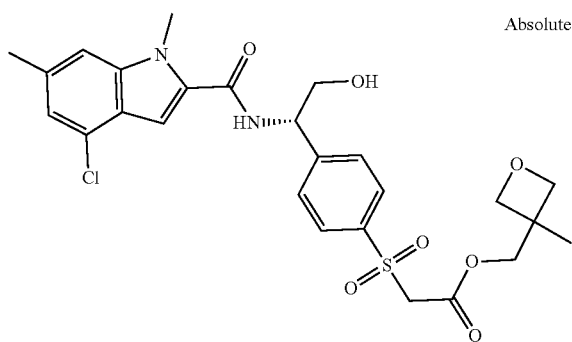 | Absolute | 1.23 | 549 | 5 |
| 09-032 | 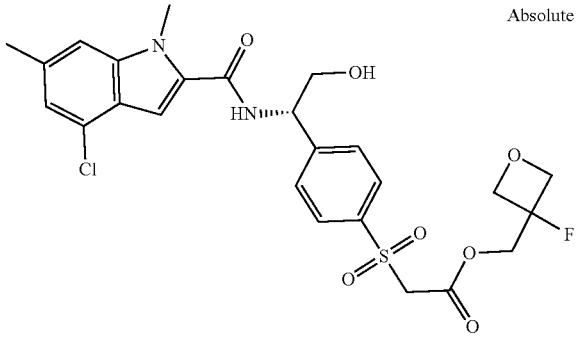 [SMILES: Cc1cc(Cl)c2cc(C(=O)N[C@H](CO)c3ccc(S(=O)(=O)CC(=O)OCC4(F)COC4)cc3)n(C)c2c1] | Absolute | 1.23 | 533 | 5 |
| 09-033 | 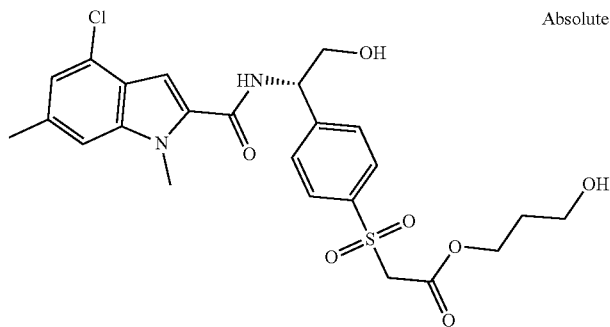 [SMILES: Cc1cc(Cl)c2cc(C(=O)N[C@H](CO)c3ccc(S(=O)(=O)CC(=O)OCCCO)cc3)n(C)c2c1] | Absolute | 1.15 | 523 | 5 |

| | | | | | |
|---|---|---|---|---|---|
| 09-034 | 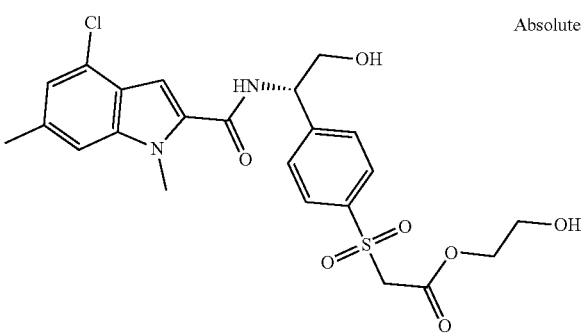 [SMILES: Cc1cc(Cl)c2cc(C(=O)N[C@H](CO)c3ccc(S(=O)(=O)CC(=O)OCCO)cc3)n(C)c2c1] | Absolute | 1.13 | 509 | 5 |
| 09-035 | 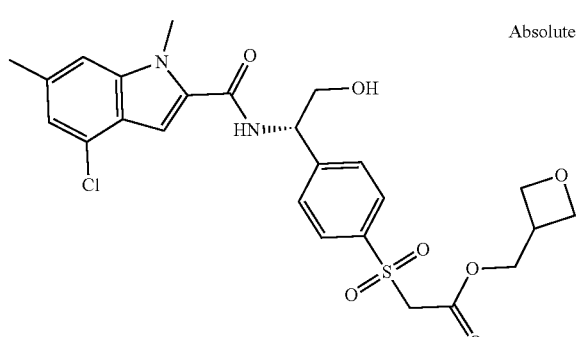 | Absolute | 1.19 | 535 | 5 |
| 09-036 | 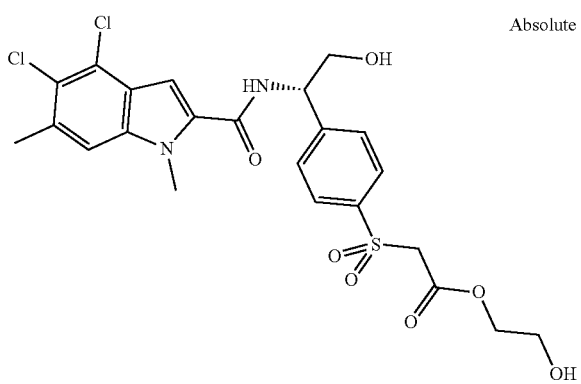 [SMILES: Cc1cc2c(cc(C(=O)N[C@H](CO)c3ccc(S(=O)(=O)CC(=O)OCCO)cc3)n2C)c(Cl)c1Cl] | Absolute | 1.24 | 543 | 5 |
| 09-037 | 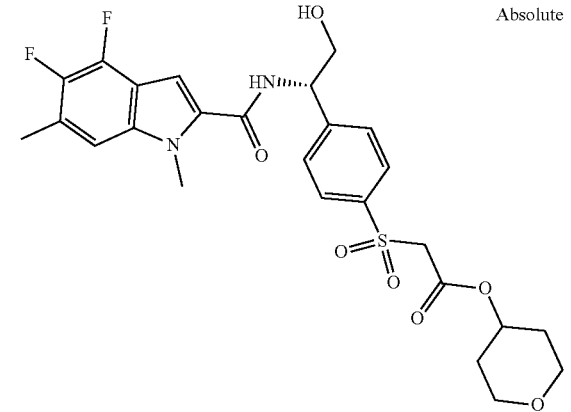 [SMILES: Cc1cc2c(cc(C(=O)N[C@H](CO)c3ccc(S(=O)(=O)CC(=O)OC4CCOCC4)cc3)n2C)c(F)c1F] | Absolute | 1.23 | 551 | 5 |

| | | | | | |
|---|---|---|---|---|---|
| 09-038 | 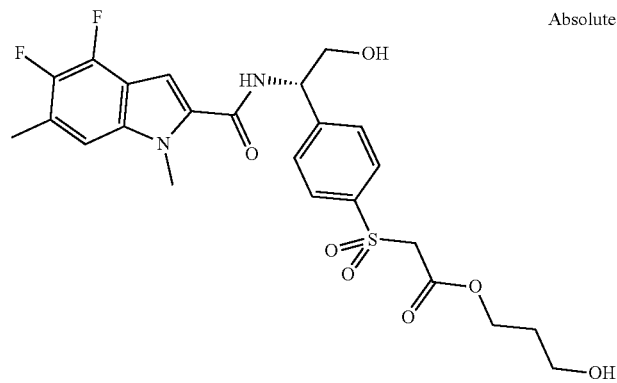 [SMILES: Cc1cc2c(cc(C(=O)N[C@H](CO)c3ccc(S(=O)(=O)CC(=O)OCCCO)cc3)n2C)c(F)c1F] | Absolute | 1.14 | 525 | 5 |
| 09-039 | 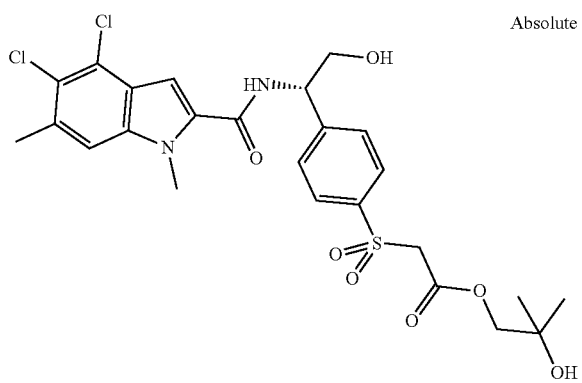 [SMILES: Cc1cc2c(cc(C(=O)N[C@H](CO)c3ccc(S(=O)(=O)CC(=O)OCC(C)(C)O)cc3)n2C)c(Cl)c1Cl] | Absolute | 1.29 | 571 | 5 |
| 09-040 | 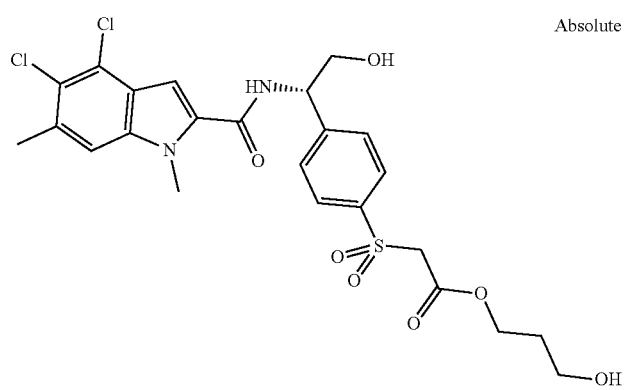 [SMILES: Cc1cc2c(cc(C(=O)N[C@H](CO)c3ccc(S(=O)(=O)CC(=O)OCCCO)cc3)n2C)c(Cl)c1Cl] | Absolute | 1.25 | 557 | 5 |
| 09-041 | 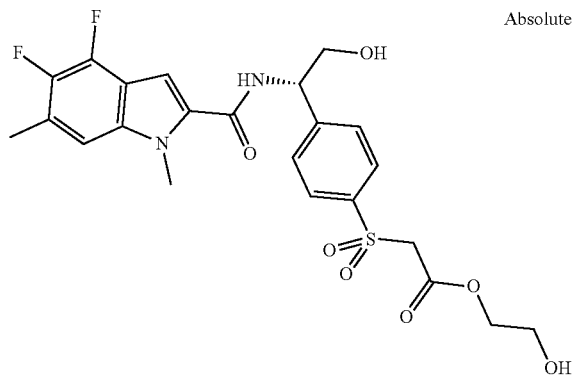 [SMILES: Cc1cc2c(cc(C(=O)N[C@H](CO)c3ccc(S(=O)(=O)CC(=O)OCCO)cc3)n2C)c(F)c1F] | Absolute | 1.12 | 511 | 5 |

-continued

| Example | Structure | | t_ret [min] | M+H | HPLC Method |
|---|---|---|---|---|---|
| 09-042 | (structure) | Absolute | 1.23 | 553 | 5 |
| 09-043 | (structure) | Absolute | 1.19 | 539 | 5 |
| 09-044 | (structure) | Absolute | 1.34 | 585 | 5 |

| Example | Structure | | t_ret [min] | M+H | HPLC Method |
|---|---|---|---|---|---|
| 10-001 | (structure) | Absolute | 1.2 | 486 | 5 |

| | | | | |
|---|---|---|---|---|
| 10-002 | 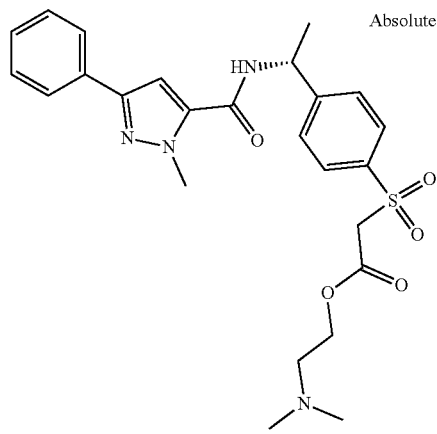 [SMILES: C[C@@H](NC(=O)c1cc(-c2ccccc2)nn1C)c1ccc(S(=O)(=O)CC(=O)OCCN(C)C)cc1] | Absolute | 1.18 | 499 | 5 |
| 10-003 | 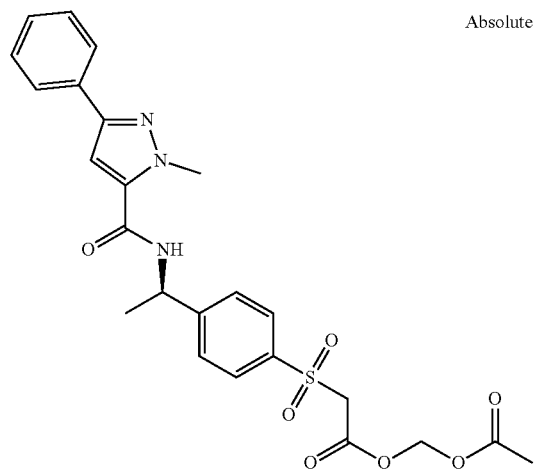 [SMILES: CC(=O)OCOC(=O)CS(=O)(=O)c1ccc([C@@H](C)NC(=O)c2cc(-c3ccccc3)nn2C)cc1] | Absolute | 1.25 | 500 | 5 |
| 10-004 | 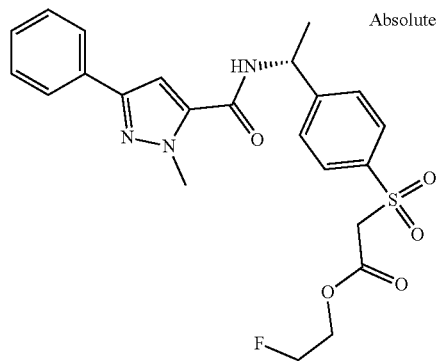 [SMILES: C[C@@H](NC(=O)c1cc(-c2ccccc2)nn1C)c1ccc(S(=O)(=O)CC(=O)OCCF)cc1] | Absolute | 1.23 | 474 | 5 |

| | | | | | |
|---|---|---|---|---|---|
| 10-005 | 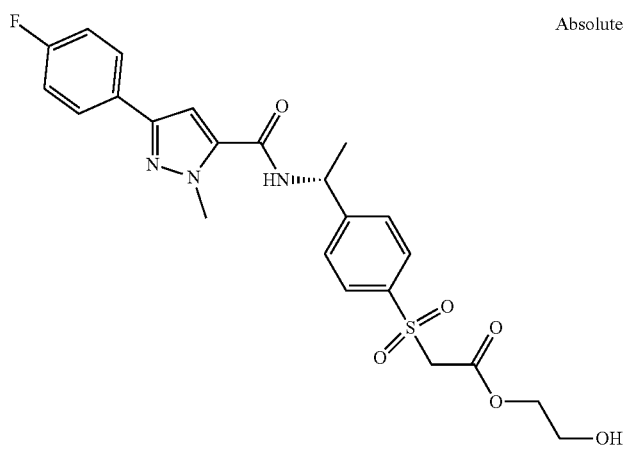 [SMILES: C[C@@H](NC(=O)c1cc(-c2ccc(F)cc2)nn1C)c1ccc(S(=O)(=O)CC(=O)OCCO)cc1] | Absolute | 1.14 | 490 | 5 |
| 10-006 | 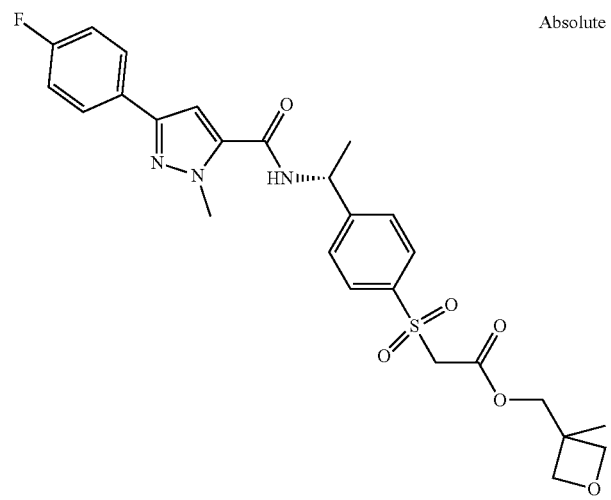 [SMILES: C[C@@H](NC(=O)c1cc(-c2ccc(F)cc2)nn1C)c1ccc(S(=O)(=O)CC(=O)OCC2(C)COC2)cc1] | Absolute | 1.26 | 530 | 5 |
| 10-007 | 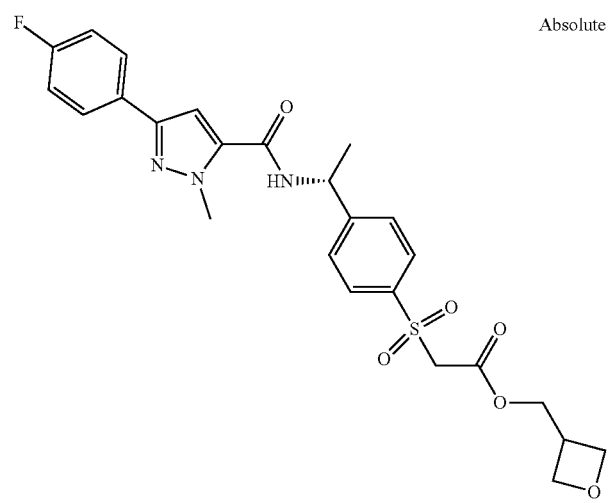 [SMILES: C[C@@H](NC(=O)c1cc(-c2ccc(F)cc2)nn1C)c1ccc(S(=O)(=O)CC(=O)OCC2COC2)cc1] | Absolute | 1.21 | 516 | 5 |

Syntheses of Sulfoxide Ester Derivatives 11-001-11-010

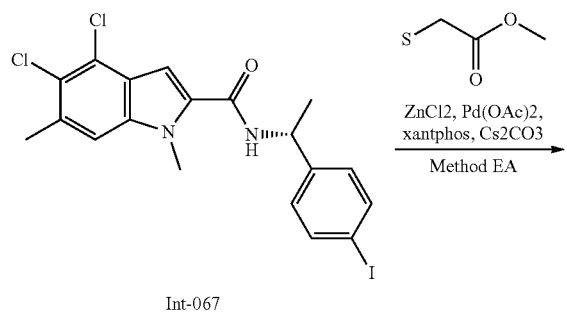

Int-067

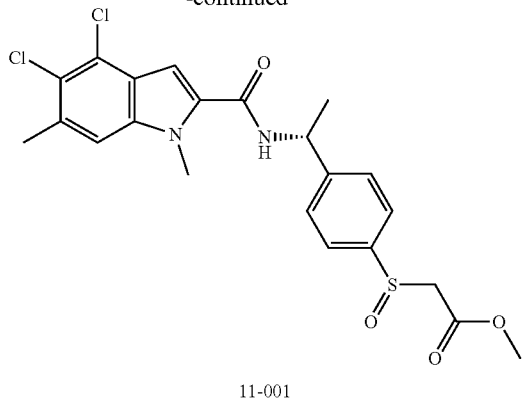

11-001

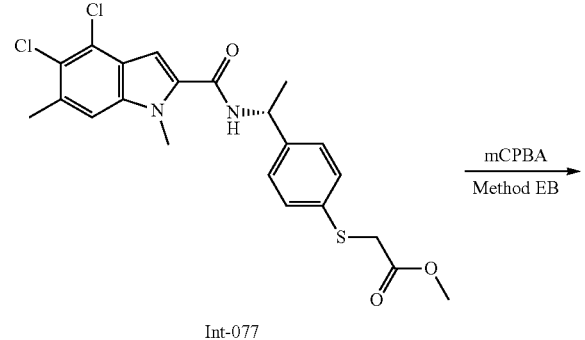

Int-077

Synthesis of Int-077 (Method EA).

An adopted procedure from Nikolovska-Coleska et al is used (J. Med. Chem. 2014, 57, 4111-4133).

Methylthioglycolate (34 µL, 0.37 mmol) is added to a suspension of $Cs_2CO_3$ (120 mg, 0.37 mmol) in dry THF (2 mL) under an argon atmosphere. The mixture is stirred at room temperature for 10 min.

At this time, a solution of $ZnCl_2$ (130 µL, 0.13 mmol, 1M in Et2O) is added and the mixture is stirred at room temperature for an additional 10 min. Meanwhile, in a separate flask, $Pd(OAc)_2$ (4.1 mg, 0.018 mmol) and xantphos (22 mg, 0.37 mmol) are premixed in dry THF (1 mL) under argon and stirred at room temperature for about 20 min. To the mixture of thiol, $Cs_2CO_3$, and $ZnCl_2$ is added Int-067 (90 mg, 0.19 mmol), LiI (12 mg, 0.09 mmol), and the premixed solution of the catalyst and ligand. The mixture was stirred at 60° C. under argon for 2 h. The reaction mixture was filtered and purified by RP-chromatography (MeCN/water 30-98%, acidic modifier).

Synthesis of 11-001 (Method EB)

To Int-077 (310 mg, 0.67 mmol) in DCM, mCPBA (77%; 164 mg, 0.73 mmol) is added and stirred for 30 min at ambient temperature. The mixture is diluted with DCM (30 mL) and washed with saturated aqueous $NaHCO_3$. The Organic layer is dried ($MgSO_4$), filtered, and the solvents removed under reduced pressure. The residue is dissolved in DMSO/MeCN and purified by RP-chromatography (MeCN/water 20-98%, acidic modifier)

The following sulfoxynyl acetates are prepared in an analogous manner. Diastereomerically enriched derivatives are prepared by SFC separation.

| Example | Structure | | $t_{ret}$ [min] | M + H | HPLC Method |
|---------|-----------|---|-----------------|-------|-------------|
| 11-001  | 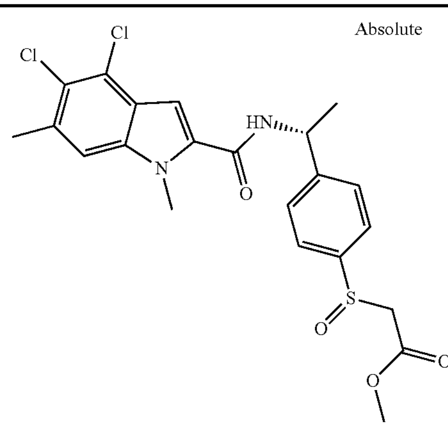          | Absolute | 1.4 | 481 | 5 |

-continued

| Example | Structure | | $t_{ret}$ [min] | M + H | HPLC Method |
|---|---|---|---|---|---|
| 11-002 | [Structure: 4,5-dichloro-1,6-dimethyl-1H-indole-2-carboxamide with (S)-2-hydroxy-1-phenylethyl group, phenyl bearing sulfoxonium -S⁺(O⁻)-CH₂-C(O)-OMe] | Absolute | 1.23 | 497 | 5 |
| 11-003 | [Structure: 4,5-dichloro-1,6-dimethyl-1H-indole-2-carboxamide with (S)-2-hydroxy-1-phenylethyl group, phenyl bearing sulfoxonium -S⁺(O⁻)-CH₂-C(O)-OMe, opposite S stereochem] | Absolute | 1.23 | 497 | 5 |
| 11-004 | [Structure: 4,5-dichloro-1,6-dimethyl-1H-indole-2-carboxamide with (S)-2-hydroxy-1-phenylethyl group, phenyl bearing sulfinyl -S(O)-CH₂-C(O)-OMe] | Absolute | 1.23 | 497 | 5 |
| 11-005 | [Structure: 4-chloro-1,6-dimethyl-1H-indole-2-carboxamide with (S)-2-hydroxy-1-phenylethyl group, phenyl bearing sulfinyl -S(O)-CH₂-C(O)-OMe] | Absolute | 1.15 | 463 | 5 |

| Example | Structure | $t_{ret}$ [min] | M + H | HPLC Method |
|---|---|---|---|---|
| 11-006 | 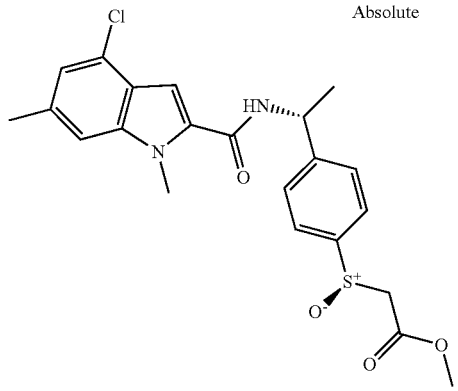 Absolute | 1.32 | 447 | 5 |
| 11-007 | 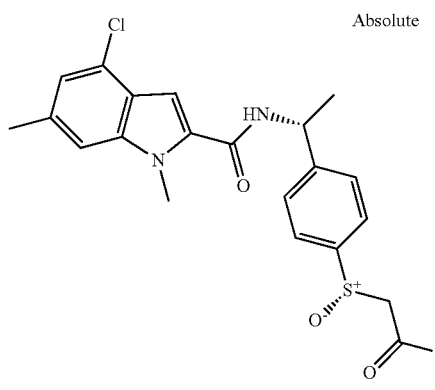 Absolute | 1.32 | 447 | 5 |
| 11-008 | 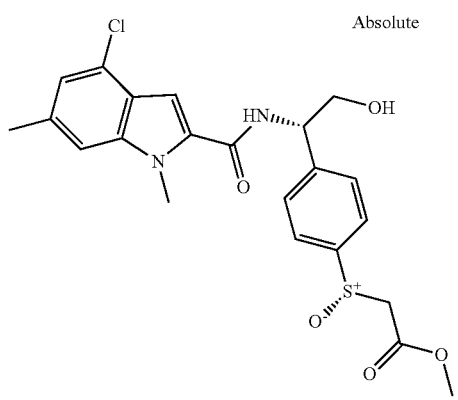 Absolute | 1.16 | 463 | 5 |

| Example | Structure | $t_{ret}$ [min] | M + H | HPLC Method |
|---|---|---|---|---|
| 11-009 | 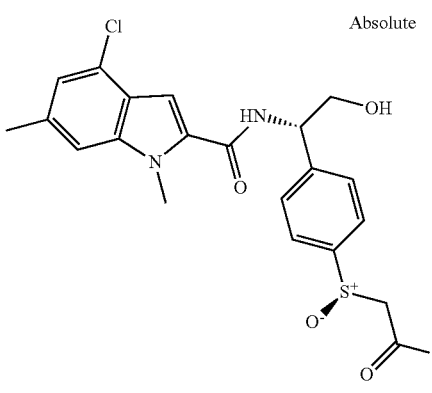 Absolute | 1.32 | 447 | 5 |
| 11-010 | Absolute | 1.16 | 463 | 5 |
Syntheses of Sulfoxide Acid Derivatives 12-001-12-010
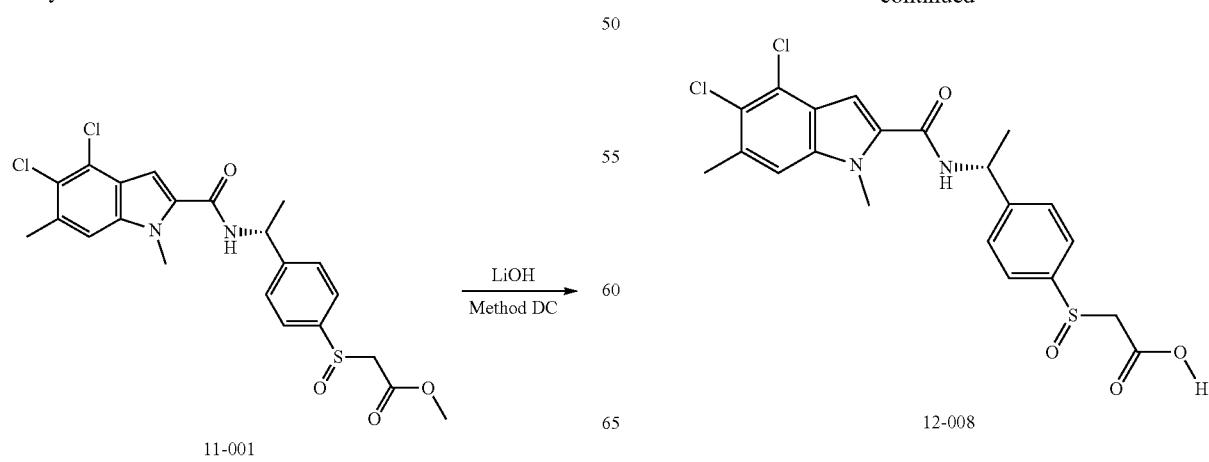

Carboxylic acids 12-001 to 12-010 are prepared using general Method DC. Diastereomerically enriched derivatives are prepared by SFC separation.

| Example | Structure | | $t_{ret}$ [min] | M + H | HPLC Method |
|---|---|---|---|---|---|
| 12-001 | 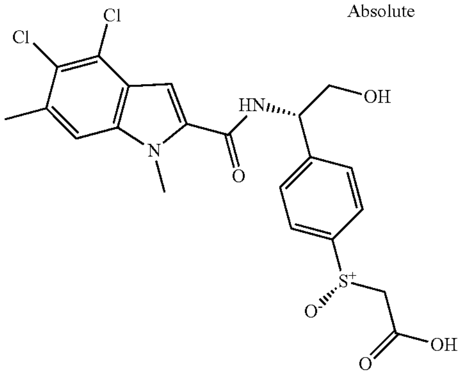 [SMILES: Cc1cc2c(cc(C(=O)N[C@H](CO)c3ccc([S@@+]([O-])CC(=O)O)cc3)n2C)c(Cl)c1Cl] | Absolute | 0.97 | 483 | 5 |
| 12-002 | 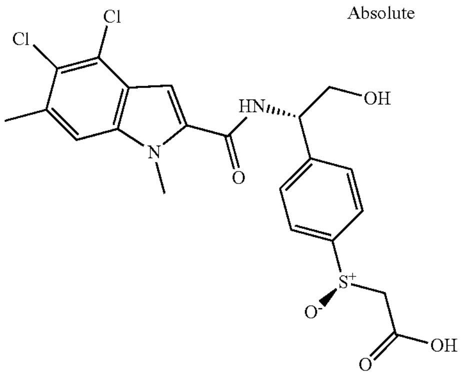 [SMILES: Cc1cc2c(cc(C(=O)N[C@H](CO)c3ccc([S@+]([O-])CC(=O)O)cc3)n2C)c(Cl)c1Cl] | Absolute | 0.97 | 483 | 5 |
| 12-003 | 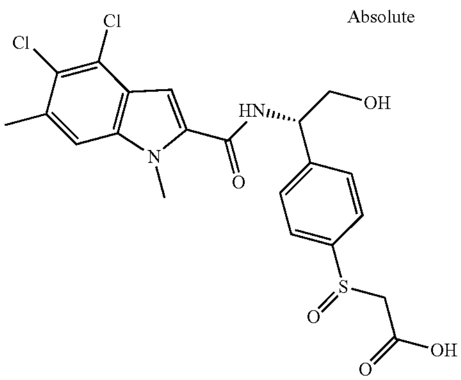 [SMILES: Cc1cc2c(cc(C(=O)N[C@H](CO)c3ccc(S(=O)CC(=O)O)cc3)n2C)c(Cl)c1Cl] | Absolute | 0.96 | 483 | 5 |
| 12-004 | 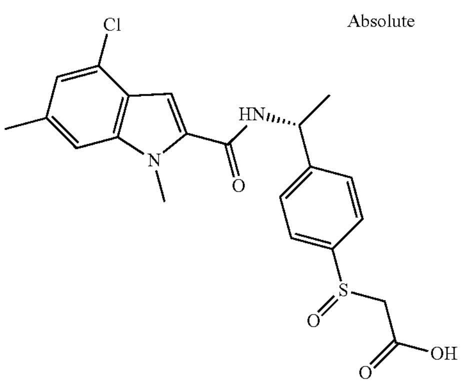 [SMILES: Cc1cc(Cl)c2cc(C(=O)N[C@H](C)c3ccc(S(=O)CC(=O)O)cc3)n(C)c2c1] | Absolute | 1.02 | 433 | 5 |

-continued

| Example | Structure | | $t_{ret}$ [min] | M + H | HPLC Method |
|---|---|---|---|---|---|
| 12-005 | 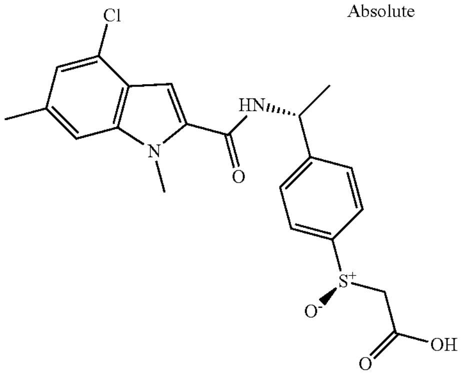 [SMILES: Cc1cc(Cl)c2cc(C(=O)N[C@H](C)c3ccc([S@+]([O-])CC(=O)O)cc3)n(C)c2c1] | Absolute | 1.01 | 433 | 5 |
| 12-006 | 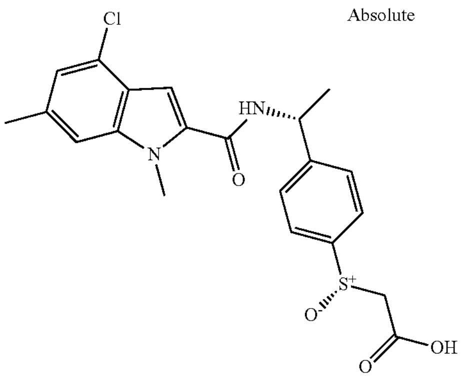 [SMILES: Cc1cc(Cl)c2cc(C(=O)N[C@H](C)c3ccc([S@@+]([O-])CC(=O)O)cc3)n(C)c2c1] | Absolute | 1.01 | 433 | 5 |
| 12-007 | 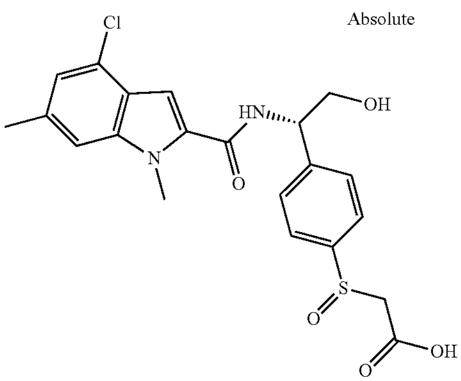 [SMILES: Cc1cc(Cl)c2cc(C(=O)N[C@H](CO)c3ccc(S(=O)CC(=O)O)cc3)n(C)c2c1] | Absolute | 0.88 | 449 | 5 |
| 12-008 | 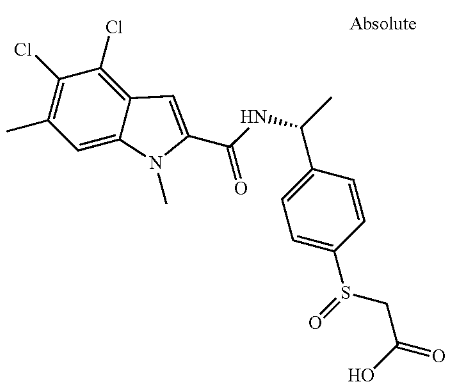 [SMILES: Cc1cc2c(cc(C(=O)N[C@H](C)c3ccc(S(=O)CC(=O)O)cc3)n2C)c(Cl)c1Cl] | Absolute | 1.02 | 467 | 5 |

-continued
| Example | Structure | $t_{ret}$ [min] | M + H | HPLC Method |
|---|---|---|---|---|
| 12-009 | 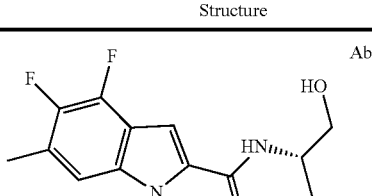 Absolute | 0.84 | 451 | 5 |
| 12-010 |  Absolute | 0.85 | 451 | 5 |
Syntheses of Sulfoxide Ester Derivatives 13-001-13-011
The following examples of solfoxyacetate esters are prepared according to the general procedure method DE
| Example | Structure | $t_{ret}$ [min] | M + H | HPLC Method |
|---|---|---|---|---|
| 13-001 | 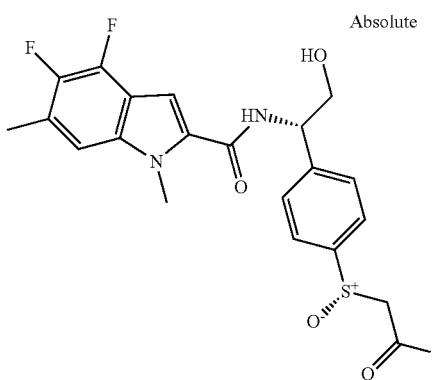 Absolute | 1.32 | 525 | 5 |

-continued
| Example | Structure | | $t_{ret}$ [min] | M + H | HPLC Method |
|---|---|---|---|---|---|
| 13-002 | 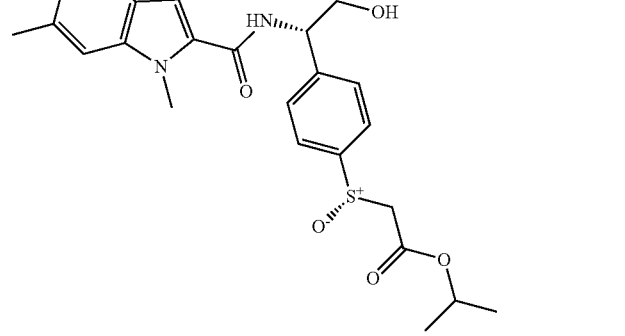 | Absolute | 1.32 | 525 | 5 |
| 13-003 | 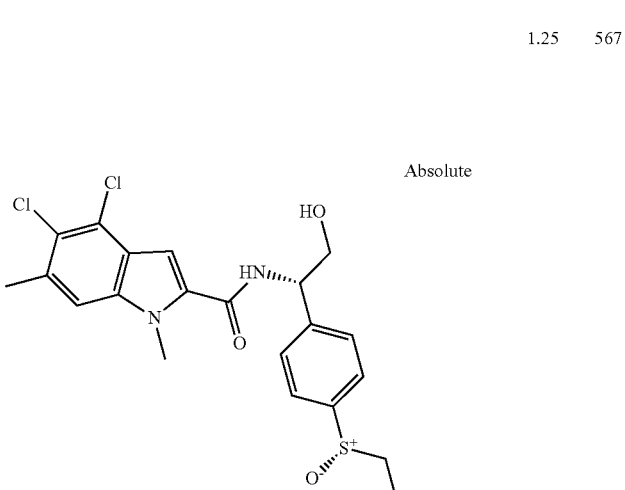 | Absolute | 1.25 | 567 | 5 |
| 13-004 | 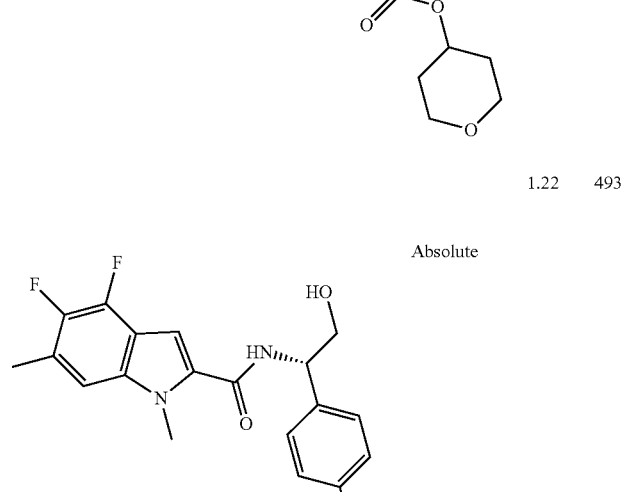 | Absolute | 1.22 | 493 | 5 |

-continued
| Example | Structure | | $t_{ret}$ [min] | M + H | HPLC Method |
|---|---|---|---|---|---|
| 13-005 | 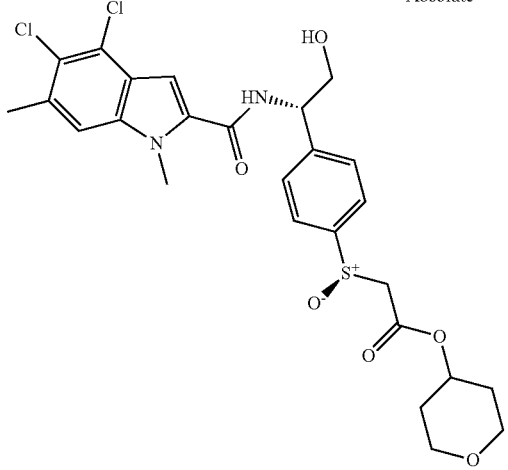 | Absolute | 1.25 | 567 | 5 |
| 13-006 | 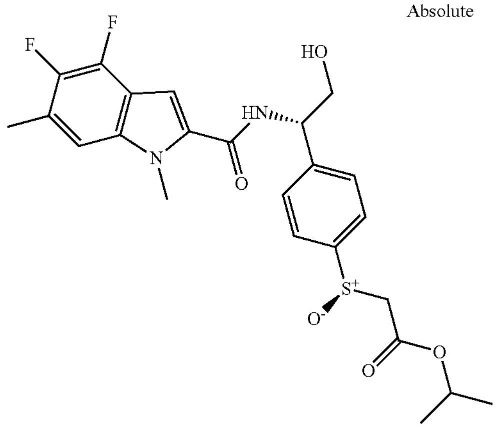 [SMILES: Cc1cc2c(cc(C(=O)N[C@H](CO)c3ccc([S@+]([O-])CC(=O)OC(C)C)cc3)n2C)c(F)c1F] | | 1.22 | 493 | 5 |
| 13-007 | 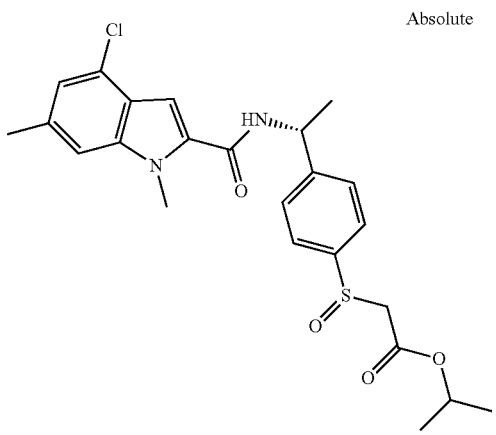 [SMILES: Cc1cc(Cl)c2cc(C(=O)N[C@H](C)c3ccc(S(=O)CC(=O)OC(C)C)cc3)n(C)c2c1] | Absolute | 1.42 | 475 | 5 |

| Example | Structure | | $t_{ret}$ [min] | M + H | HPLC Method |
|---|---|---|---|---|---|
| 13-008 | 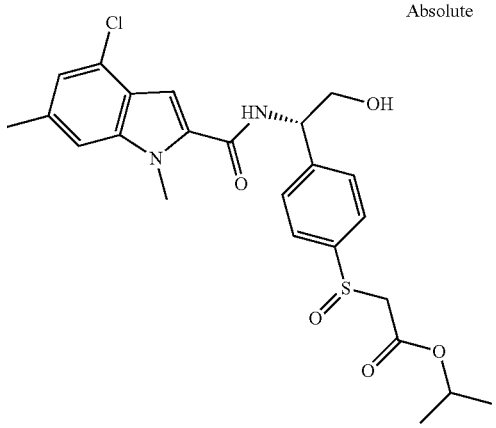 [SMILES: Cc1cc(Cl)c2cc(C(=O)N[C@H](CO)c3ccc(S(=O)CC(=O)OC(C)C)cc3)n(C)c2c1] | Absolute | 1.25 | 491 | 5 |
| 13-009 | 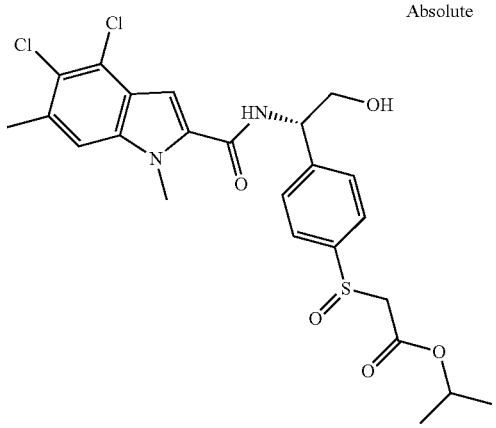 [SMILES: Cc1cc2c(cc(C(=O)N[C@H](CO)c3ccc(S(=O)CC(=O)OC(C)C)cc3)n2C)c(Cl)c1Cl] | Absolute | 1.33 | 525 | 5 |
| 13-010 | 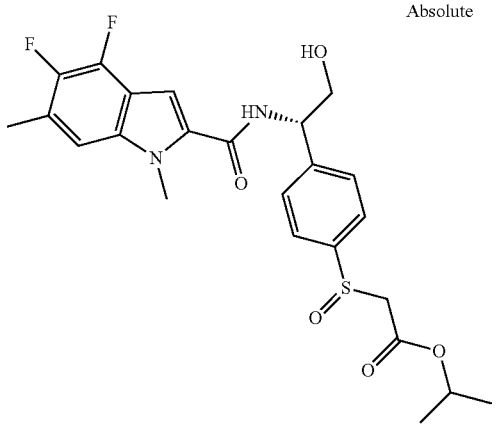 [SMILES: Cc1cc2c(cc(C(=O)N[C@H](CO)c3ccc(S(=O)CC(=O)OC(C)C)cc3)n2C)c(F)c1F] | Absolute | 1.22 | 493 | 5 |

| Example | Structure | | $t_{ret}$ [min] | M + H | HPLC Method |
|---|---|---|---|---|---|
| 13-011 | (structure) | Absolute | 1.44 | 509 | 5 |

| Example | Chemical Name |
|---|---|
| 01-036 | propan-2-yl 2-{4-[(1R)-1-({4-chloro-1,6-dimethyl-1H-pyrrolo[2,3-b]pyridin-2-yl}formamido)ethyl]benzenesulfonyl}acetate |
| 09-034 | 2-hydroxyethyl 2-{4-[(1S)-1-[(4-chloro-1,6-dimethyl-1H-indol-2-yl)formamido]-2-hydroxyethyl]benzenesulfonyl}acetate |
| 02-011 | propan-2-yl 2-{4-[(1R)-1-[(1-methyl-3-phenyl-1H-pyrazol-5-yl)formamido]ethyl]benzenesulfonyl}acetate |
| 09-028 | oxan-4-yl 2-{4-[(1S)-1-[(4-chloro-1,6-dimethyl-1H-indol-2-yl)formamido]-2-hydroxyethyl]benzenesulfonyl}acetate |
| 12-004 | 2-{4-[(1R)-1-[(4-chloro-1,6-dimethyl-1H-indol-2-yl)formamido]ethyl]benzenesulfinyl}acetic acid |
| 12-005 | 2-[(R)-4-[(1R)-1-[(4-chloro-1,6-dimethyl-1H-indol-2-yl)formamido]ethyl]benzenesulfinyl]acetic acid |
| 11-005 | methyl 2-{4-[(1S)-1-[(4-chloro-1,6-dimethyl-1H-indol-2-yl)formamido]-2-hydroxyethyl]benzenesulfinyl}acetate |
| 02-014 | propan-2-yl 2-{4-[(1R)-1-{[3-(3,4-dichlorophenyl)-1-methyl-1H-pyrazol-5-yl]formamido}ethyl]benzenesulfonyl}acetate |
| 10-007 | oxetan-3-ylmethyl 2-{4-[(1R)-1-{[3-(4-fluorophenyl)-1-methyl-1H-pyrazol-5-yl]formamido}ethyl]benzenesulfonyl}acetate |
| 06-004 | propan-2-yl 2-{4-[(1R)-1-[(1-methyl-3-phenyl-1H-pyrazol-5-yl)formamido]ethyl]benzenesulfonyl}propanoate |
| 12-006 | 2-[(S)-4-[(1R)-1-[(4-chloro-1,6-dimethyl-1H-indol-2-yl)formamido]ethyl]benzenesulfinyl]acetic acid |
| 11-006 | methyl 2-[(R)-4-[(1R)-1-[(4-chloro-1,6-dimethyl-1H-indol-2-yl)formamido]ethyl]benzenesulfinyl]acetate |
| 15-001 | 3-(4-fluorophenyl)-1-methyl-N-[(1R)-1-[4-({[2-(morpholin-4-yl)ethoxy]carbamoyl}methanesulfonyl)phenyl]ethyl]-1H-pyrazole-5-carboxamide |
| 05-021 | methyl 4-{4-[(1S)-1-[(4-chloro-1,6-dimethyl-1H-indol-2-yl)formamido]-2-hydroxyethyl]benzenesulfonyl}oxane-4-carboxylate |
| 09-031 | (3-methyloxetan-3-yl)methyl 2-{4-[(1S)-1-[(4-chloro-1,6-dimethyl-1H-indol-2-yl)formamido]-2-hydroxyethyl]benzenesulfonyl}acetate |
| 01-033 | propan-2-yl 2-{4-[(1R)-1-[(4-chloro-5-fluoro-1,6-dimethyl-1H-indol-2-yl)formamido]ethyl]benzenesulfonyl}acetate |
| 11-007 | methyl 2-[(S)-4-[(1R)-1-[(4-chloro-1,6-dimethyl-1H-indol-2-yl)formamido]ethyl]benzenesulfinyl]acetate |
| 01-018 | propan-2-yl 2-{4-[(1R)-1-[(4-chloro-1,6-dimethyl-1H-indol-2-yl)formamido]ethyl]benzenesulfonyl}acetate |
| 01-034 | propan-2-yl 2-{4-[(1S)-1-({4-chloro-1,6-dimethyl-1H-pyrrolo[2,3-b]pyridin-2-yl}formamido)-2-hydroxyethyl]benzenesulfonyl}acetate |
| 09-035 | oxetan-3-ylmethyl 2-{4-[(1S)-1-[(4-chloro-1,6-dimethyl-1H-indol-2-yl)formamido]-2-hydroxyethyl]benzenesulfonyl}acetate |
| 15-002 | 3-(4-fluorophenyl)-1-methyl-N-[(1R)-1-[4-({[(1-methylpiperidin-4-yl)oxy]carbamoyl}methanesulfonyl)phenyl]ethyl]-1H-pyrazole-5-carboxamide |
| 07-014 | 2-{4-[(1S)-1-[(4,5-dichloro-1,6-dimethyl-1H-indol-2-yl)formamido]-2-hydroxyethyl]benzenesulfonyl}-2-methylpropanoic acid |
| 03-015 | 2-{4-[(1R)-1-({4-chloro-1,6-dimethyl-1H-pyrrolo[2,3-b]pyridin-2-yl}formamido)ethyl]benzenesulfonyl}acetic acid |
| 03-013 | 2-{4-[(1S)-1-({4-chloro-1,6-dimethyl-1H-pyrrolo[2,3-b]pyridin-2-yl}formamido)-2-hydroxyethyl]benzenesulfonyl}acetic acid |

-continued

| Example | Chemical Name |
|---|---|
| 13-007 | propan-2-yl 2-{4-[(1R)-1-[(4-chloro-1,6-dimethyl-1H-indol-2-yl)formamido]ethyl]benzenesulfinyl}acetate |
| 13-008 | propan-2-yl 2-{4-[(1S)-1-[(4-chloro-1,6-dimethyl-1H-indol-2-yl)formamido]-2-hydroxyethyl]benzenesulfinyl}acetate |
| 09-032 | (3-fluorooxetan-3-yl)methyl 2-{4-[(1S)-1-[(4-chloro-1,6-dimethyl-1H-indol-2-yl)formamido]-2-hydroxyethyl]benzenesulfonyl}acetate |
| 01-035 | propan-2-yl 2-{4-[(1S)-1-[(4-chloro-5-fluoro-1,6-dimethyl-1H-indol-2-yl)formamido]-2-hydroxyethyl]benzenesulfonyl}acetate |
| 11-008 | methyl 2-[(S)-4-[(1S)-1-[(4-chloro-1,6-dimethyl-1H-indol-2-yl)formamido]-2-hydroxyethyl]benzenesulfinyl]acetate |
| 12-007 | 2-{4-[(1S)-1-[(4-chloro-1,6-dimethyl-1H-indol-2-yl)formamido]-2-hydroxyethyl]benzenesulfinyl}acetic acid |
| 01-037 | propan-2-yl 2-{4-[(1R)-1-[(4,5-dichloro-1,6-dimethyl-1H-indol-2-yl)formamido]ethyl]benzenesulfonyl}acetate |
| 06-005 | propan-2-yl 2-methyl-2-{4-[(1R)-1-[(1-methyl-3-phenyl-1H-pyrazol-5-yl)formamido]ethyl]benzenesulfonyl}propanoate |
| 10-006 | (3-methyloxetan-3-yl)methyl 2-{4-[(1R)-1-{[3-(4-fluorophenyl)-1-methyl-1H-pyrazol-5-yl]formamido}ethyl]benzenesulfonyl}acetate |
| 09-030 | (3S)-oxolan-3-yl 2-{4-[(1S)-1-[(4-chloro-1,6-dimethyl-1H-indol-2-yl)formamido]-2-hydroxyethyl]benzenesulfonyl}acetate |
| 02-013 | propan-2-yl 2-{4-[(1R)-1-{[3-(4-chloro-3-methoxyphenyl)-1-methyl-1H-pyrazol-5-yl]formamido}ethyl]benzenesulfonyl}acetate |
| 15-003 | 5-{4-[(1R)-1-[(4-chloro-1,6-dimethyl-1H-indol-2-yl)formamido]ethyl]phenyl}-4-oxopentanoic acid |
| 09-029 | 2-methoxyethyl 2-{4-[(1S)-1-[(4-chloro-1,6-dimethyl-1H-indol-2-yl)formamido]-2-hydroxyethyl]benzenesulfonyl}acetate |
| 15-004 | 3-(4-fluorophenyl)-N-[(1R)-1-{4-[(methoxycarbamoyl)methanesulfonyl]phenyl}ethyl]-1-methyl-1H-pyrazole-5-carboxamide |
| 02-015 | propan-2-yl 2-{4-[(1R)-1-{[3-(4-fluoro-3-methylphenyl)-1-methyl-1H-pyrazol-5-yl]formamido}ethyl]benzenesulfonyl}acetate |
| 02-012 | propan-2-yl 2-{4-[(1R)-1-{[3-(4-fluoro-3-methoxyphenyl)-1-methyl-1H-pyrazol-5-yl]formamido}ethyl]benzenesulfonyl}acetate |
| 11-009 | methyl 2-{4-[(1R)-1-[(4-chloro-1,6-dimethyl-1H-indol-2-yl)formamido]ethyl]benzenesulfinyl}acetate |
| 10-005 | 2-hydroxyethyl 2-{4-[(1R)-1-{[3-(4-fluorophenyl)-1-methyl-1H-pyrazol-5-yl]formamido}ethyl]benzenesulfonyl}acetate |
| 11-010 | methyl 2-[(R)-4-[(1S)-1-[(4-chloro-1,6-dimethyl-1H-indol-2-yl)formamido]-2-hydroxyethyl]benzenesulfinyl]acetate |
| 01-038 | propan-2-yl 2-{4-[(1S)-1-[(4-chloro-1,6-dimethyl-1H-indol-2-yl)formamido]-2-hydroxyethyl]benzenesulfonyl}acetate |
| 09-033 | 3-hydroxypropyl 2-{4-[(1S)-1-[(4-chloro-1,6-dimethyl-1H-indol-2-yl)formamido]-2-hydroxyethyl]benzenesulfonyl}acetate |
| 03-014 | 2-{4-[(1R)-1-[(4-chloro-5-fluoro-1,6-dimethyl-1H-indol-2-yl)formamido]ethyl]benzenesulfonyl}acetic acid |
| 02-016 | propan-2-yl 2-{4-[(1R)-1-{[3-(3,4-difluorophenyl)-1-methyl-1H-pyrazol-5-yl]formamido}ethyl]benzenesulfonyl}acetate |
| 06-006 | propan-2-yl 2-{4-[(1S)-1-{[3-(4-fluorophenyl)-1-methyl-1H-pyrazol-5-yl]formamido}-2-hydroxyethyl]benzenesulfonyl}-2-methylpropanoate |
| 02-017 | propan-2-yl 2-{4-[(1S)-1-{[3-(4-fluorophenyl)-1-methyl-1H-pyrazol-5-yl]formamido}-2-hydroxyethyl]benzenesulfonyl}acetate |
| 03-016 | 2-{4-[(1S)-1-[(4-chloro-5-fluoro-1,6-dimethyl-1H-indol-2-yl)formamido]-2-hydroxyethyl]benzenesulfonyl}acetic acid |
| 11-001 | methyl 2-{4-[(1R)-1-[(4,5-dichloro-1,6-dimethyl-1H-indol-2-yl)formamido]ethyl]benzenesulfinyl}acetate |
| 12-001 | 2-[(S)-4-[(1S)-1-[(4,5-dichloro-1,6-dimethyl-1H-indol-2-yl)formamido]-2-hydroxyethyl]benzenesulfinyl]acetic acid |
| 11-002 | methyl 2-[(R)-4-[(1S)-1-[(4,5-dichloro-1,6-dimethyl-1H-indol-2-yl)formamido]-2-hydroxyethyl]benzenesulfinyl]acetate |
| 13-009 | propan-2-yl 2-{4-[(1S)-1-[(4,5-dichloro-1,6-dimethyl-1H-indol-2-yl)formamido]-2-hydroxyethyl]benzenesulfinyl}acetate |
| 11-003 | methyl 2-[(S)-4-[(1S)-1-[(4,5-dichloro-1,6-dimethyl-1H-indol-2-yl)formamido]-2-hydroxyethyl]benzenesulfinyl]acetate |
| 06-007 | propan-2-yl 2-{4-[(1S)-1-{[3-(4-fluorophenyl)-1-methyl-1H-pyrazol-5-yl]formamido}-2-hydroxyethyl]benzenesulfonyl}propanoate |
| 04-004 | 2-{4-[(1S)-1-{[3-(4-fluorophenyl)-1-methyl-1H-pyrazol-5-yl]formamido}-2-hydroxyethyl]benzenesulfonyl}acetic acid |
| 13-001 | propan-2-yl 2-[(R)-4-[(1S)-1-[(4,5-dichloro-1,6-dimethyl-1H-indol-2-yl)formamido]-2-hydroxyethyl]benzenesulfinyl]acetate |
| 03-017 | 2-{4-[(1S)-1-{[4-chloro-1-methyl-6-(4-methylpiperazin-1-yl)-1H-indol-2-yl]formamido}-2-hydroxyethyl]benzenesulfonyl}acetic acid |
| 03-018 | 2-{4-[(1R)-1-{[4-chloro-1-methyl-6-(4-methylpiperazin-1-yl)-1H-indol-2-yl]formamido}ethyl]benzenesulfonyl}acetic acid |
| 12-002 | 2-[(R)-4-[(1S)-1-[(4,5-dichloro-1,6-dimethyl-1H-indol-2-yl)formamido]-2-hydroxyethyl]benzenesulfinyl]acetic acid |
| 11-004 | methyl 2-{4-[(1S)-1-[(4,5-dichloro-1,6-dimethyl-1H-indol-2-yl)formamido]-2-hydroxyethyl]benzenesulfinyl}acetate |

-continued

| Example | Chemical Name |
|---|---|
| 06-008 | methyl 2-{4-[(1S)-1-{[3-(4-fluorophenyl)-1-methyl-1H-pyrazol-5-yl]formamido}-2-hydroxyethyl]benzenesulfonyl}-2-methylpropanoate |
| 13-002 | propan-2-yl 2-[(S)-4-[(1S)-1-[(4,5-dichloro-1,6-dimethyl-1H-indol-2-yl)formamido]-2-hydroxyethyl]benzenesulfinyl]acetate |
| 01-039 | propan-2-yl 2-{4-[(1S)-1-[(4,5-difluoro-1,6-dimethyl-1H-indol-2-yl)formamido]-2-hydroxyethyl]benzenesulfonyl}acetate |
| 12-003 | 2-{4-[(1S)-1-[(4,5-dichloro-1,6-dimethyl-1H-indol-2-yl)formamido]-2-hydroxyethyl]benzenesulfinyl}acetic acid |
| 07-015 | 2-{4-[(1R)-1-[(4,5-dichloro-1,6-dimethyl-1H-indol-2-yl)formamido]ethyl]benzenesulfonyl}-2-methylpropanoic acid |
| 05-017 | methyl 2-{4-[(1S)-1-[(4,5-dichloro-1,6-dimethyl-1H-indol-2-yl)formamido]-2-hydroxyethyl]benzenesulfonyl}-2-methylpropanoate |
| 03-012 | 2-{4-[(1S)-1-[(4,5-difluoro-1,6-dimethyl-1H-indol-2-yl)formamido]-2-hydroxyethyl]benzenesulfonyl}acetic acid |
| 01-002 | ethyl 2-{4-[(1S)-1-[(4,5-dichloro-1,6-dimethyl-1H-indol-2-yl)formamido]-2-hydroxyethyl]benzenesulfonyl}acetate |
| 09-044 | 3-hydroxy-2,2-dimethylpropyl 2-{4-[(1S)-1-[(4,5-dichloro-1,6-dimethyl-1H-indol-2-yl)formamido]-2-hydroxyethyl]benzenesulfonyl}acetate |
| 07-001 | 2-{4-[(1R)-1-[(4-chloro-1,6-dimethyl-1H-indol-2-yl)formamido]ethyl]benzenesulfonyl}-2-ethylbutanoic acid |
| 05-023 | 4,5-dichloro-1,6-dimethyl-N-[(1R)-1-{4-[(2-oxooxolan-3-yl)sulfonyl]phenyl}ethyl]-1H-indole-2-carboxamide |
| 04-003 | 2-{4-[(1R)-1-{[3-(1H-indol-7-yl)-1-methyl-1H-pyrazol-5-yl]formamido}ethyl]benzenesulfonyl}acetic acid |
| 13-003 | oxan-4-yl 2-[(S)-4-[(1S)-1-[(4,5-dichloro-1,6-dimethyl-1H-indol-2-yl)formamido]-2-hydroxyethyl]benzenesulfinyl]acetate |
| 12-009 | 2-[(R)-4-[(1S)-1-[(4,5-difluoro-1,6-dimethyl-1H-indol-2-yl)formamido]-2-hydroxyethyl]benzenesulfinyl]acetic acid |
| 09-036 | 2-hydroxyethyl 2-{4-[(1S)-1-[(4,5-dichloro-1,6-dimethyl-1H-indol-2-yl)formamido]-2-hydroxyethyl]benzenesulfonyl}acetate |
| 09-037 | oxan-4-yl 2-{4-[(1S)-1-[(4,5-difluoro-1,6-dimethyl-1H-indol-2-yl)formamido]-2-hydroxyethyl]benzenesulfonyl}acetate |
| 03-004 | 2-{4-[(1R)-1-{[4-chloro-1-methyl-6-(1-methyl-1H-pyrazol-4-yl)-1H-indol-2-yl]formamido}ethyl]benzenesulfonyl}acetic acid |
| 09-038 | 3-hydroxypropyl 2-{4-[(1S)-1-[(4,5-difluoro-1,6-dimethyl-1H-indol-2-yl)formamido]-2-hydroxyethyl]benzenesulfonyl}acetate |
| 09-039 | 2-hydroxy-2-methylpropyl 2-{4-[(1S)-1-[(4,5-dichloro-1,6-dimethyl-1H-indol-2-yl)formamido]-2-hydroxyethyl]benzenesulfonyl}acetate |
| 09-040 | 3-hydroxypropyl 2-{4-[(1S)-1-[(4,5-dichloro-1,6-dimethyl-1H-indol-2-yl)formamido]-2-hydroxyethyl]benzenesulfonyl}acetate |
| 03-003 | 2-{4-[(1R)-1-[(4-chloro-1,6,7-trimethyl-1H-indol-2-yl)formamido]ethyl]benzenesulfonyl}acetic acid |
| 09-041 | 2-hydroxyethyl 2-{4-[(1S)-1-[(4,5-difluoro-1,6-dimethyl-1H-indol-2-yl)formamido]-2-hydroxyethyl]benzenesulfonyl}acetate |
| 05-024 | 4,5-difluoro-1,6-dimethyl-N-[(1R)-1-{4-[(2-oxooxolan-3-yl)sulfonyl]phenyl}ethyl]-1H-indole-2-carboxamide |
| 01-028 | ethyl 2-{4-[(1S)-1-[(4,5-difluoro-1,6-dimethyl-1H-indol-2-yl)formamido]-2-hydroxyethyl]benzenesulfonyl}acetate |
| 07-012 | 2-{4-[(1R)-1-[(4-chloro-1,6-dimethyl-1H-indol-2-yl)formamido]ethyl]benzenesulfonyl}pentanoic acid |
| 12-010 | 2-[(S)-4-[(1S)-1-[(4,5-difluoro-1,6-dimethyl-1H-indol-2-yl)formamido]-2-hydroxyethyl]benzenesulfinyl]acetic acid |
| 03-006 | 2-{4-[(1S)-1-[(4,5-dichloro-1,6-dimethyl-1H-indol-2-yl)formamido]-2-hydroxyethyl]benzenesulfonyl}acetic acid |
| 09-042 | 3-hydroxy-2,2-dimethylpropyl 2-{4-[(1S)-1-[(4,5-difluoro-1,6-dimethyl-1H-indol-2-yl)formamido]-2-hydroxyethyl]benzenesulfonyl}acetate |
| 13-010 | propan-2-yl 2-{4-[(1S)-1-[(4,5-difluoro-1,6-dimethyl-1H-indol-2-yl)formamido]-2-hydroxyethyl]benzenesulfinyl}acetate |
| 09-043 | 2-hydroxy-2-methylpropyl 2-{4-[(1S)-1-[(4,5-difluoro-1,6-dimethyl-1H-indol-2-yl)formamido]-2-hydroxyethyl]benzenesulfonyl}acetate |
| 13-004 | propan-2-yl 2-[(S)-4-[(1S)-1-[(4,5-difluoro-1,6-dimethyl-1H-indol-2-yl)formamido]-2-hydroxyethyl]benzenesulfinyl]acetate |
| 03-005 | 2-{4-[(1R)-1-[(4,5-dichloro-1,6-dimethyl-1H-indol-2-yl)formamido]ethyl]benzenesulfonyl}acetic acid |
| 13-005 | oxan-4-yl 2-[(R)-4-[(1S)-1-[(4,5-dichloro-1,6-dimethyl-1H-indol-2-yl)formamido]-2-hydroxyethyl]benzenesulfinyl]acetate |
| 07-013 | 1-{4-[(1R)-1-[(4-chloro-1,6-dimethyl-1H-indol-2-yl)formamido]ethyl]benzenesulfonyl}cyclopropane-1-carboxylic acid |
| 13-006 | propan-2-yl 2-[(R)-4-[(1S)-1-[(4,5-difluoro-1,6-dimethyl-1H-indol-2-yl)formamido]-2-hydroxyethyl]benzenesulfinyl]acetate |
| 05-025 | 4,5-dichloro-1,6-dimethyl-N-[(1R)-1-{4-[(2-oxooxan-3-yl)sulfonyl]phenyl}ethyl]-1H-indole-2-carboxamide |
| 07-016 | 1-acetyl-4-{4-[(1R)-1-[(4,5-dichloro-1,6-dimethyl-1H-indol-2-yl)formamido]ethyl]benzenesulfonyl}piperidine-4-carboxylic acid |
| 12-008 | 2-{4-[(1R)-1-[(4,5-dichloro-1,6-dimethyl-1H-indol-2-yl)formamido]ethyl]benzenesulfinyl}acetic acid |

-continued

| Example | Chemical Name |
| --- | --- |
| 13-011 | propan-2-yl 2-{4-[(1R)-1-[(4,5-dichloro-1,6-dimethyl-1H-indol-2-yl)formamido]ethyl]benzenesulfinyl}acetate |
| 02-008 | propan-2-yl 2-{4-[(1R)-1-{[3-(4-fluorophenyl)-1-methyl-1H-pyrazol-5-yl]formamido}ethyl]benzenesulfonyl}acetate |
| 09-014 | oxan-4-yl 2-{4-[(1R)-1-[(4-chloro-1,6-dimethyl-1H-indol-2-yl)formamido]ethyl]benzenesulfonyl}acetate |
| 15-005 | ethyl 2-{4-[(1R)-1-{[3-(1H-indol-1-yl)-1-methyl-1H-pyrazol-5-yl]formamido}ethyl]benzenesulfonyl}acetate |
| 01-029 | methyl 2-({6-[(1R)-1-[(4-chloro-1,6-dimethyl-1H-indol-2-yl)formamido]ethyl]pyridin-3-yl}sulfonyl)acetate |
| 01-006 | methyl 2-{4-[(1R)-1-({4,5-dichloro-1,6-dimethyl-1H-pyrrolo[2,3-b]pyridin-2-yl}formamido)ethyl]benzenesulfonyl}acetate |
| 09-003 | 2-methoxyethyl 2-{4-[(1R)-1-({4,5-dichloro-1,6-dimethyl-1H-pyrrolo[2,3-b]pyridin-2-yl}formamido)ethyl]benzenesulfonyl}acetate |
| 09-012 | (3-methyloxetan-3-yl)methyl 2-{4-[(1R)-1-[(4-chloro-1,6-dimethyl-1H-indol-2-yl)formamido]ethyl]benzenesulfonyl}acetate |
| 03-009 | 2-{4-[(1R)-1-[(4-chloro-1,6-dimethyl-1H-indol-2-yl)formamido]ethyl]benzenesulfonyl}acetic acid |
| 01-001 | methyl 2-{4-[(1R)-1-[(4,5-dichloro-1,6-dimethyl-1H-indol-2-yl)formamido]ethyl]benzenesulfonyl}acetate |
| 05-001 | tert-butyl 2-{4-[(1R)-1-[(4-chloro-1,6-dimethyl-1H-indol-2-yl)formamido]ethyl]benzenesulfonyl}propanoate |
| 01-011 | propan-2-yl 2-{4-[(1R)-1-{[4-chloro-1-methyl-6-(1-methyl-1H-pyrazol-4-yl)-1H-indol-2-yl]formamido}ethyl]benzenesulfonyl}acetate |
| 05-018 | 2-methoxyethyl 2-{4-[(1R)-1-({4,5-dichloro-1,6-dimethyl-1H-pyrrolo[2,3-b]pyridin-2-yl}formamido)ethyl]benzenesulfonyl}-2-methylpropanoate |
| 02-010 | methyl 2-({5-[(1R)-1-[(1-methyl-3-phenyl-1H-pyrazol-5-yl)formamido]ethyl]pyridin-2-yl}sulfonyl)acetate |
| 14-020 | 4-chloro-N-[(1R)-1-{4-[(hydroxycarbamoyl)methanesulfonyl]phenyl}ethyl]-1,6-dimethyl-1H-indole-2-carboxamide |
| 01-023 | methyl 2-{4-[(1S)-1-({4,5-dichloro-1,6-dimethyl-1H-pyrrolo[2,3-b]pyridin-2-yl}formamido)-2-hydroxyethyl]benzenesulfonyl}acetate |
| 01-027 | methyl 2-{4-[(1R)-1-[(5-chloro-1-methyl-6-{1-[2-(morpholin-4-yl)ethyl]-1H-pyrazol-4-yl}-1H-indol-2-yl)formamido]ethyl]benzenesulfonyl}acetate |
| 05-010 | methyl 4-{4-[(1R)-1-[(4-chloro-1,6-dimethyl-1H-indol-2-yl)formamido]ethyl]benzenesulfonyl}oxane-4-carboxylate |
| 01-007 | methyl 2-{4-[(1S)-1-[(4,5-dichloro-1,6-dimethyl-1H-indol-2-yl)formamido]-2-hydroxyethyl]benzenesulfonyl}acetate |
| 01-021 | propan-2-yl 2-{4-[(1S)-1-[(4,5-dichloro-1,6-dimethyl-1H-indol-2-yl)formamido]-2-hydroxyethyl]benzenesulfonyl}acetate |
| 01-012 | methyl 2-{4-[(1R)-1-[(4-chloro-1,6-dimethyl-1H-indol-2-yl)formamido]ethyl]benzenesulfonyl}acetate |
| 09-013 | 2-methylpropyl 2-{4-[(1R)-1-[(4-chloro-1,6-dimethyl-1H-indol-2-yl)formamido]ethyl]benzenesulfonyl}acetate |
| 05-012 | propan-2-yl 2-{4-[(1R)-1-[(4-chloro-1,6-dimethyl-1H-indol-2-yl)formamido]ethyl]benzenesulfonyl}-2-methylpropanoate |
| 05-013 | methyl 2-{4-[(1R)-1-[(4-chloro-1,6-dimethyl-1H-indol-2-yl)formamido]ethyl]benzenesulfonyl}butanoate |
| 15-006 | ethyl 2-{4-[(1R)-1-{[3-(1H-indazol-1-yl)-1-methyl-1H-pyrazol-5-yl]formamido}ethyl]benzenesulfonyl}acetate |
| 09-005 | 2-(2-hydroxyethoxy)ethyl 2-{4-[(1R)-1-[(4-chloro-1,6-dimethyl-1H-indol-2-yl)formamido]ethyl]benzenesulfonyl}acetate |
| 06-001 | methyl 4-{4-[(1R)-1-{[3-(4-fluorophenyl)-1-methyl-1H-pyrazol-5-yl]formamido}ethyl]benzenesulfonyl}oxane-4-carboxylate |
| 07-005 | 2-{4-[(1R)-1-[(4-chloro-1,6-dimethyl-1H-indol-2-yl)formamido]ethyl]benzenesulfonyl}-2-methylpropanoic acid |
| 05-003 | ethyl 2-{4-[(1R)-1-[(4-chloro-1,6-dimethyl-1H-indol-2-yl)formamido]ethyl]benzenesulfonyl}-2-methylpropanoate |
| 10-003 | (acetyloxy)methyl 2-{4-[(1R)-1-[(1-methyl-3-phenyl-1H-pyrazol-5-yl)formamido]ethyl]benzenesulfonyl}acetate |
| 03-011 | 2-{4-[(1S)-1-({4,5-dichloro-1,6-dimethyl-1H-pyrrolo[2,3-b]pyridin-2-yl}formamido)-2-hydroxyethyl]benzenesulfonyl}acetic acid |
| 05-009 | methyl 2-{4-[(1R)-1-[(4-chloro-1,6-dimethyl-1H-indol-2-yl)formamido]ethyl]benzenesulfonyl}propanoate |
| 01-016 | ethyl 2-{4-[(1R)-1-({4,5-dichloro-1,6-dimethyl-1H-pyrrolo[2,3-b]pyridin-2-yl}formamido)ethyl]benzenesulfonyl}acetate |
| 01-003 | methyl 2-{4-[(1R)-1-{[4-chloro-1-methyl-6-(1-methyl-1H-pyrazol-4-yl)-1H-indol-2-yl]formamido}ethyl]benzenesulfonyl}acetate |
| 09-011 | [3-(trifluoromethyl)phenyl]methyl 2-{4-[(1R)-1-[(4-chloro-1,6-dimethyl-1H-indol-2-yl)formamido]ethyl]benzenesulfonyl}acetate |
| 15-007 | N-[(1R)-1-[4-(1-carbamoyl-1-methylethanesulfonyl)phenyl]ethyl]-4-chloro-1,6-dimethyl-1H-indole-2-carboxamide |
| 01-004 | ethyl 2-{4-[(1R)-1-[(4-chloro-1,6-dimethyl-1H-indol-2-yl)formamido]ethyl]benzenesulfonyl}acetate |
| 01-009 | ethyl 2-{4-[(1R)-1-{[4-chloro-1-methyl-6-(1-methyl-1H-pyrazol-4-yl)-1H-indol-2-yl]formamido}ethyl]benzenesulfonyl}acetate |

-continued

| Example | Chemical Name |
| --- | --- |
| 05-004 | propan-2-yl 2-{4-[(1R)-1-[(4-chloro-1,6-dimethyl-1H-indol-2-yl)formamido]ethyl]benzenesulfonyl}propanoate |
| 15-008 | 4-chloro-N-[(1R)-1-[4-(3-{4-[(1R)-1-[(4-chloro-1,6-dimethyl-1H-indol-2-yl)formamido]ethyl]benzenesulfonyl}-2-oxopropanesulfonyl)phenyl]ethyl]-1,6-dimethyl-1H-indole-2-carboxamide |
| 07-002 | 4-{4-[(1R)-1-[(4-chloro-1,6-dimethyl-1H-indol-2-yl)formamido]ethyl]benzenesulfonyl}oxane-4-carboxylic acid |
| 09-002 | 2-(acetyloxy)ethyl 2-{4-[(1R)-1-[(4-chloro-1,6-dimethyl-1H-indol-2-yl)formamido]ethyl]benzenesulfonyl}acetate |
| 05-005 | methyl 2-{4-[(1R)-1-[(4-chloro-1,6-dimethyl-1H-indol-2-yl)formamido]ethyl]benzenesulfonyl}-4-methoxybutanoate |
| 02-005 | ethyl 2-{4-[(1R)-1-{[3-(1H-indol-7-yl)-1-methyl-1H-pyrazol-5-yl]formamido}ethyl]benzenesulfonyl}acetate |
| 05-019 | methyl 1-{4-[(1R)-1-[(4-chloro-1,6-dimethyl-1H-indol-2-yl)formamido]ethyl]benzenesulfonyl}cyclopropane-1-carboxylate |
| 01-026 | propan-2-yl 2-{4-[(1R)-1-[(5-chloro-1-methyl-6-{1-[2-(morpholin-4-yl)ethyl]-1H-pyrazol-4-yl}-1H-indol-2-yl)formamido]ethyl]benzenesulfonyl}acetate |
| 01-013 | methyl 2-{4-[(1S)-1-[(4-chloro-1,6-dimethyl-1H-indol-2-yl)formamido]-2-hydroxyethyl]benzenesulfonyl}acetate |
| 09-004 | (2S)-2-methoxypropyl 2-{4-[(1R)-1-[(4-chloro-1,6-dimethyl-1H-indol-2-yl)formamido]ethyl]benzenesulfonyl}acetate |
| 02-004 | ethyl 2-{4-[(1R)-1-{[3-(4-fluorophenyl)-1-methyl-1H-pyrazol-5-yl]formamido}ethyl]benzenesulfonyl}acetate |
| 02-001 | methyl 2-{4-[(1R)-1-{[3-(4-fluorophenyl)-1-methyl-1H-pyrazol-5-yl]formamido}ethyl]benzenesulfonyl}acetate |
| 06-002 | methyl 2-{4-[(1R)-1-{[3-(4-fluorophenyl)-1-methyl-1H-pyrazol-5-yl]formamido}ethyl]benzenesulfonyl}-2-methylpropanoate |
| 05-011 | ethyl 2-{4-[(1R)-1-[(4-chloro-1,6-dimethyl-1H-indol-2-yl)formamido]ethyl]benzenesulfonyl}propanoate |
| 02-007 | methyl 2-{4-[(1S)-2-hydroxy-1-[(1-methyl-3-phenyl-1H-pyrazol-5-yl)formamido]ethyl]benzenesulfonyl}acetate |
| 01-024 | propan-2-yl 2-{4-[(1R)-1-[(4-chloro-1,6-dimethyl-1H-indol-2-yl)formamido]ethyl]benzenesulfonyl}acetate |
| 15-009 | 4-chloro-N-[(1R)-1-{4-[(dimethylcarbamoyl)methanesulfonyl]phenyl}ethyl]-1,6-dimethyl-1H-indole-2-carboxamide |
| 09-020 | 2-methanesulfonylethyl 2-{4-[(1R)-1-[(4-chloro-1,6-dimethyl-1H-indol-2-yl)formamido]ethyl]benzenesulfonyl}acetate |
| 09-001 | 2-(2-ethoxyethoxy)ethyl 2-{4-[(1R)-1-[(4-chloro-1,6-dimethyl-1H-indol-2-yl)formamido]ethyl]benzenesulfonyl}acetate |
| 15-010 | ethyl 2-{4-[(1R)-1-[(1-methyl-5-phenyl-1H-pyrazol-3-yl)formamido]ethyl]benzenesulfonyl}acetate |
| 09-007 | 2-hydroxyethyl 2-{4-[(1R)-1-[(4-chloro-1,6-dimethyl-1H-indol-2-yl)formamido]ethyl]benzenesulfonyl}acetate |
| 15-011 | 2-[(2-{4-[(1R)-1-[(4-chloro-1,6-dimethyl-1H-indol-2-yl)formamido]ethyl]benzenesulfonyl}acetyl)oxy]ethyl 2-{4-[(1R)-1-[(4-chloro-1,6-dimethyl-1H-indol-2-yl)formamido]ethyl]benzenesulfonyl}acetate |
| 01-005 | ethyl 2-{4-[(1S)-1-[(4-chloro-1,6-dimethyl-1H-indol-2-yl)formamido]-2-hydroxyethyl]benzenesulfonyl}acetate |
| 03-002 | 2-{4-[(1S)-1-[(4-chloro-1,6-dimethyl-1H-indol-2-yl)formamido]-2-hydroxyethyl]benzenesulfonyl}acetic acid |
| 03-001 | 2-{4-[(1S)-1-[(4,5-dichloro-1,6-dimethyl-1H-indol-2-yl)formamido]ethyl]benzenesulfonyl}acetic acid |
| 10-001 | 2-methoxyethyl 2-{4-[(1R)-1-[(1-methyl-3-phenyl-1H-pyrazol-5-yl)formamido]ethyl]benzenesulfonyl}acetate |
| 10-002 | 2-(dimethylamino)ethyl 2-{4-[(1R)-1-[(1-methyl-3-phenyl-1H-pyrazol-5-yl)formamido]ethyl]benzenesulfonyl}acetate |
| 03-007 | 2-(4-{1-[(4-chloro-6-ethynyl-1-methyl-1H-indol-2-yl)formamido]ethyl}benzenesulfonyl)acetic acid |
| 03-008 | 2-(4-{1-[(4-chloro-6-iodo-1-methyl-1H-indol-2-yl)formamido]ethyl}benzenesulfonyl)acetic acid |
| 07-003 | 2-{4-[(1R)-1-[(4-chloro-1,6-dimethyl-1H-indol-2-yl)formamido]ethyl]benzenesulfonyl}propanoic acid |
| 07-004 | 1-{4-[(1R)-1-[(4-chloro-1,6-dimethyl-1H-indol-2-yl)formamido]ethyl]benzenesulfonyl}cyclopentane-1-carboxylic acid |
| 02-002 | methyl 2-{4-[(1R)-1-[(1-methyl-3-phenyl-1H-pyrazol-5-yl)formamido]ethyl]benzenesulfonyl}acetate |
| 09-006 | 2-{[(tert-butoxy)carbonyl]amino}ethyl 2-{4-[(1R)-1-[(4-chloro-1,6-dimethyl-1H-indol-2-yl)formamido]ethyl]benzenesulfonyl}acetate |
| 09-008 | 2-methoxyethyl 2-{4-[(1R)-1-{[1-methyl-5-(trifluoromethyl)-1H-indol-2-yl]formamido}ethyl]benzenesulfonyl}acetate |
| 07-006 | (2S)-2-{4-[(1R)-1-[(5-chloro-1-methyl-1H-indol-2-yl)formamido]ethyl]benzenesulfonyl}propanoic acid |
| 05-006 | methyl 2-{4-[(1R)-1-[(5-chloro-1-methyl-1H-indol-2-yl)formamido]ethyl]benzenesulfonyl}propanoate |
| 01-008 | methyl 2-(4-{1-[(4-chloro-6-ethynyl-1-methyl-1H-indol-2-yl)formamido]ethyl}benzenesulfonyl)acetate |

-continued

| Example | Chemical Name |
|---|---|
| 09-010 | pyridin-4-ylmethyl 2-{4-[(1R)-1-[(4-chloro-1,6-dimethyl-1H-indol-2-yl)formamido]ethyl]benzenesulfonyl}acetate |
| 04-002 | 2-{4-[(1R)-1-{[3-(4-fluorophenyl)-1-methyl-1H-pyrazol-5-yl]formamido}ethyl]benzenesulfonyl}acetic acid |
| 07-008 | (2R)-2-{4-[(1R)-1-[(5-chloro-1-methyl-1H-indol-2-yl)formamido]ethyl]benzenesulfonyl}propanoic acid |
| 07-007 | 2-{4-[(1R)-1-[(5-chloro-1-methyl-1H-indol-2-yl)formamido]ethyl]benzenesulfonyl}-2-methylpropanoic acid |
| 03-010 | 2-{4-[(1R)-1-({4,5-dichloro-1,6-dimethyl-1H-pyrrolo[2,3-b]pyridin-2-yl}formamido)ethyl]benzenesulfonyl}acetic acid |
| 01-010 | methyl 2-{4-[(1R)-1-({3,5-dimethyl-3H-benzo[e]indol-2-yl}formamido)ethyl]benzenesulfonyl}acetate |
| 07-010 | 2-{4-[(1R)-1-[(4-chloro-1,6-dimethyl-1H-indol-2-yl)formamido]ethyl]benzenesulfonyl}-4-methoxybutanoic acid |
| 05-007 | methyl 2-{4-[(1R)-1-[(4-chloro-1,6-dimethyl-1H-indol-2-yl)formamido]ethyl]benzenesulfonyl}-2-methylpropanoate |
| 01-014 | tert-butyl 2-{4-[(1R)-1-[(4-chloro-1,6-dimethyl-1H-indol-2-yl)formamido]ethyl]benzenesulfonyl}acetate |
| 01-015 | methyl 2-{4-[(1R)-1-[(4-chloro-1,6,7-trimethyl-1H-indol-2-yl)formamido]ethyl]benzenesulfonyl}acetate |
| 05-008 | methyl 1-{4-[(1R)-1-[(4-chloro-1,6-dimethyl-1H-indol-2-yl)formamido]ethyl]benzenesulfonyl}cyclopentane-1-carboxylate |
| 07-011 | 2-{4-[(1R)-1-[(4-chloro-1,6-dimethyl-1H-indol-2-yl)formamido]ethyl]benzenesulfonyl}butanoic acid |
| 07-009 | 2-{4-[(1R)-1-[(5-chloro-1-methyl-1H-indol-2-yl)formamido]ethyl]benzenesulfonyl}propanoic acid |
| 01-017 | methyl 2-{4-[(1S)-1-[(4,5-dichloro-1,6-dimethyl-1H-indol-2-yl)formamido]ethyl]benzenesulfonyl}acetate |
| 02-006 | methyl 2-{4-[(1R)-1-{[3-(1H-indol-7-yl)-1-methyl-1H-pyrazol-5-yl]formamido}ethyl]benzenesulfonyl}acetate |
| 04-001 | 2-{4-[(1R)-1-[(1-methyl-3-phenyl-1H-pyrazol-5-yl)formamido]ethyl]benzenesulfonyl}acetic acid |
| 05-015 | methyl 2-{4-[(1R)-1-[(4-chloro-1,6-dimethyl-1H-indol-2-yl)formamido]ethyl]benzenesulfonyl}pentanoate |
| 09-009 | butyl 2-{4-[(1R)-1-[(4-chloro-1,6-dimethyl-1H-indol-2-yl)formamido]ethyl]benzenesulfonyl}acetate |
| 02-003 | ethyl 2-{4-[(1R)-1-[(1-methyl-3-phenyl-1H-pyrazol-5-yl)formamido]ethyl]benzenesulfonyl}acetate |
| 01-020 | methyl 2-(4-{1-[(4-chloro-6-iodo-1-methyl-1H-indol-2-yl)formamido]ethyl}benzenesulfonyl)acetate |
| 05-014 | tert-butyl 2-{4-[(1R)-1-[(4-chloro-1,6-dimethyl-1H-indol-2-yl)formamido]ethyl]benzenesulfonyl}-2-methylpropanoate |
| 01-022 | ($^{13}$C)methyl 2-{4-[(1R)-1-[(4,5-dichloro-1,6-dimethyl-1H-indol-2-yl)formamido]ethyl]benzenesulfonyl}acetate |
| 05-002 | methyl 2-{4-[(1R)-1-[(5-chloro-1-methyl-1H-indol-2-yl)formamido]ethyl]benzenesulfonyl}-2-methylpropanoate |
| 10-004 | 2-fluoroethyl 2-{4-[(1R)-1-[(1-methyl-3-phenyl-1H-pyrazol-5-yl)formamido]ethyl]benzenesulfonyl}acetate |
| 02-009 | methyl 2-({5-[(1S)-1-[(1-methyl-3-phenyl-1H-pyrazol-5-yl)formamido]ethyl]pyridin-2-yl}sulfonyl)acetate |
| 01-019 | methyl 2-{4-[(1R)-1-[(5-chloro-1-methyl-1H-indol-2-yl)formamido]ethyl]benzenesulfonyl}acetate |
| 09-016 | cyclopropylmethyl 2-{4-[(1R)-1-[(4-chloro-1,6-dimethyl-1H-indol-2-yl)formamido]ethyl]benzenesulfonyl}acetate |
| 09-024 | 2-[(acetyloxy)methyl]-3-hydroxypropyl 2-{4-[(1R)-1-[(4-chloro-1,6-dimethyl-1H-indol-2-yl)formamido]ethyl]benzenesulfonyl}acetate |
| 09-018 | (3S)-oxolan-3-yl 2-{4-[(1R)-1-[(4-chloro-1,6-dimethyl-1H-indol-2-yl)formamido]ethyl]benzenesulfonyl}acetate |
| 09-017 | oxetan-3-ylmethyl 2-{4-[(1R)-1-[(4-chloro-1,6-dimethyl-1H-indol-2-yl)formamido]ethyl]benzenesulfonyl}acetate |
| 05-016 | ethyl 2-{4-[(1R)-1-({4,5-dichloro-1,6-dimethyl-1H-pyrrolo[2,3-b]pyridin-2-yl}formamido)ethyl]benzenesulfonyl}-2-methylpropanoate |
| 09-027 | 3-hydroxy-2-(hydroxymethyl)propyl 2-{4-[(1R)-1-[(4-chloro-1,6-dimethyl-1H-indol-2-yl)formamido]ethyl]benzenesulfonyl}acetate |
| 09-026 | 2-{[(2-{4-[(1R)-1-[(4-chloro-1,6-dimethyl-1H-indol-2-yl)formamido]ethyl]benzenesulfonyl}acetyl)oxy]methyl}-3-hydroxypropyl 2,2-dimethylpropanoate |
| 09-022 | 3-(acetyloxy)-2-[(acetyloxy)methyl]propyl 2-{4-[(1R)-1-[(4-chloro-1,6-dimethyl-1H-indol-2-yl)formamido]ethyl]benzenesulfonyl}acetate |
| 09-023 | 2-[(2-{4-[(1R)-1-[(4-chloro-1,6-dimethyl-1H-indol-2-yl)formamido]ethyl]benzenesulfonyl}acetyl)oxy]ethyl 2,2-dimethylpropanoate |
| 05-020 | methyl 2-{4-[(1R)-1-({4,5-dichloro-1,6-dimethyl-1H-pyrrolo[2,3-b]pyridin-2-yl}formamido)ethyl]benzenesulfonyl}-2-methylpropanoate |
| 01-025 | ethyl 2-{4-[(1R)-1-[(5-chloro-1-methyl-6-{1-[2-(morpholin-4-yl)ethyl]-1H-pyrazol-4-yl}-1H-indol-2-yl)formamido]ethyl]benzenesulfonyl}acetate |
| 09-019 | (3R)-oxolan-3-yl 2-{4-[(1R)-1-[(4-chloro-1,6-dimethyl-1H-indol-2-yl)formamido]ethyl]benzenesulfonyl}acetate |

-continued

| Example | Chemical Name |
|---|---|
| 09-015 | 2-{[(2-{4-[(1R)-1-[(4-chloro-1,6-dimethyl-1H-indol-2-yl)formamido]ethyl]benzenesulfonyl}acetyl)oxy]methyl}-3-[(2,2-dimethylpropanoyl)oxy]propyl 2,2-dimethylpropanoate |
| 09-021 | 2-methoxy-2-methylpropyl 2-{4-[(1R)-1-[(4-chloro-1,6-dimethyl-1H-indol-2-yl)formamido]ethyl]benzenesulfonyl}acetate |
| 09-025 | oxetan-3-yl 2-{4-[(1R)-1-[(4-chloro-1,6-dimethyl-1H-indol-2-yl)formamido]ethyl]benzenesulfonyl}acetate |
| 01-040 | propan-2-yl 2-{4-[(1S)-1-{[4-chloro-1-methyl-6-(4-methylpiperazin-1-yl)-1H-indol-2-yl]formamido}-2-hydroxyethyl]benzenesulfonyl}acetate |
| 08-002 | 1-{4-[(1R)-1-{[3-(4-fluorophenyl)-1-methyl-1H-pyrazol-5-yl]formamido}ethyl]benzenesulfonyl}cyclopentane-1-carboxylic acid |
| 01-041 | propan-2-yl 2-{4-[(1R)-1-{[4-chloro-1-methyl-6-(4-methylpiperazin-1-yl)-1H-indol-2-yl]formamido}ethyl]benzenesulfonyl}acetate |
| 08-003 | 4-{4-[(1R)-1-{[3-(4-fluorophenyl)-1-methyl-1H-pyrazol-5-yl]formamido}ethyl]benzenesulfonyl}oxane-4-carboxylic acid |
| 06-003 | methyl 1-{4-[(1R)-1-{[3-(4-fluorophenyl)-1-methyl-1H-pyrazol-5-yl]formamido}ethyl]benzenesulfonyl}cyclopentane-1-carboxylate |
| 01-031 | propan-2-yl 2-(4-{[(4-chloro-1,6-dimethyl-1H-indol-2-yl)formamido]methyl}benzenesulfonyl)acetate |
| 01-032 | ethyl 2-(4-{[(4-chloro-1,6-dimethyl-1H-indol-2-yl)formamido]methyl}benzenesulfonyl)acetate |
| 08-001 | 2-{4-[(1R)-1-{[3-(4-fluorophenyl)-1-methyl-1H-pyrazol-5-yl]formamido}ethyl]benzenesulfonyl}-2-methylpropanoic acid |
| 01-030 | methyl 2-(4-{[(4-chloro-1,6-dimethyl-1H-indol-2-yl)formamido]methyl}benzenesulfonyl)acetate |
| 05-022 | methyl 2-{4-[(1R)-1-[(4,5-dichloro-1,6-dimethyl-1H-indol-2-yl)formamido]ethyl]benzenesulfonyl}-2-methylpropanoate |

Biological Data

3-Phosphoglycerate Dehydrogenase (PHGDH) Fluorescence Intensity Assay

This assay is used to identify compounds which inhibit the enzymatic activity of PHGDH which catalyzes the reaction of 3-Phosphoglycerate (3-PG) and NAD to 3-Phosphohydroxypyruvate and NADH.

The produced NADH is used in a coupled reaction for Diaphorase mediated reduction of Resazurin to Resorufin which can be measured in a Fluorescence Intensity readout.

The full length version of PHGDH enzyme was expressed in E. coli with an N-terminal HIS-tag and a TEV cleavage site.

The 3-Phosphoglycerate substrate was purchased from Sigma. NAD, Diaphorase and Resazurin were purchased from Sigma Aldrich.

Compounds are dispensed onto assay plates (black, low volume, flat bottom 384 well, Corning) using an Access Labcyte Workstation with the Labcyte Echo 55× from a DMSO solution. For the chosen highest assay concentration of 100 µM, 150 nl of compound solution are transferred from a 10 mM DMSO compound stock solution. A series of 11 concentrations (10 1:5 steps) is transferred for each compound.

DMSO is added such that every well has a total of 150 nl compound solution.

The assay has been performed at two different NAD/3-PG ratios (final assay concentrations):

PHGDH_HIGH_NAD/3-PG: 250 µM NAD/500 µM 3-PG

PHGDH_500_NAD/3-PG: 500 µM NAD/500 µM 3-PG

5 µl of PHGDH protein (final assay concentration 100 ng/ml) in assay buffer (125 mM Tris-HCl, pH 7.5; 56.25 mM Hydrazine sulfate pH 9.0; 2.5 mM EDTA; assay specific NAD concentration; 0.0125% Tween20) are added to the 150 nl of compounds.

10 µl of a mix containing assay specific 3-PG concentration, Resazurin (25 µM final assay concentration) and Diaphorase (35 µg/ml final assay concentration) are added.

Plates are kept at room temperature. After 240 minutes incubation time the fluorescence signal is measured in a PerkinElmer Envision HTS Multilabel Reader with an excitation wavelength at 530-560 nm and an emission wavelength at 590 nm.

Each plate contains negative controls (diluted DMSO instead of test compound; reaction as described with PHGDH protein) and positive controls (diluted DMSO instead of test compound; reaction as described with buffer instead of PHGDH protein). Negative and positive control values are used for normalization.

A known inhibitor of PHGDH activity is used as internal control.

IC50 values are calculated and analyzed in the MEGA-LAB IC50 application using a 4 parametric logistic model.

| Example | IC50 (PHGDH_HIGH_NAD/ 3-PG) | IC50 (PHGDH_500_NAD/ 3-PG) |
|---|---|---|
| 01-036 | 1833 nM | |
| 09-034 | 52 nM | |
| 02-011 | 6724 nM | |
| 09-028 | 230 nM | |
| 12-004 | 11 nM | 18 nM |
| 12-005 | 17 nM | 28 nM |
| 11-005 | 221 nM | |
| 02-014 | 73347 nM | |
| 10-007 | 714 nM | |
| 06-004 | 78161 nM | |
| 12-006 | 61 nM | 95 nM |
| 11-006 | 1124 nM | |
| 05-021 | 2448 nM | |
| 09-031 | 61 nM | |
| 01-033 | 36497 nM | |
| 11-007 | 234 nM | |
| 01-018 | 3551 nM | |
| 01-034 | 1147 nM | |
| 09-035 | 54 nM | |
| 07-014 | 4 nM | 6 nM |
| 03-015 | 41 nM | |
| 03-013 | 35 nM | |

| Example | IC50 (PHGDH_HIGH_NAD/ 3-PG) | IC50 (PHGDH_500_NAD/ 3-PG) |
|---|---|---|
| 13-007 | 2143 nM | |
| 13-008 | 695 nM | 1204 nM |
| 09-032 | 27 nM | |
| 01-035 | 466 nM | |
| 11-008 | 120 nM | |
| 12-007 | 8 nM | 11 nM |
| 01-037 | 3374 nM | |
| 06-005 | 15855 nM | |
| 10-006 | 938 nM | |
| 09-030 | 85 nM | |
| 02-013 | 6115 nM | |
| 09-029 | 62 nM | |
| 02-015 | 5492 nM | |
| 02-012 | 3718 nM | |
| 11-009 | 612 nM | |
| 10-005 | 766 nM | |
| 11-010 | 447 nM | |
| 14-001 | 83 nM | |
| 01-038 | 261 nM | |
| 09-033 | 98 nM | |
| 14-002 | 58 nM | |
| 03-014 | 5 nM | 7 nM |
| 02-016 | >20000 nM | |
| 14-003 | 7 nM | 9 nM |
| 14-004 | 73 nM | 90 nM |
| 06-006 | 14468 nM | |
| 02-017 | 7706 nM | |
| 03-016 | 5 nM | 7 nM |
| 11-001 | 296 nM | 436 nM |
| 12-001 | 7 nM | 9 nM |
| 11-002 | 189 nM | 291 nM |
| 13-009 | 428 nM | 797 nM |
| 11-003 | 89 nM | 137 nM |
| 06-007 | 29552 nM | |
| 04-004 | 174 nM | 299 nM |
| 13-001 | 204 nM | 305 nM |
| 14-005 | 81 nM | 158 nM |
| 03-017 | 40 nM | 146 nM |
| 03-018 | 84 nM | 292 nM |
| 12-002 | 3 nM | 4 nM |
| 11-004 | 98 nM | 196 nM |
| 06-008 | 8340 nM | |
| 13-002 | 819 nM | 1018 nM |
| 01-039 | 1120 nM | |
| 14-006 | 39 nM | 66 nM |
| 12-003 | 3 nM | 5 nM |
| 14-007 | 38 nM | 59 nM |
| 14-008 | 20 nM | 31 nM |
| 07-015 | 5 nM | 9 nM |
| 05-017 | 1229 nM | 2956 nM |
| 03-012 | 8 nM | 17 nM |
| 01-002 | 169 nM | 258 nM |
| 09-044 | | 419 nM |
| 07-001 | 10 nM | 14 nM |
| 14-009 | | 92 nM |
| 05-023 | | 119 nM |
| 04-003 | 53 nM | 87 nM |
| 14-010 | | 4897 nM |
| 13-003 | | 211 nM |
| 12-009 | | 32 nM |
| 09-036 | | 107 nM |
| 14-011 | | 85 nM |
| 09-037 | | 578 nM |
| 03-004 | 20 nM | 29 nM |
| 14-012 | | 256 nM |
| 09-038 | | 255 nM |
| 14-013 | | 18 nM |
| 09-039 | | 168 nM |
| 09-040 | | 190 nM |
| 03-003 | 13 nM | 22 nM |
| 09-041 | | 156 nM |
| 05-024 | | 119 nM |
| 01-028 | 267 nM | 525 nM |
| 14-014 | | 16 nM |
| 07-012 | 6 nM | 16 nM |

| Example | IC50 (PHGDH_HIGH_NAD/ 3-PG) | IC50 (PHGDH_500_NAD/ 3-PG) |
|---|---|---|
| 12-010 | | 10 nM |
| 03-006 | 3 nM | 4 nM |
| 09-042 | | 509 nM |
| 14-015 | | 1128 nM |
| 14-016 | | 8 nM |
| 14-017 | | 2484 nM |
| 13-010 | | 1061 nM |
| 09-043 | | 246 nM |
| 13-004 | | 690 nM |
| 03-005 | 4 nM | 9 nM |
| 13-005 | | 191 nM |
| 14-018 | | 4542 nM |
| 07-013 | 10 nM | 15 nM |
| 13-006 | | 2084 nM |
| 05-025 | | 20 nM |
| 07-016 | | 21 nM |
| 12-008 | | 8 nM |
| 13-011 | | 1738 nM |
| 14-019 | | 21 nM |
| 14-020 | | 172 nM |
| 05-001 | | 24415 nM |
| 09-001 | | 289 nM |
| 03-001 | | 155 nM |
| 03-002 | | 6 nM |
| 10-001 | | 1452 nM |
| 10-002 | | 497 nM |
| 09-002 | | 230 nM |
| 07-002 | | 7 nM |
| 03-007 | | 29 nM |
| 09-003 | | 286 nM |
| 03-008 | | 24 nM |
| 09-004 | | 394 nM |
| 01-001 | | 441 nM |
| 05-003 | | 15891 nM |
| 02-001 | | 1262 nM |
| 07-003 | | 8 nM |
| 09-005 | | 197 nM |
| 07-004 | | 6 nM |
| 02-002 | | 1356 nM |
| 09-006 | | 701 nM |
| 01-003 | | 905 nM |
| 05-004 | | 11781 nM |
| 09-007 | | 166 nM |
| 01-004 | | 964 nM |
| 05-005 | | 652 nM |
| 01-005 | | 223 nM |
| 07-005 | | 12 nM |
| 02-004 | | 3098 nM |
| 09-008 | | 3456 nM |
| 07-006 | | 238 nM |
| 01-006 | | 485 nM |
| 01-007 | | 121 nM |
| 05-006 | | 3046 nM |
| 01-008 | | 1694 nM |
| 01-009 | | 815 nM |
| 09-010 | | 175 nM |
| 04-002 | | 76 nM |
| 07-008 | | 139 nM |
| 07-007 | | 209 nM |
| 09-011 | | 3510 nM |
| 03-010 | | 170 nM |
| 01-010 | | 943 nM |
| 01-011 | | 1929 nM |
| 07-010 | | 21 nM |
| 10-003 | | 816 nM |
| 03-009 | | 8 nM |
| 05-007 | | 4524 nM |
| 01-013 | | 87 nM |
| 01-014 | | 4251 nM |
| 09-012 | | 303 nM |
| 09-013 | | 19319 nM |
| 01-012 | | 412 nM |
| 01-015 | | 583 nM |
| 02-005 | | 3001 nM |
| 01-016 | | 1094 nM |

-continued

| Example | IC50 (PHGDH_HIGH_NAD/3-PG) | IC50 (PHGDH_500_NAD/3-PG) |
|---|---|---|
| 05-008 | 18286 nM | |
| 07-011 | 11 nM | |
| 05-009 | 1683 nM | |
| 07-009 | 190 nM | |
| 01-017 | 6719 nM | |
| 02-006 | 1270 nM | |
| 05-010 | 11169 nM | |
| 05-011 | 5017 nM | |
| 05-012 | 25095 nM | |
| 04-001 | 145 nM | |
| 05-013 | 5527 nM | |
| 02-007 | 4343 nM | |
| 05-015 | 3470 nM | |
| 01-021 | 463 nM | |
| 09-009 | 3735 nM | |
| 02-003 | 3178 nM | |
| 01-020 | 1786 nM | |
| 05-014 | 5054 nM | |
| 09-014 | 1041 nM | |
| 01-022 | 414 nM | |
| 05-002 | 33068 nM | |
| 03-011 | 9 nM | |
| 10-004 | 1437 nM | |
| 01-023 | 216 nM | |
| 02-009 | >100000 nM | |
| 02-010 | 3688 nM | |
| 01-019 | 2477 nM | |
| 01-024 | 3551 nM | |
| 09-016 | 2105 nM | |
| 09-024 | 247 nM | |
| 09-018 | 418 nM | |
| 05-019 | 5309 nM | |
| 09-017 | 177 nM | |
| 05-016 | >100000 nM | |
| 09-027 | 160 nM | |
| 09-026 | 1406 nM | |
| 09-022 | 431 nM | |
| 05-018 | 5331 nM | |
| 09-023 | 1804 nM | |
| 02-008 | 4843 nM | |
| 05-020 | >20000 nM | |
| 01-027 | 248 nM | |
| 01-025 | 742 nM | |
| 09-019 | 250 nM | |
| 09-015 | 9188 nM | |
| 01-029 | 1133 nM | |
| 09-021 | 574 nM | |
| 09-025 | 72 nM | |
| 01-026 | 1353 nM | |
| 09-020 | 54 nM | |
| 01-040 | 981 nM | |
| 08-002 | 74 nM | 95 nM |
| 01-041 | 3136 nM | |
| 08-003 | 139 nM | |
| 06-001 | 7696 nM | |
| 06-002 | 14654 nM | |
| 06-003 | 11653 nM | |
| 01-031 | >20000 nM | |
| 01-032 | 5943 nM | |
| 08-001 | 161 nM | |
| 01-030 | 3386 nM | |
| 14-021 | 127 nM | |
| 05-022 | 5585 nM | |

$^{13}C_3$ Serine Assay MDA-MB-468

Cell Line:

MDA-MB-468 (ATCC: HTB-132)

Reagents:

Medium I: DMEM Lonza BE12-604F+10% FCS

Medium II: DMEM glucose free (Gibco #A14430-01)+10% FCS+1% Na-Pyruvate (Gibco #11360)+1% Glutamax I (Gibco #35050)+13C Glucose (Aldrich #389374) (20 mM final concentration)

Assay Protocol:

Cells are cultivated in Medium I in a 75 mL flask.

Day 1: 5000 cells in 180 µL Medium I/well were seeded into a 96-well plate. Plates were incubated at 37° C. in a 5% $CO_2$ incubator overnight.

Day 2: 10 mM DMSO stock from test compounds were serially pre-diluted with Medium I (See dilution scheme: for the first well 20 µL DMSO stock are diluted with 180 µL Medium I. From this 1000 µM solution further seven 1:3 (1+2) dilution are prepared with Medium I). 20 µL of these pre-dilutions are transferred in duplicates to the 96-well plate of Day 1. After incubation at 37° C. in a $CO_2$ incubator for 1 hour the medium was removed, 100 µL PBS (tempered to room temperature) added and subsequently removed again.

180 µL Medium II were then added per well and 20 µL of serial dilutions of test compounds in Medium II (as described before) were transferred per well as above. After 180 minutes incubation at 37° C. in a $CO_2$ incubator the medium was again cautiously removed.

After the addition of 100 µL methanol: $H_2O$ (80:20, v:v, pre-cooled to −80° C.) the plates were sealed immediately and frozen at −80° C.

At day of measurement plates were thawn, centrifuged and the supernatant evaporated. The samples were resuspended in 100 µl water for tandem mass spectrometry.

$^{13}C3$ serine levels were analyzed with LC/MS/MS using Multiple Reaction Monitoring (MRM).

Data Analysis:

Detected Peak Areas with MRM transition 107.090/75.80 Da were integrated using Analyst software. IC50 values were computed from these values using a 4 parametric logistic model.

| Example | IC50 ($^{13}$CSERINE) |
|---|---|
| 01-002 | 2.9 nM |
| 01-028 | 7.3 nM |
| 03-006 | 203.3 nM |
| 03-005 | 1068.1 nM |
| 01-018 | 66.3 nM |
| 01-004 | 29.3 nM |
| 01-012 | 52.5 nM |
| 01-024 | 66.3 nM |
| 02-011 | 134.9 nM |
| 15-001 | 55358.7 nM |
| 15-002 | 85293.7 nM |
| 10-006 | 102.9 nM |
| 15-003 | 9638 nM |
| 15-004 | 6273.5 nM |
| 05-017 | 0.3 nM |
| 07-012 | 2392.2 nM |
| 02-008 | 68.4 nM |
| 09-014 | 14.7 nM |
| 15-005 | 309.2 nM |
| 01-029 | 51.4 nM |
| 01-006 | 88.8 nM |
| 09-003 | 82.8 nM |
| 09-012 | 22.2 nM |
| 03-009 | 3567.9 nM |
| 01-001 | 7 nM |
| 05-001 | 891.4 nM |
| 01-011 | 489.3 nM |
| 05-018 | 141.8 nM |
| 02-010 | 593.7 nM |
| 14-020 | 135.7 nM |
| 01-023 | 0.8 nM |
| 01-027 | 34.2 nM |
| 05-010 | 3.7 nM |
| 01-007 | 5 nM |
| 01-021 | 12.6 nM |
| 09-013 | 70.1 nM |
| 05-012 | 906.1 nM |
| 05-013 | 165.9 nM |

-continued

| Example | IC50 ($^{13}$CSERINE) |
|---|---|
| 15-006 | 73.3 nM |
| 09-005 | 138.7 nM |
| 06-001 | 25382.5 nM |
| 07-005 | 1187.5 nM |
| 05-003 | 30.2 nM |
| 10-003 | 23.7 nM |
| 03-011 | 1998 nM |
| 05-009 | 1.6 nM |
| 01-016 | 72.1 nM |
| 01-003 | 109.2 nM |
| 09-011 | 20.1 nM |
| 15-007 | 3216.7 nM |
| 01-009 | 44.1 nM |
| 05-004 | 10.1 nM |
| 15-008 | 11.9 nM |
| 07-002 | 6902.8 nM |
| 09-002 | 69 nM |
| 05-005 | 831.2 nM |
| 02-005 | 64.8 nM |
| 05-019 | 508.8 nM |
| 01-026 | 35.9 nM |
| 01-013 | 8.3 nM |
| 09-004 | 78.6 nM |
| 02-004 | 62.1 nM |
| 02-001 | 32.8 nM |
| 06-002 | 1884 nM |
| 05-011 | 3.9 nM |
| 02-007 | 166.6 nM |
| 15-009 | 3392.1 nM |
| 09-020 | 37.4 nM |
| 09-001 | 53.8 nM |
| 15-010 | 1303.4 nM |
| 09-007 | 23.9 nM |
| 15-011 | 249 nM |
| 01-005 | 3.3 nM |
| 03-002 | 1377 nM |

Therapeutic Use

Due to their biological properties the compounds of the invention, their tautomers, racemates, enantiomers, diastereomers, mixtures thereof and the salts of all the above-mentioned forms may be suitable for treating diseases characterised by excessive or abnormal cell proliferation such as cancer.

For example, the following cancers, tumors and other proliferative diseases may be treated with compounds of the invention, without being restricted thereto:

Cancers/tumors/carcinomas of the head and neck: e.g. tumors/carcinomas/cancers of the nasal cavity, paranasal sinuses, nasopharynx, oral cavity (including lip, gum, alveolar ridge, retromolar trigone, floor of mouth, tongue, hard palate, buccal mucosa), oropharynx (including base of tongue, tonsil, tonsillar pilar, soft palate, tonsillar fossa, pharyngeal wall), middle ear, larynx (including supraglottis, glottis, subglottis, vocal cords), hypopharynx, salivary glands (including minor salivary glands);

cancers/tumors/carcinomas of the lung: e.g. non-small cell lung cancer (NSCLC) (squamous cell carcinoma, spindle cell carcinoma, adenocarcinoma, large cell carcinoma, clear cell carcinoma, bronchioalveolar), small cell lung cancer (SCLC) (oat cell cancer, intermediate cell cancer, combined oat cell cancer);

neoplasms of the mediastinum: e.g. neurogenic tumors (including neurofibroma, neurilemoma, malignant schwannoma, neurosarcoma, ganglioneuroblastoma, ganglioneuroma, neuroblastoma, pheochromocytoma, paraganglioma), germ cell tumors (including seminoma, teratoma, non-seminoma), thymic tumors (including thymoma, thymolipoma, thymic carcinoma, thymic carcinoid), mesenchymal tumors (including fibroma, fibrosarcoma, lipoma, liposarcoma, myxoma, mesothelioma, leiomyoma, leiomyosarcoma, rhabdomyosarcoma, xanthogranuloma, mesenchymoma, hemangioma, hemangioendothelioma, hemangiopericytoma, lymphangioma, lymphangiopericytoma, lymphangiomyoma);

cancers/tumors/carcinomas of the gastrointestinal (GI) tract: e.g. tumors/carcinomas/cancers of the esophagus, stomach (gastric cancer), pancreas, liver and biliary tree (including hepatocellular carcinoma (HCC), e.g. childhood HCC, fibrolamellar HCC, combined HCC, spindle cell HCC, clear cell HCC, giant cell HCC, carcinosarcoma HCC, sclerosing HCC; hepatoblastoma; cholangiocarcinoma; cholangiocellular carcinoma; hepatic cystadenocarcinoma; angiosarcoma, hemangioendothelioma, leiomyosarcoma, malignant schwannoma, fibrosarcoma, Klatskin tumor), gall bladder, extrahepatic bile ducts, small intestine (including duodenum, jejunum, ileum), large intestine (including cecum, colon, rectum, anus; colorectal cancer, gastrointestinal stroma tumor (GIST)), genitourinary system (including kidney, e.g. renal pelvis, renal cell carcinoma (RCC), nephroblastoma (Wilms' tumor), hypernephroma, Grawitz tumor; ureter; urinary bladder, e.g. urachal cancer, urothelial cancer; urethra, e.g. distal, bulbomembranous, prostatic; prostate (androgen dependent, androgen independent, castration resistant, hormone independent, hormone refractory), penis);

cancers/tumors/carcinomas of the testis: e.g. seminomas, non-seminomas,

Gynecologic cancers/tumors/carcinomas: e.g. tumors/carcinomas/cancers of the ovary, fallopian tube, peritoneum, cervix, vulva, vagina, uterine body (including endometrium, fundus);

cancers/tumors/carcinomas of the breast: e.g. mammary carcinoma (infiltrating ductal, colloid, lobular invasive, tubular, adenocystic, papillary, medullary, mucinous), hormone receptor positive breast cancer (estrogen receptor positive breast cancer, progesterone receptor positive breast cancer), Her2 positive breast cancer, triple negative breast cancer, Paget's disease of the breast;

cancers/tumors/carcinomas of the endocrine system: e.g. tumors/carcinomas/cancers of the endocrine glands, thyroid gland (thyroid carcinomas/tumors; papillary, follicular, anaplastic, medullary), parathyroid gland (parathyroid carcinoma/tumor), adrenal cortex (adrenal cortical carcinoma/tumors), pituitary gland (including prolactinoma, craniopharyngioma), thymus, adrenal glands, pineal gland, carotid body, islet cell tumors, paraganglion, pancreatic endocrine tumors (PET; non-functional PET, PPoma, gastrinoma, insulinoma, VIPoma, glucagonoma, somatostatinoma, GRFoma, ACTHoma), carcinoid tumors;

sarcomas of the soft tissues: e.g. fibrosarcoma, fibrous histiocytoma, liposarcoma, leiomyosarcoma, rhabdomyosarcoma, angiosarcoma, lymphangiosarcoma, Kaposi's sarcoma, glomus tumor, hemangiopericytoma, synovial sarcoma, giant cell tumor of tendon sheath, solitary fibrous tumor of pleura and peritoneum, diffuse mesothelioma, malignant peripheral nerve sheath tumor (MPNST), granular cell tumor, clear cell sarcoma, melanocytic schwannoma, plexosarcoma, neuroblastoma, ganglioneuroblastoma, neuroepithelioma, extraskeletal Ewing's sarcoma, paraganglioma, extraskeletal chondrosarcoma, extraskeletal osteosarcoma, mesenchymoma, alveolar soft part sarcoma, epithelioid sarcoma, extrarenal rhabdoid tumor, desmoplastic small cell tumor;

sarcomas of the bone: e.g. myeloma, reticulum cell sarcoma, chondrosarcoma (including central, peripheral, clear cell, mesenchymal chondrosarcoma), osteosarcoma (including parosteal, periosteal, high-grade surface, small cell, radiation-induced osteosarcoma, Paget's sarcoma), Ewing's tumor, malignant giant cell tumor, adamantinoma, (fibrous) histiocytoma, fibrosarcoma, chordoma, small round cell sarcoma, hemangioendothelioma, hemangiopericytoma, osteochondroma, osteoid osteoma, osteoblastoma, eosinophilic granuloma, chondroblastoma;

mesothelioma: e.g. pleural mesothelioma, peritoneal mesothelioma;

cancers of the skin: e.g. basal cell carcinoma, squamous cell carcinoma, Merkel's cell carcinoma, melanoma (including cutaneous, superficial spreading, lentigo maligna, acral lentiginous, nodular, intraocular melanoma), actinic keratosis, eyelid cancer;

neoplasms of the central nervous system and brain: e.g. astrocytoma (cerebral, cerebellar, diffuse, fibrillary, anaplastic, pilocytic, protoplasmic, gemistocytary), glioblastoma, gliomas, oligodendrogliomas, oligoastrocytomas, ependymomas, ependymoblastomas, choroid plexus tumors, medulloblastomas, meningiomas, schwannomas, hemangioblastomas, hemangiomas, hemangiopericytomas, neuromas, ganglioneuromas, neuroblastomas, retinoblastomas, neurinomas (e.g. acoustic), spinal axis tumors;

lymphomas and leukemias: e.g. B-cell non-Hodgkin lymphomas (NHL) (including small lymphocytic lymphoma (SLL), lymphoplasmacytoid lymphoma (LPL), mantle cell lymphoma (MCL), follicular lymphoma (FL), diffuse large cell lymphoma (DLCL), Burkitt's lymphoma (BL)), T-cell non-Hodgkin lymphomas (including anaplastic large cell lymphoma (ALCL), adult T-cell leukemia/lymphoma (ATLL), cutaneous T-cell lymphoma (CTCL), peripheral T-cell lymphoma (PTCL)), lymphoblastic T-cell lymphoma (T-LBL), adult T-cell lymphoma, lymphoblastic B-cell lymphoma (B-LBL), immunocytoma, chronic B-cell lymphocytic leukemia (B-CLL), chronic T-cell lymphocytic leukemia (T-CLL) B-cell small lymphocytic lymphoma (B-SLL), cutaneous T-cell lymphoma (CTLC), primary central nervous system lymphoma (PCNSL), immunoblastoma, Hodgkin's disease (HD) (including nodular lymphocyte predominance HD (NLPHD), nodular sclerosis HD (NSHD), mixed-cellularity HD (MCHD), lymphocyte-rich classic HD, lymphocyte-depleted HD (LDHD)), large granular lymphocyte leukemia (LGL), chronic myelogenous leukemia (CML), acute myelogenous/myeloid leukemia (AML), acute lymphatic/lymphoblastic leukemia (ALL), acute promyelocytic leukemia (APL), chronic lymphocytic/lymphatic leukemia (CLL), prolymphocytic leukemia (PLL), hairy cell leukemia, chronic myelogenous/myeloid leukemia (CML), myeloma, plasmacytoma, multiple myeloma (MM), plasmacytoma, myelodysplastic syndromes (MDS), chronic myelomonocytic leukemia (CMML);

cancers of unknown primary site (CUP);

All cancers/tumors/carcinomas mentioned above which are characterized by their specific location/origin in the body are meant to include both the primary tumors and the metastatic tumors derived therefrom.

All cancers/tumors/carcinomas mentioned above may be further differentiated by their histopathological classification:

Epithelial cancers, e.g. squamous cell carcinoma (SCC) (carcinoma in situ, superficially invasive, verrucous carcinoma, pseudosarcoma, anaplastic, transitional cell, lymphoepithelial), adenocarcinoma (AC) (well-differentiated, mucinous, papillary, pleomorphic giant cell, ductal, small cell, signet-ring cell, spindle cell, clear cell, oat cell, colloid, adenosquamous, mucoepidermoid, adenoid cystic), mucinous cystadenocarcinoma, acinar cell carcinoma, large cell carcinoma, small cell carcinoma, neuroendocrine tumors (small cell carcinoma, paraganglioma, carcinoid); oncocytic carcinoma;

Nonepithilial cancers, e.g. sarcomas (fibrosarcoma, chondrosarcoma, rhabdomyosarcoma, leiomyosarcoma, hemangiosarcoma, giant cell sarcoma, lymphosarcoma, fibrous histiocytoma, liposarcoma, angiosarcoma, lymphangiosarcoma, neurofibrosarcoma), lymphoma, melanoma, germ cell tumors, hematological neoplasms, mixed and undifferentiated carcinomas;

The compounds of the invention may be used in therapeutic regimens in the context of first line, second line, or any further line treatments.

The compounds of the invention may be used for the prevention, short-term or long-term treatment of the above-mentioned diseases, optionally also in combination with radiotherapy and/or surgery.

Of course, the above also includes the use of the compounds of the invention in various methods of treating the above diseases by administering a therapeutically effective dose to a patient in need thereof, as well as the use of these compounds for the manufacture of medicaments for the treatment of such diseases, as well as pharmaceutical compositions including such compounds of the invention, as well as the preparation and/or manufacture of medicaments including such compounds of the invention, and the like.

Combinations with Other Active Substances

The compounds of the invention may be used on their own or in combination with one or several other pharmacologically active substances such as state-of-the-art or standard-of-care compounds, such as e.g. cell proliferation inhibitors, anti-angiogenic substances, steroids or immune modulators/checkpoint inhibitors, and the like.

Therapeutic agents (=cytostatic and/or cytotoxic active substances) which may be administered in combination with the compounds according to the invention, include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors and/or of their corresponding receptors (growth factors such as for example platelet derived growth factor (PDGF), fibroblast growth factor (FGF), vascular endothelial growth factor (VEGF), epidermal growth factor (EGF), insuline-like growth factors (IGF), human epidermal growth factor (HER, e.g. HER2, HER3, HER4) and hepatocyte growth factor (HGF) and/or their corresponding receptors), inhibitors are for example (anti-)growth factor antibodies, (anti-)growth factor receptor antibodies and tyrosine kinase inhibitors, such as for example cetuximab, gefitinib, afatinib, nintedanib, imatinib, lapatinib, bosutinib, bevacizumab and trastuzumab); antimetabolites (e.g. antifolates such as methotrexate, raltitrexed, pyrimidine analogues such as 5-fluorouracil (5-FU), ribonucleoside and deoxyribonucleoside analogues, capecitabine and gemcitabine, purine and adenosine analogues such as mercaptopurine, thioguanine, cladribine and pentostatin, cytarabine (ara C), fludarabine); antitumour antibiotics (e.g. anthracyclins such as doxorubicin, doxil (pegylated liposomal doxorubicin hydrochloride, myocet (non-pegylated liposomal doxorubicin), daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); angiogenesis inhibitors (e.g. tasquinimod), tubuline inhibitors; DNA synthesis inhibitors, PARP inhibitors, topoisomerase inhibitors (e.g. epipodophyllotoxins such as for example etoposide and etopophos, teniposide, amsacrin, topotecan, irinotecan, mitoxantrone), serine/threonine kinase inhibitors (e.g. PDK 1 inhibitors, Raf inhibitors, A-Raf inhibitors, B-Raf inhibitors, C-Raf inhibitors, mTOR inhibitors, mTORC1/2 inhibitors, PI3K inhibitors, PI3Kα inhibitors, dual mTOR/PI3K inhibitors, STK 33 inhibitors, AKT inhibitors, PLK 1 inhibitors, inhibitors of CDKs, Aurora kinase inhibitors), tyrosine kinase inhibitors (e.g. PTK2/FAK inhibitors), protein protein interaction inhibitors (e.g. IAP activator, Mcl-1, MDM2/MDMX), MEK inhibitors, ERK inhibitors, FLT3 inhibitors, BRD4 inhibitors, IGF-1R inhibitors, TRAILR2 agonists, Bcl-xL inhibitors, Bcl-2 inhibitors, Bcl-2/Bcl-xL inhibitors, ErbB receptor inhibitors, BCR-ABL inhibitors, ABL inhibitors, Src inhibitors, rapamycin analogs (e.g. everolimus, temsirolimus, ridaforolimus, sirolimus), androgen synthesis inhibitors, androgen receptor inhibitors, DNMT inhibitors, HDAC inhibitors, ANG1/2 inhibitors, CYP17 inhibitors, radiopharmaceuticals, proteasome inhibitors, immunotherapeutic agents such as immune checkpoint inhibitors (e.g. CTLA4, PD1, PD-L1, PD-L2, LAG3, and TIM3 binding molecules/immunoglobulins, such as e.g. ipilimumab, nivolumab, pembrolizumab), ADCC (antibody-dependent cell-mediated cytotoxicity) enhancers (e.g. anti-CD33 antibodies, anti-CD37 antibodies, anti-CD20 antibodies), t-cell engagers (e.g. bi-specific T-cell engagers (BiTEs®) like e.g. CD3× BCMA, CD3×CD33, CD3×CD19, PSMA×CD3), tumor vaccines and various chemotherapeutic agents such as amifostin, anagrelid, clodronat, filgrastin, interferon, interferon alpha, leucovorin, procarbazine, levamisole, mesna, mitotane, pamidronate and porfimer.

Most preferred are combinations with IAP activators, proteasome inhibitors, immunotherapeutic agents such as immune checkpoint inhibitors (e.g. CTLA4, PD1, PD-L1, PD-L2, LAG3, and TIM3 binding molecules/immunoglobulins, such as e.g. ipilimumab, nivolumab, pembrolizumab), ADCC (antibody-dependent cell-mediated cytotoxicity) enhancers (e.g. anti-CD33 antibodies, anti-CD37 antibodies, anti-CD20 antibodies), T-cell engagers (e.g. bi-specific T-cell engagers (BiTEs®) like e.g. CD3×BCMA, CD3× CD33, CD3×CD19, PSMA×CD3) and tumor vaccines.

When two or more substances or principles are to be used as part of a combined treatment regimen, they can be administered via the same route of administration or via different routes of administration, at essentially the same time (i.e. simultaneously, concurrently) or at different times (e.g. sequentially, successively, alternately, consecutively, or according to any other sort of alternating regime).

When the substances or principles are to be administered simultaneously via the same route of administration, they may be administered as different pharmaceutical formulations or compositions or as part of a combined pharmaceutical formulation or composition. Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmacological or therapeutic effect.

Of course, the above includes the preparation and methods of preparing, the compounds of the invention for the combined use with the above combination partners. Also included are the preparation, and methods of preparing, the above-mentioned combination partners for the combined use with the compounds of the invention.

Furthermore, the invention also encompasses kits comprising at least one compound of the invention and one or more other components selected from the group consisting of other drugs used for the treatment of the diseases and disorders as described above, and devices as described below.

Formulations

Suitable preparations for administering the compounds of the invention will be apparent to those with ordinary skill in the art and include for example tablets, pills, capsules, suppositories, lozenges, troches, solutions—particularly solutions for injection (s.c., i.v., i.m.) and infusion (injectables)—elixirs, syrups, sachets, emulsions, inhalatives or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) of the invention with known excipients, for example inert diluents, carriers, disintegrants, adjuvants, surfactants, binders and/or lubricants. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may of course contain, apart from the above-mentioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage range of the compounds of formula (I) applicable per day is usually from 1 mg to 2000 mg, preferably from 1 to 1000 mg.

The dosage for intravenous use is from 1 mg to 1000 mg with different infusion rates, preferably between 5 mg and 500 mg with different infusion rates.

However, it may sometimes be necessary to depart from the amounts specified, depending on the body weight, age, the route of administration, severity of the disease, the individual response to the drug, the nature of its formulation and the time or interval over which the drug is administered (continuous or intermittent treatment with one or multiple doses per day). Thus, in some cases it may be sufficient to use less than the minimum dose given above, whereas in other cases the upper limit may have to be exceeded. When administering large amounts it may be advisable to divide them up into a number of smaller doses spread over the day.

The formulation examples which follow illustrate the present invention without restricting its scope:

Examples of Pharmaceutical Formulations

| A) | |
|---|---|
| Tablets | per tablet |
| active substance according to formulae (I) | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) | |
|---|---|
| Tablets | per tablet |
| active substance according to formulae (I)) | 80 mg |
| lactose | 55 mg |
| corn starch | 190 mg |
| microcrystalline cellulose | 35 mg |
| polyvinylpyrrolidone | 15 mg |
| sodiumcarboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) | |
|---|---|
| Tablets | per tablet |
| active substance according to formulae (I) | 25 mg |
| lactose | 50 mg |
| microcrystalline cellulose | 24 mg |
| magnesium stearate | 1 mg |
| | 100 mg |

The active substance, lactose and cellulose are mixed together. The mixture is screened, then either moistened with water, kneaded, wet-granulated and dried or dry-granulated or directly final blend with the magnesium stearate and compressed to tablets of suitable shape and size. When wet-granulated, additional lactose or cellulose and magnesium stearate is added and the mixture is compressed to produce tablets of suitable shape and size.

| D) | |
|---|---|
| Ampoule solution | |
| active substance according to formulae (I) | 50 mg |
| sodium chloride | 50 mg |
| water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The invention claimed is:

1. A compound of formula (I), or a salt thereof,

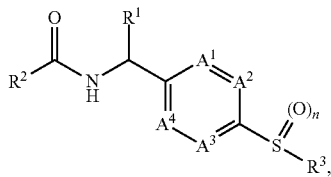

wherein n is 1 or 2;

$A^1, A^2, A^3$ and $A^4$ are independently selected from $-N=$ and $-CR^{13}=$ and wherein none, one or two independently selected $A^1, A^2, A^3$ and $A^4$ can be $-N=$;

$R^{13}$ is hydrogen, halogen, $-C_{1-3}$alkyl, $-O-C_{1-3}$alkyl;

$R^1$ is selected from the group consisting of hydrogen, $-C_{1-3}$alkyl and $-C_{1-3}$ alkyl-OH;

$R^2$ is

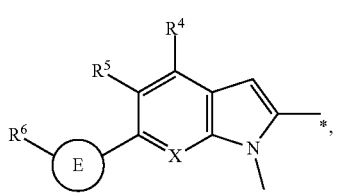

wherein

X is $-N=$ or $-CR^7-$;

$R^7$ is selected from hydrogen, halogen, $-C_{1-3}$alkyl and $-O-C_{1-3}$ alkyl;

$R^4$ is selected from the group consisting of hydrogen, halogen, $-C_{1-3}$haloalkyl, $-C_{1-3}$alkyl;

$R^5$ is selected from the group consisting of hydrogen, halogen, $-C_{1-3}$haloalkyl, $-C_{1-3}$alkyl;

or $R^4$ and $R^5$ taken together form a ring selected from a 5 or 6 membered heteroaryl, a 5 or 6 membered heterocyclyl and phenyl;

E is selected from a bond, $-C_{1-3}$alkylene-, $-C_{1-3}$haloalkylene-, $-C_{2-3}$alkynylene, 5 or 6 membered -heteroarylene- and 5 or 6 membered -heterocyclylene-;

$R^6$ is selected from hydrogen, halogen, $-C_{1-3}$alkyl, which $-C_{1-3}$alkyl is optionally substituted with one group selected from $-NH_2$, $-N(C_{1-3}alkyl)_2$ and 5 or 6 membered heterocycloalkyl;

or $R^2$ is

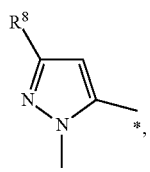

wherein $R^8$ is selected from indolyl or phenyl, each of which group is optionally substituted with one, two or three substituents independently selected from halogen, $-C_{1-3}$haloalkyl, $-C_{1-3}$alkyl, $-O-C_{1-3}$alkyl;

$R^3$ is

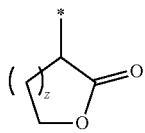

and z is 1 or 2;

or $R^3$ is $-C(R^9R^{10})-COO-R^{11}$ and $R^9$ and $R^{10}$ are the same or different, independently selected from hydrogen, $-C_{1-3}$alkyl, $-C_{1-3}$alkyl-$O-C_{1-3}$alkyl;

or $R^9$ and $R^{10}$ taken together form a $-C_{3-5}$cycloalkyl or a 6 membered heterocycloalkyl, which heterocycloalkyl is optionally substituted with $-C(O)-C_{1-3}$alkyl;

$R^{11}$ is selected from the group consisting of hydrogen, $-C_{3-6}$cycloalkyl, 4-6 membered heterocycloalkyl and $-C_{1-5}$alkyl, which $-C_{1-5}$alkyl group is optionally and independently substituted with one or two the same or different substituents, selected from $R^{12}$;

$R^{12}$ is selected from the group consisting of $-C_{3-6}$cycloalkyl, halogen, $-OH$, $-O-C_{1-4}$alkyl, $-O-C_{1-4}$alkyl-$O-C_{1-4}$alkyl, $-O-C_{1-4}$alkyl-OH, $-OC(O)-C_{1-4}$alkyl, $-NHCOO-C_{1-4}$alkyl, $-SO_2-C_{1-3}$alkyl, $-N(C_{1-3}alkyl)_2$, 5 or 6 membered heteroaryl and phenyl, which phenyl group is optionally substituted with $-C_{1-3}$haloalkyl, or $R^{12}$ is a 4 to 6 membered heterocycloalkyl, which heterocycloalkyl is optionally substituted with halogen or $-C_{1-3}$alkyl.

2. The compound according to claim 1, or a salt thereof, wherein each of $A^1, A^2, A^3$ and $A^4$ is $-CH=$.

3. The compound according to claim 1, or a salt thereof, wherein $R^1$ is selected from among hydrogen, $-CH_3$ and $-CH_2OH$.

4. The compound according to claim 3, or a salt thereof, wherein $R^1$ is selected from among $-CH_3$ and $-CH_2OH$.

5. The compound according to claim 1, or a salt thereof, wherein X is $-CR^7-$ and $R^7$ is selected from hydrogen and $-O-C_{1-3}$alkyl.

6. The compound according to claim 1, or a salt thereof, wherein $R^2$ is

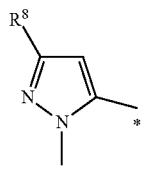

and
R[8] is selected from
indolyl and phenyl, wherein the phenyl is optionally substituted with —F, —Cl, —O—CH$_3$, —CH$_3$.

7. The compound according to claim 1, or a salt thereof, wherein R[4] is selected from among hydrogen, —F and —Cl.

8. The compound according to claim 1, or a salt thereof, wherein R[5] is selected from among hydrogen, —F, —Cl, —CF$_3$.

9. The compound according to claim 1, or a salt thereof, wherein E is a bond and R[6] is selected from hydrogen, —C$_{1-3}$alkyl and halogen; or
E is a 5 membered -heteroarylene- and R[6] is —C$_{1-3}$alkyl substituted with a 6 membered heterocycloalkyl; or
E is a 6 membered -heterocycloalkylene- and R[6] is —C$_{1-3}$ alkyl,
E is —C$_{2-3}$alkynylene- and R[6] is hydrogen.

10. The compound according to claim 9, or a salt thereof, wherein E is a bond and R[6] is —C$_{1-3}$alkyl.

11. The compound according to claim 1, or a salt thereof, wherein R[3] is selected from the group consisting of —C(R[9]R[10])—COO—R[11],

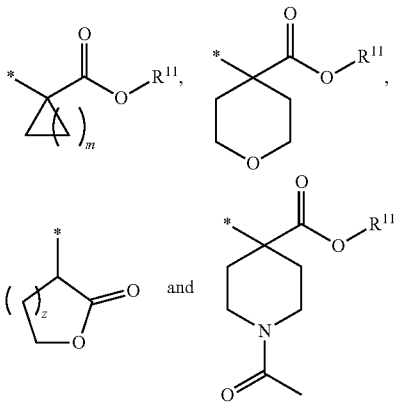

z is 1 or 2;
m is 1, 2, 3 or 4;
R[9] and R[10] are the same or different, independently selected from hydrogen, —C$_{1-3}$alkyl, —C$_{1-3}$alkyl-O—C$_{1-3}$alkyl;
R[11] is selected from the group consisting of hydrogen, 3-6 membered cycloalkyl, 3-6 membered heterocycloalkyl, or —C$_{1-5}$alkyl linear or branched, optionally substituted with 1 or 2 the same or different substituents, independently selected from R[12];
R[12] is selected from the group consisting of cycloalkyl, heterocycloalkyl, halogen, OH, —O—C$_{1-4}$alkyl, —O—C$_{1-4}$alkyl-O—C$_{1-4}$alkyl, —OC(O)—C$_{1-4}$alkyl, —NHCOO—C$_{1-4}$alkyl, —SO$_2$—C$_{1-3}$alkyl, —N(C$_{1-3}$alkyl)$_2$,

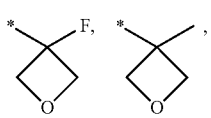

five and six membered aryl and heteroaryl.

12. The compound according to claim 1, or a salt thereof, wherein R[11] is H or —C$_{1-5}$alkyl.

13. The compound according to claim 1, or a salt thereof, wherein R[9] and R[10] are the same or different, independently selected from hydrogen and —C$_{1-3}$alkyl.

14. The compound according to claim 1, or a salt thereof, wherein R[2] is

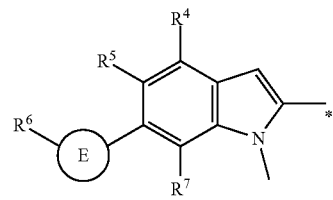

R[7] is hydrogen;
R[4] is selected from the group consisting of —F, —Cl, Br and —C$_{1-3}$alkyl;
R[5] is selected from the group consisting of —F, —Cl and Br;
E is a bond and R[6] is —C$_{1-3}$alkyl.

15. The compound according to claim 1, or a salt thereof, wherein R[3] is selected from

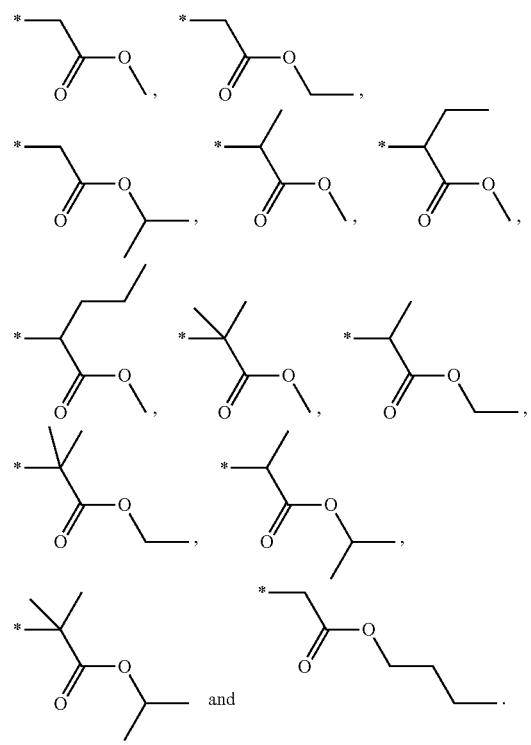

16. A pharmaceutical composition comprising a compound according to claim 1, or a pharmaceutically acceptable salt thereof, and a pharmaceutically acceptable carrier.

* * * * *